(12) United States Patent
Carry et al.

(10) Patent No.: US 8,791,255 B2
(45) Date of Patent: Jul. 29, 2014

(54) (6-OXO-1,6-DIHYDROPYRIMIDIN-2-YL)AMIDE DERIVATIVES, PREPARATION THEREOF AND PHARMACEUTICAL USE THEREOF AS AKT(PKB) PHOSPHORYLATION INHIBITORS

(75) Inventors: Jean-Christophe Carry, Paris (FR); Victor Certal, Paris (FR); Frank Halley, Paris (FR); Karl Andreas Karlsson, Paris (FR); Laurent Schio, Paris (FR); Fabienne Thompson, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/338,011

(22) Filed: Dec. 27, 2011

(65) Prior Publication Data
US 2012/0270867 A1    Oct. 25, 2012

Related U.S. Application Data

(63) Continuation of application No. PCT/FR2010/051375, filed on Jul. 1, 2010.

(60) Provisional application No. 61/241,100, filed on Sep. 10, 2009.

(30) Foreign Application Priority Data

Jul. 2, 2009  (FR) ...................................... 09 03239
Oct. 9, 2009  (FR) ...................................... 09 57070

(51) Int. Cl.
*C07D 413/04*    (2006.01)

(52) U.S. Cl.
USPC ......................................................... 544/123

(58) Field of Classification Search
USPC ........................................................... 544/123
See application file for complete search history.

(56) References Cited

FOREIGN PATENT DOCUMENTS

| CL | 201101040 | 12/2011 |
|----|-----------|---------|
| CL | 201103333 | 7/2012 |
| WO | WO 2006/005914 A1 | 1/2006 |
| WO | WO 2007/042806 A1 | 4/2007 |
| WO | WO 2007/042810 A1 | 4/2007 |
| WO | WO2009/007749 A2 | 1/2009 |
| WO | 2010056563 A1 | 5/2010 |
| WO | 2011002684 A1 | 1/2011 |

OTHER PUBLICATIONS

International Search Report dated Sep. 13, 2010 issued in PCT/FR2010/051375.

*Primary Examiner* — Rebecca Anderson
(74) *Attorney, Agent, or Firm* — Brian R. Morrill

(57) ABSTRACT

The invention relates to the novel materials of formula (I),

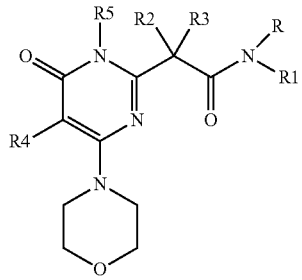

wherein each of the substituents R, R1, R2, R3, R4 and R5 is as defined herein. The materials are useful as inhibitors of AKT(PKB) phosphorylation.

3 Claims, No Drawings

(6-OXO-1,6-DIHYDROPYRIMIDIN-2-YL)AMIDE DERIVATIVES, PREPARATION THEREOF AND PHARMACEUTICAL USE THEREOF AS AKT(PKB) PHOSPHORYLATION INHIBITORS

This application claims the benefit of U.S. Provisional Application No. 61/241,100 filed on Sep. 10, 2009.

The present invention relates to novel chemical compounds (6-oxo-1,6-dihydropyrimidin-2-yl)amide), derived from pyrimidinones, to the process for the preparation thereof, to the novel intermediates obtained, to the use thereof as medicaments, to the pharmaceutical compositions containing them and to the novel use of such derivatives.

The present invention thus also relates to the use of said derivatives for the preparation of a medicament for use in the treatment of humans.

More particularly, the invention relates to novel pyrimidinone derivatives and to the pharmaceutical use thereof for the prevention and treatment of conditions capable of being modulated by inhibition of the PI3K/AKT/mTOR pathway. AKT is a key participant in the signalling pathway. A high level of AKT phosphorylation is the mark of the activation of the pathway, which is found in many human cancers.

The products of the present invention may thus in particular be used for the prevention or treatment of conditions capable of being modulated by inhibition of AKT phosphorylation (P-AKT). The inhibition of P-AKT may especially be obtained by inhibition of the PI3K/AKT/mTOR pathway, and in particular by inhibition of kinases belonging to this pathway, for instance receptor tyrosine kinases such as EGFR, IGFR, ErbB2,3'-phosphoinositide-dependent protein kinase-1 (PDK1), the PI3K phosphoinositide kinase, the AKT serine-threonine kinase, or the mTOR kinase.

The inhibition and regulation of the PI3K/AKT/mTOR pathway constitutes in particular a new and powerful mechanism of action for the treatment of a large number of cancer diseases including solid and liquid tumours.

Such conditions that can be treated by the products of the present application are solid or liquid human tumours.

Role of the PI3K/AKT/mTOR Pathway

The PI3K/AKT/mTOR signalling pathway is a complex network which regulates multiple cell functions, such as growth, survival, proliferation and cell growth, which are key processes in tumour regenesis.

This signalling pathway is an important target in the treatment of cancer since most of its effectors are altered in human tumours. The principal effectors contribute to the activation of the pathway are i) oncogenes, such as ErbB1 (EGFR), ErbB2 (HER2), PIK3CA and AKT, activated by mutation, amplification or overexpression; ii) a deficiency in tumour suppressor genes such as PTEN, TSC1/2, LKB and PML, which are inactivated following mutations or deletions (Jiang L-Z & Liu L-Z, Biochim Biophys Acta, 2008, 1784:150; Vivanco I & Sawyers C L, 2002, Nat Rev Cancer, 2:489; Cully M et al., Nature Rev. Cancer, 2006, 6:184).

The activation of the oncogenes of this signalling pathway is found in many human cancer diseases:

PIK3CA activating mutations are present in 15-30% of colon, breast, endometrial, liver, ovarian and prostate cancers (T L Yuan and L C Cantley, Oncogene, 2008, 27:5497; Y. Samuels et al. Science, 2004, 304:554; K E. Bachman et al. Cancer Biol Ther, 2004, 3:772; D A Levine et al. Clin Canc Res. 2005, 11:2875; C. Hartmann et al. Acta Neuropathol. 2005, 109:639);

amplifications, activating mutations and overexpressions of RTKs such as EGFR and HER2 in brain, breast and lung (NSCLC) cancers;

amplification and activating overexpression of AKT in brain, lung (NSCLC), breast, kidney, ovarian and pancreatic cancers (Testa J R. and Bellacosa A., Proct. Natl. Acad. Sci. USA 2001, 98:10983; Cheng et al., Proct. Natl. Acad. Sci. USA 1992, 89: 9267; Bellacosa et al., Int. J. Cancer, 1995, 64:280; Cheng et al., Proct. Natl. Acad. Sci. USA 1996, 93:3636; Yuan et al., Oncogene, 2000, 19:2324).

Deficiency in the tumour suppressor genes of this signalling pathway is also found in many human cancer diseases:

deletion of PTEN in 50% of lung (NSCLC), liver, kidney, prostate, breast, brain, pancreatic, endometrial and colon cancers (Maxwell G L et al. Canc. Res. 1998, 58:2500; Zhou X-P et al. Amer. J. Pathol., 2002, 161: 439; Endersby R & Baker S J, Oncogene, 2008, 27:5416; Li et al. Science, 1997, 275:1943; Steack P A et al., Nat. Genet., 1997, 15:356);

mutations in TSC1/2 in more than 50% of tuberous scleroses;

mutations or deletions in LKB1 (or STK11) which predispose to gastrointestinal tract cancers and to pancreatic cancer and which are found in particular in 10-38% of lung adenocarcinomas (Shah U. et al. Cancer Res. 2008, 68:3562);

modifications of PML in particular by translocation in human tumours (Gurrieri C and al, J. NAtl Cancer Inst. 2004, 96:269).

In addition, this signalling pathway is a major factor for resistance to chemotherapy, to radiotherapy and to targeted therapies such as EGFR and HER2 inhibitors, for example (C. Sawyers et al. Nat Rev 2002).

Role of AKT

AKT (proteine kinase B; PKB) is a serine-threonine kinase which occupies a central place in one of the major cell signalling pathways, the PI3K/AKT pathway. AKT is in particular involved in the growth, proliferation, and survival of tumour cells. AKT activation occurs in two steps, (i) by phosphorylation of threonine 308 (P-T308) by PDK1 and (2) by phosphorylation of serine 473-(P-S473) by mTORC2 (or mTOR-Rictor complex), resulting in complete activation. AKT in turn regulates a large number of proteins, including mTOR (mammalian target of Rapamycin), BAD, GSK3, p21, p27, FOXO or FKHRL1 (Manning B D & Cantley L C, Cell, 2007 129:1261). The activation of AKT promotes the internalisation of nutrients, thereby triggering a process of anabolising metabolisation supporting cell growth and proliferation. In particular, AKT controls the initiation of protein synthesis through a cascade of interactions that occurs by means of TSC1/2 (tuberous scleroses complex), Rheb and TOR, so as to result in two essential targets of the signalling pathway, p70S6K and 4EBP. AKT also induces inhibiting phosphorylation of the Forkhead transcription factor and inactivation of GSK3β, which result in the inhibition of apoptosis and in progression of the cell cycle (Franke T F, Oncogene, 2008, 27:6473). AKT is therefore a target for anticancer therapy and the inhibition of AKT activation by inhibition of the phosphorylation thereof may induce apoptosis of malignant cells and, by the same token, provide a treatment for cancer.

Receptor Tyrosine Kinases such as IGF1R

Abnormally high levels of protein kinase activity have been implicated in many diseases resulting from abnormal cell functions. This may originate either directly or indirectly from a dysfunction in the mechanisms for controlling the kinase activity, related to for example an inappropriate mutation, overexpression or activation of the enzyme, or owing to an overproduction or underproduction of cytokines or of growth factors, also involved in the transduction of upstream or downstream signals of kinases. In all these cases, a selective inhibition of the action of kinases leads to the hope of a beneficial effect.

The insulin-like growth factor type 1 receptor (IGF-I-R) is a transmembrane receptor tyrosine kinase which binds firstly to IGFI, but also to IGFII and to insulin with a weak affinity. The binding of IGF1 to its receptor leads to oligomerisation of the receptor, activation of the tyrosine kinase, intermolecular autophosphorylation and phosphorylation of cell substrates (principal substrates: IRS1 and Shc). The receptor activated by its ligand induces a mitogenic activity in normal cells. However, IGF-I-R plays an important role in "abnormal" growth.

Several clinical reports underline the important role of the IGF-I pathway in the development of human cancers:

IGF-I-R is often found overexpressed in many tumour types (breast, colon, lung, sarcoma, prostate, multiple myeloma) and its presence is often associated with a more aggressive phenotype.

High concentrations of circulating IGF1 are strongly correlated with a risk of prostate, lung and breast cancer.

Furthermore, it has been widely documented that IGF-I-R is necessary for the establishment and maintenance of the transformed phenotype in vitro just as in vivo [Baserga R, Exp. Cell. Res., 1999, 253, pages 1-6]. The kinase activity of IGF-I-R is essential for the transforming activity of several oncogenes: EGFR, PDGFR, SV40 virus broad T antigen, activated Ras, Raf, and v-Src. The expression of IGF-I-R in normal fibroblasts induces a neoplastic phenotype, which can subsequently lead to tumour formation in vivo. IGF-I-R expression plays an important role in substrate-independent growth. IGF-I-R has also been shown to be a protector in chemotherapy- and radiation-induced apoptosis and cytokine-induced apoptosis. Furthermore, the inhibition of endogenous IGF-I-R by a dominant negative, the formation of a triple helix or the expression of an antisense causes a suppression of the transforming activity in vitro and a decrease in tumour growth in animal models.

PDK1

3'-Phosphoinositide-dependent protein kinase-1 (PDK1) is one of the essential components of the PI3K-AKT signalling pathway. It is a serine-threonine (Ser/Thr) kinase, the role of which is to phosphorylate and activate other Ser/Thr kinases of the AGC family that are involved in the control of cell growth, proliferation and survival and in the regulation of the metabolism. These kinases include protein kinase B (PKB or AKT), SGK (or serum and glucocorticoid regulated kinase), RSK (or p90 ribosomal S6 kinase), p70S6K (or p70 ribosomal S6 kinase) and also various isoforms of protein kinase C (PKC) (Vanhaesebroeck B. & Alessi D R., Biochem J, 2000, 346:561). One of the key roles of PDK1 is therefore the activation of AKT: in the presence of PIP3, which is the second messenger generated by PI3K, PDK-1 is recruited to the plasma membrane via its PH (pleckstrin homology) domain and phosphorylates AKT on threonine 308 located in the activation loop, which is an essential modification for AKT activation. PDK1 is expressed ubiquitously and is a constitutively activate kinase. PDK1 is a key element in the PI3K/AKT signalling pathway for regulating key processes in tumour genesis, such as cell proliferation and survival. Since this pathway is activated in more than 50% of human cancers, PDK1 represents a target for anticancer therapy. The inhibition of PDK1 should result in an effective inhibition of the proliferation and survival of cancer cells and therefore provide a therapeutic benefit for human cancers (Bayascas J R, Cell cycle, 2008, 7:2978; Peifer C. & Alessi D R, Chem Med Chem, 2008, 3:1810).

Phosphoinositide 3-kinases (PI3Ks)

The PI3K lipid kinase is an important target in this signalling pathway for oncology. The class I PI3Ks are divided up into class Ia (PI3Kα,β,δ) activated by receptor tyrosine kinases (RTKs), G protein-coupled receptors (GPCRs), GTPases of the family Rho and p21-Ras, and class Ib (PI3Kγ) activated by GPCRs and p21-Ras. The class Ia PI3Ks are heterodimers which consist of a catalytic subunit p110α, β or δ and a regulatory subunit p85 or p55. The class Ib (p110γ) is monomeric. The class I PI3Ks are lipid/protein kinases which are activated by RTKs, GPCRs or Ras after recruitment to the membrane. These class I PI3Ks phosphorylate phosphatidylinositol 4,5-diphosphate (PIP2) on position 3 of the inositol so as to give phosphatidylinositol 3,4,5-triphosphate (PIP3), a key secondary messenger in this signalling pathway. In turn, PIP3 recruits AKT and PDK1 to the membrane, where they bind via their pleckstrin homology domain (PH domain), resulting in activation of AKT by PDK1 phosphorylation on threonine 308. AKT phosphorylates many substrates, thus playing a key role in many processes resulting in cell transformation, such as cell proliferation, growth and survival, and also angiogenesis.

The class I PI3Ks are implicated in human cancers: somatic mutations of the PIK3CA gene, which encodes PI3Kα, are found in 15-35% of human tumours, with in particular two principal oncogenic mutations, H1047R (in the kinase domain), and E545K/E542K (in the helical domain), (Y. Samuels et al. Science, 2004, 304:554; T L Yuan and L C Cantley, Oncogene, 2008, 27:5497). PI3K inhibitors are expected to be effective in the treatment of many human cancers exhibiting genetic alterations resulting in the activation of the PI3K/AKT/mTOR pathway (Vogt P. et al., Virology, 2006, 344:131; Zhao L & Vogt P K, Oncogene, 2008, 27:5486).

Kinase-inhibiting morpholino-pyrimidinone derivatives are known to those skilled in the art.

Application WO 2008/148074 describes products which have an mTOR-inhibiting activity. These products are pyrido[1,2-a]pyrimidin-4-ones which differ from the products of the present invention owing to their entirely aromatic nature and their substitutions.

Application WO 2008/064244 describes the application of the PI3Kβ-inhibiting products TGX-221 and TGX-155 that are of use in the treatment of cancer, and in particular of breast cancer. These products are pyrido[1,2-a]pyrimidin-4-ones previously described in applications WO 2004/016607 and WO 2001/053266, which differ from the products of the present invention owing to their entirely aromatic nature and their substitutions.

Applications WO 2006/109081, WO 2006/109084 and WO 2006/126010 describe DNA-PK-inhibiting products that are of use in the treatment of ATM-deficient cancers. These products are pyrido[1,2-a]pyrimidin-4-ones which differ from the products of the present invention owing to their entirely aromatic nature and their substitutions.

Application WO 2003/024949 describes DNA-PK-inhibiting products that are of use in the treatment of ATM-deficient cancers. These products are pyrido[1,2-a]pyrimidin-4-ones which differ from the products of the present invention owing to their entirely aromatic nature and their substitutions.

Kinase-inhibiting morpholinopyrimidine derivatives are also known to those skilled in the art.

Applications WO 2009/007748, WO 2009/007749, WO 2009/007750 and WO 2009/007751 describe products which have mTOR-inhibiting and/or PI3K-inhibiting activity, for the treatment of cancers. These products are pyrimidines substituted in the 2, 4 and 6 positions and the products of the present invention differ therefrom owing to the presence of the carbonyl group on the pyrimidinone and also by virtue of the various substituents.

The subject of the present invention is the products of formula (I):

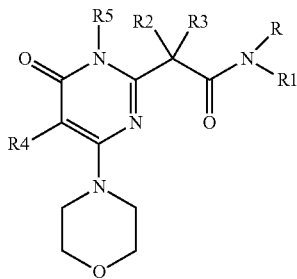

in which:
R1 represents an aryl or heteroaryl radical optionally substituted with one or more radicals, which may be identical or different, chosen from halogen atoms and hydroxyl, CN, nitro, —COOH, —COOalk, —NRxRy, —CONRxRy, —NRxCORy, —CORy, —NRxCO₂Rz, alkoxy, phenoxy, alkylthio, alkyl, alkenyl, alkynyl, cycloalkyl, O-cycloalkyl, heterocycloalkyl, aryl and heteroaryl radicals;

the latter alkoxy, phenoxy, alkylthio, alkyl, alkenyl, alkynyl, heterocycloalkyl, aryl and heteroaryl radicals being themselves optionally substituted with one or more radicals, which may be identical or different, chosen from halogen atoms and hydroxyl, alkoxy, NRvRw, heterocycloalkyl or heteroaryl radicals;

the aryl and heteroaryl radicals being, in addition, optionally substituted with one or more alkyl and alkoxy radicals, themselves optionally substituted with one or more halogen atoms;

it being possible for the heterocycloalkyl and heteroaryl radicals to additionally contain an oxo radical;

R represents a hydrogen atom or else forms, with R1, a saturated or partially or totally unsaturated 5- or 6-membered ring fused to an aryl or heteroaryl residue and optionally containing one or more other heteroatoms chosen from O, S, N, NH and Nalk, this bicyclic radical being optionally substituted with one or more radicals, which may be identical or different, chosen from halogen atoms and CO—NH₂, hydroxyl, alkyl and alkoxy radicals; the latter alkyl radical being itself optionally substituted with a hydroxyl, alkoxy, NH₂, NHalk or N(alk)₂ radical;

R2 and R3, which may be identical or different, independently represent a hydrogen atom, a halogen atom or an alkyl radical optionally substituted with one or more halogen atoms;

R4 represents a hydrogen atom;

R5 represents a hydrogen atom or an alkyl radical optionally substituted with one or more halogen atoms;

NRvRw being such that Rv represents a hydrogen atom or an alkyl radical and Rw represents a hydrogen atom or a cycloalkyl radical, CO₂alk, or an alkyl radical optionally substituted with one or more radicals, which may be identical or different, chosen from hydroxyl, alkoxy, NRvRw and heterocycloalkyl radicals; or Rx and Ry form, with the nitrogen atom to which they are attached, a cyclic radical containing from 3 to 10 ring members and optionally one or more other heteroatoms chosen from O, S, NH and N-alkyl, this cyclic radical being optionally substituted;

NRvRw being such that Rv represents a hydrogen atom or an alkyl radical and Rw represents a hydrogen atom or a cycloalkyl radical or an alkyl radical optionally substituted with one or more radicals, which may be identical or different, chosen from hydroxyl, alkoxy and heterocycloalkyl radicals; or Rv and Rw form, with the nitrogen atom to which they are attached, a cyclic radical containing from 3 to 10 ring members and optionally one or more other heteroatoms chosen from O, S, NH and N-alkyl, this cyclic radical being optionally substituted;

the cyclic radicals that Rx and Ry or Rv and Rw, respectively, can form, with the nitrogen atom to which they are attached, being optionally substituted with one or more radicals, which may be identical or different, chosen from halogen atoms and alkyl, hydroxyl, oxo, alkoxy, NH₂; NHalk and N(alk)₂ radicals;

Rz represents the values of Ry except for hydrogen;

Rx, Ry and Rz in the —NRxCORy, —CORy and NRxCO₂Rz radicals being chosen from the meanings indicated above for Rx, Ry and Rz;

all the above alkyl (alk), alkoxy and alkylthio radicals being linear or branched and containing from 1 to 6 carbon atoms, said products of formula (I) being in all the possible racemic, enantiomeric and diastereoisomeric isomer forms, and also the addition salts with inorganic and organic acids or with inorganic and organic bases, of said products of formula (I).

The products of formula (I) according to the invention are therefore such that:
either R represents H and R1 represents an aryl or heteroaryl radical optionally substituted as defined above or hereinafter,
or R forms, with R1, a saturated or partially or totally unsaturated 5- or 6-membered ring fused to an aryl or heteroaryl residue and optionally containing one or more other heteroatoms chosen from O, S, N, NH and Nalk, this bicyclic radical being optionally substituted as defined above or hereinafter,
the substituents R2, R3, R4 and R5 of said products of formula (I) having the definitions indicated above,
said products of formula (I) being in all the possible racemic, enantiomeric and diastereoisomeric isomer forms, and also the addition salts with inorganic and organic acids or with inorganic and organic bases, of said products of formula (I).

The subject of the present invention is thus the products of formula (I) as defined above, in which:
R1 represents a phenyl, pyridine, thienyl, benzoxazolyl, benzofuryl, indazolyl, indolyl, benzothienyl, benzimidazolyl, benzoxazinyl or tetrahydroquinolyl radical optionally substituted with one or more radicals, which may be identical or different, chosen from halogen atoms and CN, nitro, —COOH, —COOalk, —NRxRy, alkoxy, alkyl, alkynyl and cycloalkyl radicals;

the latter alkoxy, alkyl and alkynyl radicals being themselves optionally substituted with one or more radicals, which may be identical or different, chosen from halogen atoms and hydroxyl, alkoxy, NRvRw, piperidyl, pyrrolidinyl or heteroaryl radicals;

the phenyl and heteroaryl radicals being, in addition, optionally substituted with one or more alkyl and alkoxy radicals;

R represents a hydrogen atom or else forms, with R1, a benzoxazinyl, dihydroindolyl, tetrahydroisoquinolyl, tetrahydroquinolyl or dihydropyrrolopyridyl ring, these rings being optionally substituted with one or more radicals, which may be identical or different, chosen from halogen atoms and CO—$NH_2$, hydroxyl, alkyl and alkoxy radicals;
the latter alkyl radical being itself optionally substituted with a hydroxyl, alkoxy, $NH_2$, NHalk or N(alk)$_2$ radical;
R2 and R3, which may be identical or different, independently represent a hydrogen atom, a fluorine atom or an alkyl radical;
R4 represents a hydrogen atom;
R5 represents a hydrogen atom or an alkyl radical;
NRxRy being such that Rx represents a hydrogen atom or an alkyl radical and Ry represents a hydrogen atom or an alkyl radical; or Rx and Ry form, with the nitrogen atom to which they are attached, a cyclic radical containing from 3 to 10 ring members and optionally one or more other heteroatoms chosen from O, S, NH and N-alkyl, this cyclic radical being optionally substituted;
NRvRw being such that Rv represents a hydrogen atom or an alkyl radical and Rw represents a hydrogen atom or an alkyl radical;
all the above alkyl (alk) and alkoxy radicals being linear or branched and containing from 1 to 6 carbon atoms,
said products of formula (I) being in all the possible racemic, enantiomeric and diastereoisomeric isomer forms, and also the addition salts with inorganic and organic acids or with inorganic and organic bases, of said products of formula (I).

The subject of the present invention is the products of formula (I):

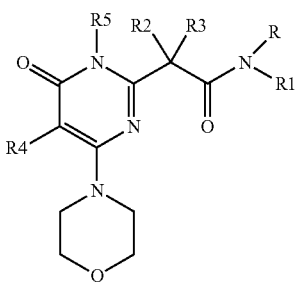

in which:
R1 represents an aryl or heteroaryl radical optionally substituted with one or more radicals, which may be identical or different, chosen from halogen atoms and hydroxyl, CN, nitro, —COOH, —COOalk, —NRxRy, —CONRxRy, —NRxCORy, —CORy, —NRxCO$_2$Rz, alkoxy, phenoxy, alkylthio, alkyl, alkenyl, alkynyl, cycloalkyl, O-cycloalkyl, heterocycloalkyl, aryl and heteroaryl radicals;
the latter alkoxy, phenoxy, alkylthio, alkyl, alkenyl, alkynyl, heterocycloalkyl, aryl and heteroaryl radicals being themselves optionally substituted with one or more radicals, which may be identical or different, chosen from halogen atoms and hydroxyl, alkoxy and NRvRw radicals;
the aryl and heteroaryl radicals being, in addition, optionally substituted with one or more alkyl and alkoxy radicals, themselves optionally substituted with one or more halogen atoms;
it being possible for the heterocycloalkyl and heteroaryl radicals to additionally contain an oxo radical;
R represents a hydrogen atom or else forms, with R1, a saturated or partially or totally unsaturated 5- or 6-membered ring fused to an aryl or heteroaryl residue and optionally containing one or more other heteroatoms chosen from O, S, N, NH and Nalk, this bicyclic radical being optionally substituted with one or more radicals, which may be identical or different, chosen from halogen atoms and hydroxyl, alkyl and alkoxy radicals;
R2 and R3, which may be identical or different, independently represent a hydrogen atom, a halogen atom or an alkyl radical optionally substituted with one or more halogen atoms;
R4 represents a hydrogen atom;
R5 represents a hydrogen atom or an alkyl radical optionally substituted with one or more halogen atoms;
NRxRy being such that Rx represents a hydrogen atom or an alkyl radical and Ry represents a hydrogen atom or a cycloalkyl radical or an alkyl radical optionally substituted with one or more radicals, which may be identical or different, chosen from hydroxyl, alkoxy, NRvRw and heterocycloalkyl radicals; or Rx and Ry form, with the nitrogen atom to which they are attached, a cyclic radical containing from 3 to 10 ring members and optionally one or more other heteroatoms chosen from O, S, NH and N-alkyl, this cyclic radical being optionally substituted;
NRvRw being such that Rv represents a hydrogen atom or an alkyl radical and Rw represents a hydrogen atom or a cycloalkyl radical or an alkyl radical optionally substituted with one or more radicals, which may be identical or different, chosen from hydroxyl, alkoxy and heterocycloalkyl radicals; or Rv and Rw form, with the nitrogen atom to which they are attached, a cyclic radical containing from 3 to 10 ring members and optionally one or more other heteroatoms chosen from O, S, NH and N-alkyl, this cyclic radical being optionally substituted;
the cyclic radicals that Rx and Ry or Rv and Rw, respectively, can form, with the nitrogen atom to which they are attached, being optionally substituted with one or more radicals, which may be identical or different, chosen from halogen atoms and alkyl, hydroxyl, oxo, alkoxy, $NH_2$; NHalk and N(alk)$_2$ radicals;
Rz represents the values of Ry except for hydrogen;
Rx, Ry and Rz in the —NRxCORy, —CORy and NRxCO$_2$Rz radicals being chosen from the meanings indicated above for Rx, Ry and Rz;
said products of formula (I) being in all the possible racemic, enantiomeric and diastereoisomeric isomer forms, and also the addition salts with inorganic and organic acids or with inorganic and organic bases, of said products of formula (I).

In the products of formula (I):
the term "alkyl (or alk) radical" denotes the linear, and where appropriate branched, radicals methyl, ethyl, propyl, isopropyl, butyl, isobutyl, sec-butyl, tert-butyl, pentyl, isopentyl, hexyl, isohexyl and also heptyl, octyl, nonyl and decyl, and also the linear or branched positional isomers thereof: the alkyl radicals containing from 1 to 6 carbon atoms and more particularly the alkyl radicals containing from 1 to 4 carbon atoms of the above list are preferred;
the term "alkoxy radical" denotes the linear, and where appropriate branched, radicals methoxy, ethoxy, propoxy, isopropoxy, linear, secondary or tertiary butoxy, pentoxy or hexoxy, and also the linear or branched positional isomers thereof: the alkoxy radicals containing from 1 to 4 carbon atoms of the above list are preferred;
the term "alkylthio radical" denotes the linear, and where appropriate branched, radicals methylthio, ethylthio, propylthio, isopropylthio, linear, secondary or tertiary butylthio, pentylthio or hexylthio, and also the linear or branched positional isomers thereof: the alkylthio radicals containing from 1 to 4 carbon atoms of the above list are preferred;

the term "halogen atom" denotes chlorine, bromine, iodine or fluorine atoms, and preferably the chlorine, bromine or fluorine atom;

the term "cycloalkyl radical" denotes a saturated carbocyclic radical containing 3 to 10 carbon atoms and thus denotes in particular cyclopropyl, cyclobutyl, cyclopentyl and cyclohexyl radicals, and most particularly cyclopropyl, cyclopentyl and cyclohexyl radicals;

in the —O-cycloalkyl radical, cycloalkyl is as defined above;

the term "heterocycloalkyl radical" thus denotes a monocyclic or bicyclic carbocyclic radical containing from 3 to 10 ring members, interrupted with one or more heteroatoms, which may be identical or different, chosen from oxygen, nitrogen or sulphur atoms: mention may, for example, be made of morpholinyl, thiomorpholinyl, homomorpholinyl, aziridyl, azetidyl, piperazinyl, piperidyl, homopiperazinyl, pyrrolidinyl, imidazolidinyl, pyrazolidinyl, tetrahydrofuryl, tetrahydrothienyl, tetrahydropyran, oxodihydropyridazinyl or else oxetanyl radicals, all these radicals being optionally substituted; mention may in particular be made of morpholinyl, thiomorpholinyl, homomorpholinyl, piperazinyl, piperidyl, homopiperazinyl or else pyrrolidinyl radicals;

the terms "aryl" and "heteroaryl" denote monocyclic or bicyclic, respectively carbocyclic and heterocyclic, unsaturated or partially unsaturated radicals containing at most 12 ring members, that may optionally contain a —C(O) ring member, the heterocyclic radicals containing one or more heteroatoms, which may be identical or different, chosen from O, N, or S, with N, where appropriate, being optionally substituted;

the term "aryl radical" thus denotes monocyclic or bicyclic radicals containing 6 to 12 ring members, such as, for example, phenyl, naphthyl, biphenyl, indenyl, fluorenyl and anthracenyl radicals, more particularly phenyl and naphthyl radicals, and even more particularly the phenyl radical. It may be noted that a carbocyclic radical containing a —C(O) ring member is, for example, the tetralone radical;

the term "heteroaryl radical" thus denotes monocyclic or bicyclic radicals containing 5 to 12 ring members: monocyclic heteroaryl radicals such as, for example, the radicals: thienyl, such as 2-thienyl and 3-thienyl, furyl, such as 2-furyl or 3-furyl, pyranyl, pyrrolyl, pyrrolinyl, pyrazolinyl, imidazolyl, pyrazolyl, pyridyl, such as 2-pyridyl, 3-pyridyl and 4-pyridyl, pyrazinyl, pyrimidinyl, pyridazinyl, oxazolyl, thiazolyl, isothiazolyl, diazolyl, thiadiazolyl, thiatriazolyl, oxadiazolyl, isoxazolyl, such as 3- or 4-isoxazolyl, furazanyl, free or salified tetrazolyl, all these radicals being optionally substituted, among which are more particularly the radicals: thienyl, such as 2-thienyl and 3-thienyl, thiazolyl, furyl, such as 2-furyl, pyrrolyl, pyrrolinyl, pyrazolinyl, imidazolyl, pyrazolyl, oxazolyl, isoxazolyl, pyridyl and pyridazinyl, these radicals being optionally substituted; bicyclic heteroaryl radicals such as, for example, the radicals: benzothienyl (benzothiophene), such as 3-benzothienyl, benzothiazolyl, quinolyl, isoquinolyl, dihydroquinolyl, quinolone, tetralone, adamentyl, benzofuryl, isobenzofuryl, dihydrobenzofuran, ethylenedioxyphenyl, thianthrenyl, benzopyrrolyl, benzimidazolyl, benzoxazinyl, benzoxazolyl, thionaphthyl, indolyl, dihydroindolyl, azaindolyl, indazolyl, purinyl, thienopyrazolyl, tetrahydroindazolyl, tetrahydroquinolyl, tetrahydroisoquinolyl, tetrahydrocyclopentapyrazolyl, dihydrofuropyrazolyl, dihydropyrrolopyridyl, tetrahydropyrrolopyrazolyl, oxotetrahydropyrrolopyrazolyl, tetrahydropyranopyrazolyl, tetrahydropyridinopyrazolyl or oxodihydropyridinopyrazolyl, all these radicals being optionally substituted.

As examples of heteroaryl or bicyclic radicals, mention may more particularly be made of pyrimidinyl, pyridyl, pyrrolyl, azaindolyl, indazolyl or pyrazolyl, benzothiazolyl or benzimidazolyl radicals optionally substituted with one or more substituents, which may be identical or different, as indicated above.

The carboxyl radical(s) of the products of formula (I) may be salified or esterified with the various groups known to those skilled in the art, among which mention may be made, for example of:

among the salification compounds, inorganic bases such as, for example, an equivalent of sodium, of potassium, of lithium, of calcium, of magnesium or of ammonium, or organic bases such as, for example, methylamine, propylamine, trimethylamine, diethylamine, triethylamine, N,N-dimethylethanolamine, tris(hydroxymethyl)aminomethane, ethanolamine, pyridine, picoline, dicyclohexylamine, morpholine, benzylamine, procaine, lysine, arginine, histidine and N-methylglucamine;

among the esterification compounds, the alkyl radicals for forming alkoxycarbonyl groups, such as, for example, methoxycarbonyl, ethoxycarbonyl, tert-butoxycarbonyl or benzyloxycarbonyl, it being possible for these alkyl radicals to be substituted with radicals chosen, for example, from halogen atoms and hydroxyl, alkoxy, acyl, acyloxy, alkylthio, amino or aryl radicals, as, for example, in chloromethyl, hydroxypropyl, methoxymethyl, propionyloxymethyl, methylthiomethyl, dimethylaminoethyl, benzyl or phenethyl groups.

The addition salts with inorganic or organic acids of the products of formula (I) may, for example, be the salts formed with hydrochloric acid, hydrobromic acid, hydroiodic acid, nitric acid, sulphuric acid, phosphoric acid, propionic acid, acetic acid, trifluoroaectic acid, formic acid, benzoic acid, maleic acid, fumaric acid, succinic acid, tartaric acid, citric acid, oxalic acid, glyoxylic acid, aspartic acid, ascorbic acid, alkoylmonosulphonic acids such as, for example, methanesulphonic acid, ethanesulphonic acid or propanesulphonic acid, alkoyldisulphonic acids such as, for example, methanedisulphonic acid or alpha, beta-ethanedisulphonic acid, arylmonosulphonic acids such as benzenesulphonic acid, and aryldisulphonic acids.

It may be recalled that stereoisomerism can be defined in its broad sense as the isomerism of compounds having the same structural formulae, but the various groups of which are arranged differently in space, such as in particular in monosubstituted cyclohexanes in which the substituent may be in the axial or equatorial position, and the various possible rotational conformations of ethane derivatives. However, another type of stereoisomerism exists, due to the different spatial arrangements of fixed substituents, on double bonds or on rings, which is often referred to as geometrical isomerism or cis-transisomerism. The term "stereoisomerism" is used in the present application in its broadest sense and therefore relates to all the compounds indicated above.

The subject of the present invention is the products of formula (I) as defined above, in which:

R₁ represents a phenyl, pyridine, thienyl, benzoxazole-4-yl or indazol-6-yl radical, optionally substituted with one or more radicals, which may be identical or different, chosen from halogen atoms and CN, nitro, —COOH, —COOalk, —NRxRy, alkoxy, alkyl, alkynyl and cycloalkyl radicals;
the latter alkoxy, alkyl and alkynyl radicals being themselves optionally substituted with one or more radicals, which may be identical or different, chosen from halogen atoms and hydroxyl, alkoxy and NRvRw radicals;
the phenyl and heteroaryl radicals being, in addition, optionally substituted with one or more alkyl and alkoxy radicals;
R represents a hydrogen atom or else forms, with R1, a 1,4-benzoxazin-4-yl or 2,3-dihydroindol-1-yl ring, these rings being optionally substituted with one or more radicals, which may be identical or different, chosen from halogen atoms and hydroxyl, alkyl and alkoxy radicals;
R2 and R3, which may be identical or different, independently represent a hydrogen atom, a fluorine atom or an alkyl radical;
R4 represents a hydrogen atom;
R5 represents a hydrogen atom or an alkyl radical;
NRxRy being such that Rx represents a hydrogen atom or an alkyl radical and Ry represents a hydrogen atom or an alkyl radical; or Rx and Ry form, with the nitrogen atom to which they are attached, a cyclic radical containing from 3 to 10 ring members and optionally one or more other heteroatoms chosen from O, S, NH and N-alkyl, this cyclic radical being optionally substituted;
NRvRw being such that Rv represents a hydrogen atom or an alkyl radical and Rw represents a hydrogen atom or an alkyl radical;
all the above alkyl (alk) and alkoxy radicals being linear or branched and containing from 1 to 6 carbon atoms,
said products of formula (I) being in all the possible racemic, enantiomeric and diastereoisomeric isomer forms, and also the addition salts with inorganic and organic acids or with inorganic and organic bases, of said products of formula (I).

In particular, when NRxRy or NRvRw forms a ring as defined above, such an amine ring may be chosen in particular from pyrrolidinyl, pyrazolidinyl, pyrazolinyl, piperidyl, azepinyl, morpholinyl, homomorpholinyl, piperazinyl or homopiperazinyl radicals, these radicals being themselves optionally substituted as indicated above or hereinafter.

The NRxRy or NRvRw ring may more particularly be chosen from the radicals: pyrrolidinyl or morpholinyl optionally substituted with one or two alkyl radicals or piperazinyl radicals optionally substituted on the second nitrogen atom with an alkyl, phenyl, or and CH₂-phenyl radical, themselves optionally substituted with one or more radicals, which may be identical or different, chosen from halogen atoms and alkyl, hydroxyl and alkoxy radicals.

The subject of the present invention is most particularly the products of formula (I) as defined above, corresponding to the following formulae:
2-[4-(morpholin-4-yl)-6-oxo-1,6-dihydropyrimidin-2-yl]-N-phenylacetamide
N-(4-fluorophenyl)-2-[4-(morpholin-4-yl)-6-oxo-1 hydropyrimidin-2-yl]acetamide
N-(3-chlorophenyl)-2-[4-(morpholin-4-yl)-6-oxo-1,6-dihydropyrimidin-2-yl]acetamide
N-[3-(dimethylamino)phenyl]-2-[4-(morpholin-4-yl)-6-oxo-1,6-dihydropyrimidin-2-yl]acetamide
N-(2,4-difluorophenyl)-2-[4-(morpholin-4-yl)-6-oxo-1,6-dihydropyrimidin-2-yl]acetamide
N-(3,4-difluorophenyl)-2-[4-(morpholin-4-yl)-6-oxo-1,6-dihydropyrimidin-2-yl]acetamide
2-[4-(morpholin-4-yl)-6-oxo-1,6-dihydropyrimidin-2-yl]-N-(thiophen-3-yl)acetamide
N-(4-fluoro-3-methoxyphenyl)-2-[4-(morpholin-4-yl)-6-oxo-1,6-dihydropyrimidin-2-yl]acetamide
N-(2-fluorophenyl)-2-[4-(morpholin-4-yl)-6-oxo-1,6-dihydropyrimidin-2-yl]acetamide
N-(2-methylphenyl)-2-[4-(morpholin-4-yl)-6-oxo-1,6-dihydropyrimidin-2-yl]acetamide
N-(2-methoxyphenyl)-2-[4-(morpholin-4-yl)-6-oxo-1,6-dihydropyrimidin-2-yl]acetamide
N-(2,3-difluorophenyl)-2-[4-(morpholin-4-yl)-6-oxo-1,6-dihydropyrimidin-2-yl]acetamide
N-(3,5-difluorophenyl)-2-[4-(morpholin-4-yl)-6-oxo-1,6-dihydropyrimidin-2-yl]acetamide
N-(3-fluorophenyl)-2-[4-(morpholin-4-yl)-6-oxo-1,6-dihydropyrimidin-2-yl]acetamide
N-(4-chlorophenyl)-2-[4-(morpholin-4-yl)-6-oxo-1,6-dihydropyrimidin-2-yl]acetamide
N-(3-methoxyphenyl)-2-[4-(morpholin-4-yl)-6-oxo-1,6-dihydropyrimidin-2-yl]acetamide
2-[4-(morpholin-4-yl)-6-oxo-1,6-dihydropyrimidin-2-yl]-N-[3-(trifluoromethyl)phenyl]acetamide
N-(3-bromophenyl)-2-[4-(morpholin-4-yl)-6-oxo-1,6-dihydropyrimidin-2-yl]acetamide
N-[3-(2-methylpropan-2-yl)phenyl]-2-[4-(morpholin-4-yl)-6-oxo-1,6-dihydropyrimidin-2-yl]acetamide
methyl 3-({[4-(morpholin-4-yl)-6-oxo-1,6-dihydropyrimidin-2-yl]acetyl}amino)benzoate
3-({[4-(morpholin-4-yl)-6-oxo-1,6-dihydropyrimidin-2-yl]acetyl}amino)benzoic acid
2-[4-(morpholin-4-yl)-6-oxo-1,6-dihydropyrimidin-2-yl]-N-[3-(propan-2-yl)phenyl]acetamide
N-(3-methylphenyl)-2-[4-(morpholin-4-yl)-6-oxo-1,6-dihydropyrimidin-2-yl]acetamide
N-(3-cyano-4-fluorophenyl)-2-[4-(morpholin-4-yl)-6-oxo-1,6-dihydropyrimidin-2-yl]acetamide
N-(1H-indazol-6-yl)-2-[4-(morpholin-4-yl)-6-oxo-1,6-dihydropyrimidin-2-yl]acetamide
N-(3-cyanophenyl)-2-[4-(morpholin-4-yl)-6-oxo-1,6-dihydropyrimidin-2-yl]acetamide
N-(5-fluoropyridin-2-yl)-2-[4-(morpholin-4-yl)-6-oxo-1,6-dihydropyrimidin-2-yl]acetamide
N-(4-fluoro-3-methylphenyl)-2-[4-(morpholin-4-yl)-6-oxo-1,6-dihydropyrimidin-2-yl]acetamide
N-(3-chloro-4-fluorophenyl)-2-[4-(morpholin-4-yl)-6-oxo-1,6-dihydropyrimidin-2-yl]acetamide
2-[4-(morpholin-4-yl)-6-oxo-1,6-dihydropyrimidin-2-yl]-N-(pyridin-3-yl)acetamide
N-(4-fluoro-2-methylphenyl)-2-[4-(morpholin-4-yl)-6-oxo-1,6-dihydropyrimidin-2-yl]acetamide
N-(3-hydroxyphenyl)-2-[4-(morpholin-4-yl)-6-oxo-1,6-dihydropyrimidin-2-yl]acetamide
N-(3-bromo-4-fluorophenyl)-2-[4-(morpholin-4-yl)-6-oxo-1,6-dihydropyrimidin-2-yl]acetamide
2-[4-(morpholin-4-yl)-6-oxo-1,6-dihydropyrimidin-2-yl]-N-(3,4,5-trifluorophenyl)acetamide
N-[4-fluoro-3-(hydroxymethyl)phenyl]-2-[4-(morpholin-4-yl)-6-oxo-1,6-dihydropyrimidin-2-yl]acetamide
N-(3-cyclopropylephenyl)-2-[4-(morpholin-4-yl)-6-oxo-1,6-dihydropyrimidin-2-yl]acetamide
N-(2-hydroxyphenyl)-2-[4-(morpholin-4-yl)-6-oxo-1,6-dihydropyrimidin-2-yl]acetamide
N-[3-(difluoromethoxy)phenyl]-2-[4-(morpholin-4-yl)-6-oxo-1,6-dihydropyrimidin-2-yl]acetamide
N-(4-fluoro-3-methoxyphenyl)-2-[4-(morpholin-4-yl)-6-oxo-1,6-dihydropyrimidin-2-yl]propanamide N-(2,3-dimethylphenyl)-2-[4-(morpholin-4-yl)-6-oxo-1,6-dihydropyrimidin-2-yl]acetamide
N-(2-fluoro-3-methylphenyl)-2-[4-(morpholin-4-yl)-6-oxo-1,6-dihydropyrimidin-2-yl]acetamide
N-(1,3-benzoxazol-4-yl)-2-[4-(morpholin-4-yl)-6-oxo-1,6-dihydropyrimidin-2-yl]acetamide
2-[4-(morpholin-4-yl)-6-oxo-1,6-dihydropyrimidin-2-yl]-N-[3-(trifluoromethoxy)phenyl]acetamide
2-[4-(morpholin-4-yl)-6-oxo-1,6-dihydropyrimidin-2-yl]-N-[3-(propan-2-yloxy)phenyl]acetamide
N-(4-fluoro-2-methoxyphenyl)-2-[4-(morpholin-4-yl)-6-oxo-1,6-dihydropyrimidin-2-yl]acetamide
2-methylpropan-2-yl {2-[3-({[4-(morpholin-4-yl)-6-oxo-1,6-dihydropyrimidin-2-yl]acetyl}amino)phenyl]ethyl}carbamate
N-[4-fluoro-3-(trifluoromethyl)phenyl]-2-[4-(morpholin-4-yl)-6-oxo-1,6-dihydropyrimidin-2-yl]acetamide
N-(3-ethynylphenyl)-2-[4-(morpholin-4-yl)-6-oxo-1,6-dihydropyrimidin-2-yl]acetamide
N-(3-cyclopentyloxy)phenyl]-2-[4-(morpholin-4-yl)-6-oxo-1,6-dihydropyrimidin-2-yl]acetamide
N-(4-fluoro-2-hydroxyphenyl)-2-[4-(morpholin-4-yl)-6-oxo-1,6-dihydropyrimidin-2-yl]acetamide
2-[2-(2,3-dihydro-1H-indol-1-yl)-2-oxoethyl]-6-(morpholin-4-yl)pyrimidin-4(3H)-one
N-(3-cyclopropyl-4-fluorophenyl)-2-[4-(morpholin-4-yl)-6-oxo-1,6-dihydropyrimidin-2-yl]acetamide
2-[4-(morpholin-4-yl)-6-oxo-1,6-dihydropyrimidin-2-yl]-N-(2,3,4-trifluorophenyl)acetamide
N-[4-fluoro-3-(trifluoromethoxy)phenyl]-2-[4-(morpholin-4-yl)-6-oxo-1,6-dihydropyrimidin-2-yl]acetamide
N-[3-(2-hydroxyethoxy)phenyl]-2-[4-(morpholin-4-yl)-6-oxo-1,6-dihydropyrimidin-2-yl]acetamide
N-(3-iodophenyl)-2-[4-(morpholin-4-yl)-6-oxo-1,6-dihydropyrimidin-2-yl]acetamide
methyl 2-fluoro-5-({[4-(morpholin-4-yl)-6-oxo-1,6-dihydropyrimidin-2-yl]acetyl}amino)benzoate
N-(3-ethoxyphenyl)-2-[4-(morpholin-4-yl)-6-oxo-1,6-dihydropyrimidin-2-yl]acetamide
N-(2,4-difluoro-3-methoxyphenyl)-2-[4-(morpholin-4-yl)-6-oxo-1,6-dihydropyrimidin-2-yl]acetamide
2-[4-(morpholin-4-yl)-6-oxo-1,6-dihydropyrimidin-2-yl]-N-(2,4,5-trifluorophenyl)acetamide
N-(3,5-dichloro-4-fluorophenyl)-2-[4-(morpholin-4-yl)-6-oxo-1,6-dihydropyrimidin-2-yl]acetamide
2-[2-(2,3-dihydro-4H-1,4-benzoxazin-4-yl)-2-oxoethyl]-6-(morpholin-4-yl)pyrimidin-4(3H)-one
N-(4-fluoro-3-nitrophenyl)-2-[4-(morpholin-4-yl)-6-oxo-1,6-dihydropyrimidin-2-yl]acetamide
2-fluoro-5-({[4-(morpholin-4-yl)-6-oxo-1,6-dihydropyrimidin-2-yl]acetyl}amino)benzoic acid
N-(5-fluoro-2-hydroxyphenyl)-2-[4-(morpholin-4-yl)-6-oxo-1,6-dihydropyrimidin-2-yl]acetamide
N-(2-bromo-4-fluorophenyl)-2-[4-(morpholin-4-yl)-6-oxo-1,6-dihydropyrimidin-2-yl]acetamide
N-(4-fluorophenyl)-2-[1-methyl-4-(morpholin-4-yl)-6-oxo-1,6-dihydropyrimidin-2-yl]acetamide
N-(3-chloro-4-fluorophenyl)-2-[1-methyl-4-(morpholin-4-yl)-6-oxo-1,6-dihydropyrimidin-2-yl]acetamide
N-(3-bromophenyl)-2-[1-methyl-4-(morpholin-4-yl)-6-oxo-1,6-dihydropyrimidin-2-yl]acetamide
2-[1-ethyl-4-(morpholin-4-yl)-6-oxo-1,6-dihydropyrimidin-2-yl]-N-(4-fluorophenyl)acetamide
N-(1H-indol-4-yl)-2-[4-(morpholin-4-yl)-6-oxo-1,6-dihydropyrimidin-2-yl]acetamide
N-(4-fluorophenyl)-3-methyl-2-[4-(morpholin-4-yl)-6-oxo-1,6-dihydropyrimidin-2-yl]butanamide
N-[4-fluoro-3-(methoxymethyl)phenyl]-2-[4-(morpholin-4-yl)-6-oxo-1,6-dihydropyrimidin-2-yl]acetamide
N-(4-fluoro-3-iodophenyl)-2-[4-(morpholin-4-yl)-6-oxo-1,6-dihydropyrimidin-2-yl]acetamide
2-[4-(morpholin-4-yl)-6-oxo-1,6-dihydropyrimidin-2-yl]-N-[3-(1,1,2,2-tetrafluoroethoxy)phenyl]acetamide
N-[3-(difluoromethyl)-4-fluorophenyl]-2-[4-(morpholin-4-yl)-6-oxo-1,6-dihydropyrimidin-2-yl]acetamide
2,2-difluoro-N-(4-fluorophenyl)-2-[4-(morpholin-4-yl)-6-oxo-1,6-dihydropyrimidin-2-yl]acetamide
N-(3,4-difluorophenyl)-2-[1-methyl-4-(morpholin-4-yl)-6-oxo-1,6-dihydropyrimidin-2-yl]acetamide
2-[2-(2,3-dihydro-1H-indol-1-yl)-2-oxoethyl]-3-methyl-6-(morpholin-4-pyrimidin-4(3H)-one
N-(3-bromo-4-fluorophenyl)-2-[1-methyl-4-(morpholin-4-yl)-6-oxo-1,6-dihydropyrimidin-2-yl]acetamide
N-[4-fluoro-3-(hydroxymethyl)phenyl]-2-[1-methyl-4-(morpholin-4-yl)-6-oxo-1,6-dihydropyrimidin-2-yl]acetamide
N-(3-cyclopropylphenyl)-2-[1-methyl-4-(morpholin-4-yl)-6-oxo-1,6-dihydropyrimidin-2-yl]acetamide
N-(4-fluoro-3-methoxyphenyl)-2-[1-methyl-4-(morpholin-4-yl)-6-oxo-1,6-dihydropyrimidin-2-yl]acetamide
N-(1-benzofur-4-yl)-2-[4-(morpholin-4-yl)-6-oxo-1,6-dihydropyrimidin-2-yl]acetamide
2-[1-methyl-4-(morpholin-4-yl)-6-oxo-1,6-dihydropyrimidin-2-yl]-N-phenylacetamide
N-(3-cyclopropyl-4-fluorophenyl)-2-[1-methyl-4-(morpholin-4-yl)-6-oxo-1,6-dihydropyrimidin-2-yl]acetamide
N-(3-fluoro-2-hydroxyphenyl)-2-[4-(morpholin-4-yl)-6-oxo-1,6-dihydropyrimidin-2-yl]acetamide
2-[2-(4-fluoro-2,3-dihydro-1H-indol-1-yl)-2-oxoethyl]-6-(morpholin-4-yl)pyrimidin-4(3H)-one
2-[2-(4-chloro-2,3-dihydro-1H-indol-1-yl)-2-oxoethyl]-6-(morpholin-4-yl)pyrimidin-4(3H)-one
N-(3-ethynyl-4-fluorophenyl)-2-[4-(morpholin-4-yl)-6-oxo-1,6-dihydropyrimidin-2-yl]acetamide
2-[2-(4-hydroxy-2,3-dihydro-1H-indol-1-yl)-2-oxoethyl]-6-(morpholin-4-yl)pyrimidin-4(3H)-one
2-[2-(4,6-difluoro-2,3-dihydro-1H-indol-1-yl)-2-oxoethyl]-6-(morpholin-4-pyrimidin-4(3H)-one
N-(4-fluoro-3-iodophenyl)-2-(1-methyl-4-morpholin-4-yl-6-oxo-1,6-dihydropyrimidin-2-yl)acetamide
2-[2-(4,5-difluoro-2,3-dihydro-1H-indol-1-yl)-2-oxoethyl]-6-(morpholin-4-pyrimidin-4(3H)-one
2-[2-(6-fluoro-2,3-dihydro-1H-indol-1-yl)-2-oxoethyl]-6-(morpholin-4-yl)pyrimidin-4(3H)-one
2-[2-(2-methyl-2,3-dihydro-1H-indol-1-yl)-2-oxoethyl]-6-(morpholin-4-pyrimidin-4(3H)-one
N-[3-(difluoromethyl)-4-fluorophenyl]-2-[1-methyl-4-(morpholin-4-yl)-6-oxo-1,6-dihydropyrimidin-2-yl]acetamide
2-[1-methyl-4-(morpholin-4-yl)-6-oxo-1,6-dihydropyrimidin-2-yl]-N-(3,4,5-trifluorophenyl)acetamide
N-(1-methyl-1H-indol-4-yl)-2-[4-(morpholin-4-yl)-6-oxo-1,6-dihydropyrimidin-2-yl]acetamide
2-[2-(4-methyl-2,3-dihydro-1H-indol-1-yl)-2-oxoethyl]-6-(morpholin-4-yl)pyrimidin-4(3H)-one
2-[2-(3-methyl-2,3-dihydro-1H-indol-1-yl)-2-oxoethyl]-6-(morpholin-4-yl)pyrimidin-4(3H)-one
2-[2-(4-fluoro-2,3-dihydro-1H-indol-1-yl)-2-oxoethyl]-3-methyl-6-(morpholin-4-yl)pyrimidin-4(3H)-one
2-[2-(5-fluoro-2,3-dihydroindol-1-yl)-2-oxoethyl]-6-morpholin-4-yl-3H-pyrimidin-4-one
2-[2-(4-chloro-2,3-dihydro-1H-indol-1-yl)-2-oxoethyl]-3-methyl-6-(morpholin-4-yl)pyrimidin-4(3H)-one N-(1-benzothiophen-4-yl)-2-[4-(morpholin-4-yl)-6-oxo-1,6-dihydropyrimidin-2-yl]acetamide 2-{2-[2-(hydroxymethyl)-2,3-dihydro-1H-indol-1-yl]-2-oxoethyl}-6-(morpholin-4-yl)pyrimidin-4(3H)-one 2-[4-(morpholin-4-yl)-6-oxo-1,6-dihydropyrimidin-2-yl]-N-{2-[2-(piperidin-1-yl)ethoxy]phenyl}acetamide N-[2-(2-methoxyethoxy)phenyl]-2-[4-(morpholin-4-yl)-6-oxo-1,6-dihydropyrimidin-2-yl]acetamide 2-[2-(4-hydroxy-2,3-dihydro-1H-indol-1-yl)-2-oxoethyl]-3-methyl-6-(morpholin-4-yl)pyrimidin-4(3H)-one 2-[2-(4-methoxy-2,3-dihydro-1H-indol-1-yl)-2-oxoethyl]-3-methyl-6-(morpholin-4-yl)pyrimidin-4(3H)-one 2-[2-(3,4-dihydroisoquinolin-2(1H)-yl)-2-oxoethyl]-6-(morpholin-4-yl)pyrimidin-4(3H)-one 2-[4-(morpholin-4-yl)-6-oxo-1,6-dihydropyrimidin-2-yl]-N-{2-[2-(pyrrolidin-1-yl)ethoxy]phenyl}acetamide 2-[4-(morpholin-4-yl)-6-oxo-1,6-dihydropyrimidin-2-yl]-N-[2-(pyridin-3-ylmethoxy)phenyl]acetamide 3-methyl-2-[2-(4-methyl-2,3-dihydro-1H-indol-1-yl)-2-oxoethyl]-6-(morpholin-4-yl)pyrimidin-4(3H)-one 2-(2-{3-[(dimethylamino)methyl]-2,3-dihydro-1H-indol-1-yl}-2-oxoethyl)-6-(morpholin-4-pyrimidin-4(3H)-one 2-[2-(4-bromo-2,3-dihydro-1H-indol-1-yl)-2-oxoethyl]-3-methyl-6-(morpholin-4-yl)pyrimidin-4(3H)-one 2-{2-[(2S)-2-methyl-2,3-dihydro-1H-indol-1-yl]-2-oxoethyl}-6-(morpholin-4-pyrimidin-4(3H)-one 2-{2-[(2R)-2-methyl-2,3-dihydro-1H-indol-1-yl]-2-oxoethyl}-6-(morpholin-4-yl)pyrimidin-4(3H)-one 3-methyl-2-[2-(3-methyl-2,3-dihydro-1H-indol-1-yl)-2-oxoethyl]-6-(morpholin-4-yl)pyrimidin-4(3H)-one 2-{2-[2-(methoxymethyl)-2,3-dihydro-1H-indol-1-yl]-2-oxoethyl}-6-(morpholin-4-yl)pyrimidin-4(3H)-one 2-[2-(4-ethoxy-2,3-dihydro-1H-indol-1-yl)-2-oxoethyl]-6-(morpholin-4-pyrimidin-4(3H)-one 1-{[4-(morpholin-4-yl)-6-oxo-1,6-d hydropyrimidin-2-yl] acetyl}-2,3-dihydro-1 H-indole-2-carboxamide 3-methyl-2-[2-(2-methyl-2,3-dihydro-1H-indol-1-yl)-2-oxoethyl]-6-(morpholin-4-yl)pyrimidin-4(3H)-one 2-[2-(6-fluoro-2,3-dihydro-1H-indol-1-yl)-2-oxoethyl]-3-methyl-6-(morpholin-4-yl)pyrimidin-4(3H)-one 2-{2-[(3S)-3-methyl-2,3-dihydro-1H-indol-1-yl]-2-oxoethyl}-6-(morpholin-4-yl)pyrimidin-4(3H)-one 2-{2-[(3R)-3-methyl-2,3-dihydro-1H-indol-1-yl]-2-oxoethyl}-6-(morpholin-4-pyrimidin-4(3H)-one 2-[2-(5,6-difluoro-2,3-dihydro-1H-indol-1-yl)-2-oxoethyl]-3-methyl-6-(morpholin-4-yl)pyrimidin-4(3H)-one 2-[2-(4,5-difluoro-2,3-dihydro-1H-indol-1-yl)-2-oxoethyl]-3-methyl-6-(morpholin-4-yl)pyrimidin-4(3H)-one 2-[2-(1,3-dihydro-2H-isoindol-2-yl)-2-oxoethyl]-6-(morpholin-4-yl)pyrimidin-4(3H)-one N-(1-benzothiophen-4-yl)-2-[1-methyl-4-(morpholin-4-yl)-6-oxo-1,6-dihydropyrimidin-2-yl]acetamide 2-[2-(5-chloro-3,4-dihydroquinolin-1(2H)-yl)-2-oxoethyl]-6-(morpholin-4-yl)pyrimidin-4(3H)-one 2-{2-[4-(hydroxymethyl)-2,3-dihydro-1H-indol-1-yl]-2-oxoethyl}-6-(morpholin-4-yl)pyrimidin-4(3H)-one N-[4-fluoro-2-(piperidin-4-ylmethoxy)phenyl]-2-[4-(morpholin-4-yl)-6-oxo-1,6-dihydropyrimidin-2-yl]acetamide 2-[2-(5-chloro-2,3-dihydroindol-1-yl)-2-oxoethyl]-6-morpholin-4-yl-3H-pyrimidin-4-one 2-[2-(4-bromo-2,3-dihydroindol-1-yl)-2-oxoethyl]-6-morpholin-4-yl-3H-pyrimidin-4-one 2-(2-{(3S)-3-[(dimethylamino)methyl]-2,3-dihydro-1H-indol-1-yl}-2-oxoethyl)-6-(morpholin-4-yl)pyrimidin-4(3H)-one 2-(2-{(3R)-3-[(dimethylamino)methyl]-2,3-dihydro-1H-indol-1-yl}-2-oxoethyl)-6-(morpholin-4-yl)pyrimidin-4(3H)-one N-[4-fluoro-2-(2-methoxyethoxy)phenyl]-2-[4-(morpholin-4-yl)-6-oxo-1,6-dihydropyrimidin-2-yl]acetamide N-(1H-benzimidazol-4-yl)-2-[4-(morpholin-4-yl)-6-oxo-1,6-dihydropyrimidin-2-yl]acetamide methyl 2-hydroxy-3-({[4-(morpholin-4-yl)-6-oxo-1,6-dihydropyrimidin-2-yl]acetyl}amino)benzoate 2-[2-(4-methoxy-2,3-dihydroindol-1-yl)-2-oxoethyl]-6-morpholin-4-yl-3H-pyrimidin-4-one N-(3-bromo-2-hydroxyphenyl)-2-[4-(morpholin-4-yl)-6-oxo-1,6-dihydropyrimidin-2-yl]acetamide N-(3,4-dihydro-2H-1,4-benzoxazin-8-yl)-2-[4-(morpholin-4-yl)-6-oxo-1,6-dihydropyrimidin-2-yl]acetamide methyl 5-fluoro-2-({[4-(morpholin-4-yl)-6-oxo-1,6-dihydropyrimidin-2-yl]acetyl}amino) benzoate 2-(2-{3-[(diethylamino)methyl]-2,3-dihydro-1H-indol-1-yl}-2-oxoethyl)-6-(morpholin-4-pyrimidin-4(3H)-one 2-[2-(2,3-dihydro-1H-pyrrolo[3,2-b]pyridin-1-yl)-2-oxoethyl]-6-(morpholin-4-yl)pyrimidin-4(3H)-one 2-[2-(5,6-difluoro-2,3-dihydroindol-1-yl)-2-oxoethyl]-6-morpholin-4-yl-3H-pyrimidin-4-one 2-[4-(morpholin-4-yl)-6-oxo-1,6-dihydropyrimidin-2-yl]-N-(1,2,3,4-tetrahydroquinolin-8-yl)acetamide 2-[2-(8-chloro-2,3-dihydro-4H-1,4-benzoxazin-4-yl)-2-oxoethyl]-6-(morpholin-4-yl)pyrimidin-4(3H)-one N-(2-hydroxy-3-methylphenyl)-2-[4-(morpholin-4-yl)-6-oxo-1,6-dihydropyrimidin-2-yl]acetamide N-(2-hydroxy-3-nitrophenyl)-2-[4-(morpholin-4-yl)-6-oxo-1,6-dihydropyrimidin-2-yl]acetamide N-(3-cyano-2-hydroxyphenyl)-2-[4-(morpholin-4-yl)-6-oxo-1,6-dihydropyrimidin-2-yl]acetamide N-[2-hydroxy-3-(trifluoromethyl)phenyl]-2-[4-(morpholin-4-yl)-6-oxo-1,6-dihydropyrimidin-2-yl]acetamide 2-[2-(3,3-dimethyl-2,3-dihydro-1H-indol-1-yl)-2-oxoethyl]-6-(morpholin-4-pyrimidin-4(3H)-one and also the addition salts with inorganic and organic acids or with inorganic and organic bases, of said products of formula (I).

The subject of the present invention is most particularly the products of formula (I) as defined above, corresponding to the following formulae:

2-[4-(morpholin-4-yl)-6-oxo-1,6-dihydropyrimidin-2-yl]-N-phenylacetamide

N-(4-fluorophenyl)-2-[4-(morpholin-4-yl)-6-oxo-1,6-dihydropyrimidin-2-yl]acetamide N-(3-chlorophenyl)-2-[4-(morpholin-4-yl)-6-oxo-1,6-dihydropyrimidin-2-yl]acetamide N-[3-(dimethylamino)phenyl]-2-[4-(morpholin-4-yl)-6-oxo-1,6-dihydropyrimidin-2-yl]acetamide N-(2,4-difluorophenyl)-2-[4-(morpholin-4-yl)-6-oxo-1,6-dihydropyrimidin-2-yl]acetamide N-(3,4-difluorophenyl)-2-[4-(morpholin-4-yl)-6-oxo-1,6-dihydropyrimidin-2-yl]acetamide 2-[4-(morpholin-4-yl)-6-oxo-1,6-dihydropyrimidin-2-yl]-N-(thiophen-3-yl)acetamide N-(4-fluoro-3-methoxyphenyl)-2-[4-(morpholin-4-yl)-6-oxo-1,6-dihydropyrimidin-2-yl]acetamide N-(2-fluorophenyl)-2-[4-(morpholin-4-yl)-6-oxo-1,6-dihydropyrimidin-2-yl]acetamide N-(2-methylphenyl)-2-[4-(morpholin-4-yl)-6-oxo-1,6-dihydropyrimidin-2-yl]acetamide N-(2-methoxyphenyl)-2-[4-(morpholin-4-yl)-6-oxo-1,6-dihydropyrimidin-2-yl]acetamide N-(2,3-difluorophenyl)-2-[4-(morpholin-4-yl)-6-oxo-1,6-dihydropyrimidin-2-yl]acetamide N-(3,5-difluorophenyl)-2-[4-(morpholin-4-yl)-6-oxo-1,6-dihydropyrimidin-2-yl]acetamide
N-(3-fluorophenyl)-2-[4-(morpholin-4-yl)-6-oxo-1,6-dihydropyrimidin-2-yl]acetamide
N-(4-chlorophenyl)-2-[4-(morpholin-4-yl)-6-oxo-1,6-dihydropyrimidin-2-yl]acetamide
N-(3-methoxyphenyl)-2-[4-(morpholin-4-yl)-6-oxo-1,6-dihydropyrimidin-2-yl]acetamide
2-[4-(morpholin-4-yl)-6-oxo-1,6-dihydropyrimidin-2-yl]-N-[3-(trifluoromethyl)phenyl]acetamide
N-(3-bromophenyl)-2-[4-(morpholin-4-yl)-6-oxo-1,6-dihydropyrimidin-2-yl]acetamide
N-[3-(2-methylpropan-2-yl)phenyl]-2-[4-(morpholin-4-yl)-6-oxo-1,6-dihydropyrimidin-2-yl]acetamide
methyl 3-({[4-(morpholin-4-yl)-6-oxo-1,6-dihydropyrimidin-2-yl]acetyl}amino) benzoate
3-({[4-(morpholin-4-yl)-6-oxo-1,6-dihydropyrimidin-2-yl]acetyl}amino)benzoic acid
2-[4-(morpholin-4-yl)-6-oxo-1,6-dihydropyrimidin-2-yl]-N-[3-(propan-2-yl)phenyl]acetamide
N-(3-methylphenyl)-2-[4-(morpholin-4-yl)-6-oxo-1,6-dihydropyrimidin-2-yl]acetamide
N-(3-cyano-4-fluorophenyl)-2-[4-(morpholin-4-yl)-6-oxo-1,6-dihydropyrimidin-2-yl]acetamide
N-(1H-indazol-6-yl)-2-[4-(morpholin-4-yl)-6-oxo-1,6-dihydropyrimidin-2-yl]acetamide
N-(3-cyanophenyl)-2-[4-(morpholin-4-yl)-6-oxo-1,6-dihydropyrimidin-2-yl]acetamide
N-(5-fluoropyridin-2-yl)-2-[4-(morpholin-4-yl)-6-oxo-1,6-dihydropyrimidin-2-yl]acetamide
N-(4-fluoro-3-methylphenyl)-2-[4-(morpholin-4-yl)-6-oxo-1,6-dihydropyrimidin-2-yl]acetamide
N-(3-chloro-4-fluorophenyl)-2-[4-(morpholin-4-yl)-6-oxo-1,6-dihydropyrimidin-2-yl]acetamide
2-[4-(morpholin-4-yl)-6-oxo-1,6-dihydropyrimidin-2-yl]-N-(pyridin-3-yl)acetamide
N-(4-fluoro-2-methylphenyl)-2-[4-(morpholin-4-yl)-6-oxo-1,6-dihydropyrimidin-2-yl]acetamide
N-(3-hydroxyphenyl)-2-[4-(morpholin-4-yl)-6-oxo-1,6-dihydropyrimidin-2-yl]acetamide
N-(3-bromo-4-fluorophenyl)-2-[4-(morpholin-4-yl)-6-oxo-1,6-dihydropyrimidin-2-yl]acetamide
2-[4-(morpholin-4-yl)-6-oxo-1,6-dihydropyrimidin-2-yl]-N-(3,4,5-trifluorophenyl)acetamide
N-[4-fluoro-3-(hydroxymethyl)phenyl]-2-[4-(morpholin-4-yl)-6-oxo-1,6-dihydropyrimidin-2-yl]acetamide
N-(3-cyclopropylphenyl)-2-[4-(morpholin-4-yl)-6-oxo-1,6-dihydropyrimidin-2-yl]acetamide
N-(2-hydroxyphenyl)-2-[4-(morpholin-4-yl)-6-oxo-1,6-dihydropyrimidin-2-yl]acetamide
N-[3-(difluoromethoxy)phenyl]-2-[4-(morpholin-4-yl)-6-oxo-1,6-dihydropyrimidin-2-yl]acetamide
N-(4-fluoro-3-methoxyphenyl)-2-[4-(morpholin-4-yl)-6-oxo-1,6-dihydropyrimidin-2-yl]propanamide
N-(2,3-dimethylphenyl)-2-[4-(morpholin-4-yl)-6-oxo-1,6-dihydropyrimidin-2-yl]acetamide
N-(2-fluoro-3-methylphenyl)-2-[4-(morpholin-4-yl)-6-oxo-1,6-dihydropyrimidin-2-yl]acetamide
N-(1,3-benzoxazol-4-yl)-2-[4-(morpholin-4-yl)-6-oxo-1,6-dihydropyrimidin-2-yl]acetamide
2-[4-(morpholin-4-yl)-6-oxo-1,6-dihydropyrimidin-2-yl]-N-[3-(trifluoromethoxy)phenyl]acetamide
2-[4-(morpholin-4-yl)-6-oxo-1,6-dihydropyrimidin-2-yl]-N-[3-(propan-2-yloxy)phenyl]acetamide
N-(4-fluoro-2-methoxyphenyl)-2-[4-(morpholin-4-yl)-6-oxo-1,6-dihydropyrimidin-2-yl]acetamide
2-methylpropan-2-yl {2-[3-({[4-(morpholin-4-yl)-6-oxo-1,6-dihydropyrimidin-2-yl]acetyl}amino)phenyl]ethyl}carbamate
N-[4-fluoro-3-(trifluoromethyl)phenyl]-2-[4-(morpholin-4-yl)-6-oxo-1,6-dihydropyrimidin-2-yl]acetamide
N-(3-ethynylphenyl)-2-[4-(morpholin-4-yl)-6-oxo-1,6-dihydropyrimidin-2-yl]acetamide
N-[3-(cyclopentyloxy)phenyl]-2-[4-(morpholin-4-yl)-6-oxo-1,6-dihydropyrimidin-2-yl]acetamide
N-(4-fluoro-2-hydroxyphenyl)-2-[4-(morpholin-4-yl)-6-oxo-1,6-dihydropyrimidin-2-yl]acetamide
2-[2-(2,3-dihydro-1H-indol-1-yl)-2-oxoethyl]-6-(morpholin-4-yl)pyrimidin-4(3H)-one
N-(3-cyclopropyl-4-fluorophenyl)-2-[4-(morpholin-4-yl)-6-oxo-1,6-dihydropyrimidin-2-yl]acetamide
2-[4-(morpholin-4-yl)-6-oxo-1,6-dihydropyrimidin-2-yl]-N-(2,3,4-trifluorophenyl)acetamide
N-[4-fluoro-3-(trifluoromethoxy)phenyl]-2-[4-(morpholin-4-yl)-6-oxo-1,6-dihydropyrimidin-2-yl]acetamide
N-[3-(2-hydroxyethoxy)phenyl]-2-[4-(morpholin-4-yl)-6-oxo-1,6-dihydropyrimidin-2-yl]acetamide
N-(3-iodophenyl)-2-[4-(morpholin-4-yl)-6-oxo-1,6-dihydropyrimidin-2-yl]acetamide
methyl 2-fluoro-5-({[4-(morpholin-4-yl)-6-oxo-1,6-dihydropyrimidin-2-yl]acetyl}amino)benzoate
N-(3-ethoxyphenyl)-2-[4-(morpholin-4-yl)-6-oxo-1,6-dihydropyrimidin-2-yl]acetamide
N-(2,4-difluoro-3-methoxyphenyl)-2-[4-(morpholin-4-yl)-6-oxo-1,6-dihydropyrimidin-2-yl]acetamide
2-[4-(morpholin-4-yl)-6-oxo-1,6-dihydropyrimidin-2-yl]-N-(2,4,5-trifluorophenyl)acetamide
N-(3,5-dichloro-4-fluorophenyl)-2-[4-(morpholin-4-yl)-6-oxo-1,6-dihydropyrimidin-2-yl]acetamide
2-[2-(2,3-dihydro-4H-1,4-benzoxazin-4-yl)-2-oxoethyl]-6-(morpholin-4-yl)pyrimidin-4(3H)-one
N-(4-fluoro-3-nitrophenyl)-2-[4-(morpholin-4-yl)-6-oxo-1,6-dihydropyrimidin-2-yl]acetamide
2-fluoro-5-({[4-(morpholin-4-yl)-6-oxo-1,6-dihydropyrimidin-2-yl]acetyl}amino)benzoic acid
N-(5-fluoro-2-hydroxyphenyl)-2-[4-(morpholin-4-yl)-6-oxo-1,6-dihydropyrimidin-2-yl]acetamide
N-(2-bromo-4-fluorophenyl)-2-[4-(morpholin-4-yl)-6-oxo-1,6-dihydropyrimidin-2-yl]acetamide
N-(4-fluorophenyl)-2-[1-methyl-4-(morpholin-4-yl)-6-oxo-1,6-dihydropyrimidin-2-yl]acetamide
N-(3-chloro-4-fluorophenyl)-2-[1-methyl-4-(morpholin-4-yl)-6-oxo-1,6-dihydropyrimidin-2-yl]acetamide
N-(3-bromophenyl)-2-[1-methyl-4-(morpholin-4-yl)-6-oxo-1,6-dihydropyrimidin-2-yl]acetamide
2-[1-ethyl-4-(morpholin-4-yl)-6-oxo-1,6-dihydropyrimidin-2-yl]-N-(4-fluorophenyl)acetamide
N-(1H-indol-4-yl)-2-[4-(morpholin-4-yl)-6-oxo-1,6-dihydropyrimidin-2-yl]acetamide
N-(4-fluorophenyl)-3-methyl-2-[4-(morpholin-4-yl)-6-oxo-1,6-dihydropyrimidin-2-yl]butanamide
N-[4-fluoro-3-(methoxymethyl)phenyl]-2-[4-(morpholin-4-yl)-6-oxo-1,6-dihydropyrimidin-2-yl]acetamide
N-(4-fluoro-3-iodophenyl)-2-[4-(morpholin-4-yl)-6-oxo-1,6-dihydropyrimidin-2-yl]acetamide
2-[4-(morpholin-4-yl)-6-oxo-1,6-dihydropyrimidin-2-yl]-N-[3-(1,1,2,2-tetrafluoroethoxy)phenyl]acetamide
N-[3-(difluoromethyl)-4-fluorophenyl]-2-[4-(morpholin-4-yl)-6-oxo-1,6-dihydropyrimidin-2-yl]acetamide
2,2-difluoro-N-(4-fluorophenyl)-2-[4-(morpholin-4-yl)-6-oxo-1,6-dihydropyrimidin-2-yl]acetamide
N-(3,4-difluorophenyl)-2-[1-methyl-4-(morpholin-4-yl)-6-oxo-1,6-dihydropyrimidin-2-yl]acetamide 2-[2-(2,3-dihydro-1H-indol-1-yl)-2-oxoethyl]-3-methyl-6-(morpholin-4-yl)pyrimidin-4(3H)-one N-(3-bromo-4-fluorophenyl)-2-[1-methyl-4-(morpholin-4-yl)-6-oxo-1,6-dihydropyrimidin-2-yl]acetamide N-[4-fluoro-3-(hydroxymethyl)phenyl]-2-[1-methyl-4-(morpholin-4-yl)-6-oxo-1,6-dihydropyrimidin-2-yl]acetamide N-(3-cyclopropylphenyl)-2-[1-methyl-4-(morpholin-4-yl)-6-oxo-1,6-dihydropyrimidin-2-yl]acetamide N-(4-fluoro-3-methoxyphenyl)-2-[1-methyl-4-(morpholin-4-yl)-6-oxo-1,6-dihydropyrimidin-2-yl]acetamide N-(1-benzofur-4-yl)-2-[4-(morpholin-4-yl)-6-oxo-1,6-dihydropyrimidin-2-yl]acetamide 2-[1-methyl-4-(morpholin-4-yl)-6-oxo-1,6-dihydropyrimidin-2-yl]-N-phenylacetamide N-(3-cyclopropyl-4-fluorophenyl)-2-[1-methyl-4-(morpholin-4-yl)-6-oxo-1,6-dihydropyrimidin-2-yl]acetamide N-(3-fluoro-2-hydroxyphenyl)-2-[4-(morpholin-4-yl)-6-oxo-1,6-dihydropyrimidin-2-yl]acetamide 2-[2-(4-fluoro-2,3-dihydro-1H-indol-1-yl)-2-oxoethyl]-6-(morpholin-4-pyrimidin-4(3H)-one 2-[2-(4-chloro-2,3-dihydro-1H-indol-1-yl)-2-oxoethyl]-6-(morpholin-4-pyrimidin-4(3H)-one N-(3-ethynyl-4-fluorophenyl)-2-[4-(morpholin-4-yl)-6-oxo-1,6-dihydropyrimidin-2-yl]acetamide 2-[2-(4-hydroxy-2,3-dihydro-1H-indol-1-yl)-2-oxoethyl]-6-(morpholin-4-yl)pyrimidin-4(3H)-one 2-[2-(4,6-difluoro-2,3-dihydro-1H-indol-1-yl)-2-oxoethyl]-6-(morpholin-4-pyrimidin-4(3H)-one and also the addition salts with inorganic and organic acids or with inorganic and organic bases, also products of formula (I).

A subject of the present invention is also any process for preparing the products of formula (I) as defined above.

The products according to the invention may be prepared using conventional organic chemistry methods.

Preparation of Compounds of Formula (I)

The products of general formula (I) according to the present invention may in particular be prepared as indicated in general schemes 1A-1C below. In this respect, the methods described cannot constitute a limitation of the scope of the invention, as regards the methods for preparing the claimed compounds.

The preparations of the examples of the present invention give illustrations of the schemes below.

Such synthesis schemes are part of the present invention: a subject of the present invention is thus also the processes for preparing the products of formula C to (I)-d as defined in general schemes 1A-1C below.

General scheme 1A:

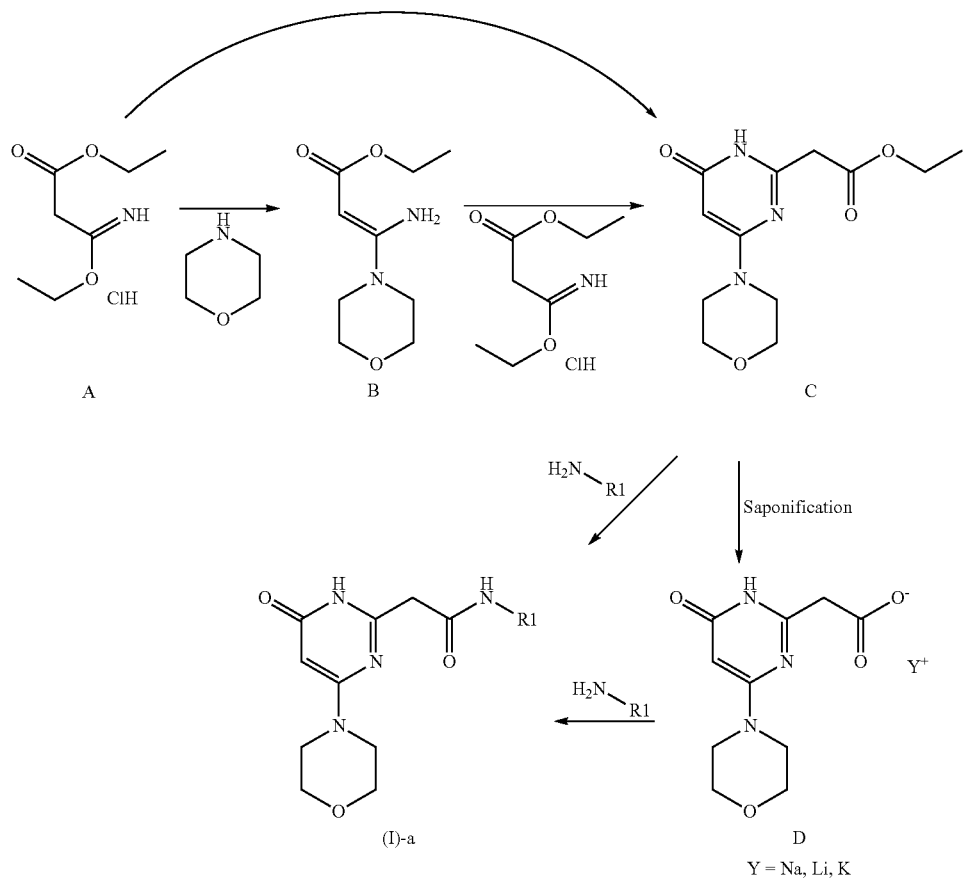

In general scheme 1A:

The aminal ketene B can be obtained from the iminoether A or from the commercially available aminoacrylate tautomer thereof, by reaction with morpholine in a solvent such as ethanol, at a temperature of between 0° C. and the boiling point of the solvent, according to the process described by Landwehr J. et al. in J. Med. Chem. 2006, 49, 4327-4332.

The ester C can be obtained by reaction of the aminal ketene B with the iminoether A, or the aminoacrylate tautomer thereof, in a solvent such as ethanol, at a temperature of between 20° C. and the boiling point of the solvent.

Alternatively, the ester C can be obtained by "one-pot" reaction between morpholine and an excess (for example 3 equivalents) of iminoether A (or of the aminoacrylate tautomer thereof), in a solvent such as ethanol, at a temperature of between 20° C. and the boiling point of the solvent.

The carboxylate D can be obtained by hydrolysis of the ester C in the presence of a base such as sodium hydroxide or lithium hydroxide, in a solvent such as tetrahydrofuran or methanol, at a temperature of between 0° C. and 30° C.

The amides (I)-a can be obtained from the carboxylate D by condensation of an amine $R1-NH_2$ in the presence of a peptide coupling agent such as, for example, EDCI (ethyl dimethylaminopropyl carbodiimide), DMT-MM [4-(4,6-dimethoxy-1,2,3-triazin-2-yl)-4-methylmorpholinium chloride], BOP [benzotriazol-1-yloxytrisdimethylaminophosphonium hexafluorophosphate], PyBOP [benzotriazol-1-yloxytrispyrrolidinophosphonium hexafluorophosphate], PyBROP [bromotrispyrrolidinophosphonium hexafluorophosphate], HATU [O-(7-azabenzotriazol-1-yl)-1,1,3,3-tetramethyluronium) hexafluorophosphate] or an HOBT/EDCI [hydroxybenzotriazole/ethyl dimethylaminopropyl carbodiimide mixture], in a solvent such as N,N-dimethylformamide, pyridine, ethanol, water or methanol, at a temperature of between 20° C. and 50° C., for instance under the conditions described by Kunishima M. et al. in Tetrahedron 2001, 57, 1551-1558.

The amides (I)-a can also be obtained from the ester C by reaction of an amine $R1-NH_2$ in the presence of an agent such as trimethylaluminium or potassium tert-butoxide, in a solvent such as toluene, tetrahydrofuran or N,N-dimethylformamide, at a temperature of between 20° C. and 150° C., for instance under the conditions described by Perreux L. et al. in Tetrahedron 2003 (59) 2185-2189 and by Auzeloux, P et al. in J. Med. Chem. 2000, 43 (2), 190-197.

General scheme 1B:

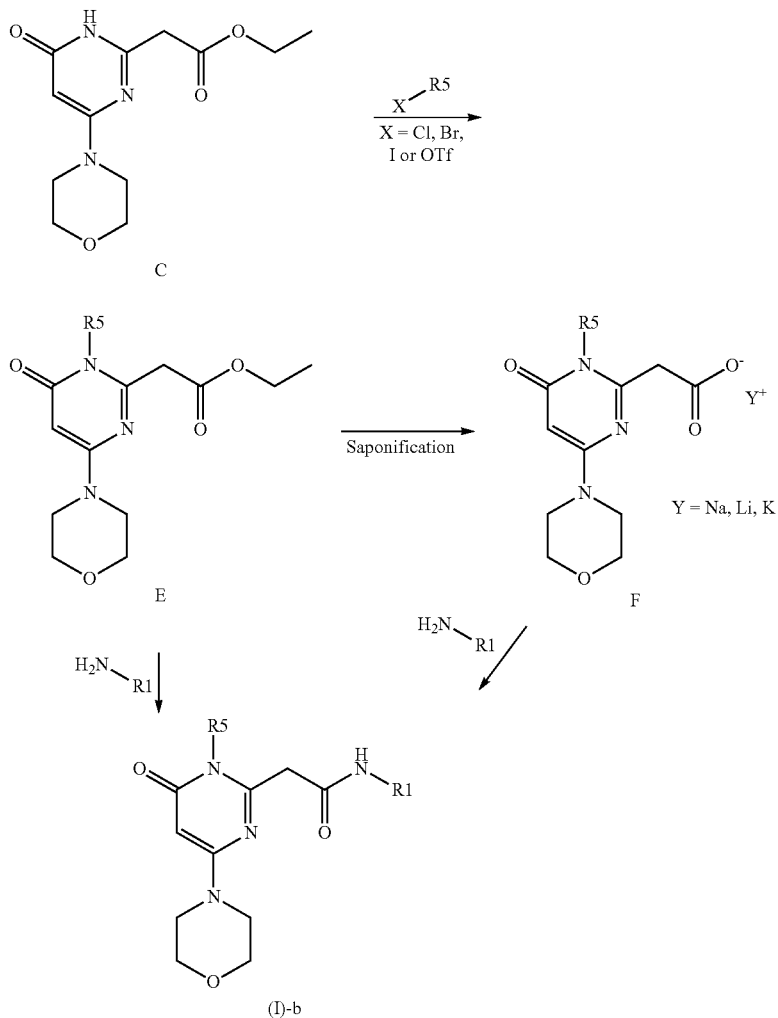

In General Scheme 1B:

The esters E can be obtained from the ester C by reaction with a compound R5-X (X=Cl, Br, I or triflate), in the presence of a base such as sodium hydroxide, potassium tertbutylate or caesium carbonate, in a solvent such as methanol, ethanol or dioxane, at a temperature of between 0° C. and 50°

C., according to, for example, the process described by Noël D. D'Angelo et al. in J. Med. Chem. 2008, 51, 5766-5779.

The carboxylates F can be obtained by hydrolysis of the esters E, in the presence of a base such as sodium hydroxide or lithium hydroxide, in a solvent such as tetrahydrofuran or methanol, at a temperature of between 0° C. and 30° C.

The amides (I)-b can be obtained from the carboxylates F by condensation of an amine R1-NH$_2$ in the presence of a peptide coupling agent such as, for example, EDCI (ethyl dimethylaminopropyl carbodiimide), DMT-MM [4-(4,6-dimethoxy-1,2,3-triazin-2-yl)-4-methylmorpholinium chloride], BOP [benzotriazol-1-yloxytrisdimethylaminophosphonium hexafluorophosphate], PyBOP [benzotriazol-1-yloxytrispyrrolidinophosphonium hexafluorophosphate], PyBROP [bromotrispyrrolidinophosphonium hexafluorophosphate], HATU [O-(7-azabenzotriazol-1-yl)-1,1,3,3-tetramethyluronium) hexafluorophosphate] or an HOBT/EDCI [hydroxybenzotriazole/ethyl dimethylaminopropyl carbodiimide mixture], in a solvent such as N,N-dimethylformamide, pyridine, ethanol, water or methanol, at a temperature of between 20° C. and 50° C., for instance under the conditions described by Kunishima M. et al. in Tetrahedron 2001, 57, 1551-1558.

The amides (I)-b can also be obtained from the esters E by reaction of an amine R1-NH$_2$, in the presence of an agent such as trimethyl aluminium, in a solvent such as toluene, at a temperature of between 20° C. and the boiling point of the solvent, for instance under the conditions described by Auzeloux, P et al. in J. Med. Chem. 2000, 43 (2), 190-197.

General scheme 1C:

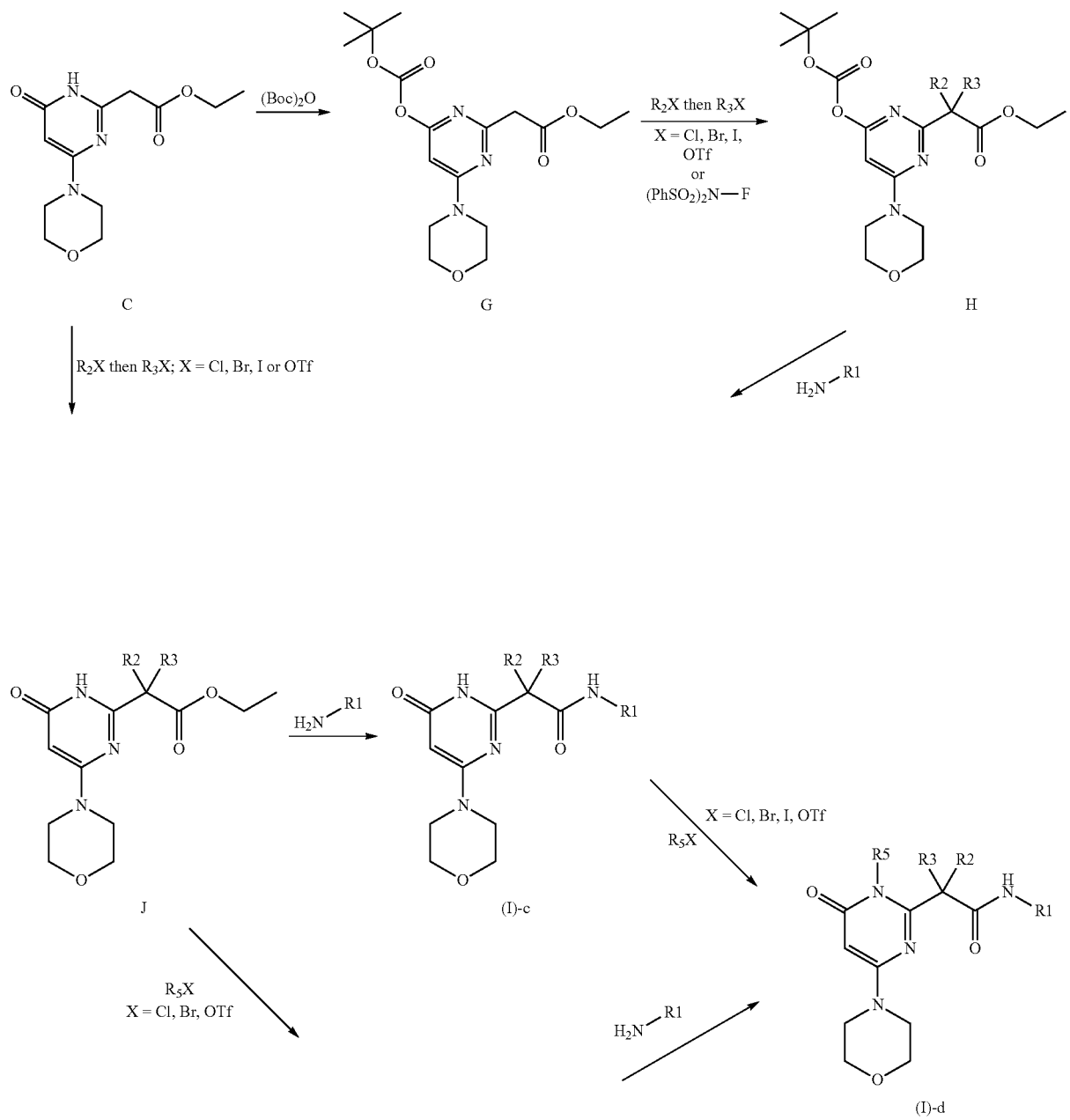

-continued

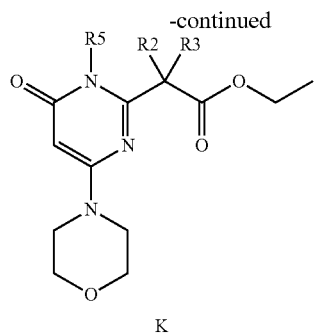

K

In General Scheme 1C:

the ester G can be obtained from the ester C by reaction with (Boc)₂O (tert-butyl dicarbonate), in a solvent such as N,N-dimethylformamide, dioxane, acetonitrile or dichloromethane, in the presence of a base such as, for example, sodium hydride, triethylamine, N,N-diisopropylethylamine or pyridine, at a temperature of between 0° C. and 60° C., according to, for example, the process described by Hioki K. et al. Synthesis 2006, 12, 1931-1933

The products H can be obtained from the ester G by reaction with R2-X and then, optionally, with R3-X (X=Cl, Br, I or OTf, and R2 and R3 are alkyl groups), in the presence of a base such as sodium hydroxide, potassium tert-butoxide or caesium carbonate, in a solvent such as methanol, ethanol or dioxane, at a temperature of between 0° C. and 100° C., according to, for example, the process described by Noël D. D'Angelo et al. in J. Med. Chem. 2008, 51, 5766-5779.

The product H where R2=R3=F can be obtained by reaction of the product G with N-fluorobenzenesulphonimide, in the presence of a base such as the potassium salt of hexamethyldisilylazane, in a solvent such as tetrahydrofuran, at a temperature of between −78° C. and 20° C., according to, for example, the process described by Christopher S. Burgey et al. in J. Med. Chem. 2003, 46, 461-473.

The esters J where the R2 and R3 groups are alkyl radicals can be obtained from the ester C in the same way as the products H, in the presence of a base such as butyllithium, sodium hydride, potassium tert-butoxide or caesium carbonate, in a solvent such as methanol, ethanol, tetrahydrofuran, N,N-dimethylformamide or dioxane, at a temperature of between 0° C. and 50° C.

The amides (I)-c can be obtained from the esters H or J by reaction of an amine R1-NH₂, in the presence of an agent such as trimethyl aluminium, in a solvent such as toluene, at a temperature of between 20° C. and the boiling point of the solvent, for instance under the conditions described by Auzeloux, P et al. in J. Med. Chem. 2000, 43 (2), 190-197.

The amides (I)-d can be obtained from the amides (I)-c by reaction with a compound R5-X (X=Cl, Br, I or triflate), in the presence of a base such as sodium hydroxide, potassium tert-butoxide or caesium carbonate, in a solvent such as methanol, ethanol or dioxane, at a temperature of between 0° C. and 50° C., according to, for example, the process described by Noël D. D'Angelo et al., in J. Med. Chem. 2008, 51, 5766-5779.

Alternatively, the amides (I)-d can be obtained from the esters K by reaction of an amine R1-NH₂, in the presence of an agent such as trimethylaluminium, in a solvent such as toluene, at a temperature of between 20° C. and the boiling point of the solvent, for instance under the conditions described by Auzeloux, P et al. in J. Med. Chem. 2000, 43 (2), 190-197.

The esters K can be obtained from the esters J by reaction with a compound R5-X (X=Cl, Br, I or triflate), in the presence of a base such as sodium hydroxide, potassium tert-butoxide or caesium carbonate, in a solvent such as methanol, ethanol or dioxane, at a temperature of between 0° C. and 50° C., according to, for example, the process described by Noël D. D'Angelo et al. in J. Med. Chem. 2008, 51, 5766-5779.

Among the starting products of formula A or B, some are known and can be obtained either commercially, or according to the usual methods known to those skilled in the art, for example from commercially available products.

It is understood, for those skilled in the art, that, in order to implement the processes according to the invention, described above, it may be necessary to introduce protective groups for amino, carboxyl and alcohol functions in order to prevent side reactions.

The following nonexhaustive list of examples of protection of reactive functions may be mentioned:
hydroxyl groups can be protected, for example, with alkyl radicals such as tert-butyl, trimethylsilyl, tert-butyldimethylsilyl, methoxymethyl, tetrahydropyranyl, benzyl or acetyl,
amino groups can be protected, for example, with acetyl, trityl, benzyl, tert-butoxycarbonyl, BOC, benzyloxycarbonyl or phthalimido radicals or other radicals known in peptide chemistry.

Acid functions can be protected, for example, in the form of esters formed with readily cleavable esters such as benzyl or tert-butyl esters, or esters known in peptide chemistry.

A list of various protective groups that can be used will be found in the manuals known to those skilled in the art, and for example in patent BF 2 499 995.

It may be noted that it is possible, if desired and if necessary, to subject intermediate products or products of formula (I) thus obtained by means of the processes indicated above, in order to obtain other intermediates or other products of formula (I), to one or more conversion reactions known to those skilled in the art, such as, for example:

a) a reaction for esterification of an acid function, b) a reaction for saponification of an ester function to give an acid function, c) a reaction for reduction of the free or esterified carboxyl function to give an alcohol function, d) a reaction for conversion of an alkoxy function to give a hydroxyl function, or else of a hydroxyl function to give an alkoxy function, e) a reaction for removal of the protective groups that the protected reactive functions may be carrying, f) a reaction for salification with an inorganic or organic acid or with a base so as to obtain the corresponding salt, g) a reaction for resolving the racemic forms to give resolved products, said products of formula (I) thus obtained being in all the possible racemic, enantiomeric and diastereoisomeric isomer forms.

The reactions a) to g) can be carried out under the usual conditions known to those skilled in the art, such as, for example, those indicated hereinafter.

a) The products described above may, if desired, be the subject, on the possible carboxyl functions, of esterification reactions which can be carried out according to the usual methods known to those skilled in the art.

b) The possible conversions of ester functions to give acid functions of the products described above may, if desired, be carried out under the usual conditions known to those skilled in the art, in particular by acid or alkaline hydrolysis, for example with sodium hydroxide or potassium hydroxide in an alcohol medium such as, for example, in methanol, or else with hydrochloric acid or sulphuric acid.

The saponification reaction can be carried out according to the usual methods known to those skilled in the art, such as, for example, in a solvent such as methanol or ethanol, dioxane or dimethoxyethane, in the presence of sodium hydroxide or of potassium hydroxide.

c) The possible free or esterified carboxyl functions of the products described above may, if desired, be reduced to give alcohol functions by means of the methods known to those skilled in the art: the possible esterified carboxyl functions may, if desired, be reduced to give alcohol functions by means of the methods known to those skilled in the art, and in particular with lithium aluminium hydride in a solvent such as, for example, tetrahydrofuran, or else dioxane or ethyl ether.

The possible free carboxyl functions of the products described above may, if desired, be reduced to give alcohol functions in particular with boron hydride.

d) The possible alkoxy functions, such as in particular methoxy functions, of the products described above may, if necessary, be converted to hydroxyl functions under the usual conditions known to those skilled in the art, for example with boron tribromide in a solvent such as, for example, methylene chloride, with pyridine hydrobromide or hydrochloride or else with hydrobromic acid or hydrochloric acid in water or trifluoroacetic acid at reflux.

e) The removal of protective groups such as, for example, those indicated above can be carried out under the usual conditions known to those skilled in the art, in particular by acid hydrolysis carried out with an acid such as hydrochloric acid, benzenesulphonic acid, para-toluenesulphonic acid, formic acid or trifluoroacetic acid, or else by catalytic hydrogenation.

The phthalimido group may be removed with hydrazine.

f) The products described above may, if desired, be the subject of salification reactions, for example with an inorganic or organic acid or with an inorganic or organic base, according to the usual methods known to those skilled in the art: such a salification reaction can be carried out, for example, in the presence of hydrochloric acid, or else of tartaric acid, citric acid or methanesulphonic acid, in an alcohol such as, for example, ethanol or methanol.

g) The possible optically active forms of the products described above can be prepared by resolving the racemic mixtures according to the usual methods known to those skilled in the art.

The products of formula (I) as defined above, and also the addition salts thereof with acids, have advantageous pharmacological properties, in particular due to their kinase-inhibiting properties, as is indicated above.

The products of the present invention are in particular of use in tumour therapy.

The products of the invention may also thus increase the therapeutic effects of commonly used antitumour agents.

These properties justify the use thereof in therapy, and a subject of the invention is in particular, as medicaments, the products of formula (I) as defined above, said products of formula (I) being in all the possible racemic, enantiomeric and diastereoisomeric isomer forms, and also the pharmaceutically acceptable addition salts with inorganic and organic acids or with inorganic and organic bases, of said products of formula (I).

The subject of the invention is most particularly, as medicaments, the products corresponding to the following formulae:

2-[4-(morpholin-4-yl)-6-oxo-1,6-dihydropyrimidin-2-yl]-N-phenylacetamide

N-(4-fluorophenyl)-2-[4-(morpholin-4-yl)-6-oxo-1,6-dihydropyrimidin-2-yl]acetamide N-(3-chlorophenyl)-2-[4-(morpholin-4-yl)-6-oxo-1,6-dihydropyrimidin-2-yl]acetamide N-[3-(dimethylamino)phenyl]-2-[4-(morpholin-4-yl)-6-oxo-1,6-dihydropyrimidin-2-yl]acetamide N-(2,4-difluorophenyl)-2-[4-(morpholin-4-yl)-6-oxo-1,6-dihydropyrimidin-2-yl]acetamide N-(3,4-difluorophenyl)-2-[4-(morpholin-4-yl)-6-oxo-1,6-dihydropyrimidin-2-yl]acetamide 2-[4-(morpholin-4-yl)-6-oxo-1,6-dihydropyrimidin-2-yl]-N-(thiophen-3-yl)acetamide N-(4-fluoro-3-methoxyphenyl)-2-[4-(morpholin-4-yl)-6-oxo-1,6-dihydropyrimidin-2-yl]acetamide N-(2-fluorophenyl)-2-[4-(morpholin-4-yl)-6-oxo-1,6-dihydropyrimidin-2-yl]acetamide N-(2-methylphenyl)-2-[4-(morpholin-4-yl)-6-oxo-1,6-dihydropyrimidin-2-yl]acetamide N-(2-methoxyphenyl)-2-[4-(morpholin-4-yl)-6-oxo-1,6-dihydropyrimidin-2-yl]acetamide N-(2,3-difluorophenyl)-2-[4-(morpholin-4-yl)-6-oxo-1,6-dihydropyrimidin-2-yl]acetamide N-(3,5-difluorophenyl)-2-[4-(morpholin-4-yl)-6-oxo-1,6-dihydropyrimidin-2-yl]acetamide N-(3-fluorophenyl)-2-[4-(morpholin-4-yl)-6-oxo-1,6-dihydropyrimidin-2-yl]acetamide N-(4-chlorophenyl)-2-[4-(morpholin-4-yl)-6-oxo-1,6-dihydropyrimidin-2-yl]acetamide N-(3-methoxyphenyl)-2-[4-(morpholin-4-yl)-6-oxo-1,6-dihydropyrimidin-2-yl]acetamide 2-[4-(morpholin-4-yl)-6-oxo-1,6-dihydropyrimidin-2-yl]-N-[3-(trifluoromethyl)phenyl]acetamide N-(3-bromophenyl)-2-[4-(morpholin-4-yl)-6-oxo-1,6-dihydropyrimidin-2-yl]acetamide N-[3-(2-methylpropan-2-yl)phenyl]-2-[4-(morpholin-4-yl)-6-oxo-1,6-dihydropyrimidin-2-yl]acetamide methyl 3-({[4-(morpholin-4-yl)-6-oxo-1,6-dihydropyrimidin-2-yl]acetyl}amino)benzoate 3-({[4-(morpholin-4-yl)-6-oxo-1,6-dihydropyrimidin-2-yl]acetyl}amino)benzoic acid 2-[4-(morpholin-4-yl)-6-oxo-1,6-dihydropyrimidin-2-yl]-N-[3-(propan-2-yl)phenyl]acetamide N-(3-methylphenyl)-2-[4-(morpholin-4-yl)-6-oxo-1,6-dihydropyrimidin-2-yl]acetamide N-(3-cyano-4-fluorophenyl)-2-[4-(morpholin-4-yl)-6-oxo-1,6-dihydropyrimidin-2-yl]acetamide N-(1H-indazol-6-yl)-2-[4-(morpholin-4-yl)-6-oxo-1,6-dihydropyrimidin-2-yl]acetamide N-(3-cyanophenyl)-2-[4-(morpholin-4-yl)-6-oxo-1,6-dihydropyrimidin-2-yl]acetamide N-(5-fluoropyridin-2-yl)-2-[4-(morpholin-4-yl)-6-oxo-1,6-dihydropyrimidin-2-yl]acetamide
N-(4-fluoro-3-methylphenyl)-2-[4-(morpholin-4-yl)-6-oxo-1,6-dihydropyrimidin-2-yl]acetamide
N-(3-chloro-4-fluorophenyl)-2-[4-(morpholin-4-yl)-6-oxo-1,6-dihydropyrimidin-2-yl]acetamide
2-[4-(morpholin-4-yl)-6-oxo-1,6-dihydropyrimidin-2-yl]-N-(pyridin-3-yl)acetamide
N-(4-fluoro-2-methylphenyl)-2-[4-(morpholin-4-yl)-6-oxo-1,6-dihydropyrimidin-2-yl]acetamide
N-(3-hydroxyphenyl)-2-[4-(morpholin-4-yl)-6-oxo-1,6-dihydropyrimidin-2-yl]acetamide
N-(3-bromo-4-fluorophenyl)-2-[4-(morpholin-4-yl)-6-oxo-1,6-dihydropyrimidin-2-yl]acetamide
2-[4-(morpholin-4-yl)-6-oxo-1,6-dihydropyrimidin-2-yl]-N-(3,4,5-trifluorophenyl)acetamide
N-[4-fluoro-3-(hydroxymethyl)phenyl]-2-[4-(morpholin-4-yl)-6-oxo-1,6-dihydropyrimidin-2-yl]acetamide
N-(3-cyclopropylephenyl)-2-[4-(morpholin-4-yl)-6-oxo-1,6-dihydropyrimidin-2-yl]acetamide
N-(2-hydroxyphenyl)-2-[4-(morpholin-4-yl)-6-oxo-1,6-dihydropyrimidin-2-yl]acetamide
N-[3-(difluoromethoxy)phenyl]-2-[4-(morpholin-4-yl)-6-oxo-1,6-dihydropyrimidin-2-yl]acetamide
N-(4-fluoro-3-methoxyphenyl)-2-[4-(morpholin-4-yl)-6-oxo-1,6-dihydropyrimidin-2-yl]propanamide
N-(2,3-dimethylphenyl)-2-[4-(morpholin-4-yl)-6-oxo-1,6-dihydropyrimidin-2-yl]acetamide
N-(2-fluoro-3-methylphenyl)-2-[4-(morpholin-4-yl)-6-oxo-1,6-dihydropyrimidin-2-yl]acetamide
N-(1,3-benzoxazol-4-yl)-2-[4-(morpholin-4-yl)-6-oxo-1,6-dihydropyrimidin-2-yl]acetamide
2-[4-(morpholin-4-yl)-6-oxo-1,6-dihydropyrimidin-2-yl]-N-[3-(trifluoromethoxy)phenyl]acetamide
2-[4-(morpholin-4-yl)-6-oxo-1,6-dihydropyrimidin-2-yl]-N-[3-(propan-2-yloxy)phenyl]acetamide
N-(4-fluoro-2-methoxyphenyl)-2-[4-(morpholin-4-yl)-6-oxo-1,6-dihydropyrimidin-2-yl]acetamide
2-methylpropan-2-yl {2-[3-({[4-(morpholin-4-yl)-6-oxo-1,6-dihydropyrimidin-2-yl]acetyl}amino)phenyl]ethyl}carbamate
N-[4-fluoro-3-(trifluoromethyl)phenyl]-2-[4-(morpholin-4-yl)-6-oxo-1,6-dihydropyrimidin-2-yl]acetamide
N-(3-ethynylphenyl)-2-[4-(morpholin-4-yl)-6-oxo-1,6-dihydropyrimidin-2-yl]acetamide
N-[3-(cyclopentyloxy)phenyl]-2-[4-(morpholin-4-yl)-6-oxo-1,6-dihydropyrimidin-2-yl]acetamide
N-(4-fluoro-2-hydroxyphenyl)-2-[4-(morpholin-4-yl)-6-oxo-1,6-dihydropyrimidin-2-yl]acetamide
2-[2-(2,3-dihydro-1H-indol-1-yl)-2-oxoethyl]-6-(morpholin-4-yl)pyrimidin-4(3H)-one
N-(3-cyclopropyl-4-fluorophenyl)-2-[4-(morpholin-4-yl)-6-oxo-1,6-dihydropyrimidin-2-yl]acetamide
2-[4-(morpholin-4-yl)-6-oxo-1,6-dihydropyrimidin-2-yl]-N-(2,3,4-trifluorophenyl)acetamide
N-[4-fluoro-3-(trifluoromethoxy)phenyl]-2-[4-(morpholin-4-yl)-6-oxo-1,6-dihydropyrimidin-2-yl]acetamide
N-[3-(2-hydroxyethoxy)phenyl]-2-[4-(morpholin-4-yl)-6-oxo-1,6-dihydropyrimidin-2-yl]acetamide
N-(3-iodophenyl)-2-[4-(morpholin-4-yl)-6-oxo-1,6-dihydropyrimidin-2-yl]acetamide
methyl 2-fluoro-5-({[4-(morpholin-4-yl)-6-oxo-1,6-dihydropyrimidin-2-yl]acetyl}amino)benzoate
N-(3-ethoxyphenyl)-2-[4-(morpholin-4-yl)-6-oxo-1,6-dihydropyrimidin-2-yl]acetamide
N-(2,4-difluoro-3-methoxyphenyl)-2-[4-(morpholin-4-yl)-6-oxo-1,6-dihydropyrimidin-2-yl]acetamide
2-[4-(morpholin-4-yl)-6-oxo-1,6-dihydropyrimidin-2-yl]-N-(2,4,5-trifluorophenyl)acetamide
N-(3,5-dichloro-4-fluorophenyl)-2-[4-(morpholin-4-yl)-6-oxo-1,6-dihydropyrimidin-2-yl]acetamide
2-[2-(2,3-dihydro-4H-1,4-benzoxazin-4-yl)-2-oxoethyl]-6-(morpholin-4-yl)pyrimidin-4(3H)-one
N-(4-fluoro-3-nitrophenyl)-2-[4-(morpholin-4-yl)-6-oxo-1,6-dihydropyrimidin-2-yl]acetamide
2-fluoro-5-({[4-(morpholin-4-yl)-6-oxo-1,6-dihydropyrimidin-2-yl]acetyl}amino)benzoic acid
N-(5-fluoro-2-hydroxyphenyl)-2-[4-(morpholin-4-yl)-6-oxo-1,6-dihydropyrimidin-2-yl]acetamide
N-(2-bromo-4-fluorophenyl)-2-[4-(morpholin-4-yl)-6-oxo-1,6-dihydropyrimidin-2-yl]acetamide
N-(4-fluorophenyl)-2-[1-methyl-4-(morpholin-4-yl)-6-oxo-1,6-dihydropyrimidin-2-yl]acetamide
N-(3-chloro-4-fluorophenyl)-2-[1-methyl-4-(morpholin-4-yl)-6-oxo-1,6-dihydropyrimidin-2-yl]acetamide
N-(3-bromophenyl)-2-[1-methyl-4-(morpholin-4-yl)-6-oxo-1,6-dihydropyrimidin-2-yl]acetamide
2-[1-ethyl-4-(morpholin-4-yl)-6-oxo-1,6-dihydropyrimidin-2-yl]-N-(4-fluorophenyl)acetamide
N-(1H-indol-4-yl)-2-[4-(morpholin-4-yl)-6-oxo-1,6-dihydropyrimidin-2-yl]acetamide
N-(4-fluorophenyl)-3-methyl-2-[4-(morpholin-4-yl)-6-oxo-1,6-dihydropyrimidin-2-yl]butanamide
N-[4-fluoro-3-(methoxymethyl)phenyl]-2-[4-(morpholin-4-yl)-6-oxo-1,6-dihydropyrimidin-2-yl]acetamide
N-(4-fluoro-3-iodophenyl)-2-[4-(morpholin-4-yl)-6-oxo-1,6-dihydropyrimidin-2-yl]acetamide
2-[4-(morpholin-4-yl)-6-oxo-1,6-dihydropyrimidin-2-yl]-N-[3-(1,1,2,2-tetrafluoroethoxy)phenyl]acetamide
N-[3-(difluoromethyl)-4-fluorophenyl]-2-[4-(morpholin-4-yl)-6-oxo-1,6-dihydropyrimidin-2-yl]acetamide
2,2-difluoro-N-(4-fluorophenyl)-2-[4-(morpholin-4-yl)-6-oxo-1,6-dihydropyrimidin-2-yl]acetamide
N-(3,4-difluorophenyl)-2-[1-methyl-4-(morpholin-4-yl)-6-oxo-1,6-dihydropyrimidin-2-yl]acetamide
2-[2-(2,3-dihydro-1H-indol-1-yl)-2-oxoethyl]-3-methyl-6-(morpholin-4-yl)pyrimidin-4(3H)-one
N-(3-bromo-4-fluorophenyl)-2-[1-methyl-4-(morpholin-4-yl)-6-oxo-1,6-dihydropyrimidin-2-yl]acetamide
N-[4-fluoro-3-(hydroxymethyl)phenyl]-2-[1-methyl-4-(morpholin-4-yl)-6-oxo-1,6-dihydropyrimidin-2-yl]acetamide
N-(3-cyclopropylphenyl)-2-[1-methyl-4-(morpholin-4-yl)-6-oxo-1,6-dihydropyrimidin-2-yl]acetamide
N-(4-fluoro-3-methoxyphenyl)-2-[1-methyl-4-(morpholin-4-yl)-6-oxo-1,6-dihydropyrimidin-2-yl]acetamide
N-(1-benzofur-4-yl)-2-[4-(morpholin-4-yl)-6-oxo-1,6-dihydropyrimidin-2-yl]acetamide
2-[1-methyl-4-(morpholin-4-yl)-6-oxo-1,6-dihydropyrimidin-2-yl]-N-phenylacetamide
N-(3-cyclopropyl-4-fluorophenyl)-2-[1-methyl-4-(morpholin-4-yl)-6-oxo-1,6-dihydropyrimidin-2-yl]acetamide
N-(3-fluoro-2-hydroxyphenyl)-2-[4-(morpholin-4-yl)-6-oxo-1,6-dihydropyrimidin-2-yl]acetamide
2-[2-(4-fluoro-2,3-dihydro-1H-indol-1-yl)-2-oxoethyl]-6-(morpholin-4-yl)pyrimidin-4(3H)-one
2-[2-(4-chloro-2,3-dihydro-1H-indol-1-yl)-2-oxoethyl]-6-(morpholin-4-yl)pyrimidin-4(3H)-one
N-(3-ethynyl-4-fluorophenyl)-2-[4-(morpholin-4-yl)-6-oxo-1,6-dihydropyrimidin-2-yl]acetamide
2-[2-(4-hydroxy-2,3-dihydro-1H-indol-1-yl)-2-oxoethyl]-6-(morpholin-4-yl)pyrimidin-4(3H)-one
2-[2-(4,6-difluoro-2,3-dihydro-1H-indol-1-yl)-2-oxoethyl]-6-(morpholin-4-yl)pyrimidin-4(3H)-one N-(4-fluoro-3-iodophenyl)-2-(1-methyl-4-morpholin-4-yl-6-oxo-1,6-dihydropyrimidin-2-yl)acetamide
2-[2-(4,5-difluoro-2,3-dihydro-1H-indol-1-yl)-2-oxoethyl]-6-(morpholin-4-yl)pyrimidin-4(3H)-one
2-[2-(6-fluoro-2,3-dihydro-1H-indol-1-yl)-2-oxoethyl]-6-(morpholin-4-yl)pyrimidin-4(3H)-one
2-[2-(2-methyl-2,3-dihydro-1H-indol-1-yl)-2-oxoethyl]-6-(morpholin-4-yl)pyrimidin-4(3H)-one
N-[3-(difluoromethyl)-4-fluorophenyl]-2-[1-methyl-4-(morpholin-4-yl)-6-oxo-1,6-dihydropyrimidin-2-yl]acetamide
2-[1-methyl-4-(morpholin-4-yl)-6-oxo-1,6-dihydropyrimidin-2-yl]-N-(3,4,5-trifluorophenyl)acetamide
N-(1-methyl-1H-indol-4-yl)-2-[4-(morpholin-4-yl)-6-oxo-1,6-dihydropyrimidin-2-yl]acetamide
2-[2-(4-methyl-2,3-dihydro-1H-indol-1-yl)-2-oxoethyl]-6-(morpholin-4-pyrimidin-4(3H)-one
2-[2-(3-methyl-2,3-dihydro-1H-indol-1-yl)-2-oxoethyl]-6-(morpholin-4-yl)pyrimidin-4(3H)-one
2-[2-(4-fluoro-2,3-dihydro-1H-indol-1-yl)-2-oxoethyl]-3-methyl-6-(morpholin-4-yl)pyrimidin-4(3H)-one
2-[2-(5-fluoro-2,3-dihydroindol-1-yl)-2-oxoethyl]-6-morpholin-4-yl-3H-pyrimidin-4-one
2-[2-(4-chloro-2,3-dihydro-1H-indol-1-yl)-2-oxoethyl]-3-methyl-6-(morpholin-4-yl)pyrimidin-4(3H)-one
N-(1-benzothiophen-4-yl)-2-[4-(morpholin-4-yl)-6-oxo-1,6-dihydropyrimidin-2-yl]acetamide
2-{2-[2-(hydroxymethyl)-2,3-dihydro-1H-indol-1-yl]-2-oxoethyl}-6-(morpholin-4-yl)pyrimidin-4(3H)-one
2-[4-(morpholin-4-yl)-6-oxo-1,6-dihydropyrimidin-2-yl]-N-{2-[2-(piperidin-1-yl)ethoxy]phenyl}acetamide
N-[2-(2-methoxyethoxy)phenyl]-2-[4-(morpholin-4-yl)-6-oxo-1,6-dihydropyrimidin-2-yl]acetamide
2-[2-(4-hydroxy-2,3-dihydro-1H-indol-1-yl)-2-oxoethyl]-3-methyl-6-(morpholin-4-yl)pyrimidin-4(3H)-one
2-[2-(4-methoxy-2,3-dihydro-1H-indol-1-yl)-2-oxoethyl]-3-methyl-6-(morpholin-4-yl)pyrimidin-4(3H)-one
2-[2-(3,4-dihydroisoquinolin-2(1H)-yl)-2-oxoethyl]-6-(morpholin-4-pyrimidin-4(3H)-one
2-[4-(morpholin-4-yl)-6-oxo-1,6-dihydropyrimidin-2-yl]-N-{2-[2-(pyrrolidin-1-yl)ethoxy]phenyl}acetamide
2-[4-(morpholin-4-yl)-6-oxo-1,6-dihydropyrimidin-2-yl]-N-[2-(pyridin-3-ylmethoxy)phenyl]acetamide
3-methyl-2-[2-(4-methyl-2,3-dihydro-1H-indol-1-yl)-2-oxoethyl]-6-(morpholin-4-yl)pyrimidin-4(3H)-one
2-(2-{3-[(dimethylamino)methyl]-2,3-dihydro-1H-indol-1-yl}-2-oxoethyl)-6-(morpholin-4-yl)pyrimidin-4(3H)-one
2-[2-(4-bromo-2,3-dihydro-1H-indol-1-yl)-2-oxoethyl]-3-methyl-6-(morpholin-4-yl)pyrimidin-4(3H)-one
2-{2-[(2S)-2-methyl-2,3-dihydro-1H-indol-1-yl]-2-oxoethyl}-6-(morpholin-4-pyrimidin-4(3H)-one
2-{2-[(2R)-2-methyl-2,3-dihydro-1H-indol-1-yl]-2-oxoethyl}-6-(morpholin-4-pyrimidin-4(3H)-one
3-methyl-2-[2-(3-methyl-2,3-dihydro-1H-indol-1-yl)-2-oxoethyl]-6-(morpholin-4-pyrimidin-4(3H)-one
2-{2-[2-(methoxymethyl)-2,3-dihydro-1H-indol-1-yl]-2-oxoethyl}-6-(morpholin-4-yl)pyrimidin-4(3H)-one
2-[2-(4-ethoxy-2,3-dihydro-1H-indol-1-yl)-2-oxoethyl]-6-(morpholin-4-yl)pyrimidin-4(3H)-one
1-{[4-(morpholin-4-yl)-6-oxo-1,6-dihydropyrimidin-2-yl]acetyl}-2,3-dihydro-1H-indole-2-carboxamide
3-methyl-2-[2-(2-methyl-2,3-dihydro-1H-indol-1-yl)-2-oxoethyl]-6-(morpholin-4-yl)pyrimidin-4(3H)-one
2-[2-(6-fluoro-2,3-dihydro-1H-indol-1-yl)-2-oxoethyl]-3-methyl-6-(morpholin-4-pyrimidin-4(3H)-one
2-{2-[(3S)-3-methyl-2,3-dihydro-1H-indol-1-yl]-2-oxoethyl}-6-(morpholin-4-pyrimidin-4(3H)-one
2-{2-[(3R)-3-methyl-2,3-dihydro-1H-indol-1-yl]-2-oxoethyl}-6-(morpholin-4-yl)pyrimidin-4(3H)-one
2-[2-(5,6-difluoro-2,3-dihydro-1H-indol-1-yl)-2-oxoethyl]-3-methyl-6-(morpholin-4-yl)pyrimidin-4(3H)-one
2-[2-(4,5-difluoro-2,3-dihydro-1H-indol-1-yl)-2-oxoethyl]-3-methyl-6-(morpholin-4-yl)pyrimidin-4(3H)-one
2-[2-(1,3-dihydro-2H-isoindol-2-yl)-2-oxoethyl]-6-(morpholin-4-yl)pyrimidin-4(3H)-one
N-(1-benzothiophen-4-yl)-2-[1-methyl-4-(morpholin-4-yl)-6-oxo-1,6-dihydropyrimidin-2-yl]acetamide
2-[2-(5-chloro-3,4-dihydroquinolin-1(2H)-yl)-2-oxoethyl]-6-(morpholin-4-yl)pyrimidin-4(3H)-one
2-{2-[4-(hydroxymethyl)-2,3-dihydro-1H-indol-1-yl]-2-oxoethyl}-6-(morpholin-4-pyrimidin-4(3H)-one
N-[4-fluoro-2-(piperidin-4-ylmethoxy)phenyl]-2-[4-(morpholin-4-yl)-6-oxo-1,6-dihydropyrimidin-2-yl]acetamide
2-[2-(5-chloro-2,3-dihydroindol-1-yl)-2-oxoethyl]-6-morpholin-4-yl-3H-pyrimidin-4-one
2-[2-(4-bromo-2,3-dihydroindol-1-yl)-2-oxoethyl]-6-morpholin-4-yl-3H-pyrimidin-4-one
2-(2-{(3S)-3-[(dimethylamino)methyl]-2,3-dihydro-1H-indol-1-yl}-2-oxoethyl)-6-(morpholin-4-yl)pyrimidin-4(3H)-one
2-(2-{(3R)-3-[(dimethylamino)methyl]-2,3-dihydro-1H-indol-1-yl}-2-oxoethyl)-6-(morpholin-4-yl)pyrimidin-4(3H)-one
N-[4-fluoro-2-(2-methoxyethoxy)phenyl]-2-[4-(morpholin-4-yl)-6-oxo-1,6-dihydropyrimidin-2-yl]acetamide
N-(1H-benzimidazol-4-yl)-2-[4-(morpholin-4-yl)-6-oxo-1,6-dihydropyrimidin-2-yl]acetamide
methyl 2-hydroxy-3-({[4-(morpholin-4-yl)-6-oxo-1,6-dihydropyrimidin-2-yl]acetyl}amino)benzoate
2-[2-(4-methoxy-2,3-dihydroindol-1-yl)-2-oxoethyl]-6-morpholin-4-yl-3H-pyrimidin-4-one
N-(3-bromo-2-hydroxyphenyl)-2-[4-(morpholin-4-yl)-6-oxo-1,6-dihydropyrimidin-2-yl]acetamide
N-(3,4-dihydro-2H-1,4-benzoxazin-8-yl)-2-[4-(morpholin-4-yl)-6-oxo-1,6-dihydropyrimidin-2-yl]acetamide
methyl 5-fluoro-2-({[4-(morpholin-4-yl)-6-oxo-1,6-dihydropyrimidin-2-yl]acetyl}amino) benzoate
2-(2-{3-[(diethylamino)methyl]-2,3-dihydro-1H-indol-1-yl}-2-oxoethyl)-6-(morpholin-4-yl)pyrimidin-4(3H)-one
2-[2-(2,3-dihydro-1H-pyrrolo[3,2-b]pyridin-1-yl)-2-oxoethyl]-6-(morpholin-4-yl)pyrimidin-4(3H)-one
2-[2-(5,6-difluoro-2,3-dihydroindol-1-yl)-2-oxoethyl]-6-morpholin-4-yl-3H-pyrimidin-4-one
2-[4-(morpholin-4-yl)-6-oxo-1,6-dihydropyrimidin-2-yl]-N-(1,2,3,4-tetrahydroquinolin-8-yl)acetamide
2-[2-(8-chloro-2,3-dihydro-4H-1,4-benzoxazin-4-yl)-2-oxoethyl]-6-(morpholin-4-yl)pyrimidin-4(3H)-one
N-(2-hydroxy-3-methylphenyl)-2-[4-(morpholin-4-yl)-6-oxo-1,6-dihydropyrimidin-2-yl]acetamide
N-(2-hydroxy-3-nitrophenyl)-2-[4-(morpholin-4-yl)-6-oxo-1,6-dihydropyrimidin-2-yl]acetamide
N-(3-cyano-2-hydroxyphenyl)-2-[4-(morpholin-4-yl)-6-oxo-1,6-dihydropyrimidin-2-yl]acetamide
N-[2-hydroxy-3-(trifluoromethyl)phenyl]-2-[4-(morpholin-4-yl)-6-oxo-1,6-dihydropyrimidin-2-yl]acetamide
2-[2-(3,3-dimethyl-2,3-dihydro-1H-indol-1-yl)-2-oxoethyl]-6-(morpholin-4-yl)pyrimidin-4(3H)-one
and also the pharmaceutically acceptable addition salts with inorganic and organic acids or with inorganic and organic bases of said products of formula (I).

The invention also relates to pharmaceutical compositions containing, as active ingredient, at least one of the products of formula (I) as defined above or a pharmaceutically acceptable salt of this product or a prodrug of this product, and, where appropriate, a pharmaceutically acceptable carrier.

The invention also extends to the pharmaceutical compositions containing, as active ingredient, at least one of the medicaments as defined above.

Such pharmaceutical compositions of the present invention may also, where appropriate, contain active ingredients of other antimitotic medicaments, such as, in particular, those based on taxol, cis-platin, DNA-intercalating agents, and the like.

These pharmaceutical compositions may be administered orally, parenterally or locally by topical application to the skin and the mucous membranes, or by intravenous or intramuscular injection.

These compositions may be solid or liquid and may be in all the pharmaceutical forms commonly used in human medicine, such as, for example, simple or sugar-coated tablets, pills, lozenges, gel capsules, drops, granules, injectable preparations, ointments, creams or gels; they are prepared according to the usual methods. The active ingredient may be incorporated therein in excipients customarily used in pharmaceutical compositions, such as talc, gum arabic, lactose, starch, magnesium stearate, cocoa butter, aqueous or non-aqueous carriers, fatty substances of animal or plant origin, paraffin derivatives, glycols, various wetting agents, dispersants or emulsifiers, and preservatives.

The usual dosage, which is variable according to the product used, the individual treated and the condition in question, may, for example, be from 0.05 to 5 g per day in adults, or preferably from 0.1 to 2 g per day.

Such a medicament may in particular be for use in the treatment or prevention of a disease in a mammal.

The subject of the present invention is in particular the use of a product of formula (I) as defined above, for the preparation of a medicament for use in the prevention or treatment of diseases associated with an uncontrolled proliferation.

The subject of the present invention is thus most particularly the use of a product of formula (I) as defined above, for the preparation of a medicament for use in the treatment or prevention of diseases in oncology, and in particular for use in the treatment of cancers.

Among these cancers, the focus is on the treatment of solid or liquid tumours, and on the treatment of cancers resistant to cytotoxic agents.

The cited products of the present invention may especially be used in the treatment of primary tumours and/or of metastases, in particular in gastric, hepatic, renal, ovarian, colon, prostate, endometrial and lung (NSCLC and SCLC) cancers, glioblastomas, thyroid, bladder and breast cancers, in melanoma, in lymphoid or myeloid hematopoietic tumours, in sarcomas, in brain, larynx and lymphatic system cancers, bone and pancreatic cancers, and in hamartomas.

The subject of the present invention is also the use of the products of formula (I) as defined above, for the preparation of medicaments for use in cancer chemotherapy.

The subject of the present invention is thus the products of formula (I) as defined above, for their use in the treatment of cancers.

The subject of the present invention is the products of formula (I) as defined above, for their use in the treatment of solid or liquid tumours.

The subject of the present invention is therefore the products of formula (I) as defined above, for their use in the treatment of cancers resistant to cytotoxic agents.

The subject of the present invention is therefore the products of formula (I) as defined above, for their use in the treatment of primary tumours and/or of metastases, in particular in gastric, hepatic, renal, ovarian, colon, prostate, endometrial and lung (NSCLC and SCLC) cancers, glioblastomas, thyroid, bladder and breast cancers, in melanoma, in lymphoid or myeloid hematopoietic tumours, in sarcomas, in brain, larynx and lymphatic system cancers, bone and pancreatic cancers, and in hamartomas.

The subject of the present invention is therefore the products of formula (I) as defined above, for their use in cancer chemotherapy.

Such medicaments for use in cancer chemotherapy may be used alone or in combination.

The subject of the present invention is therefore the products of formula (I) as defined above, for their use in cancer chemotherapy, alone or in combination.

The products of the present application can in particular be administered alone or in combination with chemotherapy or radiotherapy, or else in combination, for example, with other therapeutic agents.

Such therapeutic agents may be commonly used antitumour agents.

A subject of the present invention is also, as novel industrial products, the synthesis intermediates of formulae C, D, E and F as defined and recalled below:

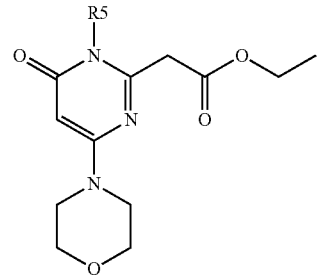

C, E

D, F $Y = Na, Li, K$ in which R5 has the definition indicated in either one of Claims 1 and 2.

The following examples, which are products of formula (I), illustrate the invention without, however, limiting it.

EXPERIMENTAL SECTION

The nomenclature of the compounds of this present invention was carried out with the ACDLABS software, version 10.0.

The microwave oven used is a Biotage, Initiator™ 2.0, 400 W max, 2450 MHz instrument.

The $^1$H NMR spectra at 400 MHz and the $^1$H NMR spectra at 500 MHz were performed on a Bruker Avance DRX-400 or Bruker Avance DPX-500 spectrometer with the chemical shifts (δ in ppm) in the solvent dimethyl sulphoxide-d₆ (DMSO-d₆) referenced at 2.5 ppm at a temperature of 303 K.

The mass spectra (MS) were obtained either by method A or by method B:

Method A:

Waters HPLC-SQD instrument; ionization: positive and/or negative mode electrospray (ES+/−); chromatographic conditions: column: Acquity BEH C18 1.7 μm—2.1×50 mm; solvents: A: H₂O (0.1% formic acid) B: CH₃CN (0.1% formic acid); column temperature: 50° C.; flow rate: 1 ml/min; gradient (2 min): from 5% to 50% of B in 0.8 min; 1.2 min: 100% of B; 1.85 min: 100% of B; 1.95: 5% of B; retention time=Tr (min).

Method B:

Waters ZQ instrument; ionization: positive and/or negative mode electrospray (ES+/−); chromatographic conditions: column: XBridge C₁₈ 2.5 μm—3×50 mm; solvents: A: H₂O (0.1% formic acid) B: CH₃CN (0.1% formic acid); column temperature: 70° C.; flow rate: 0.9 ml/min; gradient (7 min): from 5% to 100% of B in 5.3 min; 5.5 min: 100% of B; 6.3 min: 5% of B; retention time=Tr (min).

EXAMPLE 1

Synthesis of 2-[4-(morpholin-4-yl)-6-oxo-1,6-dihydropyrimidin-2-yl]-N-phenylacetamide Stage 1:

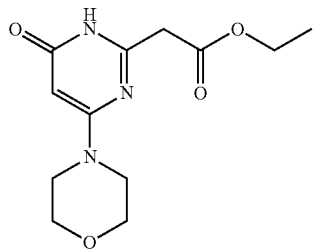 [SMILES: CCOC(=O)Cc1nc(N2CCOCC2)cc(=O)[nH]1]

168.5 ml of ethyl 3-ethoxy-3-iminopropanoate hydrochloride, and then 155 ml of N,N-diisopropylethylamine in 200 ml of ethanol are added to a solution of 25 g of morpholine in 400 ml of ethanol heated to 95° C. The reaction mixture is heated at 95° C. for 30 hours and then allowed to return to ambient temperature. The precipitate formed is filtered off through sintered glass and then washed with 100 ml of ethanol, twice 500 ml of water and, finally, 500 ml of ethyl ether. The solid is dried under vacuum so as to give 35 g of ethyl [4-(morpholin-4-yl)-6-oxo-1,6-dihydropyrimidin-2-yl]acetate in the form of a white solid, the characteristics of which are the following:

¹H NMR spectrum (400 MHz): 1.19 (t, J=7.1 Hz, 3 H); 3.38 to 3.44 (m, 4 H); 3.56 (s, 2H); 3.61 (dd, J=4.0 and 5.7 Hz, 4 H); 4.12 (q, J=7.1 Hz, 2 H); 5.20 (s, 1 H); 11.69 (broad s, 1 H).

Mass spectrometry: method A

Retention time Tr (min)=0.48;

[M+H]⁺: m/z 268; [M−H]⁻: m/z 266.

Stage 2:

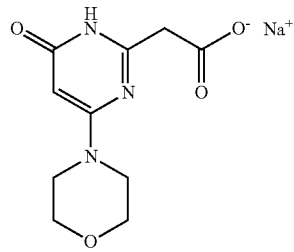 [SMILES: O=C([O-])Cc1nc(N2CCOCC2)cc(=O)[nH]1 ; [Na+]]

18.7 ml of 2M sodium hydroxide are added to a solution of 10 g of ethyl [4-(morpholin-4-yl)-6-oxo-1,6-dihydropyrimidin-2-yl]acetate prepared in stage 1 of Example 1 in 300 ml of tetrahydrofuran. The reaction mixture is stirred for 48 hours at ambient temperature. The precipitate formed is filtered off through sintered glass, washed with ethyl acetate and rinsed several times with ethyl ether. The solid obtained is then dried in a rotary evaporator so as to give 8.7 g of sodium [4-(morpholin-4-yl)-6-oxo-1,6-dihydropyrimidin-2-yl]acetate in the form of a white solid, the characteristics of which are the following:

¹H NMR spectrum: 3.08 (s, 2 H); 3.38 (t, J=4.6 Hz, 4 H); 3.61 (t, J=4.6 Hz, 4 H); 5.08 (s, 1 H); 13.16 (broad s, 1 H).

Mass spectrometry: method A

Retention time Tr (min)=0.29;

[M+H]⁺: m/z 240; [M−H]⁻: m/z 238.

Stage 2':

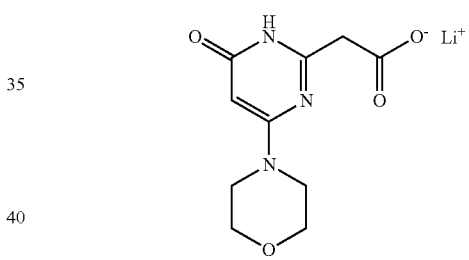

7.5 ml of water and 197 mg of lithium hydroxide are added to a solution of 2 g of ethyl [4-(morpholin-4-yl)-6-oxo-1,6-dihydropyrimidin-2-yl]acetate prepared in stage 1 of Example 1 in 75 ml of methanol. After stirring for 48 hours at ambient temperature, the reaction mixture is concentrated under reduced pressure. 50 ml of water are added. The aqueous phase is then washed with ethyl acetate and then lyophilized. 1.73 g of lithium [4-(morpholin-4-yl)-6-oxo-1,6-dihydropyrimidin-2-yl]acetate are obtained in the form of a white solid, the characteristics of which are similar to the product of stage 2.

Stage 3:

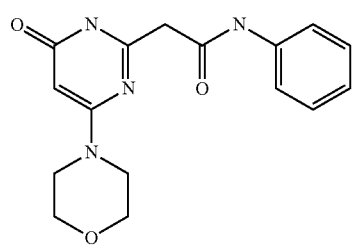 [SMILES: O=C(Cc1nc(N2CCOCC2)cc(=O)[nH]1)Nc1ccccc1]

370 mg of benzotriazol-1-yloxytris(dimethylamino)phosphonium hexafluorophosphate, 113 mg of 1-hydroxybenzotriazole and 0.140 ml of aniline are added to a solution of 200 mg of sodium [4-(morpholin-4-yl)-6-oxo-1,6-dihydropyrimidin-2-yl]acetate prepared in stage 2 of Example 1 in 3 ml of N,N-dimethylformamide. The reaction mixture is stirred at ambient temperature for 3 hours, and then concentrated under reduced pressure. Water and ethyl acetate are added and the resulting mixture is thus stirred for 30 minutes. The precipitate formed is filtered off and dried in a rotary evaporator. After purification by silica column chromatography, eluent: dichloromethane/methanol 90/10, 161 mg of 2-[4-(morpholin-4-yl)-6-oxo-1,6-dihydropyrimidin-2-yl]-N-phenylacetamide are obtained in the form of a white solid, the characteristics of which are the following:

$^1$H NMR spectrum: 3.38 to 3.44 (m, 4 H); 3.56 to 3.63 (m, 6 H); 5.20 (s, 1H); 7.06 (t, J=7.8 Hz, 1 H); 7.31 (t, J=8.6 Hz, 2 H); 7.56 (d, J=8.6 Hz, 2 H); 10.14 (s, 1 H); 11.64 (broad s, 1H).

Mass spectrometry: method A

Retention time Tr (min)=0.55;

[M+H]$^+$: m/z 315; [M−H]$^-$: m/z 313.

EXAMPLE 2

Synthesis of N-(4-fluorophenyl)-2-[4-(morpholin-4-yl)-6-oxo-1,6-dihydropyrimidin-2-yl]acetamide

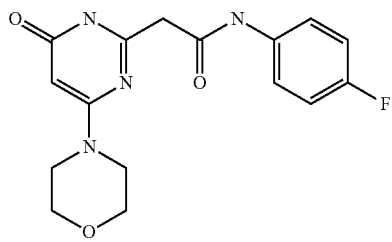 [SMILES: O=C(Cc1nc(N2CCOCC2)cc(=O)[nH]1)Nc1ccc(F)cc1]

The product is prepared according to the procedure described in stage 3 of Example 1, using 300 mg of sodium [4-(morpholin-4-yl)-6-oxo-1,6-dihydropyrimidin-2-yl]acetate prepared in stage 2 of Example 1, 595 mg of benzotriazol-1-yloxytris(dimethylamino)phosphonium hexafluorophosphate, 182 mg of 1-hydroxybenzotriazole and 0.235 ml of 4-fluoroaniline in place of aniline. 110 mg of N-(4-fluorophenyl)-2-[4-(morpholin-4-yl)-6-oxo-1,6-dihydropyrimidin-2-yl]acetamide are obtained in the form of an off-white solid, the characteristics of which are the following:

$^1$H NMR spectrum: 3.41 (t, J=4.9 Hz, 4 H); 3.55 to 3.64 (m, 6 H); 5.20 (s, 1H); 7.15 (t, J=8.9 Hz, 2 H); 7.58 (dd, J=5.6 and 9.0 Hz, 2 H); 10.20 (s, 1 H); 11.65 (broad s, 1 H).

Mass spectrometry: method B

Retention time Tr (min)=2.86;

[M+H]$^+$: m/z 333; [M−H]$^-$: m/z 331.

EXAMPLE 3

Synthesis of N-(3-chlorophenyl)-2-[4-(morpholin-4-yl)-6-oxo-1,6-dihydropyrimidin-2-yl]acetamide

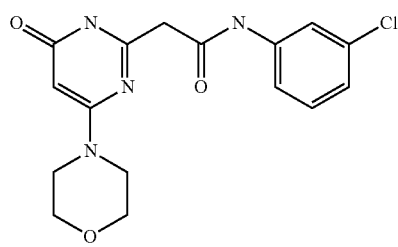 [SMILES: O=C(Cc1nc(N2CCOCC2)cc(=O)[nH]1)Nc1cccc(Cl)c1]

The product is prepared according to the procedure described in stage 3 of Example 1, using 300 mg of lithium [4-(morpholin-4-yl)-6-oxo-1,6-dihydropyrimidin-2-yl]acetate obtained in stage 2' of Example 1 and 0.235 ml of 3-chloroaniline in place of aniline. After purification by silica column chromatography, eluent: dichloromethane/methanol/acetonitrile 90/5/5, 71 mg of N-(3-chlorophenyl)-2-[4-(morpholin-4-yl)-6-oxo-1,6-dihydropyrimidin-2-yl]acetamide are obtained, the characteristics of which are the following:

$^1$H NMR spectrum: 3.42 (d, J=5.1 Hz, 4 H); 3.53 to 3.69 (m, 6 H); 5.20 (s, 1 H); 7.12 (d, J=9.0 Hz, 1 H); 7.34 (t, J=8.1 Hz, 1 H); 7.42 (dt, J=1.3 and 7.8 Hz, 1 H); 7.77 (t, J=2.1 Hz, 1H); 10.34 (broad s, 1 H); 11.66 (broad s, 1 H).

Mass spectrometry: method B

Retention time Tr (min)=0.68;

[M+H]$^+$: m/z 349; [M−H]$^-$: m/z 347.

EXAMPLE 4

Synthesis of N-[3-(dimethylamino)phenyl]-2-[4-(morpholin-4-yl)-6-oxo-1,6-dihydropyrimidin-2-yl]acetamide

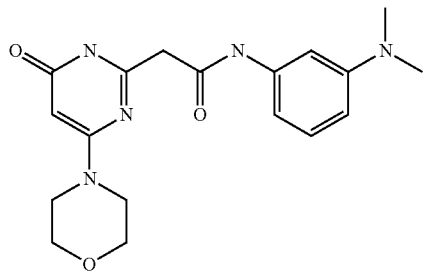 [SMILES: CN(C)c1cccc(NC(=O)Cc2nc(N3CCOCC3)cc(=O)[nH]2)c1]

0.160 ml of pyridine, 240 mg of N-[3-(dimethylamino)propyl]-N'-ethylcarbodiimide hydrochloride and 400 mg of N,N-dimethyl-m-phenylenediamine are added to a solution of 250 mg of sodium [4-(morpholin-4-yl)-6-oxo-1,6-dihydropyrimidin-2-yl]acetate prepared in stage 2 of Example 1 in 4 ml of N,N-dimethylformamide. The reaction mixture is stirred at ambient temperature overnight and is then concentrated under reduced pressure. Water and ethyl acetate are added and the resulting mixture is thus stirred for 30 minutes. The precipitate formed is filtered off, rinsed with ethyl ether and dried in a rotary evaporator. After purification by silica column chromatography as a solid deposit, eluent: dichloromethane/methanol 95/05, a solid is obtained which is taken up in a mixture of dichloromethane, methanol and ethyl ether. The solid is filtered off and dried. 30 mg of N-[3-(dimethylamino)phenyl]-2-[4-(morpholin-4-yl)-6-oxo-1,6-dihydropyrimidin-2-yl]acetamide are obtained in the form of a yellow solid, the characteristics of which are the following:

$^1$H NMR spectrum: 2.86 (s, 6 H); 3.41 (t, J=5.0 Hz, 4 H); 3.57 (s, 2 H); 3.60 (t, J=4.9 Hz, 4 H); 5.19 (s, 1 H); 6.44 (d, J=9.3 Hz, 1 H); 6.86 (d, J=7.8 Hz, 1 H); 7.01 (s, 1 H); 7.09(t, J=8.3 Hz, 1 H); 9.98 (broad s, 1 H); 11.61 (broad s, 1 H).

Mass spectrometry: method B

Retention time Tr (min)=0.40;

[M+H]$^+$: m/z 358; [M–H]$^-$: m/z 356.

EXAMPLE 5

Synthesis of N-(2,4-difluorophenyl)-2-[4-(morpholin-4-yl)-6-oxo-1,6-dihydropyrimidin-2-yl]acetamide

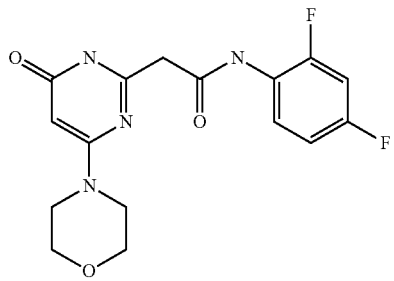 [SMILES: O=C(Cc1nc(N2CCOCC2)cc(=O)[nH]1)Nc1ccc(F)cc1F]

2.5 ml of pyridine, 233 mg of N-[3-(dimethylamino)propyl]-N'-ethylcarbodiimide hydrochloride and 400 mg of 2,4-difluoroaniline are added to a solution of 260 mg of sodium [4-(morpholin-4-yl)-6-oxo-1,6-dihydropyrimidin-2-yl]acetate prepared in stage 2 of Example 1 in 2 ml of N,N-dimethylformamide. The reaction mixture is stirred at ambient temperature for 16 hours, and then concentrated under reduced pressure. Water and ethyl acetate are added and the resulting mixture is thus stirred for 30 minutes. The precipitate formed is filtered off, and rinced with water, ethyl ether and petroleum ether. The solid obtained is dried under vacuum. 205 mg of N-(2,4-difluorophenyl)-2-[4-(morpholin-4-yl)-6-oxo-1,6-dihydropyrimidin-2-yl]acetamide are obtained in the form of a pinkish solid, the characteristics of which are the following:

$^1$H NMR spectrum: 3.43 (t, J=5.0 Hz, 4 H); 3.61 (t, J=5.0 Hz, 4 H); 3.66 (s, 2 H); 5.20 (s, 1 H); 7.01 to 7.13 (m, 1 H); 7.25 to 7.40 (m, 1 H); 7.83 (q, J=7.1 Hz, 1H); 9.97 (broad s, 1H); 11.67 (broad s, 1 H).

Mass spectrometry: method B

Retention time Tr (min)=0.59;

[M+H]$^+$: m/z 351; [M–H]$^-$: m/z 349.

EXAMPLE 6

Synthesis of N-(3,4-difluorophenyl)-2-[4-(morpholin-4-yl)-6-oxo-1,6-dihydropyrimidin-2-yl]acetamide

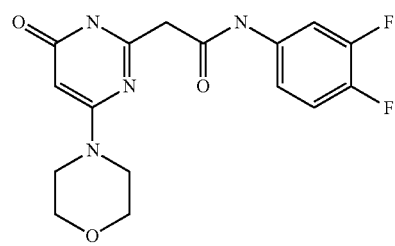 [SMILES: O=C(Cc1nc(N2CCOCC2)cc(=O)[nH]1)Nc1ccc(F)c(F)c1]

The product is prepared according to the procedure described in Example 5, using 260 mg of sodium [4-(morpholin-4-yl)-6-oxo-1,6-dihydropyrimidin-2-yl]acetate and 400 mg of 3,4-difluoroaniline in place of the 2,4-difluoroaniline. 210 mg of N-(3,4-difluorophenyl)-2-[4-(morpholin-4-yl)-6-oxo-1,6-dihydropyrimidin-2-yl]acetamide are obtained in the form of a white solid, the characteristics of which are the following:

$^1$H NMR spectrum (400 MHz): 3.41 (t, J=4.9 Hz, 4 H); 3.54 to 3.64 (m, 6 H); 5.20 (s, 1H); 7.27 (d, J=8.8 Hz, 1H); 7.39 (dt, J=9.0 and 10.6 Hz, 1 H); 7.64 to 7.79 (m, 1 H); 10.38 (s, 1 H); 11.66 (broad s, 1 H).

Mass spectrometry: method A

Retention time Tr (min)=0.64;

[M+H]$^+$: m/z 351; [M–H]$^-$: m/z 349.

EXAMPLE 7

Synthesis of 2-[4-(morpholin-4-yl)-6-oxo-1,6-dihydropyrimidin-2-yl]-N-(thiophen-3-yl)acetamide

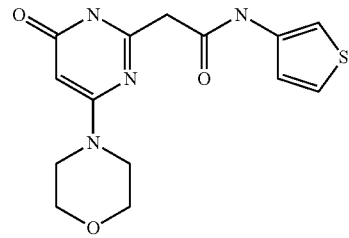 [SMILES: O=C(Cc1nc(N2CCOCC2)cc(=O)[nH]1)Nc1ccsc1]

The product is prepared according to the procedure described in Example 5, using 250 mg of sodium [4-(morpholin-4-yl)-6-oxo-1,6-dihydropyrimidin-2-yl]acetate and 400 mg of 3-aminothiophene hydrochloride in place of the 2,4-difluoroaniline. 252 mg of 2-[4-(morpholin-4-yl)-6-oxo-1,6-dihydropyrimidin-2-yl]-N-(thiophen-3-yl)acetamide are obtained in the form of a beige solid, the characteristics of which are the following:

$^1$H NMR spectrum: 3.41 (t, J=5.0 Hz, 4 H); 3.51 to 3.64 (m, 6 H); 5.20 (s, 1H); 7.08 (d, J=5.6 Hz, 1 H); 7.35 to 7.56 (m, 2 H); 10.55 (broad s, 1 H); 11.64 (broad s, 1 H).

Mass spectrometry: method A

Retention time Tr (min)=0.52;

[M+H]$^+$: m/z 321; [M–H]$^-$: m/z 319.

EXAMPLE 8

Synthesis of N-(4-fluoro-3-methoxyphenyl)-2-[4-(morpholin-4-yl)-6-oxo-1,6-dihydropyrimidin-2-yl]acetamide

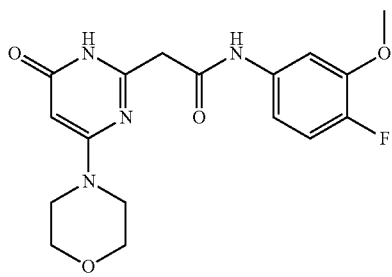 [SMILES: COc1cc(NC(=O)Cc2nc(N3CCOCC3)cc(=O)[nH]2)ccc1F]

The product is prepared according to the procedure described in Example 5, using 250 mg of sodium [4-(morpholin-4-yl)-6-oxo-1,6-dihydropyrimidin-2-yl]acetate and 520 mg of 4-fluoro-3-methoxyaniline in place of the 2,4-difluoroaniline. 262 mg of N-(4-fluoro-3-methoxyphenyl)-2-[4-(morpholin-4-yl)-6-oxo-1,6-dihydropyrimidin-2-yl]acetamide are obtained in the form of a white solid, the characteristics of which are the following:

$^1$H NMR spectrum (400 MHz): 3.41 (t, J=4.9 Hz, 4 H); 3.56 to 3.62 (m, 6 H); 3.79 (s, 3H); 5.20 (s, 1 H); 7.02 to 7.09 (m, 1 H); 7.10 to 7.17 (m, 1 H); 7.47 (dd, J=2.4 and 8.1 Hz, 1 H); 10.20 (s, 1 H); 11.64 (broad s, 1 H).

Mass spectrometry: method A
Retention time Tr (min)=0.60;
[M+H]$^+$: m/z 363; [M−H]$^-$: m/z 361.

EXAMPLE 9

Synthesis of N-(2-fluorophenyl)-2-[4-(morpholin-4-yl)-6-oxo-1,6-dihydropyrimidin-2-yl]acetamide

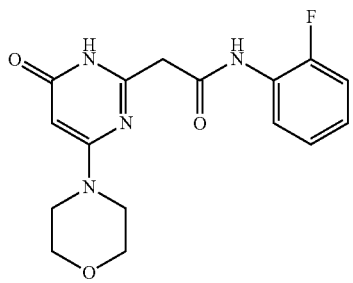 [SMILES: O=C(Cc1nc(N2CCOCC2)cc(=O)[nH]1)Nc1ccccc1F]

In a microwave tube, 300 mg of ethyl [4-(morpholin-4-yl)-6-oxo-1,6-dihydropyrimidin-2-yl]acetate prepared in stage 1 of Example 1 are introduced into 1 ml of N,N-dimethylformamide, 623 mg of 2-fluoroaniline and 378 mg of potassium tert-butoxide. 2 ml of N,N-dimethylformamide are then added. The tube is then microwave-heated at 150° C. for 20 minutes. The reaction mixture is concentrated under reduced pressure. 30 ml of water and 10 ml of ethyl acetate are added and the resulting mixture is thus stirred for 1 h 30. The precipitate formed is filtered off and rinsed with ethyl acetate, ethyl ether and then petroleum ether. The solid obtained is dried in a rotary evaporator and 93 mg of N-(2-fluorophenyl)-2-[4-(morpholin-4-yl)-6-oxo-1,6-dihydropyrimidin-2-yl]acetamide are thus obtained in the form of a white solid, the characteristics of which are the following:

$^1$H NMR spectrum: 3.42 (t, J=4.9 Hz, 4 H); 3.61 (t, J=4.6 Hz, 4 H); 3.67(s, 2 H); 5.19 (s, 1 H); 7.12 to 7.20 (m, 2 H); 7.21 to 7.32 (m, 1 H); 7.81 to 7.98 (m, J=8.3 and 8.3 Hz, 1 H); 10.00 (broad s, 1 H); 11.66 (broad s, 1 H).

Mass spectrometry: method A
Retention time Tr (min)=0.56;
[M+H]$^+$: m/z 333; [M−H]$^-$: m/z 331
Purity: 94%
Melting point (Kofler bench): 279° C.

EXAMPLE 10

Synthesis of N-(2-methylphenyl)-2-[4-(morpholin-4-yl)-6-oxo-1,6-dihydropyrimidin-2-yl]acetamide

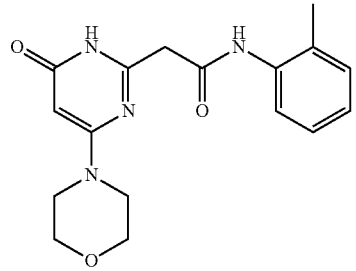 [SMILES: Cc1ccccc1NC(=O)Cc1nc(N2CCOCC2)cc(=O)[nH]1]

The product is prepared according to the procedure described in Example 9, using 300 mg of ethyl [4-(morpholin-4-yl)-6-oxo-1,6-dihydropyrimidin-2-yl]acetate prepared in stage 1 of Example 1 and 582 mg of 2-methylaniline in place of the 2-fluoroaniline. 76 mg of N-(2-methylphenyl)-2-[4-(morpholin-4-yl)-6-oxo-1,6-dihydropyrimidin-2-yl]acetamide are obtained in the form of a white solid, the characteristics of which are the following:

$^1$H NMR spectrum: 2.21 (s, 3 H); 3.43 (t, J=5.0 Hz, 4 H); 3.55 to 3.67 (m, 6H); 5.18 (s, 1 H); 7.08 (t, J=7.8 Hz, 1 H); 7.16 (t, J=7.8 Hz, 1 H); 7.21 (d, J=7.8 Hz, 1H); 7.42 (d, J=7.8 Hz, 1 H); 9.65 (broad s, 1 H); 11.70 (s, 1 H).

Mass spectrometry: method B
Retention time Tr (min)=2.81;
[M+H]$^+$: m/z 329; [M−H]$^-$: m/z 327
Melting point (Kofler bench): 194° C.

EXAMPLE 11

Synthesis of N-(2-methoxyphenyl)-2-[4-(morpholin-4-yl)-6-oxo-1,6-dihydropyrimidin-2-yl]acetamide

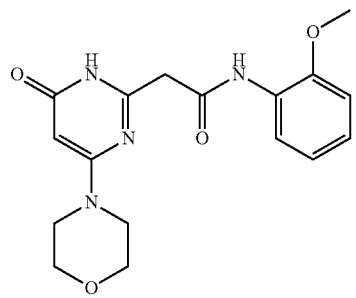 [SMILES: COc1ccccc1NC(=O)Cc1nc(N2CCOCC2)cc(=O)[nH]1]

The product is prepared according to the procedure described in Example 9, using 300 mg of ethyl [4-(morpholin-4-yl)-6-oxo-1,6-dihydropyrimidin-2-yl]acetate prepared in stage 1 of Example 1 in 2 ml of N,N-dimethylformamide, 637 mg of 2-methoxyaniline in place of the 2-fluoroaniline, and 300 mg of potassium tert-butoxide. 3 ml of N,N-dimethylformamide are added and the tube is microwave-heated at 150° C. for 20 minutes. The reaction mixture is concentrated under reduced pressure. 15 ml of water and 5 ml of ethyl acetate are added and the resulting mixture is thus stirred for 2 hours. The aqueous phase is extracted with 5 ml of ethyl acetate. The combined organic phases are dried over magnesium sulphate. filtered, and concentrated under reduced pressure. After purification of the solid obtained, on a preparative plate (thickness: 2 mm), elution being carried out with a mixture of dichloromethane and methanol (90/10 by volume), 7 mg of N-(2-methoxyphenyl)-2-[4-(morpholin-4-yl)-6-oxo-1,6-dihydropyrimidin-2-yl]acetamide are thus obtained in the form of a pinkish solid, the characteristics of which are the following:

$^1$H NMR spectrum: 3.43 (t, J=4.9 Hz, 4 H); 3.59 to 3.65 (m, 4 H); 3.69 (s, 2H); 3.83 (s, 3 H); 5.20 (s, 1 H); 6.90 (ddd, J=2.2 and 6.5 and 8.2 Hz, 1 H); 6.99 to 7.13 (m, 2 H); 7.97 (d, J=8.6 Hz, 1 H); 9.44 (broad s, 1 H); 11.66 (broad s, 1 H).

Mass spectrometry: method A

Retention time Tr (min)=0.59;

[M+H]$^+$: m/z 345; [M−H]$^-$: m/z 343.

EXAMPLE 12

Synthesis of N-(2,3-difluorophenyl)-2-[4-(morpholin-4-yl)-6-oxo-1,6-dihydropyrimidin-2-yl]acetamide

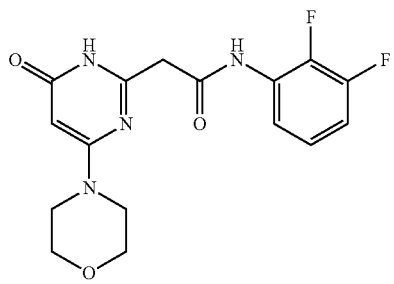 [SMILES: O=C(Cc1nc(N2CCOCC2)cc(=O)[nH]1)Nc1cccc(F)c1F]

The product is prepared according to the procedure described in Example 9, using 300 mg of ethyl [4-(morpholin-4-yl)-6-oxo-1,6-dihydropyrimidin-2-yl]acetate prepared in stage 1 of Example 1 and 840 mg of 2,3-difluoroaniline in place of the 2-fluoroaniline. 83 mg of N-(2,3-difluorophenyl)-2-[4-(morpholin-4-yl)-6-oxo-1,6-dihydropyrimidin-2-yl]acetamide are obtained in the form of a white solid, the characteristics of which are the following:

$^1$H NMR spectrum: 3.42 (t, J=5.1 Hz, 4H); 3.61 (t, J=5.1 Hz, 4 H); 3.69 (s, 2 H); 5.20 (s, 1 H); 7.18 (t, J=7.0 Hz, 2 H); 7.69 (broad s, 1 H); 10.24 (broad s, 1 H); 11.63 (broad s, 1 H).

Mass spectrometry: method A

Retention time Tr (min)=0.61;

[M+H]$^+$: m/z 351; [M−H]$^-$: m/z 349

Melting point (Kofler bench): 248° C.

EXAMPLE 13

Synthesis of N-(3,5-difluorophenyl)-2-[4-(morpholin-4-yl)-6-oxo-1,6-dihydropyrimidin-2-yl]acetamide

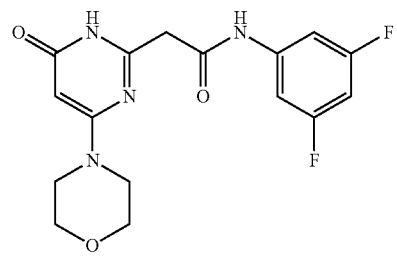 [SMILES: O=C(Cc1nc(N2CCOCC2)cc(=O)[nH]1)Nc1cc(F)cc(F)c1]

The product is prepared according to the procedure described in Example 9, using 300 mg of ethyl [4-(morpholin-4-yl)-6-oxo-1,6-dihydropyrimidin-2-yl]acetate prepared in stage 1 of Example 1 and 780 mg of 3,5-difluoroaniline in place of the 2-fluoroaniline. 133 mg of N-(3,5-difluorophenyl)-2-[4-(morpholin-4-yl)-6-oxo-1,6-dihydropyrimidin-2-yl]acetamide are obtained in the form of a white solid, the characteristics of which are the following:

$^1$H NMR spectrum: 3.41 (t, J=4.9 Hz, 4 H); 3.56 to 3.65 (m, 6 H); 5.20 (s, 1H); 6.92 (t, J=9.3 Hz, 1 H); 7.28 (dd, J=2.2 and 9.5 Hz, 2 H); 10.55 (broad s, 1 H); 11.66 (broad s, 1 H).

Mass spectrometry: method A

Retention time Tr (min)=0.66;

[M+H]$^+$: m/z 351; [M−H]$^-$: m/z 349

Melting point (Kofler bench)>260° C.

EXAMPLE 14

Synthesis of N-(3-fluorophenyl)-2-[4-(morpholin-4-yl)-6-oxo-1,6-dihydropyrimidin-2-yl]acetamide

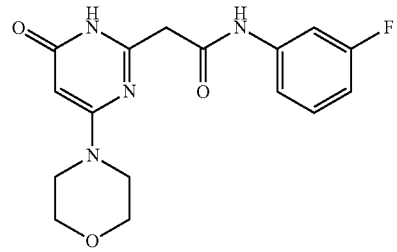 [SMILES: O=C(Cc1nc(N2CCOCC2)cc(=O)[nH]1)Nc1cccc(F)c1]

The product is prepared according to the procedure described in Example 9, using 250 mg of ethyl [4-(morpholin-4-yl)-6-oxo-1,6-dihydropyrimidin-2-yl]acetate prepared in stage 1 of Example 1 and 0.90 ml of 3-fluoroaniline in place of the 2-fluoroaniline. 160 mg of N-(3-fluorophenyl)-2-[4-(morpholin-4-yl)-6-oxo-1,6-dihydropyrimidin-2-yl]acetamide are obtained in the form of a white solid, the characteristics of which are the following:

$^1$H NMR spectrum (400 MHz): 3.42 (d, J=5.0 Hz, 4 H); 3.57 to 3.62 (m, 6 H); 5.20 (s, 1 H); 6.89 (t, J=9.0 Hz, 1 H); 7.27 (d, J=7.5 Hz, 1 H); 7.31 to 7.40 (m, 1 H); 7.55 (d, J=12.1 Hz, 1 H); 10.38 (broad s, 1 H); 11.66 (broad s, 1H).

Mass spectrometry: method A

Retention time Tr (min)=2.93;

[M+H]$^+$: m/z 333; [M−H]$^-$: m/z 331.

EXAMPLE 15

Synthesis of N-(4-chlorophenyl)-2-[4-(morpholin-4-yl)-6-oxo-1,6-dihydropyrimidin-2-yl]acetamide

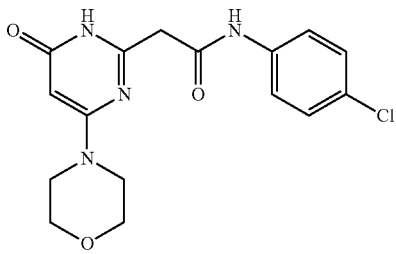 [SMILES: O=C(Cc1nc(N2CCOCC2)cc(=O)[nH]1)Nc1ccc(Cl)cc1]

The product is prepared according to the procedure described in Example 9, using 250 mg of ethyl [4-(morpholin-4-yl)-6-oxo-1,6-dihydropyrimidin-2-yl]acetate prepared in stage 1 of Example 1 and 1.193 g of 4-chloroaniline in place of the 2-fluoroaniline. 140 mg of N-(4-chlorophenyl)-2-[4-(morpholin-4-yl)-6-oxo-1,6-dihydropyrimidin-2-yl]acetamide are obtained in the form of a white solid, the characteristics of which are the following:

$^1$H NMR spectrum: 3.37 to 3.46 (m, J=4.9 Hz, 4 H); 3.51 to 3.66 (m, 6 H); 5.21 (s, 1 H); 7.38 (d, J=8.8 Hz, 2 H); 7.60 (d, J=8.8 Hz, 2 H); 10.34 (broad s, 1 H); 11.71 (broad s, 1 H)

Mass spectrometry: method A
Retention time Tr (min)=0.68;
[M+H]$^+$: m/z 349; [M−H]$^-$: m/z 347.

EXAMPLE 16

Synthesis of N-(3-methoxyphenyl)-2-[4-(morpholin-4-yl)-6-oxo-1,6-dihydropyrimidin-2-yl]acetamide

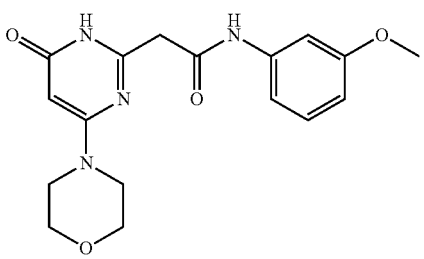 [SMILES: COc1cccc(NC(=O)Cc2nc(N3CCOCC3)cc(=O)[nH]2)c1]

The product is prepared according to the procedure described in Example 9, using 300 mg of ethyl [4-(morpholin-4-yl)-6-oxo-1,6-dihydropyrimidin-2-yl]acetate prepared in stage 1 of Example 1 and 1.254 ml of 3-methoxyaniline in place of the 2-fluoroaniline. 56 mg of N-(3-methoxyphenyl)-2-[4-(morpholin-4-yl)-6-oxo-1,6-dihydropyrimidin-2-yl]acetamide are obtained in the form of a white solid, the characteristics of which are the following:

$^1$H NMR spectrum: 3.41 (t, J=5.0 Hz, 4 H); 3.55 to 3.63 (m, 6 H); 3.72 (s, 3H); 5.20 (s, 1 H); 6.64 (dd, J=2.4 and 8.1 Hz, 1 H); 7.08 (ddd, J=0.9 and 1.0 and 8.1 Hz, 1 H); 7.21 (t, J=8.3 Hz, 1 H); 7.27 (s, 1 H); 10.14 (broad s, 1 H); 11.63 (broad s, 1 H).

Mass spectrometry: method A
Retention time Tr (min)=0.58;
[M+H]$^+$: m/z 345; [M−H]$^-$: m/z 343.

EXAMPLE 17

Synthesis of 2-[4-(morpholin-4-yl)-6-oxo-1,6-dihydropyrimidin-2-yl]-N-[3-(trifluoromethyl)phenyl]acetamide

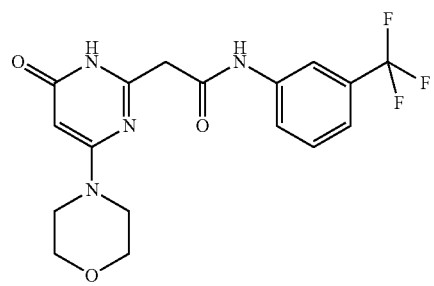 [SMILES: O=C(Cc1nc(N2CCOCC2)cc(=O)[nH]1)Nc1cccc(C(F)(F)F)c1]

The product is prepared according to the procedure described in Example 9, using 300 mg of ethyl [4-(morpholin-4-yl)-6-oxo-1,6-dihydropyrimidin-2-yl]acetate prepared in stage 1 of Example 1 and 0.705 ml of 3-(trifluoromethyl)aniline in place of the 2-fluoroaniline. 228 mg of 2-[4-(morpholin-4-yl)-6-oxo-1,6-dihydropyrimidin-2-yl]-N-[3-(trifluoromethyl)phenyl]acetamide are obtained in the form of a white solid, the characteristics of which are the following:

$^1$H NMR spectrum: 3.37 to 3.46 (m, 4 H); 3.54 to 3.66 (m, 6 H); 5.21 (broad s, 1 H); 7.42 (d, J=8.1 Hz, 1 H); 7.57 (t, J=8.1 Hz, 1 H); 7.75 (d, J=8.3 Hz, 1 H); 8.05 (broad s, 1 H); 10.50 (broad s, 1 H); 11.67 (broad s, 1 H).

Mass spectrometry: method A
Retention time Tr (min)=3.39;
[M+H]$^+$: m/z 383; [M−H]$^-$: m/z 381.

EXAMPLE 18

Synthesis of N-(3-bromophenyl)-2-[4-(morpholin-4-yl)-6-oxo-1,6-dihydropyrimidin-2-yl]acetamide

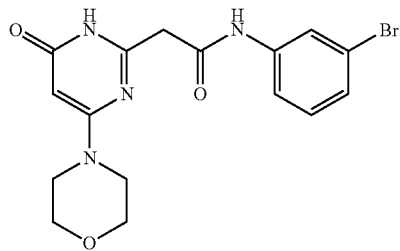 [SMILES: O=C(Cc1nc(N2CCOCC2)cc(=O)[nH]1)Nc1cccc(Br)c1]

The product is prepared according to the procedure described in Example 9, using 300 mg of ethyl [4-(morpholin-4-yl)-6-oxo-1,6-dihydropyrimidin-2-yl]acetate prepared in stage 1 of Example 1 and 0.61 ml of 3-bromoaniline in place of the 2-fluoroaniline. 105 mg of N-(3-bromophenyl)-2-[4-(morpholin-4-yl)-6-oxo-1,6-dihydropyrimidin-2-yl]acetamide are obtained in the form of a white solid, the characteristics of which are the following:

$^1$H NMR spectrum (400 MHz): 3.37 to 3.46 (m, 4 H); 3.54 to 3.66 (m, 6 H); 5.20 (broad s, 1 H); 7.15 to 7.34 (m, 2 H); 7.47 (d, J=8.1 Hz, 1 H); 7.91 (broad s, 1 H); 10.33 (broad s, 1 H); 11.66 (broad s, 1 H)

Mass spectrometry: method A

Retention time Tr (min)=0.70;
[M+H]⁺: m/z 395; [M−H]⁻: m/z 393.

EXAMPLE 19

Synthesis of N-[3-(2-methylpropan-2-yl)phenyl]-2-[4-(morpholin-4-yl)-6-oxo-1,6-dihydropyrimidin-2-yl]acetamide

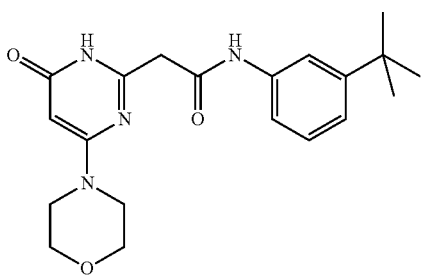 [SMILES: CC(C)(C)c1cccc(NC(=O)Cc2nc(N3CCOCC3)cc(=O)[nH]2)c1]

224 mg of 3-(tert-butyl)aniline are added to a solution of 261 mg of sodium [4-(morpholin-4-yl)-6-oxo-1,6-dihydropyrimidin-2-yl]acetate prepared in stage 2 of Example 1 in 10 ml of methanol. The reaction mixture is stirred at ambient temperature for 5 minutes and then 442 mg of 4-(4,6-dimethoxy-1,3,5-triazin-2-yl)-4-methylmorpholin-4-ium chloride hydrate are added. The resulting mixture is thus stirred for 30 minutes at ambient temperature. The reaction mixture is concentrated under reduced pressure. The evaporation residue is taken up with 10 ml of water and 10 ml of ethyl acetate. The resulting product is then stirred for 30 minutes. The precipitate formed is filtered off. 235 mg of N-[3-(2-methylpropan-2-yl)phenyl]-2-[4-(morpholin-4-yl)-6-oxo-1,6-dihydropyrimidin-2-yl]acetamide are thus obtained in the form of a white solid, the characteristics of which are the following:

¹H NMR spectrum: 1.26 (s, 9 H); 3.42 (t, J=4.8 Hz, 4 H); 3.53 to 3.64 (m, 6H); 5.20 (s, 1 H); 7.10 (d, J=8.1 Hz, 1 H); 7.23 (t, J=8.1 Hz, 1 H); 7.41 (d, J=8.1 Hz, 1 H); 7.58 (broad s, 1H); 10.09 (broad s, 1 H); 11.65 (broad s, 1 H)

Mass spectrometry: method A
Retention time Tr (min)=0.83;
[M+H]⁺: m/z 371; [M−H]⁻: m/z 369.

EXAMPLE 20

Synthesis of methyl 3-({[4-(morpholin-4-yl)-6-oxo-1,6-dihydropyrimidin-2-yl]acetyl}amino)benzoate

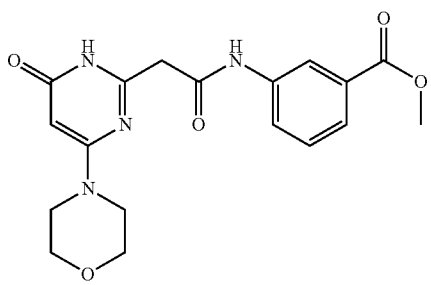 [SMILES: COC(=O)c1cccc(NC(=O)Cc2nc(N3CCOCC3)cc(=O)[nH]2)c1]

The product is prepared according to the procedure described in Example 19, using 653 mg of sodium [4-(morpholin-4-yl)-6-oxo-1,6-dihydropyrimidin-2-yl]acetate prepared in stage 2 of Example 1 and 567 mg of methyl 3-aminobenzoate in place of the 3-(tert-butyl)aniline. 400 mg of methyl 3-({[4-(morpholin-4-yl)-6-oxo-1,6-dihydropyrimidin-2-yl]acetyl}amino)benzoate are obtained in the form of a white solid, the characteristics of which are the following:

¹H NMR spectrum: 3.41 (dd, J=4.8 and 5.3 Hz, 4 H); 3.53 to 3.68 (m, 6 H); 3.85 (broad s, 3 H); 5.21 (broad s, 1 H); 7.47 (t, J=8.1 Hz, 1 H); 7.66 (d, J=8.1 Hz, 1 H); 7.80 (d, J=8.3 Hz, 1 H); 8.24 (s, 1 H); 10.00 to 10.64 (m, 1 H); 11.67 (broad s, 1 H).

Mass spectrometry: method A
Retention time Tr (min)=0.59;
[M+H]⁺: m/z 373; [M−H]⁻: m/z 371
Purity: 95%.

EXAMPLE 21

Synthesis of 3-({[4-(morpholin-4-yl)-6-oxo-1,6-dihydropyrimidin-2-yl]acetyl}amino)benzoic acid

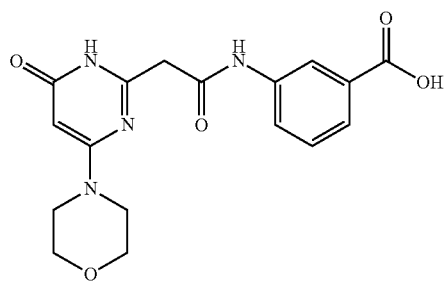 [SMILES: O=C(Cc1nc(N2CCOCC2)cc(=O)[nH]1)Nc1cccc(C(=O)O)c1]

1.8 ml of 2 M sodium hydroxide are added to a solution of 335 mg of methyl 3-({[4-(morpholin-4-yl)-6-oxo-1,6-dihydropyrimidin-2-yl]acetyl}amino)benzoate in 25 ml of methanol. The reaction mixture is heated at 60° C. for 2 h 30, and it is then concentrated under reduced pressure. The evaporation residue is taken up in 50 ml of water. The aqueous phase is extracted with ethyl acetate and then acidified (pH=6) by adding a 1N solution of hydrochloric acid. The precipitate formed is filtered off and then washed with 20 ml of water, 5 ml of ethyl acetate and, finally, 20 ml of ethyl ether. The solid is dried under vacuum and 175 mg of 3-({[4-(morpholin-4-yl)-6-oxo-1,6-dihydropyrimidin-2-yl]acetyl}amino)benzoic acid are thus obtained in the form of a white solid, the characteristics of which are the following:

¹H NMR spectrum (400 MHz): 3.42 (t, J=4.9 Hz, 4 H); 3.52 to 3.72 (m, 6 H); 5.21 (s, 1H); 7.43 (t, J=7.9 Hz, 1 H); 7.64 (d, J=7.8 Hz, 1 H); 7.79 (ddd, J=1.5 and 1.6 and 8.2 Hz, 1 H); 8.19 (s, 1 H); 10.36 (s, 1 H); 11.77 (broad s, 1 H); 12.94 (broad s, 1 H).

Mass spectrometry: method A
Retention time Tr (min)=0.46;
[M+H]⁺: m/z 359; [M−H]⁻: m/z 357.

EXAMPLE 22

Synthesis of 2-[4-(morpholin-4-yl)-6-oxo-1,6-dihydropyrimidin-2-yl]-N-[3-(propan-2-yl)phenyl]acetamide

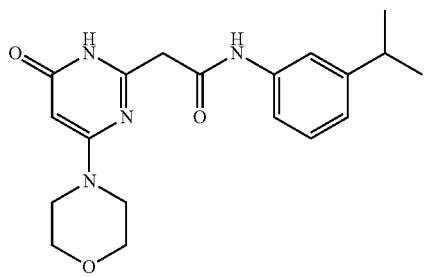 [SMILES: CC(C)c1cccc(NC(=O)Cc2nc(N3CCOCC3)cc(=O)[nH]2)c1]

The product is prepared according to the procedure described in Example 19, using 653 mg of sodium [4-(morpholin-4-yl)-6-oxo-1,6-dihydropyrimidin-2-yl]acetate prepared in stage 2 of Example 1 and using a mixture of 10 ml of water and 2 ml of tetrahydrofuran in place of the methanol and 270 mg of isopropylaniline in place of the 3-(tert-butyl) aniline. 235 mg of 2-[4-(morpholin-4-yl)-6-oxo-1,6-dihydropyrimidin-2-yl]-N-[3-(propan-2-yl)phenyl]acetamide are obtained in the form of a white solid, the characteristics of which are the following:

$^1$H NMR spectrum: 1.18 (d, J=6.8 Hz, 6 H); 2.84 (quin, J=6.9 Hz, 1 H); 3.42 (t, J=4.9 Hz, 4 H); 3.54 to 3.65 (m, 6 H); 5.20 (s, 1 H); 6.94 (d, J=7.6 Hz, 1 H); 7.22 (t, J=7.8 Hz, 1 H); 7.38 (d, J=8.8 Hz, 1 H); 7.45 (s, 1 H); 10.09 (s, 1 H); 11.64 (broad s, 1 H)

Mass spectrometry: method A
Retention time Tr (min)=0.78;
[M+H]$^+$: m/z 357; [M−H]$^-$: m/z 355.

EXAMPLE 23

Synthesis of N-(3-methylphenyl)-2-[4-(morpholin-4-yl)-6-oxo-1,6-dihydropyrimidin-2-yl]acetamide

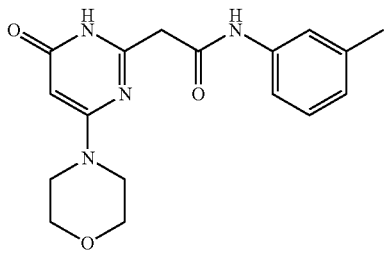 [SMILES: Cc1cccc(NC(=O)Cc2nc(N3CCOCC3)cc(=O)[nH]2)c1]

The product is prepared according to the procedure described in Example 19, using 261 mg of sodium [4-(morpholin-4-yl)-6-oxo-1,6-dihydropyrimidin-2-yl]acetate prepared in stage 2 of Example 1 and using a mixture of 1 ml of water and 9 ml of ethanol in place of the methanol and 214 mg of 3-methylaniline in place of the 3-(tert-butyl)aniline. 196 mg of N-(3-methylphenyl)-2-[4-(morpholin-4-yl)-6-oxo-1,6-dihydropyrimidin-2-yl]acetamide are obtained in the form of a white solid, the characteristics of which are the following:

$^1$H NMR spectrum: 2.27 (s, 3 H); 3.38 to 3.45 (m, 4 H); 3.54 to 3.64 (m, 6H); 5.20 (s, 1 H); 6.88 (d, J=7.8 Hz, 1 H); 7.19 (t, J=7.8 Hz, 1 H); 7.35 (d, J=8.8 Hz, 1 H); 7.39 (s, 1 H); 10.07 (s, 1 H); 11.65 (broad s, 1 H)

Mass spectrometry: method A
Retention time Tr (min)=0.63;
[M+H]$^+$: m/z 329; [M−H]$^-$: m/z 327.

EXAMPLE 24

Synthesis of N-(3-cyano-4-fluorophenyl)-2-[4-(morpholin-4-yl)-6-oxo-1,6-dihydropyrimidin-2-yl]acetamide

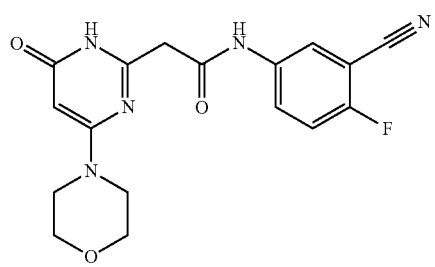 [SMILES: N#Cc1cc(NC(=O)Cc2nc(N3CCOCC3)cc(=O)[nH]2)ccc1F]

The product is prepared according to the procedure described in Example 19, using 261 mg of sodium [4-(morpholin-4-yl)-6-oxo-1,6-dihydropyrimidin-2-yl]acetate prepared in stage 2 of Example 1 and 163 mg of 5-amino-2-fluorobenzonitrile in place of the 3-(tert-butyl)aniline. The reaction mixture is concentrated to dryness under reduced pressure and the residue is then purified by silica column chromatography, elution being carried out with a gradient of the eluent $CH_2Cl_2$/MeOH: 90/10 in dichloromethane of 0% to 100%. 81 mg of N-(3-cyano-4-fluorophenyl)-2-[4-(morpholin-4-yl)-6-oxo-1,6-dihydropyrimidin-2-yl]acetamide are obtained in the form of an amber solid, the characteristics of which are the following:

$^1$H NMR spectrum: 3.34 to 3.47 (m, 4 H); 3.53 to 3.67 (m, 6 H); 5.21 (s, 1H); 7.51 (t, J=9.2 Hz, 1 H); 7.73 to 7.89 (m, 1 H); 8.07 (dd, J=2.8 and 5.7 Hz, 1 H); 10.53 (s, 1 H); 11.68 (broad s, 1 H).

Mass spectrometry: method A
Retention time Tr (min)=0.60;
[M+H]$^+$: m/z 358; [M−H]$^-$: m/z 356
Purity: 95%.

EXAMPLE 25

Synthesis of N-(1H-indazol-6-yl)-2-[4-(morpholin-4-yl)-6-oxo-1,6-dihydropyrimidin-2-yl]acetamide

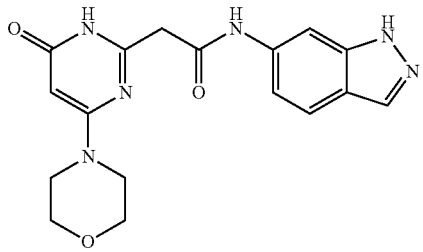 [SMILES: O=C(Cc1nc(N2CCOCC2)cc(=O)[nH]1)Nc1ccc2cn[nH]c2c1]

The product is prepared according to the procedure described in Example 19, using 261 mg of sodium [4-(morpholin-4-yl)-6-oxo-1,6-dihydropyrimidin-2-yl]acetate prepared in stage 2 of Example 1 and 280 mg of 1-Boc-6-aminoindazole in place of the 3-(tert-butyl)aniline. The reaction mixture is concentrated under reduced pressure and taken up in 13 ml of 1,4-dioxane and 3 ml of 1N hydrochloric acid, and is then microwave-heated for 10 minutes at 100° C. After cooling to ambient temperature, the reaction mixture is concentrated under reduced pressure and taken up in 30 ml of water, and then a saturated aqueous solution of sodium bicarbonate is added so as to obtain a pH in the region of 8. The precipitate formed is filtered off and washed with water, ethyl acetate and ethyl ether. After purification by silica column chromatography, elution being carried out with a gradient of the eluent $CH_2Cl_2$/MeOH: 70/30 in dichloromethane of 0% to 100%, 20 mg of N-(1H-indazol-6-yl)-2-[4-(morpholin-4-yl)-6-oxo-1,6-dihydropyrimidin-2-yl]acetamide are obtained in the form of a white solid, the characteristics of which are the following:

$^1$H NMR spectrum: 3.42 (t, J=4.9 Hz, 4 H); 3.60 (dd, J=4.0 and 5.7 Hz, 4H); 3.64 (s, 2 H); 5.20 (s, 1 H); 7.08 (dd, J=1.8 and 8.6 Hz, 1 H); 7.67 (d, J=8.6 Hz, 1 H); 7.96 (s, 1 H); 8.09 (s, 1 H); 10.32 (broad s, 1 H); 11.67 (broad s, 1 H); 12.88 (broad s, 1 H)

Mass spectrometry: method A

Retention time Tr (min)=0.45;

[M+H]$^+$: m/z 355; [M−H]$^-$: m/z 353

EXAMPLE 26

Synthesis of N-(3-cyanophenyl)-2-[4-(morpholin-4-yl)-6-oxo-1,6-dihydropyrimidin-2-yl]acetamide

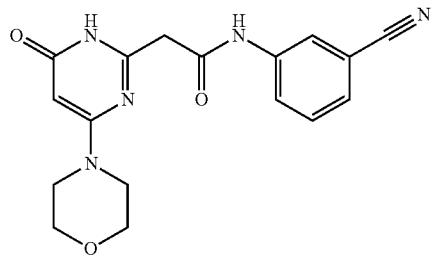 [SMILES: N#Cc1cccc(NC(=O)Cc2nc(N3CCOCC3)cc(=O)[nH]2)c1]

The product is prepared according to the procedure described in Example 19, using 261 mg of sodium [4-(morpholin-4-yl)-6-oxo-1,6-dihydropyrimidin-2-yl]acetate prepared in stage 2 of Example 1 and using a mixture of 6 ml of water and 1 ml of ethyl acetate in place of the methanol, and 118 mg of 3-aminobenzonitrile in place of the 3-(tert-butyl) aniline. 120 mg of N-(3-cyanophenyl)-2-[4-(morpholin-4-yl)-6-oxo-1,6-dihydropyrimidin-2-yl]acetamide are obtained in the form of an off-white solid, the characteristics of which are the following:

$^1$H NMR spectrum: 3.41 (t, J=4.8 Hz, 4 H); 3.60 (dd, J=4.8 and 5.3 Hz, 4H); 3.63 (s, 2 H); 5.21 (s, 1 H); 7.49 to 7.59 (m, 2 H); 7.78 (dt, J=2.3 and 6.8 Hz, 1 H); 8.04 (s, 1 H); 10.51 (broad s, 1 H); 11.69 (broad s, 1 H).

Mass spectrometry: method A

Retention time Tr (min)=0.55;

[M+H]$^+$: m/z 340; [M−H]$^-$: m/z 338.

EXAMPLE 27

Synthesis of N-(5-fluoropyridin-2-yl)-2-[4-(morpholin-4-yl)-6-oxo-1,6-dihydropyrimidin-2-yl]acetamide

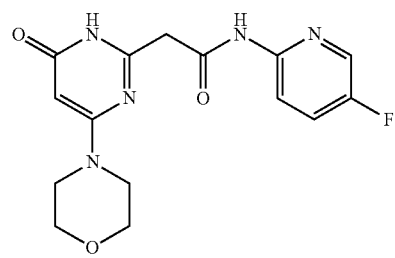 [SMILES: O=C(Cc1nc(N2CCOCC2)cc(=O)[nH]1)Nc1ccc(F)cn1]

The product is prepared according to the procedure described in Example 19, using 261 mg of sodium [4-(morpholin-4-yl)-6-oxo-1,6-dihydropyrimidin-2-yl]acetate prepared in stage 2 of Example 1 and using a mixture of 7 ml of water and 1.5 ml of tetrahydrofuran in place of the methanol, and 134 mg of 2-amino-5-fluoropyridine in place of the 3-(tert-butyl)aniline. After stirring for 1 h 30 at ambient temperature, a precipitate forms. The reaction mixture is filtered through sintered glass. The solid obtained is washed with water, ethyl acetate and ethyl ether. 130 mg of N-(5-fluoropyridin-2-yl)-2-[4-(morpholin-4-yl)-6-oxo-1,6-dihydropyrimidin-2-yl]acetamide are obtained in the form of an off-white solid, the characteristics of which are the following:

$^1$H NMR spectrum: 3.36 to 3.46 (m, 4 H); 3.60 (t, J=5.0 Hz, 4 H); 3.67 (s, 2H); 5.20 (s, 1 H); 7.75 (td, J=2.7 and 6.1 Hz, 1 H); 8.07 (dd, J=9.4 and 4 Hz, 1 H); 8.33 (d, J=2.7 Hz, 1 H); 10.80 (s, 1 H); 11.66 (broad s, 1 H)

Mass spectrometry: method A

Retention time Tr (min)=2.67;

[M+H]$^+$: m/z 334; [M−H]$^-$: m/z 332.

EXAMPLE 28

Synthesis of N-(4-fluoro-3-methylphenyl)-2-[4-(morpholin-4-yl)-6-oxo-1,6-dihydropyrimidin-2-yl] acetamide

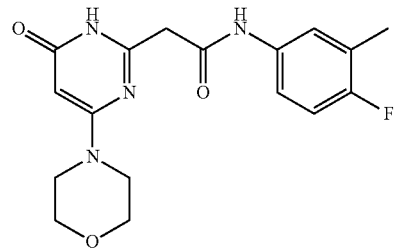 [SMILES: Cc1cc(NC(=O)Cc2nc(N3CCOCC3)cc(=O)[nH]2)ccc1F]

The product is prepared according to the procedure described in Example 5, using 250 mg of sodium [4-(morpholin-4-yl)-6-oxo-1,6-dihydropyrimidin-2-yl]acetate and 240 mg of 4-fluoro-3-methylaniline in place of the 2,4-difluoroaniline. 204 mg of N-(4-fluoro-3-methylphenyl)-2-[4-(morpholin-4-yl)-6-oxo-1,6-dihydropyrimidin-2-yl]acetamide are obtained in the form of a white solid, the characteristics of which are the following:

¹H NMR spectrum: 2.20 (d, J=1.2 Hz, 3 H); 3.41 (t, J=4.9 Hz, 4 H); 3.55 to 3.63 (m, 6 H); 5.20 (s, 1 H); 7.07 (t, J=9.2 Hz, 1 H); 7.33 to 7.41 (m, 1 H); 7.46 (dd, J=2.7 and 6.8 Hz, 1 H); 10.13 (s, 1 H); 11.63 (broad s, 1 H)
Mass spectrometry: method A
Retention time Tr (min)=0.66;
[M+H]⁺: m/z 347; [M−H]⁻: m/z 345.

EXAMPLE 29

Synthesis of N-(3-chloro-4-fluorophenyl)-2-[4-(morpholin-4-yl)-6-oxo-1,6-dihydropyrimidin-2-yl]acetamide

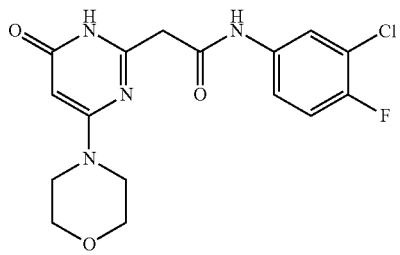 [SMILES: O=C(Cc1nc(N2CCOCC2)cc(=O)[nH]1)Nc1ccc(F)c(Cl)c1]

The product is prepared according to the procedure described in Example 5, using 250 mg of sodium [4-(morpholin-4-yl)-6-oxo-1,6-dihydropyrimidin-2-yl]acetate and 278 mg of 3-chloro-4-fluoroaniline in place of the 2,4-difluoroaniline. 218 mg of N-(3-chloro-4-fluorophenyl)-2-[4-(morpholin-4-yl)-6-oxo-1,6-dihydropyrimidin-2-yl]acetamide are obtained in the form of a white solid, the characteristics of which are the following:
¹H NMR spectrum: 3.41 (t, J=5.0 Hz, 4 H); 3.56 to 3.63 (m, 6 H); 5.20 (s, 1H); 7.38 (t, J=8.8 Hz, 1 H); 7.41 to 7.50 (m, 1 H); 7.88 (dd, J=2.7 and 6.8 Hz, 1 H); 10.38 (s, 1 H); 11.66 (broad s, 1 H).
Mass spectrometry: method A
Retention time Tr (min)=0.70;
[M+H]⁺: m/z 367; [M−H]⁻: m/z 365.

EXAMPLE 30

Synthesis of 2-[4-(morpholin-4-yl)-6-oxo-1,6-dihydropyrimidin-2-yl]-N-(pyridin-3-yl)acetamide

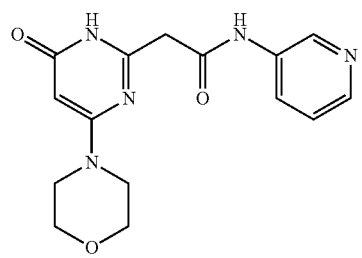 [SMILES: O=C(Cc1nc(N2CCOCC2)cc(=O)[nH]1)Nc1cccnc1]

The product is prepared according to the procedure described in Example 5, using 250 mg of sodium [4-(morpholin-4-yl)-6-oxo-1,6-dihydropyrimidin-2-yl]acetate and 427 mg of 3-aminopyridine in place of the 2,4-difluoroaniline. 168 mg of 2-[4-(morpholin-4-yl)-6-oxo-1,6-dihydropyrimidin-2-yl]-N-(pyridin-3-yl)acetamide are obtained in the form of a white solid, the characteristics of which are the following:
¹H NMR spectrum: 3.39 to 3.46 (m, 4 H); 3.56 to 3.66 (m, 6 H); 5.20 (broad s, 1 H); 7.35 (broad s, 1 H); 8.00 (d, J=8.6 Hz, 1 H); 8.28 (broad s, 1 H); 8.71 (broad s, 1 H); 10.37 (broad s, 1 H); 11.67 (broad s, 1 H).
Mass spectrometry: method A
Retention time Tr (min)=0.25;
[M+H]⁺: m/z 316; [M−H]⁻: m/z 314.

EXAMPLE 31

Synthesis of N-(4-fluoro-2-methylphenyl)-2-[4-(morpholin-4-yl)-6-oxo-1,6-dihydropyrimidin-2-yl]acetamide

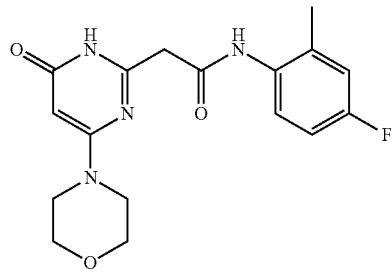 [SMILES: Cc1cc(F)ccc1NC(=O)Cc1nc(N2CCOCC2)cc(=O)[nH]1]

The product is prepared according to the procedure described in Example 5, using 200 mg of sodium [4-(morpholin-4-yl)-6-oxo-1,6-dihydropyrimidin-2-yl]acetate prepared in stage 2 of Example 1 and 278 mg of 4-fluoro-2-methylaniline in place of the 2,4-difluoroaniline. 92 mg of N-(4-fluoro-2-methylphenyl)-2-[4-(morpholin-4-yl)-6-oxo-1,6-dihydropyrimidin-2-yl]acetamide are obtained in the form of a pinkish solid, the characteristics of which are the following:
¹H NMR spectrum: 2.21 (s, 3 H); 3.44 (t, J=4.9 Hz, 4 H); 3.57 to 3.66 (m, 6H); 5.19 (s, 1 H); 6.99 (td, J=3.2 and 8.6 Hz, 1 H); 7.08 (dd, J=3.1 and 9.7 Hz, 1 H); 7.36 (dd, J=5.6 and 8.6 Hz, 1 H); 9.56 (broad s, 1 H); 11.67 (broad s, 1 H).
Mass spectrometry: method A
Retention time Tr (min)=0.59;
[M+H]⁺: m/z 347; [M−H]⁻: m/z 345.

EXAMPLE 32

Synthesis of N-(3-hydroxyphenyl)-2-[4-(morpholin-4-yl)-6-oxo-1,6-dihydropyrimidin-2-yl]acetamide

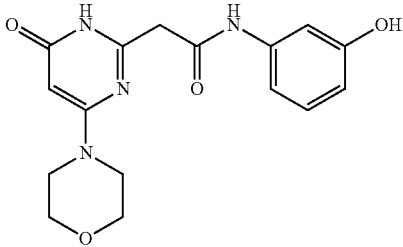 [SMILES: O=C(Cc1nc(N2CCOCC2)cc(=O)[nH]1)Nc1cccc(O)c1]

The product is prepared according to the procedure described in Example 5, using 250 mg of sodium [4-(morpholin-4-yl)-6-oxo-1,6-dihydropyrimidin-2-yl]acetate and 418 mg of 3-aminophenol in place of the 2,4-difluoroaniline. 210 mg of N-(3-hydroxyphenyl)-2-[4-(morpholin-4-yl)-6-oxo-1,6-dihydropyrimidin-2-yl]acetamide are obtained in the form of a pinkish solid, the characteristics of which are the following:

$^1$H NMR spectrum: 3.37 to 3.47 (m, 4 H); 3.51 to 3.63 (m, 6 H); 5.20 (s, 1H); 6.45 (d, J=8.6 Hz, 1 H); 6.93 (d, J=8.6 Hz, 1 H); 7.07 (t, J=8.6 Hz, 1 H); 7.12 (broad s, 1 H); 9.36 (broad s, 1 H); 10.00 (broad s, 1 H); 11.63 (broad s, 1 H).

Mass spectrometry: method A

Retention time Tr (min)=0.43;

[M+H]$^+$: m/z 331; [M−H]$^-$: m/z 329.

EXAMPLE 33

Synthesis of N-(3-bromo-4-fluorophenyl)-2-[4-(morpholin-4-yl)-6-oxo-1,6-dihydropyrimidin-2-yl]acetamide

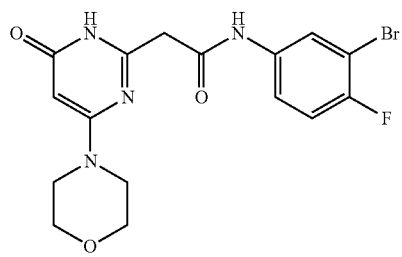 [SMILES: O=C(Cc1nc(N2CCOCC2)cc(=O)[nH]1)Nc1ccc(F)c(Br)c1]

The product is prepared according to the procedure described in Example 19, using 261 mg of sodium [4-(morpholin-4-yl)-6-oxo-1,6-dihydropyrimidin-2-yl]acetate prepared in stage 2 of Example 1 and using a mixture of 7 ml of water and 1.5 ml of tetrahydrofuran in place of the methanol, and 190 mg of 3-bromo-4-fluoroaniline in place of the 3-(tert-butyl)aniline. 266 mg of N-(3-bromo-4-fluorophenyl)-2-[4-(morpholin-4-yl)-6-oxo-1,6-dihydropyrimidin-2-yl]acetamide are obtained in the form of a white solid, the characteristics of which are the following:

$^1$H NMR spectrum: 3.41 (t, J=4.9 Hz, 4 H); 3.55 to 3.65 (m, 6 H); 5.20 (s, 1H); 7.34 (t, J=8.8 Hz, 1 H); 7.44 to 7.53 (m, 1 H); 8.00 (dd, J=2.2 and 6.1 Hz, 1 H); 10.35 (broad s, 1 H); 11.67 (broad s, 1 H).

Mass spectrometry: method A

Retention time Tr (min)=3.30;

[M+H]$^+$: m/z 411; [M−H]$^-$: m/z 409

EXAMPLE 34

Synthesis of 2-[4-(morpholin-4-yl)-6-oxo-1,6-dihydropyrimidin-2-yl]-N-(3,4,5-trifluorophenyl)acetamide

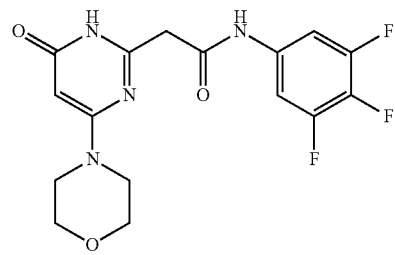 [SMILES: O=C(Cc1nc(N2CCOCC2)cc(=O)[nH]1)Nc1cc(F)c(F)c(F)c1]

The product is prepared according to the procedure described in Example 5, using 200 mg of sodium [4-(morpholin-4-yl)-6-oxo-1,6-dihydropyrimidin-2-yl]acetate prepared in stage 2 of Example 1 and 113 mg of 3,4,5-trifluoroaniline in place of the 2,4-difluoroaniline. 33 mg of 2-[4-(morpholin-4-yl)-6-oxo-1,6-dihydropyrimidin-2-yl]-N-(3,4,5-trifluorophenyl)acetamide are obtained, the characteristics of which are the following:

$^1$H NMR spectrum: 3.41 (dd, J=4.8 and 5.3 Hz, 4 H); 3.54 to 3.66 (m, 6 H); 5.20 (s, 1 H); 7.46 (dd, J=6.5 and 10.1 Hz, 2 H); 10.55 (s, 1 H); 11.64 (s, 1 H).

EXAMPLE 35

Synthesis of N-[4-fluoro-3-(hydroxymethyl)phenyl]-2-[4-(morpholin-4-yl)-6-oxo-1,6-dihydropyrimidin-2-yl]acetamide

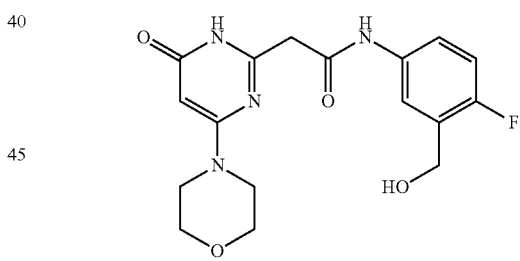

The product is prepared according to the procedure described in Example 5, using 250 mg of sodium [4-(morpholin-4-yl)-6-oxo-1,6-dihydropyrimidin-2-yl]acetate and 525 mg of (5-amino-2-fluorophenyl)methanol in place of the 2,4-difluoroaniline. 218 mg of N-[4-fluoro-3-(hydroxymethyl)phenyl]-2-[4-(morpholin-4-yl)-6-oxo-1,6-dihydropyrimidin-2-yl]acetamide are obtained in the form of a beige solid, the characteristics of which are the following:

$^1$H NMR spectrum: 3.42 (d, J=4.9 Hz, 4 H); 3.55 to 3.64 (m, 6 H); 4.51 (d, J=6.1 Hz, 2 H); 5.20 (broad s, 1 H); 5.27 (t, J=6.0 Hz, 1 H); 7.08 (t, J=9.4 Hz, 1 H); 7.46 to 7.54 (m, 1 H); 7.63 (d, J=7.3 Hz, 1 H); 10.18 (broad s, 1 H); 11.64 (broad s, 1 H).

Mass spectrometry: method A

Retention time Tr (min)=0.46

[M+H]$^+$: m/z 363; [M−H]$^-$: m/z 361

Melting point (Kofler bench)>260° C.

EXAMPLE 36

Synthesis of N-(3-cyclopropylephenyl)-2-[4-(morpholin-4-yl)-6-oxo-1,6-dihydropyrimidin-2-yl]acetamide

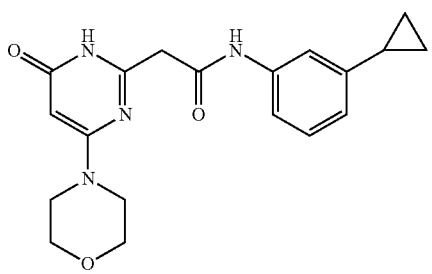 [SMILES: O=C(Cc1nc(N2CCOCC2)cc(=O)[nH]1)Nc1cccc(C2CC2)c1]

The product is prepared according to the following procedure, using 250 mg of sodium [4-(morpholin-4-yl)-6-oxo-1,6-dihydropyrimidin-2-yl]acetate and 395 mg of 3-cyclopropylaniline (prepared according to Wallace et al., in Tetrahedron Lett. 2002, 43, 6987) in place of the 2,4-difluoroaniline. 225 mg of N-(3-cyclopropylphenyl)-2-[4-(morpholin-4-yl)-6-oxo-1,6-dihydropyrimidin-2-yl]acetamide are obtained in the form of a white solid, the characteristics of which are the following:

$^1$H NMR spectrum: 0.50 to 0.68 (m, J=2.0 and 4.9 Hz, 2 H); 0.88 to 1.02 (m, 2H); 1.79 to 1.94 (m, J=4.4 and 4.4 Hz, 1 H); 3.42 (t, J=5.1 Hz, 4 H); 3.51 to 3.68 (m, 6 H); 5.20 (s, 1 H); 6.80 (d, J=8.3 Hz, 1 H); 7.17 (t, J=7.8 Hz, 1 H); 7.26 to 7.36 (m, 2 H); 10.06 (broad s, 1 H); 11.63 (broad s, 1 H)

Mass spectrometry: method A
Retention time Tr (min)=0.72
[M+H]$^+$: m/z 353; [M−H]$^-$: m/z 355
Melting point (Kofler bench)=246° C.

EXAMPLE 37

Synthesis of N-(2-hydroxyphenyl)-2-[4-(morpholin-4-yl)-6-oxo-1,6-dihydropyrimidin-2-yl]acetamide

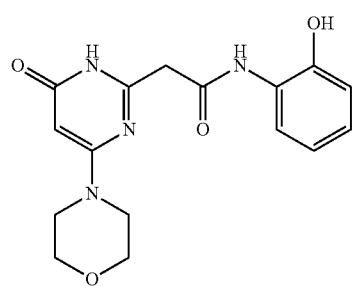 [SMILES: O=C(Cc1nc(N2CCOCC2)cc(=O)[nH]1)Nc1ccccc1O]

The product is prepared according to the procedure described in Example 5, using 500 mg of sodium [4-(morpholin-4-yl)-6-oxo-1,6-dihydropyrimidin-2-yl]acetate and 278 mg of 2-aminophenol in place of the 2,4-difluoroaniline. 370 mg of N-(2-hydroxyphenyl)-2-[4-(morpholin-4-yl)-6-oxo-1,6-dihydropyrimidin-2-yl]acetamide are obtained in the form of a white solid, the characteristics of which are the following:

$^1$H NMR spectrum: 3.45 (t, J=5.0 Hz, 4 H); 3.59 to 3.65 (m, 4 H); 3.69 (s, 2H); 5.21 (s, 1 H); 6.76 (t, J=7.8 Hz, 1 H); 6.87 (d, J=7.8 Hz, 1 H); 6.92 (t, J=8.5 Hz, 1 H); 7.86 (d, J=7.3 Hz, 1 H); 9.46 (broad s, 1 H); 9.82 (broad s, 1 H); 11.63 (broad s, 1 H)

Mass spectrometry: method A
Retention time Tr (min)=2.58;
[M+H]$^+$: m/z 331; [M−H]$^-$: m/z 329
Melting point (Kofler bench)>260° C.

EXAMPLE 38

Synthesis of N-[3-(difluoromethoxy)phenyl]-2-[4-(morpholin-4-yl)-6-oxo-1,6-dihydropyrimidin-2-yl]acetamide

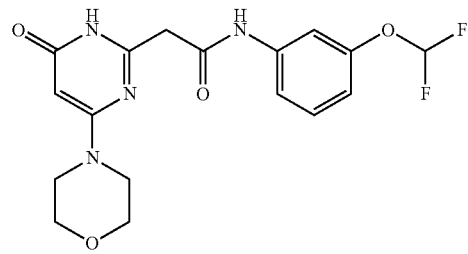 [SMILES: O=C(Cc1nc(N2CCOCC2)cc(=O)[nH]1)Nc1cccc(OC(F)F)c1]

The product is prepared according to the procedure described in Example 5, using 200 mg of sodium [4-(morpholin-4-yl)-6-oxo-1,6-dihydropyrimidin-2-yl]acetate and 520 mg of 3-(difluoromethoxy)aniline in place of the 2,4-difluoroaniline. 135 mg of N-[3-(difluoromethoxy)phenyl]-2-[4-(morpholin-4-yl)-6-oxo-1,6-dihydropyrimidin-2-yl]acetamide are obtained in the form of a white solid, the characteristics of which are the following:

$^1$H NMR spectrum (400 MHz): 3.36 to 3.48 (m, 4 H); 3.54 to 3.65 (m, 6 H); 5.20 (broad s, 1 H); 6.88 (broad s, 2 H); 7.17 (t, J=69.0 Hz, 1 H); 7.36 (s, 1 H); 7.48 to 7.57 (m, 1 H); 10.34 (broad s, 1 H); 11.66 (broad s, 1 H).

Mass spectrometry: method A
Retention time Tr (min)=0.67;
[M+H]$^+$: m/z 381; [M−H]$^-$: m/z 379.

EXAMPLE 39

Synthesis of N-(4-fluoro-3-methoxyphenyl)-2-[4-(morpholin-4-yl)-6-oxo-1,6-dihydropyrimidin-2-yl]propanamide

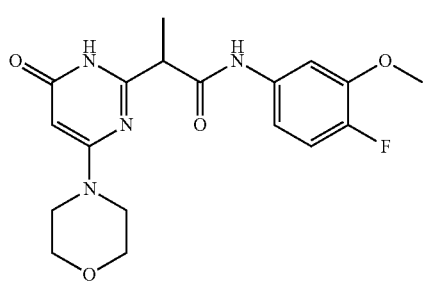 [SMILES: COc1cc(NC(=O)C(C)c2nc(N3CCOCC3)cc(=O)[nH]2)ccc1F]

Stage 1:

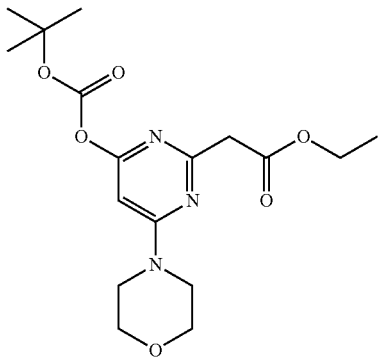 [SMILES: CCOC(=O)Cc1nc(OC(=O)OC(C)(C)C)cc(N2CCOCC2)n1]

88 mg of sodium hydride are added to a solution of 535 mg of ethyl [4-(morpholin-4-yl)-6-oxo-1,6-dihydropyrimidin-2-yl]acetate prepared in stage 1 of Example 1 in 9 ml of N,N-dimethylformamide under argon. The reaction mixture is then stirred for 5 minutes at ambient temperature, and then a solution of 655 mg of di-tert-butyl dicarbonate in 2 ml of N,N-dimethylformamide is added. After stirring overnight at ambient temperature, the reaction mixture is concentrated under reduced pressure. 10 ml of water are added, followed by 1N solution of hydrochloric acid until a pH close to 6 is obtained. The resulting mixture is extracted with ethyl acetate, and the organic phase is dried over magnesium sulphate and then concentrated to dryness under reduced pressure. 735 mg of ethyl [4-({[(2-methylpropan-2-yl)oxy]carbonyl}oxy)-6-(morpholin-4-yl)pyrimidin-2-yl]acetate are obtained in the form of a yellow oil.

Stage 2:

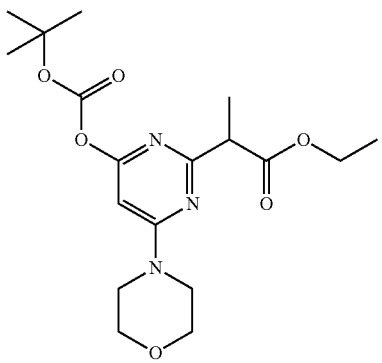 [SMILES: CCOC(=O)C(C)c1nc(OC(=O)OC(C)(C)C)cc(N2CCOCC2)n1]

84 mg of sodium hydride are added to a solution of 700 mg of ethyl [4-({[(2-methylpropan-2-yl)oxy]carbonyl}oxy)-6-(morpholin-4-yl)pyrimidin-2-yl]acetate in 8 ml of N,N-dimethylformamide under argon. The reaction mixture is then stirred for 15 minutes at 0° C. 0.130 ml of methane iodide is then added and the resulting mixture is stirred at ambient temperature overnight. 0.5 ml of water is added and the reaction mixture is concentrated to dryness under reduced pressure. After purification by silica column chromatography, elution being carried out with a gradient of heptane/ethyl acetate eluent of 0% to 50% and then with ethyl acetate at 100%. 150 mg of ethyl 2-[4-({[(2-methylpropan-2-yl)oxy]carbonyl}oxy)-6-(morpholin-4-yl)pyrimidin-2-yl]propanoate are obtained in the form of a colourless oil.

Stage 3:

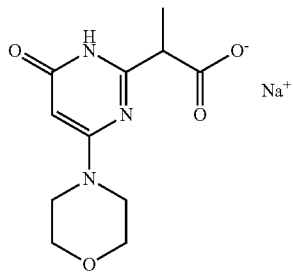 [SMILES: CC(C(=O)[O-])c1nc(N2CCOCC2)cc(=O)[nH]1 ; [Na+]]

0.190 ml of 1M sodium hydroxide is added to a solution of 145 mg of ethyl 2-[4-({[(2-methylpropan-2-yl)oxy]carbonyl}oxy)-6-(morpholin-4-yl)pyrimidin-2-yl]propanoate in 5 ml of tetrahydrofuran. After stirring overnight at ambient temperature, the reaction mixture is concentrated to dryness under reduced pressure. 100 mg of sodium 2-[4-(morpholin-4-yl)-6-oxo-1,6-dihydropyrimidin-2-yl]propanoate are obtained in the form of a solid which is used as it is in the subsequent stage.

Stage 4:

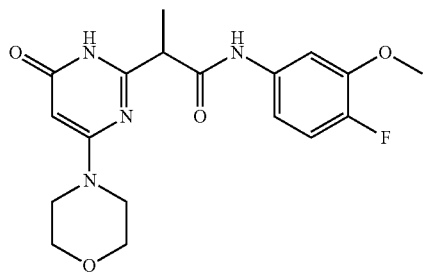 [SMILES: COc1cc(NC(=O)C(C)c2nc(N3CCOCC3)cc(=O)[nH]2)ccc1F]

The product is prepared according to the procedure described in Example 5, using 100 mg of sodium 2-[4-(morpholin-4-yl)-6-oxo-1,6-dihydropyrimidin-2-yl]propanoate and 195 mg of 4-fluoro-3-methoxyaniline in place of the 2,4-difluoroaniline. 30 mg of N-(4-fluoro-3-methoxyphenyl)-2-[4-(morpholin-4-yl)-6-oxo-1,6-dihydropyrimidin-2-yl]propanamide are obtained in the form of a white solid, the characteristics of which are the following:

$^1$H NMR spectrum (400 MHz): 1.44 (d, J=7.1 Hz, 3 H); 3.36 to 3.47 (m, 4 H); 3.50 to 3.65 (m, 4 H); 3.71 (q, J=6.8 Hz, 1 H); 3.79 (s, 3 H); 5.19 (broad s, 1 H); 7.01 to 7.18 (m, 2 H); 7.47 (dd, J=2.0 and 7.8 Hz, 1 H); 10.00 (s, 1 H); 11.55 (broad s, 1 H)

Mass spectrometry: method A
Retention time Tr (min)=0.65
[M+H]$^+$: m/z 377; [M−H]$^-$: m/z 375.

EXAMPLE 40

Synthesis of N-(2,3-dimethylphenyl)-2-[4-(morpholin-4-yl)-6-oxo-1,6-dihydropyrimidin-2-yl]acetamide

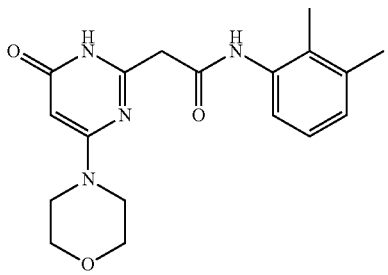 [SMILES: Cc1cccc(NC(=O)Cc2nc(N3CCOCC3)cc(=O)[nH]2)c1C]

The product is prepared according to the procedure described in Example 5, using 260 mg of sodium [4-(morpholin-4-yl)-6-oxo-1,6-dihydropyrimidin-2-yl]acetate and 242 mg of 2,3-dimethylaniline in place of the 2,4-difluoroaniline. 190 mg of N-(2,3-dimethylphenyl)-2-[4-(morpholin-4-yl)-6-oxo-1,6-dihydropyrimidin-2-yl]acetamide are obtained in the form of a white solid, the characteristics of which are the following:

$^1$H NMR spectrum: 2.08 (s, 3 H); 2.24 (s, 3 H); 3.41 to 3.47 (m, 4 H); 3.58 to 3.65 (m, 6 H); 5.20 (s, 1 H); 6.99 to 7.08 (m, 2 H); 7.13 (d, J=7.6 Hz, 1H); 9.57 (s, 1 H); 11.67 (broad s, 1H)

Mass spectrometry: method A
Retention time Tr (min)=0.62
[M+H]$^+$: m/z 343; [M−H]$^-$: m/z 341.

EXAMPLE 41

Synthesis of N-(2-fluoro-3-methylphenyl)-2-[4-(morpholin-4-yl)-6-oxo-1,6-dihydropyrimidin-2-yl]acetamide

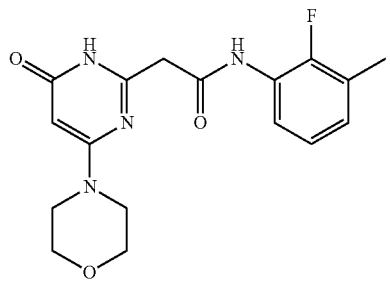

The product is prepared according to the procedure described in Example 5, using 260 mg of sodium [4-(morpholin-4-yl)-6-oxo-1,6-dihydropyrimidin-2-yl]acetate and 250 mg of 2-fluoro-3-methylaniline in place of the 2,4-difluoroaniline. 208 mg of N-(2-fluoro-3-methylphenyl)-2-[4-(morpholin-4-yl)-6-oxo-1,6-dihydropyrimidin-2-yl]acetamide are obtained in the form of a white solid, the characteristics of which are the following:

$^1$H NMR spectrum: 2.24 (broad s, 3 H); 3.37 to 3.48 (m, 4 H); 3.56 to 3.72 (m, 6 H); 5.20 (broad s, 1 H); 6.97 to 7.08 (m, 2 H); 7.71 (broad s, 1 H); 9.89 (broad s, 1 H); 11.66 (broad s, 1H)

Mass spectrometry: method A
Retention time Tr (min)=0.65
[M+H]$^+$: m/z 347; [M−H]$^-$: m/z 345.

EXAMPLE 42

Synthesis of N-(1,3-benzoxazol-4-yl)-2-[4-(morpholin-4-yl)-6-oxo-1,6-dihydropyrimidin-2-yl]acetamide

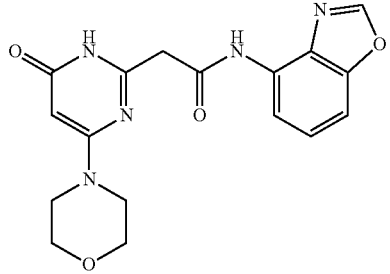 [SMILES: O=C(Cc1nc(N2CCOCC2)cc(=O)[nH]1)Nc1cccc2ocnc12]

The product is prepared according to the procedure described in Example 5, using 260 mg of sodium [4-(morpholin-4-yl)-6-oxo-1,6-dihydropyrimidin-2-yl]acetate and 268 mg of 1,3-benzoxazol-4-amine in place of the 2,4-difluoroaniline. 193 mg of N-(1,3-benzoxazol-4-yl)-2-[4-(morpholin-4-yl)-6-oxo-1,6-dihydropyrimidin-2-yl]acetamide are obtained in the form of an ecru solid, the characteristics of which are the following:

$^1$H NMR spectrum (400 MHz): 3.43 to 3.48 (m, 4 H); 3.62 (t, J=4.9 Hz, 4 H); 3.80 (s, 2H); 5.21 (s, 1 H); 7.36 to 7.42 (m, 1 H); 7.49 (d, J=8.3 Hz, 1 H); 8.08 (d, J=7.8 Hz, 1 H); 8.78 (s, 1 H); 10.44 (broad s, 1 H); 11.73 (broad s, 1 H).

Mass spectrometry: method A
Retention time Tr (min)=0.55
[M+H]$^+$: m/z 356; [M−H]$^-$: m/z 354.

EXAMPLE 43

Synthesis of 2-[4-(morpholin-4-yl)-6-oxo-1,6-dihydropyrimidin-2-yl]-N-[3-(trifluoromethoxy)phenyl]acetamide

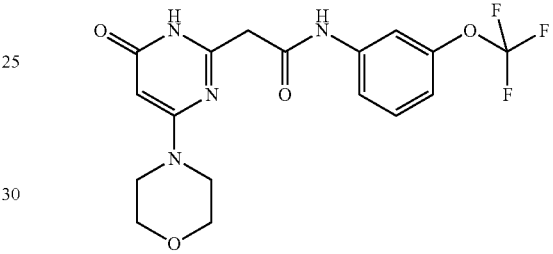

The product is prepared according to the procedure described in Example 5, using 250 mg of sodium [4-(morpholin-4-yl)-6-oxo-1,6-dihydropyrimidin-2-yl]acetate and 270 mg of 3-(trifluoromethoxy)aniline in place of the 2,4-difluoroaniline. 230 mg of 2-[4-(morpholin-4-yl)-6-oxo-1,6-dihydropyrimidin-2-yl]-N-[3-(trifluoromethoxy)phenyl]acetamide are obtained in the form of a white solid, the characteristics of which are the following:

$^1$H NMR spectrum: 3.37 to 3.44 (m, 4 H); 3.54 to 3.64 (m, 6 H); 5.20 (s, 1H); 7.05 (d, J=6.6 Hz, 1 H); 7.41 to 7.48 (m, 2 H); 7.74 (s, 1 H); 10.45 (broad s, 1 H); 11.66 (broad s, 1 H).

Mass spectrometry: method A
Retention time Tr (min)=0.78;
[M+H]$^+$: m/z 399; [M−H]$^-$: m/z 397.

EXAMPLE 44

Synthesis of 2-[4-(morpholin-4-yl)-6-oxo-1,6-dihydropyrimidin-2-yl]-N-[3-(propan-2-yloxy)phenyl]acetamide

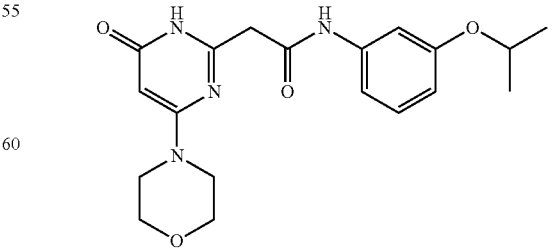

The product is prepared according to the procedure described in Example 5, using 250 mg of sodium [4-(morpholin-4-yl)-6-oxo-1,6-dihydropyrimidin-2-yl]acetate and 572 mg of 3-isopropoxyaniline in place of the 2,4-difluoroaniline. 228 mg of 2-[4-(morpholin-4-yl)-6-oxo-1,6-dihydropyrimidin-2-yl]-N-[3-(propan-2-yloxy)phenyl]acetamide are obtained in the form of a white solid, the characteristics of which are the following:

¹H NMR spectrum: 3.35 (t, J=5.0 Hz, 4 H); 3.56 (t, J=4.9 Hz, 4 H); 4.25(s, 2 H); 5.25 (broad s, 1 H); 7.31 to 7.40 (m, 2 H); 7.62 to 7.74 (m, 2 H); 11.92 (broad s, 1 H).

Mass spectrometry: method A
Retention time Tr (min)=0.60;
[M+H]⁺: m/z 313; [M−H]⁻: m/z 311.

EXAMPLE 45

Synthesis of N-(4-fluoro-2-methoxyphenyl)-2-[4-(morpholin-4-yl)-6-oxo-1,6-dihydropyrimidin-2-yl]acetamide

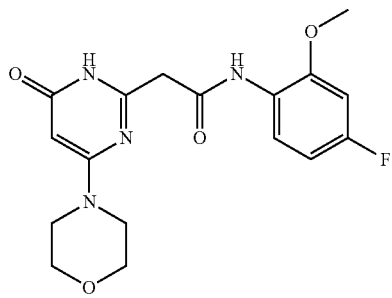 [SMILES: COc1cc(F)ccc1NC(=O)Cc1nc(N2CCOCC2)cc(=O)[nH]1]

The product is prepared according to the procedure described in Example 5, using 250 mg of sodium [4-(morpholin-4-yl)-6-oxo-1,6-dihydropyrimidin-2-yl]acetate and 460 mg of 4-fluoro-2-methoxyaniline in place of the 2,4-difluoroaniline. 245 mg of N-(4-fluoro-2-methoxyphenyl)-2-[4-(morpholin-4-yl)-6-oxo-1,6-dihydropyrimidin-2-yl]acetamide are obtained in the form of a pinkish solid, the characteristics of which are the following:

¹H NMR spectrum: 3.43 (m, 4 H); 3.62 (m, 4 H); 3.67 (s, 2 H); 3.85 (s,3H); 5.20 (s, 1 H); 6.74 (dt, J=2.8 and 8.6 Hz, 1 H); 6.98 (dd, J=2.8 and 10.9 Hz, 1 H); 7.88 (dd, J=6.7 and 8.6 Hz, 1 H); 9.44 (s, 1 H); 11.67 (broad s, 1 H).

Mass spectrometry: method A
Retention time Tr (min)=0.62;
[M+H]⁺: m/z 363; [M−H]⁻: m/z 361.

EXAMPLE 46

Synthesis of 2-methylpropan-2-yl {2-[3-({[4-(morpholin-4-yl)-6-oxo-1,6-dihydropyrimidin-2-yl]acetyl}amino)phenyl]ethyl}-carbamate

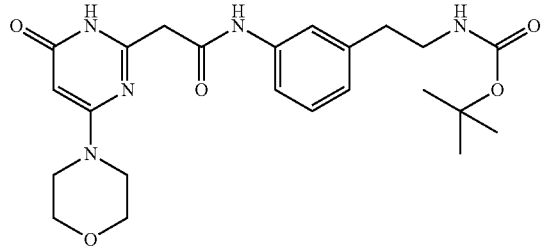 [SMILES: CC(C)(C)OC(=O)NCCc1cccc(NC(=O)Cc2nc(N3CCOCC3)cc(=O)[nH]2)c1]

The product is prepared according to the procedure described in Example 5, using 250 mg of sodium [4-(morpholin-4-yl)-6-oxo-1,6-dihydropyrimidin-2-yl]acetate and 930 mg of 2-methylpropan-2-yl [2-(3-aminophenyl)ethyl]carbamate in place of the 2,4-difluoroaniline. 285 mg of 2-methylpropan-2-yl {2-[3-({[4-(morpholin-4-yl)-6-oxo-1,6-dihydropyrimidin-2-yl]acetyl}amino)phenyl]ethyl}carbamate are obtained in the form of a pinkish solid, the characteristics of which are the following:

¹H NMR spectrum: 1.36 (s, 9 H); 2.61 to 2.68 (m, 2 H); 3.04 to 3.14 (m, 2 H); 3.41 m, 4 H); 3.56 to 3.63 (m, 6 H); 5.20 (s, 1 H); 6.84 (broad t, J=6.7 Hz, 1H); 6.89 (d, J=8.1 Hz, 1H); 7.22 (t, J=8.1 Hz, 1 H); 7.36 to 7.44 (m, 2 H); 10.09 (broad s, 1 H); 11.63 (broad s, 1 H).

Mass spectrometry: method A
Retention time Tr (min)=0.75;
[M+H]⁺: m/z 458; [M−H]⁻: m/z 456
Melting point=194° C.

EXAMPLE 47

Synthesis of N-[4-fluoro-3-(trifluoromethyl)phenyl]-2-[4-(morpholin-4-yl)-6-oxo-1,6-dihydropyrimidin-2-yl]acetamide

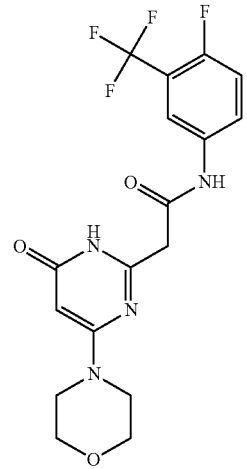 [SMILES: O=C(Cc1nc(N2CCOCC2)cc(=O)[nH]1)Nc1ccc(F)c(C(F)(F)F)c1]

The product is prepared according to the procedure described in Example 5, using 260 mg of sodium [4-(morpholin-4-yl)-6-oxo-1,6-dihydropyrimidin-2-yl]acetate and 358 mg of 4-fluoro-3-(trifluoromethyl)aniline in place of the 2,4-difluoroaniline. 222 mg of N-[4-fluoro-3-(trifluoromethyl)phenyl]-2-[4-(morpholin-4-yl)-6-oxo-1,6-dihydropyrimidin-2-yl]acetamide are obtained in the form of a white solid, the characteristics of which are the following:

¹H NMR spectrum: 3.39 to 3.42 (m, 4 H); 3.57 to 3.61 (m, 4 H); 3.62 (s,2 H); 5.21 (s, 1 H); 7.49 (t, J=9.8 Hz, 1 H); 7.75 to 7.83 (m, 1 H); 8.06 (dd, J=2.4 and 6.4 Hz, 1 H); 10.53 (broad s, 1 H); 11.68 (broad s, 1 H).

Mass spectrometry: method A
Retention time Tr (min)=0.77;
[M+H]⁺: m/z 401; [M−H]⁻: m/z 399.

EXAMPLE 48

Synthesis of N-(3-ethynylphenyl)-2-[4-(morpholin-4-yl)-6-oxo-1,6-dihydropyrimidin-2-yl]acetamide

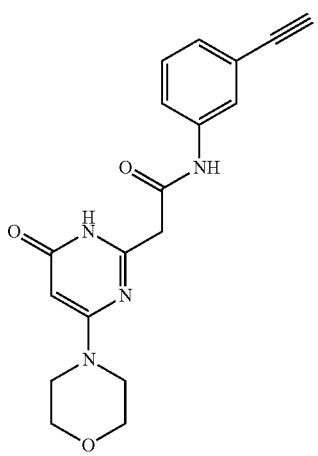 [SMILES: C#Cc1cccc(NC(=O)Cc2nc(N3CCOCC3)cc(=O)[nH]2)c1]

The product is prepared according to the procedure described in Example 5, using 260 mg of sodium [4-(morpholin-4-yl)-6-oxo-1,6-dihydropyrimidin-2-yl]acetate and 201 mg of 3-aminophenylacetylene in place of the 2,4-difluoroaniline. 190 mg of N-(3-ethynylphenyl)-2-[4-(morpholin-4-yl)-6-oxo-1,6-dihydropyrimidin-2-yl]acetamide are obtained in the form of a white solid, the characteristics of which are the following:

$^1$H NMR spectrum: 3.39 to 3.44 (m, 4 H); 3.58 to 3.64 (m, 6 H); 4.16 (s,1 H); 5.20 (s, 1 H); 7.17 (d, J=7.8 Hz, 1 H); 7.33 (t, J=7.8 Hz, 1 H); 7.54 (d, J=7.8 Hz, 1 H); 7.75 (s, 1H); 10.27 (s, 1 H); 11.66 (broad s, 1 H).

Mass spectrometry: method A
Retention time Tr (min)=0.64;
[M+H]$^+$: m/z 339; [M–H]$^-$: m/z 337.

EXAMPLE 49

Synthesis of N-[3-(cyclopentyloxy)phenyl]-2-[4-(morpholin-4-yl)-6-oxo-1,6-dihydropyrimidin-2-yl]acetamide

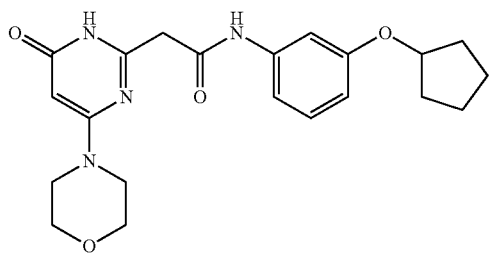 [SMILES: O=C(Cc1nc(N2CCOCC2)cc(=O)[nH]1)Nc1cccc(OC2CCCC2)c1]

The product is prepared according to the procedure described in Example 5, using 260 mg of sodium [4-(morpholin-4-yl)-6-oxo-1,6-dihydropyrimidin-2-yl]acetate and 354 mg of 3-(cyclopentyloxy)aniline in place of the 2,4-difluoroaniline. 269 mg of N-[3-(cyclopentyloxy)phenyl]-2-[4-(morpholin-4-yl)-6-oxo-1,6-dihydropyrimidin-2-yl]acetamide are obtained in the form of a white solid, the characteristics of which are the following:

$^1$H NMR spectrum: 1.50 to 1.75 (m, 6 H); 1.83 to 1.96 (m, 2 H); 3.39 to 3.44 (m, 4 H); 3.54 to 3.63 (m, 6 H); 4.73 (m, 1 H); 5.20 (s, 1 H); 6.60 (dd, J=2.0 and 8.3 Hz, 1 H); 7.03 (broad d, J=8.3 Hz, 1 H); 7.18 (t, J=8.3 Hz, 1 H); 7.26 (t, J=2.2 Hz, 1 H); 10.10 (s, 1 H); 11.64 (broad s, 1 H).

Mass spectrometry: method A
Retention time Tr (min)=0.84;
[M+H]$^+$: m/z 399; [M–H]$^-$: m/z 397.

EXAMPLE 50

Synthesis of N-(4-fluoro-2-hydroxyphenyl)-2-[4-(morpholin-4-yl)-6-oxo-1,6-dihydropyrimidin-2-yl]acetamide (VAC.SON4.056.1)

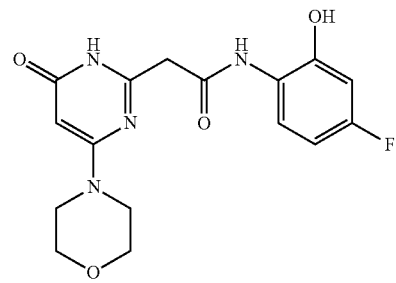 [SMILES: O=C(Cc1nc(N2CCOCC2)cc(=O)[nH]1)Nc1ccc(F)cc1O]

The product is prepared according to the procedure described in Example 5, using 500 mg of sodium [4-(morpholin-4-yl)-6-oxo-1,6-dihydropyrimidin-2-yl]acetate and 815 mg of 2-amino-5-fluorophenol in place of the 2,4-difluoroaniline. After purification by silica column chromatography, eluent: CH$_2$Cl$_2$/MeOH 95/5, 149 mg of N-(4-fluoro-2-hydroxyphenyl)-2-[4-(morpholin-4-yl)-6-oxo-1,6-dihydropyrimidin-2-yl]acetamide are obtained in the form of a grey solid, the characteristics of which are the following:

$^1$H NMR spectrum: 3.41 to 3.47 (m, 4 H); 3.59 to 3.64 (m, 4 H); 3.67 (s, 2 H); 5.20 (s, 1 H); 6.58 (dt, J=2.8 and 8.8 Hz, 1 H); 6.66 (dd, J=2.8 and 10.4 Hz, 1 H); 7.80 (dd, J=6.4 and 8.8 Hz, 1 H); 8.66 to 12.13 (broad m, 3 H)

Mass spectrometry: method B
Retention time Tr (min)=2.74
[M+H]$^+$: m/z 349; [M–H]$^-$: m/z 347.

EXAMPLE 51

Synthesis of 2-[2-(2,3-dihydro-1H-indol-1-yl)-2-oxoethyl]-6-(morpholin-4-yl)pyrimidin-4(3H)-one (VAC.PSB2.078.6)

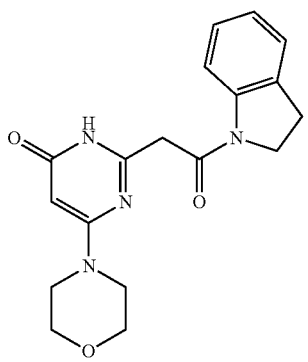 [SMILES: O=C(Cc1nc(N2CCOCC2)cc(=O)[nH]1)N1CCc2ccccc21]

The product is prepared according to the procedure described in Example 5, using 260 mg of sodium [4-(morpholin-4-yl)-6-oxo-1,6-dihydropyrimidin-2-yl]acetate and 238 mg of indoline in place of the 2,4-difluoroaniline. 230 mg of 2-[2-(2,3-dihydro-1H-indol-1-yl)-2-oxoethyl]-6-(morpholin-4-pyrimidin-4(3H)-one are obtained in the form of a pale pink solid, the characteristics of which are the following:

$^1$H NMR spectrum: 3.17 (t, J=8.3 Hz, 2 H); 3.41 (m, 4 H); 3.60 (m, 4 H); 3.75 (s, 2 H); 4.14 (t, J=8.3 Hz, 2 H); 5.21 (s, 1 H); 7.01 (t, J=7.6 Hz, 1 H); 7.16 (t, J=7.6 Hz, 1 H); 7.25 (d, J=7.6 Hz, 1 H); 8.02 (d, J=7.6 Hz, 1 H); 11.61 (broad s, 1 H)

Mass spectrometry: method A
Retention time Tr (min)=0.64
[M+H]$^+$: m/z 341; [M−H]$^-$: m/z 339.

EXAMPLE 52

Synthesis of N-(3-cyclopropyle-4-fluorophenyl)-2-[4-(morpholin-4-yl)-6-oxo-1,6-dihydropyrimidin-2-yl]acetamide (VAC.PSB2.078.11)

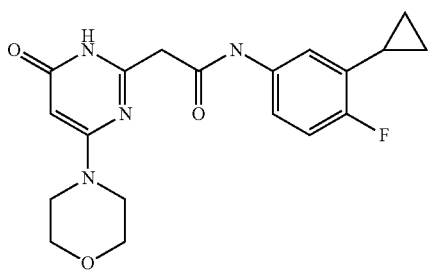 [SMILES: O=C(Cc1nc(N2CCOCC2)cc(=O)[nH]1)Nc1ccc(F)c(C2CC2)c1]

The product is prepared according to the procedure described in Example 5, using 260 mg of sodium [4-(morpholin-4-yl)-6-oxo-1,6-dihydropyrimidin-2-yl]acetate and 302 mg of 3-cyclopropyle-4-fluoroaniline (prepared according to patent application US 2007/0185058) in place of the 2,4-difluoroaniline. 225 mg of N-(3-cyclopropyle-4-fluorophenyl)-2-[4-(morpholin-4-yl)-6-oxo-1,6-dihydropyrimidin-2-yl]acetamide are obtained in the form of a pale yellow solid, the characteristics of which are the following:

$^1$H NMR spectrum: 0.62 (m, 2 H); 0.99 (m, 2 H); 1.97 to 2.09 (m, 1 H); 3.41 (m, 4 H); 3.56 (s, 2 H); 3.58 to 3.63 (m, 4 H); 5.20 (s, 1 H); 7.07 (t, J=9.5 Hz, 1 H); 7.18 (dd, J=2.3 and 7.0 Hz, 1 H); 7.30 to 7.37 (m, 1 H); 10.11 (s, 1H); 11.63 (broad s, 1 H)

Mass spectrometry: method A
Retention time Tr (min)=0.75
[M+H]$^+$: m/z 373; [M−H]$^-$: m/z 371.

EXAMPLE 53

Synthesis of 2-[4-(morpholin-4-yl)-6-oxo-1,6-dihydropyrimidin-2-yl]-N-(2,3,4-trifluorophenyl)acetamide (VAC.PSB2.078.12)

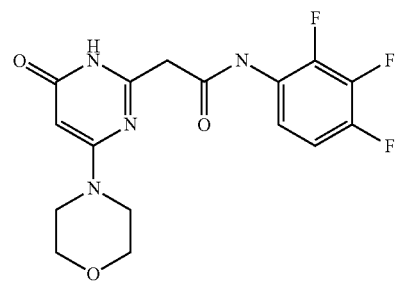 [SMILES: O=C(Cc1nc(N2CCOCC2)cc(=O)[nH]1)Nc1ccc(F)c(F)c1F]

The product is prepared according to the procedure described in Example 5, using 260 mg of sodium [4-(morpholin-4-yl)-6-oxo-1,6-dihydropyrimidin-2-yl]acetate and 294 mg of 2,3,4-trifluoroaniline in place of the 2,4-difluoroaniline. 195 mg of 2-[4-(morpholin-4-yl)-6-oxo-1,6-dihydropyrimidin-2-yl]-N-(2,3,4-trifluorophenyl)acetamide are obtained in the form of a white solid, the characteristics of which are the following:

$^1$H NMR spectrum: 3.43 (m, 4 H); 3.61 (m, 4 H); 3.67 (s, 2 H); 5.20 (s, 1 H); 7.24 to 7.35 (m, 1 H); 7.56 to 7.67 (m, 1 H); 10.18 (broad s, 1 H); 11.67 (broad s, 1 H)

Mass spectrometry: method A
Retention time Tr (min)=0.65
[M+H]$^+$: m/z 369; [M−H]$^-$: m/z 367.

EXAMPLE 54

Synthesis of N-[4-fluoro-3-(trifluoromethoxy)phenyl]-2-[4-(morpholin-4-yl)-6-oxo-1,6-dihydropyrimidin-2-yl]acetamide

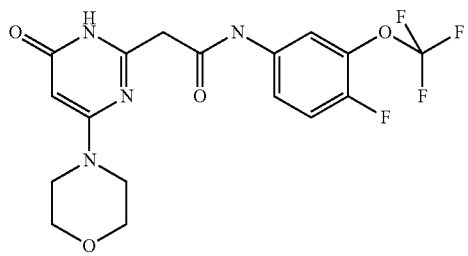 [SMILES: O=C(Cc1nc(N2CCOCC2)cc(=O)[nH]1)Nc1ccc(F)c(OC(F)(F)F)c1]

The product is prepared according to the procedure described in Example 5, using 250 mg of sodium [4-(morpholin-4-yl)-6-oxo-1,6-dihydropyrimidin-2-yl]acetate and 270 mg of 4-fluoro-3-(trifluoromethoxy)aniline in place of the 2,4-difluoroaniline. 270 mg of N-[4-fluoro-3-(trifluoromethoxy)phenyl]-2-[4-(morpholin-4-yl)-6-oxo-1,6-dihydropyrimidin-2-yl]acetamide are obtained in the form of a white solid, the characteristics of which are the following:

¹H NMR spectrum (400 MHz):
3.37 to 3.44 (m, 4 H); 3.55 to 3.65 (m, 6 H); 5.20 (s, 1 H); 7.40 to 7.59 (m, 2 H); 7.90 (broad d, J=6.8 Hz, 1 H); 10.48 (broad s, 1 H); 11.66 (broad s, 1 H)

Mass spectrometry: method A
Retention time Tr (min)=0.80
[M+H]⁺: m/z 417; [M−H]⁻: m/z 415.

EXAMPLE 55

Synthesis of N-[3-(2-hydroxyethoxy)phenyl]-2-[4-(morpholin-4-O-6-oxo-1,6-dihydropyrimidin-2-yl]acetamide

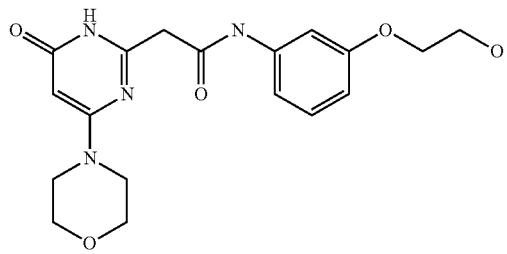 [SMILES: O=C(Cc1nc(N2CCOCC2)cc(=O)[nH]1)Nc1cccc(OCCO)c1]

The product is prepared according to the procedure described in Example 5, using 260 mg of sodium [4-(morpholin-4-yl)-6-oxo-1,6-dihydropyrimidin-2-yl]acetate and 294 mg of 2-(3-aminophenoxy)ethanol in place of the 2,4-difluoroaniline. 180 mg of N-[3-(2-hydroxyethoxy)phenyl]-2-[4-(morpholin-4-yl)-6-oxo-1,6-dihydropyrimidin-2-yl]acetamide are obtained in the form of a pinkish solid, the characteristics of which are the following:

¹H NMR spectrum (400 MHz):
For this batch, broad signals are observed, with: 3.42 (m, 4 H); 3.59 (m, 6 H); 3.70 (m, 2 H); 3.93 (m, 2 H); 4.82 (m, 1 H); 5.20 (s, 1 H); 6.64 (d, J=8.1 Hz, 1 H); 7.07 (d, J=8.1 Hz, 1 H); 7.15 to 7.23 (t, J=8.1 Hz, 1 H); 7.28 (s, 1 H); 10.12 (s, 1 H); 11.65 (s, 1 H)

Mass spectrometry: method A
Retention time Tr (min)=0.46
[M+H]⁺: m/z 375; [M−H]⁻: m/z 373.

EXAMPLE 56

Synthesis of N-(3-iodophenyl)-2-[4-(morpholin-4-yl)-6-oxo-1,6-dihydropyrimidin-2-yl]acetamide

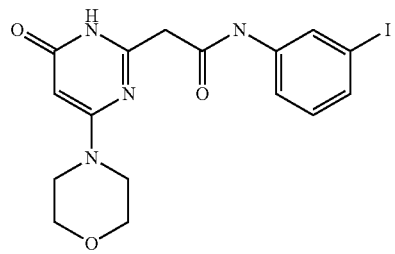 [SMILES: O=C(Cc1nc(N2CCOCC2)cc(=O)[nH]1)Nc1cccc(I)c1]

The product is prepared according to the procedure described in Example 5, using 268 mg of sodium [4-(morpholin-4-yl)-6-oxo-1,6-dihydropyrimidin-2-yl]acetate and 324 mg of 3-iodoaniline in place of the 2,4-difluoroaniline. 345 mg of N-(3-iodophenyl)-2-[4-(morpholin-4-yl)-6-oxo-1,6-dihydropyrimidin-2-yl]acetamide are obtained in the form of a white solid, the characteristics of which are the following:

¹H NMR spectrum (400 MHz):
3.41 (m, 4 H); 3.58 to 3.64 (m, 6 H); 5.20 (s, 1 H); 7.12 (t, J=8.1 Hz, 1 H); 7.42 (d, J=8.1 Hz, 1 H); 7.50 (d, J=8.1 Hz, 1 H); 8.06 (s, 1 H); 10.26 (broad s, 1 H); 11.66 (broad s, 1 H)

Mass spectrometry: method B
Retention time Tr (min)=3.41
[M+H]⁺: m/z 441; [M−H]⁻: m/z 439.

EXAMPLE 57

Synthesis of methyl 2-fluoro-5-({[4-(morpholin-4-yl)-6-oxo-1,6-dihydropyrimidin-2-yl]acetyl}amino)benzoate

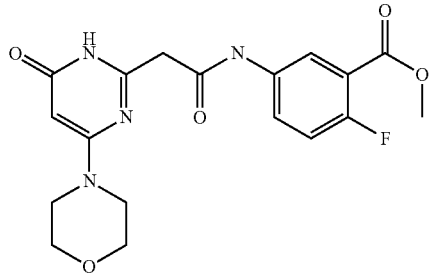 [SMILES: COC(=O)c1cc(NC(=O)Cc2nc(N3CCOCC3)cc(=O)[nH]2)ccc1F]

The product is prepared according to the procedure described in Example 5, using 500 mg of sodium [4-(morpholin-4-yl)-6-oxo-1,6-dihydropyrimidin-2-yl]acetate and 466 mg of methyl 5-amino-2-fluorobenzoate in place of the 2,4-difluoroaniline. 625 mg of methyl 2-fluoro-5-({[4-(morpholin-4-yl)-6-oxo-1,6-dihydropyrimidin-2-yl]acetyl}amino)benzoate are obtained in the form of a pinkish solid, the characteristics of which are the following:

¹H NMR spectrum (400 MHz):
3.41 (m, 4 H); 3.57 to 3.62 (m, 6 H); 3.85 (s, 3 H); 5.20 (s, 1 H); 7.32 (dd, J=9.0 and 10.6 Hz, 1 H); 7.79 (ddd, J=2.9 and 4.1 and 9.0 Hz, 1 H); 8.15 (dd, J=2.9 and 6.4 Hz, 1 H); 10.40 (s, 1 H); 11.67 (broad s, 1 H)

Mass spectrometry: method A
Retention time Tr (min)=0.59
[M+H]⁺: m/z 391; [M−H]⁻: m/z 389.

EXAMPLE 58

Synthesis of N-(3-ethoxyphenyl)-2-[4-(morpholin-4-yl)-6-oxo-1,6-dihydropyrimidin-2-yl]acetamide

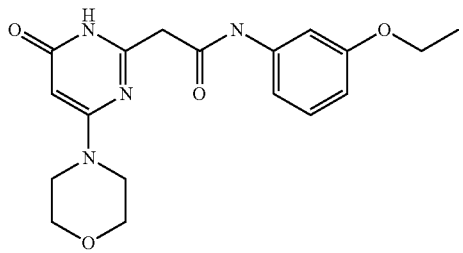

The product is prepared according to the procedure described in Example 5, using 250 mg of sodium [4-(morpholin-4-yl)-6-oxo-1,6-dihydropyrimidin-2-yl]acetate and 540 mg of 3-ethoxyaniline in place of the 2,4-difluoroaniline. 235 mg of N-(3-ethoxyphenyl)-2-[4-(morpholin-4-yl)-6-oxo-1,6-dihydropyrimidin-2-yl]acetamide are obtained in the form of a white solid, the characteristics of which are the following:

$^1$H NMR spectrum (400 MHz):
1.31 (t, J=7.0 Hz, 3 H); 3.41 (m, 4 H); 3.55 to 3.64 (m, 6 H); 3.98 (q, J=7.0 Hz, 2 H); 5.20 (s, 1 H); 6.62 (d, J=8.0 Hz, 1 H); 7.06 (d, J=8.0 Hz, 1 H); 7.19 (t, J=8.0 Hz, 1 H); 7.26 (broad s, 1 H); 10.12 (broad s, 1 H); 11.64 (broad s, 1 H)
Mass spectrometry: method A
Retention time Tr (min)=0.66
[M+H]$^+$: m/z 359; [M−H]$^−$: m/z 357.

EXAMPLE 59

Synthesis of N-(2,4-difluoro-3-methoxyphenyl)-2-[4-(morpholin-4-yl)-6-oxo-1,6-dihydropyrimidin-2-yl]acetamide

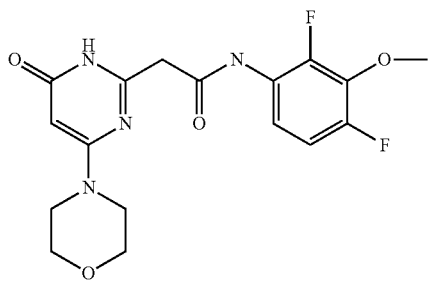 [SMILES: COc1c(F)ccc(NC(=O)Cc2nc(N3CCOCC3)cc(=O)[nH]2)c1F]

The product is prepared according to the procedure described in Example 5, using 260 mg of sodium [4-(morpholin-4-yl)-6-oxo-1,6-dihydropyrimidin-2-yl]acetate and 318 mg of 2,4-difluoro-3-methoxyaniline in place of the 2,4-difluoroaniline. 255 mg of N-(2,4-difluoro-3-methoxyphenyl)-2-[4-(morpholin-4-yl)-6-oxo-1,6-dihydropyrimidin-2-yl]acetamide are obtained in the form of a white solid, the characteristics of which are the following:

$^1$H NMR spectrum (400 MHz):
3.43 (m, 4 H); 3.61 (m, 4 H); 3.66 (s, 2 H); 3.93 (s, 3 H); 5.20 (s, 1 H); 7.11 (ddd, J=2.1 and 9.0 and 10.9 Hz, 1 H); 7.50 (dt, J=5.5 and 9.0 Hz, 1 H); 10.00 (s, 1 H); 11.65 (broad s, 1 H)
Mass spectrometry: method B
Retention time Tr (min)=3.01
[M+H]$^+$: m/z 381; [M−H]$^−$: m/z 379.

EXAMPLE 60

Synthesis of 2-[4-(morpholin-4-yl)-6-oxo-1,6-dihydropyrimidin-2-yl]-N-(2,4,5-trifluorophenyl)acetamide

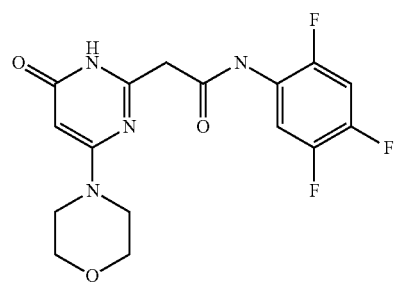 [SMILES: O=C(Cc1nc(N2CCOCC2)cc(=O)[nH]1)Nc1cc(F)c(F)cc1F]

The product is prepared according to the procedure described in Example 5, using 260 mg of sodium [4-(morpholin-4-yl)-6-oxo-1,6-dihydropyrimidin-2-yl]acetate and 294 mg of 2,4,5-trifluoroaniline in place of the 2,4-difluoroaniline. 230 mg of 2-[4-(morpholin-4-yl)-6-oxo-1,6-dihydropyrimidin-2-yl]-N-(2,4,5-trifluorophenyl)acetamide are obtained in the form of a white solid, the characteristics of which are the following:

$^1$H NMR spectrum (400 MHz):
3.42 (m, 4 H); 3.61 (m, 4 H); 3.69 (s, 2 H); 5.20 (s, 1 H); 7.65 (dt, J=7.6 and 10.8 Hz, 1 H); 8.01 (td, J=8.0 and 12.3 Hz, 1 H); 10.18 (broad s, 1 H); 11.67 (broad s, 1 H)
Mass spectrometry: method B
Retention time Tr (min)=3.10
[M+H]$^+$: m/z 369; [M−H]$^−$: m/z 367.

EXAMPLE 61

Synthesis of N-(3,5-dichloro-4-fluorophenyl)-2-[4-(morpholin-4-yl)-6-oxo-1,6-dihydropyrimidin-2-yl]acetamide

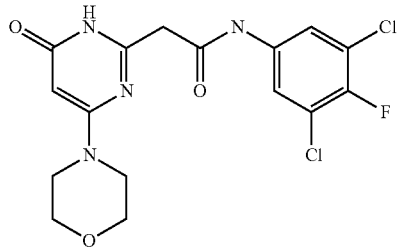 [SMILES: O=C(Cc1nc(N2CCOCC2)cc(=O)[nH]1)Nc1cc(Cl)c(F)c(Cl)c1]

The product is prepared according to the procedure described in Example 5, using 260 mg of sodium [4-(morpholin-4-yl)-6-oxo-1,6-dihydropyrimidin-2-yl]acetate and 360 mg of 3,5-dichloro-4-fluoroaniline in place of the 2,4-difluoroaniline. 259 mg of N-(3,5-dichloro-4-fluorophenyl)-2-[4-(morpholin-4-yl)-6-oxo-1,6-dihydropyrimidin-2-yl]acetamide are obtained in the form of a white solid, the characteristics of which are the following:

$^1$H NMR spectrum (400 MHz):
3.41 (m, 4 H); 3.56 to 3.64 (m, 6 H); 5.21 (s, 1 H); 7.74 (d, J=6.1 Hz, 2H); 10.50 (broad s, 1 H); 11.66 (broad s, 1 H)

EXAMPLE 62

Synthesis of 2-[2-(2,3-dihydro-4H-1,4-benzoxazin-4-yl)-2-oxoethyl]-6-(morpholin-4-yl)pyrimidin-4(3H)-one

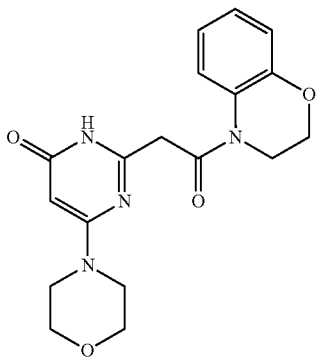 [SMILES: O=C(Cc1nc(N2CCOCC2)cc(=O)[nH]1)N1CCOc2ccccc21]

The product is prepared according to the procedure described in Example 5, using 260 mg of sodium [4-(morpholin-4-yl)-6-oxo-1,6-dihydropyrimidin-2-yl]acetate and 270 mg of 3,4-dihydro-2H-1,4-benzoxazine in place of the 2,4-difluoroaniline. After purification by silica column chromatography, elution being carried out with $CH_2Cl_2$/MeOH 95/05, 150 mg of 2-[2-(2,3-dihydro-4H-1,4-benzoxazin-4-yl)-2-oxoethyl]-6-(morpholin-4-yl)pyrimidin-4(3H)-one are obtained in the form of a white solid, the characteristics of which are the following:

$^1$H NMR spectrum (400 MHz):
3.36 to 3.45 (m, 4 H); 3.52 to 3.70 (m, 4 H); 3.81 to 3.95 (m, 4 H); 4.30 (m, 2 H); 5.18 (s, 1 H); 6.81 to 6.95 (m, 2 H); 6.99 to 7.16 (m, 1 H); 7.22 to 8.18 (m, 1 H); 11.59 (broad s, 1 H)

Mass spectrometry: method A
Retention time Tr (min)=0.62
[M+H]$^+$: m/z 357; [M−H]$^−$: m/z 355.

EXAMPLE 63

Synthesis of N-(4-fluoro-3-nitrophenyl)-2-[4-(morpholin-4-yl)-6-oxo-1,6-dihydropyrimidin-2-yl]acetamide

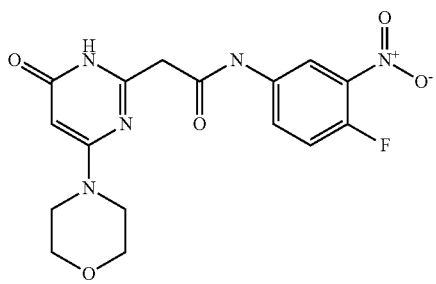 [SMILES: O=C(Cc1nc(N2CCOCC2)cc(=O)[nH]1)Nc1ccc(F)c([N+](=O)[O-])c1]

The product is prepared according to the procedure described in Example 5, using 500 mg of sodium [4-(morpholin-4-yl)-6-oxo-1,6-dihydropyrimidin-2-yl]acetate and 510 mg of 4-fluoro-3-nitroaniline in place of the 2,4-difluoroaniline. 339 mg of N-(4-fluoro-3-nitrophenyl)-2-[4-(morpholin-4-yl)-6-oxo-1,6-dihydropyrimidin-2-yl]acetamide are obtained in the form of a white solid, the characteristics of which are the following:

$^1$H NMR spectrum (400 MHz):
3.41 (m, 4 H); 3.58 to 3.62 (m, 4 H); 3.64 (s, 2 H); 5.21 (s, 1 H); 7.56 (dd, J=9.0 and 11.2 Hz, 1 H); 7.83 to 7.88 (ddd, J=2.9 and 4.0 and 9.0 Hz, 1 H); 8.47 (dd, J=2.9 and 6.8 Hz, 1 H); 10.63 (broad s, 1 H); 11.69 (broad s, 1 H)

Mass spectrometry: method A
Retention time Tr (min)=0.63
[M+H]$^+$: m/z 378; [M−H]$^−$: m/z 376.

EXAMPLE 64

Synthesis of 2-fluoro-5-({[4-(morpholin-4-yl)-6-oxo-1,6-dihydropyrimidin-2-yl]acetyl}amino)benzoic acid

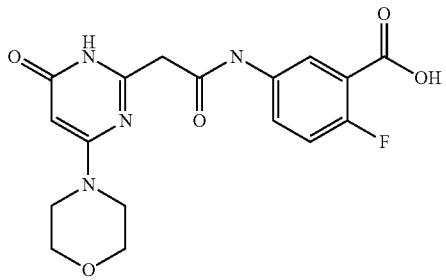 [SMILES: O=C(Cc1nc(N2CCOCC2)cc(=O)[nH]1)Nc1ccc(F)c(C(=O)O)c1]

0.4 ml of 2M sodium hydroxide is added to a solution of 310 mg of methyl 2-fluoro-5-({[4-(morpholin-4-yl)-6-oxo-1,6-dihydropyrimidin-2-yl]acetyl}amino)benzoate prepared in Example 57, in 7 ml of methanol. After stirring overnight at ambient temperature, a further 0.4 ml of 2M sodium hydroxide is added and the resulting mixture is brought to reflux for 3 hours. After cooling, the reaction mixture is concentrated under reduced pressure. The evaporation residue is taken up with water. The aqueous phase is extracted with ethyl acetate and then acidified with a 1N aqueous solution of hydrochloric acid (pH=5). The insoluble material is filtered off. The filtrate is concentrated under reduced pressure and then taken up with water and a few drops of a 1N aqueous solution of hydrochloric acid. The precipitate formed is filtered off, rinsed with petroleum ether and concentrated to dryness under reduced pressure. 52 mg of 2-fluoro-5-({[4-(morpholin-4-yl)-6-oxo-1,6-dihydropyrimidin-2-yl]acetyl}amino)benzoic acid are obtained in the form of a pale pink solid, the characteristics of which are the following:

$^1$H NMR spectrum (400 MHz):
3.41 (m, 4 H); 3.60 (t, J=4.9 Hz, 6 H); 5.20 (s, 1 H); 7.24 (t, J=9.8 Hz, 1H); 7.75 (m, 1 H); 8.06 (m, 1 H); 10.34 (broad s, 1 H); 11.67 (broad s, 1 H)

Mass spectrometry: method A
Retention time Tr (min)=0.46
[M+H]$^+$: m/z 377; [M−H]$^−$: m/z 375.

EXAMPLE 65

Synthesis of N-(5-fluoro-2-hydroxyphenyl)-2-[4-(morpholin-4-yl)-6-oxo-1,6-dihydropyrimidin-2-yl]acetamide

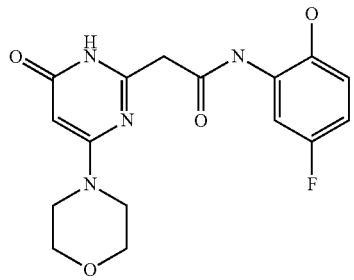 [SMILES: O=C(Cc1nc(N2CCOCC2)cc(=O)[nH]1)Nc1cc(F)ccc1O]

The product is prepared according to the procedure described in Example 5, using 1 g of sodium [4-(morpholin-4-yl)-6-oxo-1,6-dihydropyrimidin-2-yl]acetate and 466 mg of 2-amino-4-fluorophenol in place of the 2,4-difluoroaniline. 795 mg of 2-N-(5-fluoro-2-hydroxyphenyl)-2-[4-(morpholin-4-yl)-6-oxo-1,6-dihydropyrimidin-2-yl]acetamide are obtained in the form of a brown solid, the characteristics of which are the following:

$^1$H NMR spectrum (400 MHz):
3.44 (m, 4 H); 3.59 to 3.65 (m, 4 H); 3.72 (s, 2 H); 5.21 (s, 1 H); 6.70 to 6.78 (m, 1 H); 6.81 to 6.87 (m, 1 H); 7.85 (dd, J=3.0 and 10.8 Hz, 1 H); 9.10 to 10.09 (broad m, 1 H); 10.64 to 11.96 (broad m, 1 H)

Mass spectrometry: method A
Retention time Tr (min)=0.55
[M+H]$^+$: m/z 349; [M–H]$^-$: m/z 347.

EXAMPLE 66

Synthesis of N-(2-bromo-4-fluorophenyl)-2-[4-(morpholin-4-yl)-6-oxo-1,6-dihydropyrimidin-2-yl]acetamide

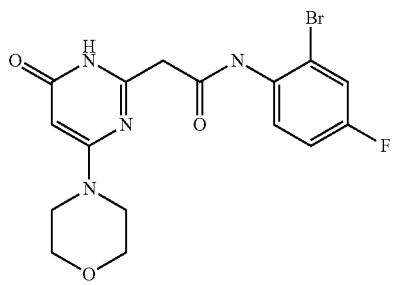 [SMILES: O=C(Cc1nc(N2CCOCC2)cc(=O)[nH]1)Nc1ccc(F)cc1Br]

The product is prepared according to the procedure described in Example 5, using 250 mg of sodium [4-(morpholin-4-yl)-6-oxo-1,6-dihydropyrimidin-2-yl]acetate and 260 mg of 2-bromo-4-fluoroaniline in place of the 2,4-difluoroaniline. 310 mg of N-(2-bromo-4-fluorophenyl)-2-[4-(morpholin-4-yl)-6-oxo-1,6-dihydropyrimidin-2-yl]acetamide are obtained in the form of a brown solid, the characteristics of which are the following:

$^1$H NMR spectrum (400 MHz):

For this batch, all the signals are broad, with: 3.44 (m, 4 H); 3.62 (m, 4H); 3.65 (s, 2 H); 5.20 (s, 1 H); 7.22 to 7.32 (m, 1 H); 7.58 to 7.67 (m, 2 H); 9.73 (s, 1 H); 11.68 (s, 1 H)

Mass spectrometry: method A
Retention time Tr (min)=0.65
[M+H]$^+$: m/z 411; [M–H]$^-$: m/z 409.

EXAMPLE 67

Synthesis of N-(4-fluorophenyl)-2-[1-methyl-4-(morpholin-4-yl)-6-oxo-1,6-dihydropyrimidin-2-yl]acetamide Stage 1:

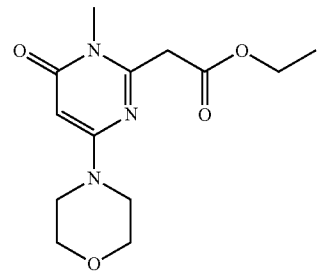 [SMILES: CCOC(=O)Cc1nc(N2CCOCC2)cc(=O)n1C]

Added to a solution of 500 mg of ethyl [4-(morpholin-4-yl)-6-oxo-1,6-dihydropyrimidin-2-yl]acetate prepared in stage 1 of Example 1 in 1.5 ml of dioxane, are 330 mg of potassium carbonate and 150 ml of methyl iodide. The reaction mixture is heated at 40° C. for 16 minutes, and then cooled to ambient temperature. The suspension is filtered through sintered glass and then rinsed with dioxane and the filtrate is concentrated under reduced pressure. The residue is purified by silica column chromatography, elution being carried out with a mixture of dichloromethane, acetonitrile and methanol (98/01/01, 96/02/02, then 90/05/05 V/V/V). 200 mg of ethyl [1-methyl-4-(morpholin-4-yl)-6-oxo-1,6-dihydropyrimidin-2-yl]acetate are obtained in the form of a white solid, the characteristics of which are the following:

Mass spectrometry: method A
Retention time Tr (min)=0.53
[M+H]$^+$: m/z 282; [M–H]$^-$: m/z 280.

Stage 2:

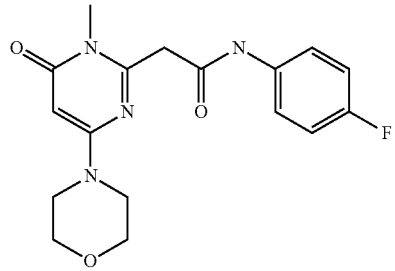 [SMILES: Cn1c(CC(=O)Nc2ccc(F)cc2)nc(N2CCOCC2)cc1=O]

0.135 ml of 4-fluoroaniline and 0.670 ml of a 2M solution of trimethylaluminium are added, dropwise, to a solution of 190 mg of ethyl [1-methyl-4-(morpholin-4-yl)-6-oxo-1,6-dihydropyrimidin-2-yl]acetate in 10 ml of toluene. After stirring for 30 minutes at ambient temperature, 10 ml of toluene are added. After stirring for 4 hours at ambient temperature, the reaction mixture is poured into water and a 1M solution of potassium phosphate is added. The precipitate is filtered through sintered glass and then rinsed with ethyl acetate. The filtrate is then washed with water and then with a saturated aqueous solution of sodium chloride. The organic phase is extracted and then dried over magnesium sulphate, filtered through sintered glass, and concentrated under reduced pressure. After purification of the residue by silica column chromatography, elution being carried out with a mixture of dichloromethane and methanol (95/05, V/V), 20 mg of N-(4-fluorophenyl)-2-[1-methyl-4-(morpholin-4-yl)-6-oxo-1,6-dihydropyrimidin-2-yl]acetamide are obtained in the form of a white solid, the characteristics of which are the following:

$^1$H NMR spectrum (400 MHz):

3.34 (s, 3 H); 3.40 (m, 4 H); 3.58 (m, 4 H); 3.90 (s, 2 H); 5.35 (s, 1 H); 7.15 (t, J=9.0 Hz, 2 H); 7.57 (dd, J=5.1 and 9.0 Hz, 2 H); 10.25 (s, 1 H)

Mass spectrometry: method A

Retention time Tr (min)=0.62

$[M-H]^+$: m/z 347; $[M-H]^-$: m/z 345.

EXAMPLE 68

Synthesis of N-(3-chloro-4-fluorophenyl)-2-[1-methyl-4-(morpholin-4-yl)-6-oxo-1,6-dihydropyrimidin-2-yl]acetamide Stage 1:

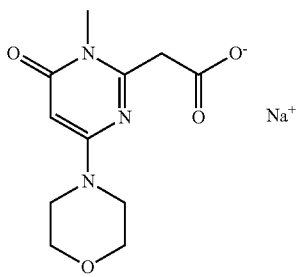 [SMILES: Cn1c(CC(=O)[O-])nc(N2CCOCC2)cc1=O ; [Na+]]

2.88 ml of 2M sodium hydroxide are added to a solution of 1.62 g of ethyl [1-methyl-4-(morpholin-4-yl)-6-oxo-1,6-dihydropyrimidin-2-yl]acetate prepared in stage 1 of Example 67, in 20 ml of tetrahydrofuran. The reaction mixture is stirred for 48 hours at ambient temperature. The precipitate formed is filtered through sintered glass, washed with ethyl acetate and rinsed several times with ethyl ether. The solid obtained is then dried in a rotary evaporator. 730 mg of sodium [1-methyl-4-(morpholin-4-yl)-6-oxo-1,6-dihydropyrimidin-2-yl] acetate are obtained in the form of a white solid, the characteristics of which are the following:

Mass spectrometry: method B

Retention time Tr (min)=1.67

$[M+H]^+$: m/z 254; $[M-H]^-$: m/z 252.

Stage 2:

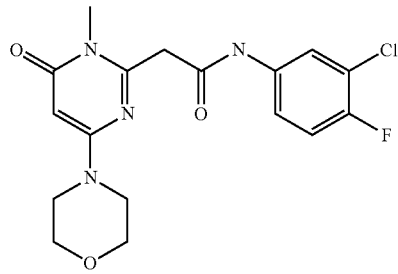 [SMILES: Cn1c(CC(=O)Nc2ccc(F)c(Cl)c2)nc(N2CCOCC2)cc1=O]

120 ml of pyridine, 182 mg of N-[3-(dimethylamino)propyl]-N'-ethylcarbodiimide hydrochloride and 210 mg of 3-chloro-4-fluoroaniline are added to a solution of 200 mg of sodium [1-methyl-4-(morpholin-4-yl)-6-oxo-1,6-dihydropyrimidin-2-yl]acetate in 2.5 ml of N,N-dimethylformamide. The reaction mixture is stirred at ambient temperature overnight and is then concentrated under reduced pressure. Water is added, followed by extraction with ethyl acetate, further washing with water, and concentration under reduced pressure. The residue obtained is washed with ethyl acetate and then rinsed with ethyl ether. 76 mg of N-(3-chloro-4-fluorophenyl)-2-[1-methyl-4-(morpholin-4-yl)-6-oxo-1,6-dihydropyrimidin-2-yl]acetamide are obtained in the form of a violet solid, the characteristics of which are the following:

$^1$H NMR spectrum (400 MHz):

3.34 (s, 3 H); 3.37 to 3.42 (m, 4 H); 3.55 to 3.60 (m, 4 H); 3.91 (s, 2 H); 5.36 (s, 1 H); 7.38 (t, J=9.0 Hz, 1 H); 7.41 to 7.47 (m, 1 H); 7.87 (dd, J=2.4 and 6.8 Hz, 1 H); 10.42 (s, 1 H)

Mass spectrometry: method A

Retention time Tr (min)=0.75

$[M+H]^+$: m/z 381; $[M-H]^-$: m/z 379

Melting point (Kofler bench): 248° C.

EXAMPLE 69

Synthesis of N-(3-bromophenyl)-2-[1-methyl-4-(morpholin-4-yl)-6-oxo-1,6-dihydropyrimidin-2-yl]acetamide

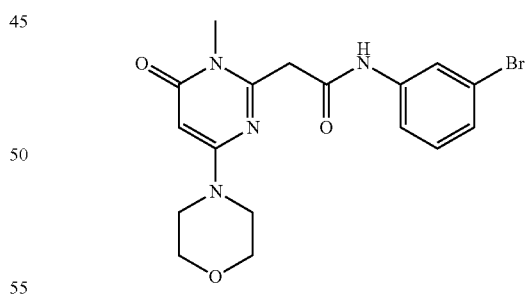

The product is prepared according to the procedure described in Example 68, using 200 mg of sodium [1-methyl-4-(morpholin-4-yl)-6-oxo-1,6-dihydropyrimidin-2-yl]acetate and 257 mg of 3-bromoaniline. 51 mg of N-(3-bromophenyl)-2-[1-methyl-4-(morpholin-4-yl)-6-oxo-1,6-dihydropyrimidin-2-yl]acetamide are obtained in the form of a white solid, the characteristics of which are the following:

$^1$H NMR spectrum (400 MHz):

3.34 (s, 3 H); 3.37 to 3.42 (m, 4 H); 3.58 (m, 4 H); 3.92 (s, 2 H); 5.36 (s, 1 H); 7.19 to 7.33 (m, 2 H); 7.45 (m, 1 H); 7.91 (broad s, 1 H); 10.37 (broad s, 1 H)

Mass spectrometry: method A
Retention time Tr (min)=0.75
[M+H]⁺: m/z 407; [M−H]⁻: m/z 405
Melting point (Kofler bench): 266° C.

EXAMPLE 70

Synthesis of 2-[1-ethyl-4-(morpholin-4-yl)-6-oxo-1,6-dihydropyrimidin-2-yl]-N-(4-fluorophenyl)acetamide Stage 1:

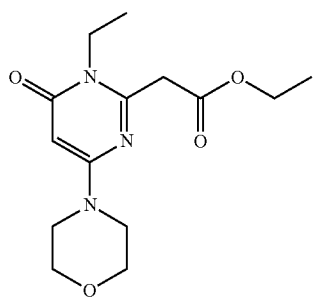 [SMILES: CCOC(=O)Cc1nc(N2CCOCC2)cc(=O)n1CC]

The product is prepared according to the procedure described in example 67, using 600 mg of ethyl [4-(morpholin-4-yl)-6-oxo-1,6-dihydropyrimidin-2-yl]acetate prepared in stage 1 of example 1 and 0.23 ml of ethyl iodide in place of the methyl iodide, and replacing the potassium carbonate with cesium carbonate. After purification by silica column chromatography, eluent: 96/02/02 CH$_2$Cl$_2$/CH$_3$CN/MeOH, 190 mg of ethyl [1-ethyl-4-(morpholin-4-yl)-6-oxo-1,6-dihydropyrimidin-2-yl]acetate are obtained in the form of a white solid the characteristics of which are the following:
Mass spectrometry: method A
Retention time Tr (min)=0.59;
[M+H]⁺: m/z 296; [M−H]⁻: m/z 294
Purity: 86%.

Stage 2:

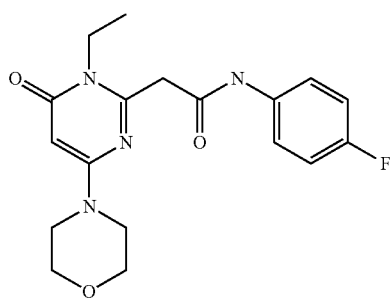 [SMILES: CCn1c(CC(=O)Nc2ccc(F)cc2)nc(N2CCOCC2)cc1=O]

0.640 ml of a 2M solution of trimethylaluminium in toluene, and then, after stirring for 40 minutes at ambient temperature, a solution of 190 mg of ethyl [1-ethyl-4-(morpholin-4-yl)-6-oxo-1,6-dihydropyrimidin-2-yl]acetate in 6 ml of toluene are successively added, dropwise, to a solution of 0.13 ml of 4-fluoroaniline in 4 ml of toluene. The reaction mixture is heated at 80° C. for 4 hours, cooled using an ice bath and run into water. A 1M solution of potassium sulphate and ethyl acetate are then added, and the organic phase is extracted, washed again with a 1M solution of potassium phosphate and then dried over magnesium phosphate, filtered and, finally, concentrated under reduced pressure. After purification by silica column chromatography, eluent: 98/01/01 then 96/02/02 CH$_2$Cl$_2$/CH$_3$CN/MeOH, 60 mg of 2-[1-ethyl-4-(morpholin-4-yl)-6-oxo-1,6-dihydropyrimidin-2-yl]-N-(4-fluorophenyl)acetamide are obtained in the form of a white solid, the characteristics of which are the following:
¹H NMR spectrum (400 MHz):
1.16 (t, J=7.1 Hz, 3 H); 3.39 (m, 4 H); 3.57 (m, 4 H); 3.88 (s, 2 H); 3.91 (q, J=7.1 Hz, 2 H); 5.33 (s, 1 H); 7.15 (t, J=8.9 Hz, 2 H); 7.57 (dd, J=5.0 and 8.9 Hz, 2 H); 10.26 (s, 1 H)
Mass spectrometry: method A
Retention time Tr (min)=0.66
[M+H]⁺: m/z 361; [M−H]⁻: m/z 359
Melting point (Kofler bench): 238° C.

EXAMPLE 71

Synthesis of N-(1H-indol-4-yl)-2-[4-(morpholin-4-yl)-6-oxo-1,6-dihydropyrimidin-2-yl]acetamide

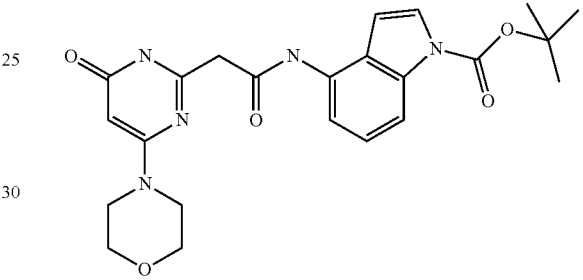

Stage 1:
The product is prepared according to the procedure described in example 5, using 500 mg of sodium [4-(morpholin-4-yl)-6-oxo-1,6-dihydropyrimidin-2-yl]acetate and 445 mg of 2-methylpropan-2-yl 4-amino-1H-indole-1-carboxylate in place of the 2,4-difluoroaniline. 500 mg of 2-dimethylpropan-2-yl 4-({[4-(morpholin-4-yl)-6-oxo-1,6-dihydropyrimidin-2-yl]acetyl}amino)-1H-indole-1-carboxylate are obtained in the form of a brown solid, the characteristics of which are the following:
Mass spectrometry: method A
Retention time Tr (min)=0.88
[M+H]⁺: m/z 454; [M−H]⁻: m/z 452.

Step 2:

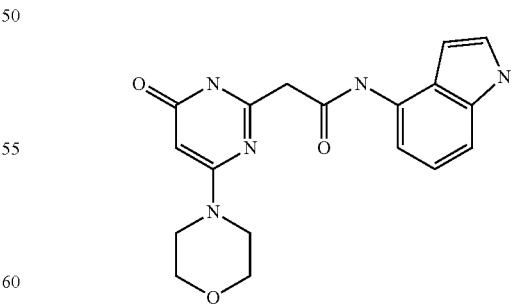

0.940 ml of trifluoroacetic acid is added dropwise to a solution of 200 mg of 2-methylpropan-2-yl 4-({[4-(morpholin-4-yl)-6-oxo-1,6-dihydropyrimidin-2-yl]acetyl}amino)-1H-indole-1-carboxylate in 8 ml of dichloromethane. After stirring at ambient temperature for 3 hours, the reaction medium is concentrated under reduced pressure, taken up with toluene and concentrated under reduced pressure. After purification by silica column chromatography, eluent: 90/10 CH$_2$Cl$_2$/MeOH, 48 mg of N-(1H-indol-4-yl)-2-[4-(morpholin-4-yl)-6-oxo-1,6-dihydropyrimidin-2-yl]acetamide are obtained, the characteristics of which are the following:

$^1$H NMR spectrum (400 MHz):
3.43 (m, 4 H); 3.60 (m, 4 H); 3.73 (s, 2 H); 5.21 (s, 1 H); 6.68 (broad s, 1 H); 7.01 (t, J=7.9 Hz, 1 H); 7.16 (d, J=7.9 Hz, 1 H); 7.30 (t, J=2.4 Hz, 1 H); 7.55 (d, J=7.9 Hz, 1 H); 9.80 (broad s, 1 H); 11.11 (broad s, 1 H); 11.67 (broad m, 1 H)

Mass spectrometry: method A
Retention time Tr (min)=0.48
[M+H]$^+$: m/z 354; [M–H]$^-$: m/z 352.

EXAMPLE 72

Synthesis of N-(4-fluorophenyl)-3-methyl-2-[4-(morpholin-4-yl)-6-oxo-1,6-dihydropyrimidin-2-yl]butanamide Stage 1:

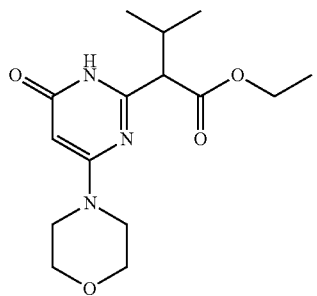 [SMILES: CCOC(=O)C(c1nc(N2CCOCC2)cc(=O)[nH]1)C(C)C]

The product is prepared according to the procedure described in example 67, using 600 mg of ethyl [4-(morpholin-4-yl)-6-oxo-1,6-dihydropyrimidin-2-yl]acetate prepared in stage 1 of example 1 and 0.29 ml of 2-iodopropane in place of the methyl iodide, and replacing the potassium carbonate with cesium carbonate. After purification by silica column chromatography, eluent: 90/05/05 CH$_2$Cl$_2$/CH$_3$CN/MeOH, 20 mg of ethyl 3-methyl-2-[4-(morpholin-4-yl)-6-oxo-1,6-dihydropyrimidin-2-yl]]butanoate are obtained in the form of a white solid, the characteristics of which are the following:

Mass spectrometry: method A
Retention time Tr (min)=0.70
[M+H]$^+$: m/z 310; [M–H]$^-$: m/z 308.

Stage 2:

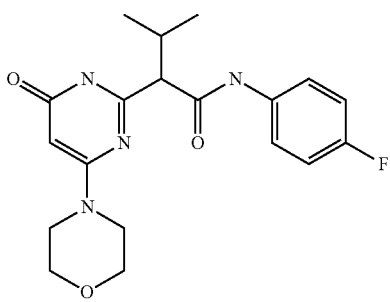 [SMILES: CC(C)C(C(=O)Nc1ccc(F)cc1)c1nc(N2CCOCC2)cc(=O)[nH]1]

The product is prepared according to the procedure described in example 70, using 0.023 ml of 4-fluoroaniline and 36 mg of ethyl 3-methyl-2-[4-(morpholin-4-yl)-6-oxo-1,6-dihydropyrimidin-2-yl]butanoate in place of the ethyl [1-ethyl-4-(morpholin-4-yl)-6-oxo-1,6-dihydropyrimidin-2-yl]acetate. After purification by silica column chromatography, eluent: 94/03/03 CH$_2$Cl$_2$/CH$_3$CN/MeOH, 15 mg of N-(4-fluorophenyl)-3-methyl-2-[4-(morpholin-4-yl)-6-oxo-1,6-dihydropyrimidin-2-yl]butanamide are obtained in the form of a white solid, the characteristics of which are the following:

$^1$H NMR spectrum (400 MHz):
0.87 (d, J=6.6 Hz, 3 H); 0.97 (d, J=6.6 Hz, 3 H); 2.53 to 2.57 (m, 1 H); 3.24 (d, J=10.3 Hz, 1 H); 3.42 to 3.47 (m, 4 H); 3.59 to 3.65 (m, 4 H); 5.21 (s, 1 H); 7.15 (t, J=8.8 Hz, 2 H); 7.59 (dd, J=5.1 and 8.8 Hz, 2 H); 10.09 (broad s, 1 H); 11.30 (broad s, 1 H)

Mass spectrometry: method A
Retention time Tr (min)=0.76
[M+H]$^+$: m/z 375; [M–H]$^-$: m/z 373
Melting point (Kofler bench): 266° C.

EXAMPLE 73

Synthesis of N-[4-fluoro-3-(methoxymethyl)phenyl]-2-[4-(morpholin-4-yl)-6-oxo-1,6-dihydropyrimidin-2-yl]acetamide

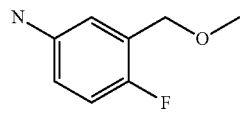

Stage 1:
In a round-bottomed flask, 374 mg of sodium hydride at 60% are introduced into 10 ml of tetrahydrofuran, 1 g of (5-amino-2-fluorophenyl)methanol and 0.441 ml of methyl iodide. After stirring at ambient temperature for one hour, a solution of sodium chloride and diethyl ether are added. The organic phase is extracted and then washed with water until pH=7. It is then dried over magnesium sulphate, filtered, and concentrated under reduced pressure. 900 mg of 4-fluoro-3-(methoxymethyl)aniline are obtained in the form of a black oil, which is used as it is in the next stage.

Stage 2:

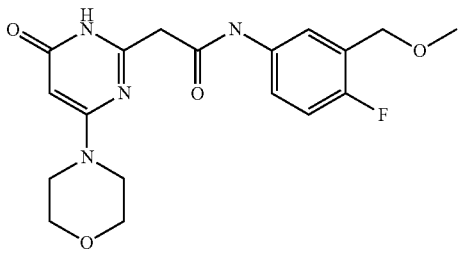 [SMILES: COCc1cc(NC(=O)Cc2nc(N3CCOCC3)cc(=O)[nH]2)ccc1F]

The product is prepared according to the procedure described in example 5, using 250 mg of sodium [4-(morpholin-4-yl)-6-oxo-1,6-dihydropyrimidin-2-yl]acetate and 900 mg of 4-fluoro-3-(methoxymethyl)aniline prepared previously, in place of the 2,4-difluoroaniline. 168 mg of N-[4-fluoro-3-(methoxymethyl)phenyl]-2-[4-(morpholin-4-yl)-6-oxo-1,6-dihydropyrimidin-2-yl]acetamide are obtained in the form of a white solid, the characteristics of which are the following:

¹H NMR spectrum (400 MHz):
3.31 (s partially masked, 3 H); 3.41 (m, 4 H); 3.59 (m, 6 H); 4.43 (s, 2 H); 5.20 (s, 1 H); 7.14 (t, J=9.3 Hz, 1 H); 7.51 (m, 1 H); 7.63 (m, 1 H); 10.21 (broad s, 1 H); 11.63 (broad s, 1 H)

Mass spectrometry: method A

Retention time Tr (min)=0.60

[M+H]⁺: m/z 377; [M−H]⁻: m/z 375

Melting point (Kofler bench): 220° C.

EXAMPLE 74

Synthesis of N-(4-fluoro-3-iodophenyl)-2-[4-(morpholin-4-yl)-6-oxo-1,6-dihydropyrimidin-2-yl]acetamide

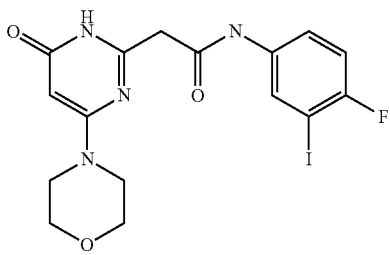 [SMILES: O=C(Cc1nc(N2CCOCC2)cc(=O)[nH]1)Nc1ccc(F)c(I)c1]

Stage 1:

1 g of 4-fluoro-3-nitrobenzene solubilized in 5 ml of ethanol is added to a suspension of 1 g of iron filings in 10 ml of ethanol, 5 ml of water and 250.4 mg of ammonium chloride, brought to reflux. After refluxing for 1 hour, the reaction mixture is filtered and the organic extracts are evaporated off. The evaporation residue is taken up in a mixture of water and dichloromethane. The aqueous phase is extracted with 3 times dichloromethane. The organic extracts are combined, dried over magnesium sulphate and concentrated under reduced pressure. 840 mg of 4-fluoro-3-iodoaniline are obtained, the characteristics of which are the following:

Mass spectrometry: method A

Retention time Tr (min)=0.60

[M+H]⁺: m/z 238.

Stage 2:

The product is prepared according to the procedure described in example 5, using 300 mg of sodium [4-(morpholin-4-yl)-6-oxo-1,6-dihydropyrimidin-2-yl]acetate and 272 mg of 4-fluoro-3-iodoaniline. 309 mg of N-(4-fluoro-3-iodophenyl)-2-[4-(morpholin-4-yl)-6-oxo-1,6-dihydropyrimidin-2-yl]acetamide are obtained, the characteristics of which are the following:

¹H NMR spectrum (400 MHz):
3.42 (m, 4 H); 3.57 to 3.63 (m, 6 H); 5.21 (s, 1 H); 7.23 (t, J=8.6 Hz, 1 H); 7.52 (ddd, J=2.5 and 4.4 and 8.6 Hz, 1 H); 8.12 (dd, J=2.5 and 5.4 Hz, 1 H); 10.29 (broad s, 1 H); 11.65 (broad s, 1 H)

Mass spectrometry: method A

Retention time Tr (min)=0.74

[M+H]⁺: m/z 459; [M−H]⁻: m/z 457.

EXAMPLE 75

Synthesis of 2-[4-(morpholin-4-yl)-6-oxo-1,6-dihydropyrimidin-2-yl]-N-[3-(1,1,2,2-tetrafluoroethoxy)phenyl]acetamide

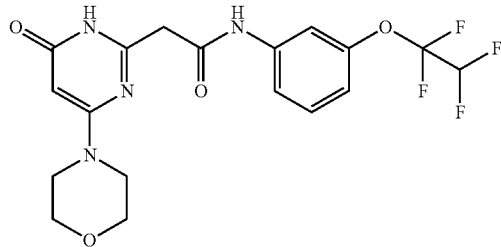 [SMILES: O=C(Cc1nc(N2CCOCC2)cc(=O)[nH]1)Nc1cccc(OC(F)(F)C(F)F)c1]

The product is prepared according to the procedure described in example 5, using 250 mg of sodium [4-(morpholin-4-yl)-6-oxo-1,6-dihydropyrimidin-2-yl]acetate, 300 mg of 3-(1,1,2,2-tetrafluoroethoxy)aniline, and 300 mg of N-[3-(dimethylamino)propyl]-N'-ethylcarbodiimide hydrochloride in a mixture of 2 ml of pyridine and 2 ml of N,N-dimethylformamide. 300 mg of 2-[4-(morpholin-4-yl)-6-oxo-1,6-dihydropyrimidin-2-yl]-N-[3-(1,1,2,2-tetrafluoroethoxy)phenyl]acetamide are obtained in the form of a white solid, the characteristics of which are the following:

¹H NMR spectrum (400 MHz):
all the signals are broad, with: 3.41 (m, 4 H); 3.60 (m, 6 H); 5.20 (s, 1H); 6.79 (t, J=52.5 Hz, 1 H); 6.94 to 7.01 (m, 1 H); 7.35 to 7.50 (m, 2 H); 7.69 (s, 1 H); 10.40 (s, 1 H); 11.66 (s, 1 H)

Mass spectrometry: method A

Retention time Tr (min)=0.77

[M+H]⁺: m/z 431; [M−H]⁻: m/z 429

Melting point (Kofler bench): 229° C.

EXAMPLE 76

Synthesis of N-[3-(difluoromethyl)-4-fluorophenyl]-2-[4-(morpholin-4-yl)-6-oxo-1,6-dihydropyrimidin-2-yl]acetamide

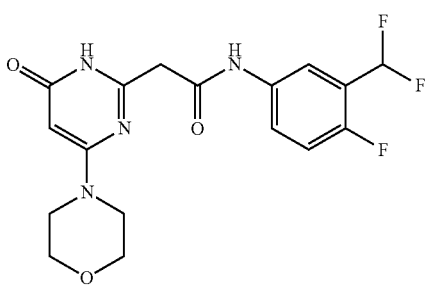 [SMILES: O=C(Cc1nc(N2CCOCC2)cc(=O)[nH]1)Nc1ccc(F)c(C(F)F)c1]

Stage 1:

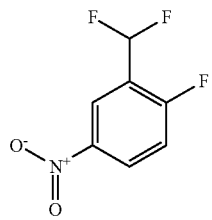 [SMILES: O=[N+]([O-])c1ccc(F)c(C(F)F)c1]

4.48 g (3.5 ml) of N-ethyl-N-(trifluoro-λ⁴-sulphanyl)ethanamine are added, at a temperature in the region of 20° C. and under argon, to a solution of 3.36 g of 2-fluoro-5-nitrobenzaldehyde in 100 ml of dichloromethane. After stirring for 3 h 30 at a temperature in the region of 20° C., 300 ml of a saturated aqueous solution of sodium hydrogen carbonate are slowly added. After stirring for one hour, the organic phase is washed with 40 ml of water, and then dried over anhydrous magnesium sulphate, filtered and concentrated to dryness under reduced pressure. 3.6 g of 2-(difluoromethyl)-1-fluoro-4-nitrobenzene are obtained in the form of a yellow liquid, the characteristics of which are the following:

Mass spectrometry: The spectra are performed by direct introduction on a Waters GCTOF apparatus (direct introduction without LC): EI: [M]⁺. m/z=191.

Stage 2:

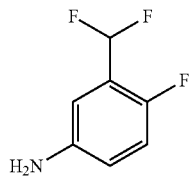 [SMILES: Nc1ccc(F)c(C(F)F)c1]

A solution of 2 g of 2-(difluoromethyl)-1-fluoro-4-nitrobenzene in 10 ml of acetic acid is added slowly to a suspension of 7 g of iron, in 30 ml of acetic acid at reflux, under argon. The reaction mixture is stirred for 1 hour at reflux, and then cooled to ambient temperature. 20 ml of ethyl acetate are then added and the reaction medium is filtered through Clarcel, rinsed with ethyl acetate and then concentrated to dryness under reduced pressure. The residue is taken up with 100 ml of ethyl acetate and again filtered through Clarcel and concentrated to dryness under reduced pressure. After silica column purification of the oily residue, eluent: 95/05 $CH_2Cl_2$/MeOH, 1.1 g of a mixture containing 3-(difluoromethyl)-4-fluoroaniline are obtained in the form of a brown liquid, which is used as it is in the next stage.

Stage 3:

The product is prepared according to the procedure described in example 5, using 250 mg of sodium [4-(morpholin-4-yl)-6-oxo-1,6-dihydropyrimidin-2-yl]acetate, 1.1 g of 3-(difluoromethyl)-4-fluoroaniline (stage 2) and 300 mg of N-[3-(dimethylamino)propyl]-N'-ethylcarbodiimide hydrochloride in a mixture of 2 ml of pyridine and 2 ml of N,N-dimethylformamide. 260 mg of N-[3-(difluoromethyl)-4-fluorophenyl]-2-[4-(morpholin-4-yl)-6-oxo-1,6-dihydropyrimidin-2-yl]acetamide are obtained in the form of a white solid, the characteristics of which are the following:

¹H NMR spectrum (400 MHz):

3.41 (m, 4 H); 3.52 to 3.67 (m, 6 H); 5.21 (s, 1 H); 7.20 (t, J=54.3 Hz, 1H); 7.34 (t, J=8.9 Hz, 1 H); 7.68 (m, 1 H); 7.90 (m, 1 H); 10.41 (s, 1 H); 11.67 (broad s, 1 H)

Mass spectrometry: method A
Retention time Tr (min)=0.67
[M+H]⁺: m/z 383; [M−H]⁻: m/z 381
Melting point (Kofler bench): above 260° C.

EXAMPLE 77

Synthesis of 2,2-difluoro-N-(4-fluorophenyl)-2-[4-(morpholin-4-yl)-6-oxo-1,6-dihydropyrimidin-2-yl]acetamide

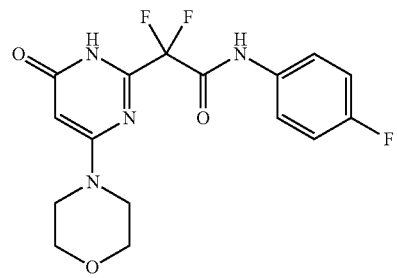 [SMILES: O=C(Nc1ccc(F)cc1)C(F)(F)c1nc(N2CCOCC2)cc(=O)[nH]1]

Stage 1:

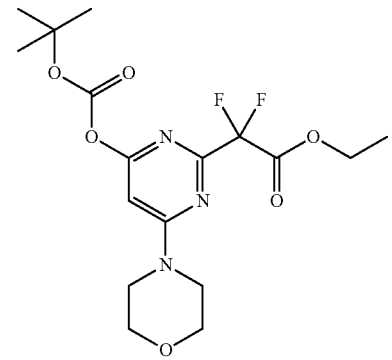 [SMILES: CCOC(=O)C(F)(F)c1nc(OC(=O)OC(C)(C)C)cc(N2CCOCC2)n1]

350 mg of ethyl [4-({[(2-methylpropan-2-yl)oxy]carbonyl}oxy)-6-(morpholin-4-yl)pyrimidin-2-yl]acetate dissolved beforehand in 6 ml of tetrahydrofuran are added to a solution of 570 mg of potassium 1,1,1,3,3,3-hexamethyldisilazan-2-ide in 9 ml of tetrahydrofuran, placed at a temperature of −78° C. and under argon. After stirring at this temperature for 45 min, 409 mg of manganese (2+) dibromide are added. After the suspension obtained has been stirred for thirty minutes, still at a temperature of −78° C., 847 mg of N-fluoro-N-(phenylsulphonyl)benzenesulphonamide are added. After a return to a temperature in the region of 20° C., the suspension is stirred overnight. The medium is run into a saturated aqueous solution of sodium bicarbonate, and extracted with ethyl acetate, and the organic phase is washed with a saturated aqueous solution of sodium chloride, dried over anhydrous magnesium sulphate, filtered and concentrated to dryness under reduced pressure. The residue is taken up with 10 ml of methylene chloride and then the insoluble material is filtered off and washed with three times 5 ml of methylene chloride. The filtrate is concentrated to dryness under reduced pressure and, after silica column purification of the oily residue, eluent: 95/05 $CH_2Cl_2$/EtOAc, 278 mg of ethyl difluoro[4-({[(2-methylpropan-2-yl)oxy]carbonyl}oxy)-6-(morpholin-4-yl)pyrimidin-2-yl]acetate are obtained in the form of a colourless oil, the characteristics of which are the following:

Mass spectrometry: method A
Retention time Tr (min)=1.06
[M+Na]⁺: m/z 426; base peak: m/z 304.

Stage 2:

0.756 ml of a solution of aluminium trichloride (2N) in toluene are added slowly to a solution of 0.136 ml of 4-fluoroaniline in 5 ml of toluene at a temperature of between 0° C. and 10° C. After stirring for 40 min at a temperature in the region of 20° C., 271 mg of ethyl difluoro[4-({[(2-methylpropan-2-yl)oxy]carbonyl}oxy)-6-(morpholin-4-yl)pyrimidin-2-yl]acetate solubilized in 6 ml of toluene, are slowly added. After refluxing for 2 h30, the temperature returns to a temperature in the region of 20° C. and then, at 0° C., 26 ml of water and 26 ml of a molar solution of potassium dihydrogen phosphate are added and the resulting mixture is extracted with ethyl acetate. The organic phase is washed with a saturated aqueous solution of sodium chloride, dried over anhydrous magnesium sulphate, filtered and concentrated to dryness under reduced pressure. After silica column purification of the residue, eluent: 95/05 CH₂Cl₂/MeOH, the solid is taken up with 5 ml of dichloromethane, the mixture is heated at 40° C. for 5 min, and then the temperature is returned to a temperature in the region of 20° C. The insoluble material is spin-filter-dried, and washed by triturating, from 1 ml of dichloromethane, three times, and then dried in a vacuum bell jar. 28 mg of 2,2-difluoro-N-(4-fluorophenyl)-2-[4-(morpholin-4-yl)-6-oxo-1,6-dihydropyrimidin-2-yl]acetamide are obtained in the form of a white powder, the characteristics of which are the following:

¹H NMR spectrum (400 MHz):

3.51 (m, 4 H); 3.58 to 3.64 (m, 4 H); 5.92 (broad s, 1 H); 7.20 (t, J=9.0 Hz, 2 H); 7.70 (dd, J=5.2 and 9.0 Hz, 2 H); 10.70 (broad s, 1 H); 11.82 (broad m, 1 H)

Mass spectrometry: method A
Retention time Tr (min)=0.69
[M+H]⁺: m/z 369; [M−H]⁻: m/z 367.

EXAMPLE 78

Synthesis of N-(3,4-difluorophenyl)-2-[1-methyl-4-(morpholin-4-yl)-6-oxo-1,6-dihydropyrimidin-2-yl]acetamide

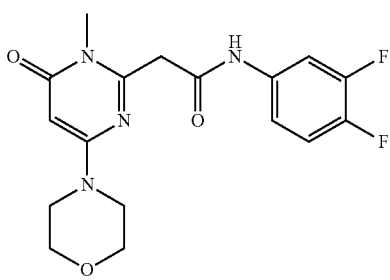 [SMILES: Cn1c(CC(=O)Nc2ccc(F)c(F)c2)nc(N2CCOCC2)cc1=O]

The product is prepared according to the procedure described in example 5, using 250 mg of sodium [1-methyl-4-(morpholin-4-yl)-6-oxo-1,6-dihydropyrimidin-2-yl]acetate prepared in stage 1 of example 68, 169 mg of 3,4-difluoroaniline, and 285 mg of N-[3-(dimethylamino)propyl]-N'ethylcarbodiimide hydrochloride in a mixture of 2 ml of pyridine and 2 ml of N,N-dimethylformamide. 180 mg of N-(3,4-difluorophenyl)-2-[1-methyl-4-(morpholin-4-yl)-6-oxo-1,6-dihydropyrimidin-2-yl]acetamide are obtained in the form of a white solid, the characteristics of which are the following:

¹H NMR spectrum (400 MHz):

3.33 (s, 3 H); 3.39 (m, 4 H); 3.58 (m, 4 H); 3.91 (s, 2 H); 5.36 (s, 1 H); 7.26 (m, 1 H); 7.39 (q, J=9.5 Hz, 1 H); 7.73 (ddd, J=2.2 and 7.5 and 13.0 Hz, 1 H); 10.43 (s, 1 H)

Mass spectrometry: method A
Retention time Tr (min)=0.69
[M+H]⁺: m/z 365; [M−H]⁻: m/z 363
Melting point (Kofler bench): above 260° C.

EXAMPLE 79

Synthesis of 2-[2-(2,3-dihydro-1H-indol-1-yl)-2-oxoethyl]-3-methyl-6-(morpholin-4-yl)pyrimidin-4(3H)-one

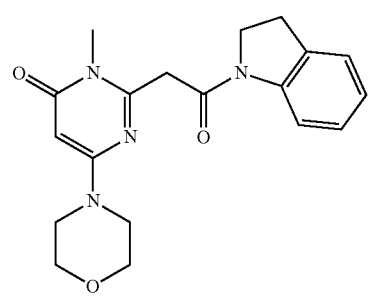 [SMILES: Cn1c(CC(=O)N2CCc3ccccc32)nc(N2CCOCC2)cc1=O]

The product is prepared according to the procedure described in example 5, using 200 mg of sodium [1-methyl-4-(morpholin-4-yl)-6-oxo-1,6-dihydropyrimidin-2-yl]acetate prepared in stage 1 of example 68, 174 mg of 2,3-dihydro-1H-indole, and 185 mg of N-[3-(dimethylamino)propyl]-N'-ethylcarbodiimide hydrochloride in a mixture of 0.12 ml of pyridine and 3 ml of N,N-dimethylformamide. After silica column purification, eluent: 93/07 CH₂Cl₂/MeOH, the solid is taken up with 4 ml of methanol and a few drops of acetone. The suspension is heated at a temperature of 80° C., filtered while hot, and then recrystallized at a temperature of 20° C. and then of 0° C. The solid is filtered off, rinsed with diethyl ether, and then dried under a vacuum bell jar. 52 mg of 2-[2-(2,3-dihydro-1H-indol-1-yl)-2-oxoethyl]-3-methyl-6-(morpholin-4-yl)pyrimidin-4(3H)-one are obtained in the form of white crystals, the characteristics of which are the following:

¹H NMR spectrum (400 MHz):

3.17 (t, J=8.4 Hz, 2 H); 3.32 (s, 3 H); 3.39 (m, 4 H); 3.58 (m, 4 H); 4.11 (s, 2 H); 4.17 (t, J=8.4 Hz, 2 H); 5.36 (s, 1 H); 7.02 (t, J=7.5 Hz, 1 H); 7.16 (t, J=7.5 Hz, 1 H); 7.26 (d, J=7.5 Hz, 1 H); 8.01 (d, J=7.5 Hz, 1 H)

Mass spectrometry: method A
Retention time Tr (min)=0.68
[M+H]⁺: m/z 355; [M−H]⁻: m/z 353
Melting point (Kofler bench): above 250° C.

EXAMPLE 80

Synthesis of N-(3-bromo-4-fluorophenyl)-2-[1-methyl-4-(morpholin-4-yl)-6-oxo-1,6-dihydropyrimidin-2-yl]acetamide

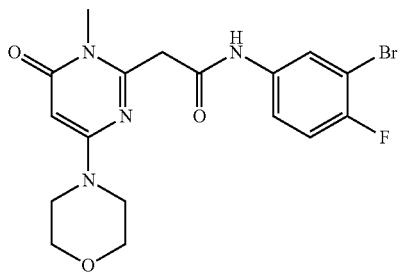 [SMILES: Cn1c(CC(=O)Nc2ccc(F)c(Br)c2)nc(N2CCOCC2)cc1=O]

The product is prepared according to the procedure described in example 5, using 200 mg of sodium [1-methyl-4-(morpholin-4-yl)-6-oxo-1,6-dihydropyrimidin-2-yl]acetate prepared in stage 1 of example 68, 199 mg of 3-bromo-4-fluoroaniline, and 228 mg of N-[3-(dimethylamino)propyl]-N'-ethylcarbodiimide hydrochloride in a mixture of 1.5 ml of pyridine and 1.5 ml of N,N-dimethylformamide. 185 mg of N-(3-bromo-4-fluorophenyl)-2-[1-methyl-4-(morpholin-4-yl)-6-oxo-1,6-dihydropyrimidin-2-yl]acetamide are obtained in the form of a white solid, the characteristics of which are the following:

$^1$H NMR spectrum (400 MHz):

3.34 (s, 3 H); 3.39 (m, 4 H); 3.58 (m, 4 H); 3.91 (s, 2 H); 5.36 (s, 1 H); 7.30 to 7.38 (t, J=8.9 Hz, 1 H); 7.48 (ddd, J=2.7 and 4.4 and 8.9 Hz, 1 H); 7.99 (dd, J=2.7 and 6.4 Hz, 1 H); 10.40 (s, 1 H)

Mass spectrometry: method A
Retention time Tr (min)=0.76
[M+H]$^+$: m/z 425; [M−H]$^−$: m/z 423
Melting point (Kofler bench): above 262° C.

EXAMPLE 81

Synthesis of N-[4-fluoro-3-(hydroxymethyl)phenyl]-2-[1-methyl-4-(morpholin-4-yl)-6-oxo-1,6-dihydropyrimidin-2-yl]acetamide

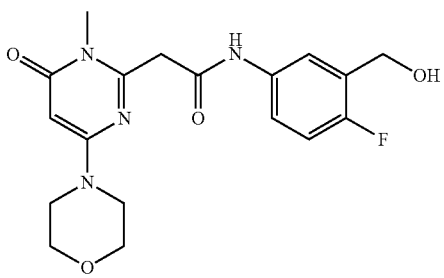 [SMILES: Cn1c(CC(=O)Nc2ccc(F)c(CO)c2)nc(N2CCOCC2)cc1=O]

The product is prepared according to the procedure described in example 5, using 250 mg of sodium [1-methyl-4-(morpholin-4-yl)-6-oxo-1,6-dihydropyrimidin-2-yl]acetate prepared in stage 1 of example 68, 184 mg of (5-amino-2-fluorophenyl)methanol, and 285 mg of N-[3-(dimethylamino)propyl]-N'-ethylcarbodiimide hydrochloride in a mixture of 2 ml of pyridine and 2 ml of N,N-dimethylformamide. 157 mg of N-[4-fluoro-3-(hydroxymethyl)phenyl]-2-[1-methyl-4-(morpholin-4-yl)-6-oxo-1,6-dihydropyrimidin-2-yl]acetamide are obtained in the form of a grey solid, the characteristics of which are the following:

$^1$H NMR spectrum (400 MHz):

3.34 (s, 3 H); 3.40 (m, 4 H); 3.59 (m, 4 H); 3.90 (s, 2 H); 4.52 (d, J=5.6 Hz, 2 H); 5.27 (t, J=5.6 Hz, 1 H); 5.35 (s, 1 H); 7.08 (t, J=9.3 Hz, 1 H); 7.43 to 7.53 (m, 1 H); 7.64 (dd, J=2.7 and 6.6 Hz, 1 H); 10.23 (s, 1 H)

Mass spectrometry: method A
Retention time Tr (min)=0.49
[M+H]$^+$: m/z 377; [M−H]$^−$: m/z 375
Melting point (Kofler bench): above 224° C.

EXAMPLE 82

Synthesis of N-(3-cyclopropylphenyl)-2-[1-methyl-4-(morpholin-4-yl)-6-oxo-1,6-dihydropyrimidin-2-yl]acetamide

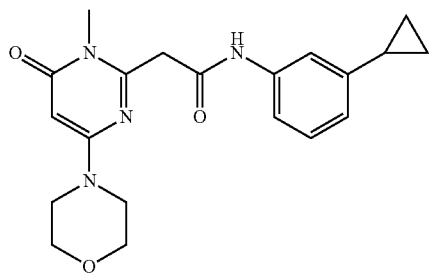 [SMILES: Cn1c(CC(=O)Nc2cccc(C3CC3)c2)nc(N2CCOCC2)cc1=O]

The product is prepared according to the procedure described in example 5, using 200 mg of sodium [1-methyl-4-(morpholin-4-yl)-6-oxo-1,6-dihydropyrimidin-2-yl]acetate prepared in stage 1 of example 68, 194 mg of 3-cyclopropylaniline (prepared according to Wallace et al. in Tetrahedron Lett. 2002, 43, 6987), and 185 mg of N-[3-(dimethylamino)propyl]-N'-ethylcarbodiimide hydrochloride in a mixture of 0.12 ml of pyridine and 4 ml of N,N-dimethylformamide. After extractions with ethyl acetate and silica column purification of the residue obtained, eluent: 95/05 CH$_2$Cl$_2$/MeOH, 129 mg of N-(3-cyclopropylphenyl)-2-[1-methyl-4-(morpholin-4-yl)-6-oxo-1,6-dihydropyrimidin-2-yl]acetamide are obtained in the form of a white solid, the characteristics of which are the following:

$^1$H NMR spectrum (400 MHz):

0.57 to 0.64 (m, 2 H); 0.90 to 0.98 (m, 2 H); 1.82 to 1.91 (m, 1 H); 3.33 (s, 3 H); 3.38 to 3.43 (m, 4 H); 3.57 to 3.62 (m, 4 H); 3.89 (s, 2 H); 5.35 (s, 1 H); 6.79 (broad d, J=7.8 Hz, 1 H); 7.17 (t, J=7.8 Hz, 1 H); 7.28 (t, J=1.5 Hz, 1H); 7.31 (broad d, J=7.8 Hz, 1 H); 10.11 (s, 1 H)

Mass spectrometry: method A
Retention time Tr (min)=0.76
[M+H]$^+$: m/z 369; [M−H]$^−$: m/z 367
Melting point (Kofler bench): 216° C.

EXAMPLE 83

Synthesis of N-(4-fluoro-3-methoxyphenyl)-2-[1-methyl-4-(morpholin-4-yl)-6-oxo-1,6-dihydropyrimidin-2-yl]acetamide

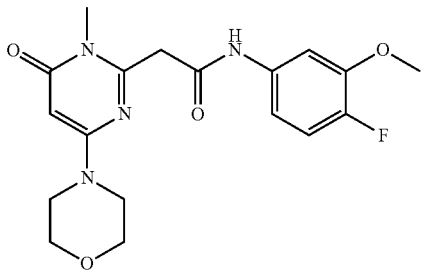 [SMILES: COc1cc(NC(=O)Cc2nc(N3CCOCC3)cc(=O)n2C)ccc1F]

The product is prepared according to the procedure described in example 5, using 200 mg of sodium [1-methyl-4-(morpholin-4-yl)-6-oxo-1,6-dihydropyrimidin-2-yl]acetate prepared in stage 1 of example 68, 205 mg of 4-fluoro-3-methoxyaniline, and 185 mg of N-[3-(dimethylamino)propyl]-N'-ethylcarbodiimide hydrochloride in a mixture of 0.12 ml of pyridine and 3 ml of N,N-dimethylformamide. After extractions with ethyl acetate and silica column purification of the residue obtained, eluent: 95/05 then 90/10 $CH_2Cl_2$/MeOH, 42 mg of N-(4-fluoro-3-methoxyphenyl)-2-[1-methyl-4-(morpholin-4-yl)-6-oxo-1,6-dihydropyrimidin-2-yl]acetamide are obtained in the form of a white solid, the characteristics of which are the following:

$^1$H NMR spectrum (400 MHz):

3.34 (s, 3 H); 3.38 to 3.42 (m, 4 H); 3.55 to 3.62 (m, 4 H); 3.79 (s, 3 H); 3.90 (s, 2 H); 5.35 (s, 1 H); 7.05 (ddd, J=2.4 and 4.0 and 8.8 Hz, 1 H); 7.14 (dd, J=8.8 and 11.2 Hz, 1 H); 7.47 (dd, J=2.4 and 8.1 Hz, 1 H); 10.26 (s, 1 H)

Mass spectrometry: method A
Retention time Tr (min)=0.64
[M+H]$^+$: m/z 377; [M–H]$^-$: m/z 375
Melting point (Kofler bench): above 260° C.

EXAMPLE 84

Synthesis of N-(1-benzofur-4-yl)-2-[4-(morpholin-4-yl)-6-oxo-1,6-dihydropyrimidin-2-yl]acetamide

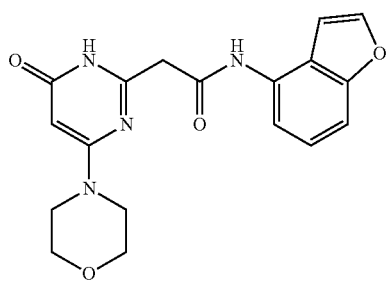

The product is prepared according to the procedure described in example 5, using 250 mg of sodium [4-(morpholin-4-yl)-6-oxo-1,6-dihydropyrimidin-2-yl]acetate, 178 mg of 1-benzofuran-4-amine, and 300 mg of N-[3-(dimethylamino)propyl]-N'-ethylcarbodiimide hydrochloride in a mixture of 2 ml of pyridine and 3 ml of N,N-dimethylformamide. 275 mg of 2-[1-methyl-4-(morpholin-4-yl)-6-oxo-1,6-dihydropyrimidin-2-yl]-N-phenylacetamide are obtained in the form of an off-white solid, the characteristics of which are the following:

$^1$H NMR spectrum (400 MHz):

3.43 (m, 4 H); 3.60 (m, 4 H); 3.73 (s, 2 H); 5.21 (s, 1 H); 7.12 (broad d, J=2.2 Hz, 1 H); 7.25 (t, J=8.1 Hz, 1 H); 7.35 (broad d, J=8.1 Hz, 1 H); 7.71 (d, J=8.1 Hz, 1 H); 7.94 (d, J=2.2 Hz, 1 H); 10.12 (s, 1 H); 11.70 (broad m, 1 H)

Mass spectrometry: method B
Retention time Tr (min)=2.96
[M+H]$^+$: m/z 355; [M–H]$^-$: m/z 353
Melting point (Kofler bench): above 260° C.

EXAMPLE 85

Synthesis of 2-[1-methyl-4-(morpholin-4-yl)-6-oxo-1,6-dihydropyrimidin-2-yl]-N-phenylacetamide

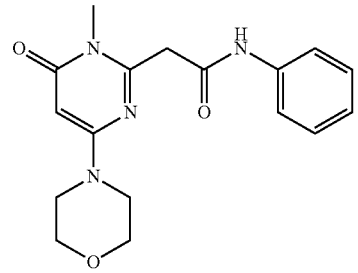 [SMILES: Cn1c(CC(=O)Nc2ccccc2)nc(N2CCOCC2)cc1=O]

The product is prepared according to the procedure described in example 5, using 200 mg of sodium [1-methyl-4-(morpholin-4-yl)-6-oxo-1,6-dihydropyrimidin-2-yl]acetate prepared in stage 1 of example 68, 134 mg of aniline, and 180 mg of N-[3-(dimethylamino)propyl]-N'-ethylcarbodiimide hydrochloride in a mixture of 0.12 ml of pyridine and 2.5 ml of N,N-dimethylformamide. 95 mg of 2-[1-methyl-4-(morpholin-4-yl)-6-oxo-1,6-dihydropyrimidin-2-yl]-N-phenylacetamide are obtained in the form of a purple solid, the characteristics of which are the following:

$^1$H NMR spectrum (400 MHz):

3.35 (s, 3 H); 3.41 (m, 4 H); 3.58 (m, 4 H); 3.91 (s, 2 H); 5.35 (s, 1 H); 7.06 (t, J=7.8 Hz, 1 H); 7.31 (t, J=7.8 Hz, 2 H); 7.55 (d, J=7.8 Hz, 2 H); 10.19 (s, 1 H)

Mass spectrometry: method B
Retention time Tr (min)=2.87
[M+H]$^+$: m/z 329; [M–H]$^-$: m/z 327
Melting point (Kofler bench): 212° C.

EXAMPLE 86

Synthesis of N-(3-cyclopropyl-4-fluorophenyl)-2-[1-methyl-4-(morpholin-4-yl)-6-oxo-1,6-dihydropyrimidin-2-yl]acetamide

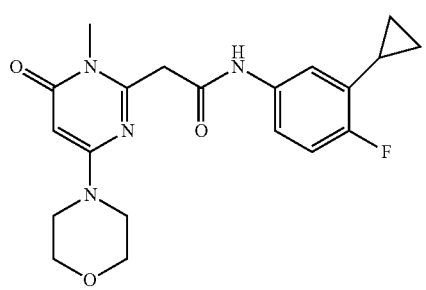 [SMILES: Cn1c(CC(=O)Nc2ccc(F)c(C3CC3)c2)nc(N2CCOCC2)cc1=O]

93

Stage 1:

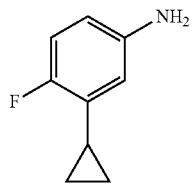

558 mg of cyclopropylboronic acid, 3.7 g of tribasic potassium phosphonate, 70 mg of tricyclohexylphosphane and 56 mg of palladium(2+) diacetate in 1.5 ml of water are added to a solution of 950 mg of 3-bromo-4-fluoroaniline in 20 ml of toluene, with stirring and under argon. The mixture is degassed and then heated to a temperature of 100° C. After 15 hours, the reaction medium is cooled to a temperature in the region of 20° C., run into 100 ml of water, and then extracted with four times 60 ml of diethyl ether. The combined organic phases are dried over anhydrous magnesium sulphate, filtered and concentrated under reduced pressure. The residue is purified on a silica column, eluent: 70/30 cyclohexane/ethyl acetate. 494 mg of 3-cyclopropyl-4-fluoroaniline are obtained in the form of a brown oil, the characteristics of which are the following:
Mass spectrometry: method A
Retention time Tr (min)=0.40
[M+H]$^+$: m/z 152;

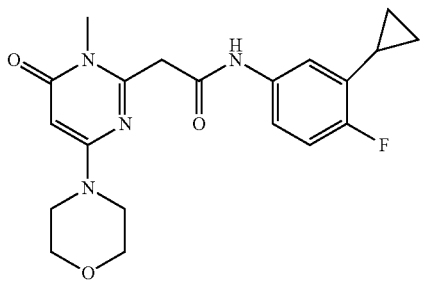 [SMILES: Cn1c(CC(=O)Nc2ccc(F)c(C3CC3)c2)nc(N2CCOCC2)cc1=O]

Stage 2:
The product is prepared according to the procedure described in example 5, using 200 mg of sodium [1-methyl-4-(morpholin-4-yl)-6-oxo-1,6-dihydropyrimidin-2-yl]acetate prepared in stage 1 of example 68, 220 mg of 3-cyclopropyl-4-fluoroaniline, and 180 mg of N-[3-(dimethylamino)propyl]-N'-ethylcarbodiimide hydrochloride in a mixture of 0.12 ml of pyridine and 2.5 ml of N,N-dimethylformamide. After extractions with ethyl acetate and silica column purification, eluent 90/10 CH$_2$Cl$_2$/MeOH, the residue is taken up with ml of diisopropyl ether, and the precipitate is spin-filter-dried and dried under vacuum, so as to obtain 69 mg of N-(3-cyclopropyl-4-fluorophenyl)-2-[1-methyl-4-(morpholin-4-yl)-6-oxo-1,6-dihydropyrimidin-2-yl]acetamide in the form of a yellow solid, the characteristics of which are the following:
$^1$H NMR spectrum (400 MHz):
0.57 to 0.66 (m, 2 H); 0.94 to 1.03 (m, 2 H); 1.93 to 2.08 (m, 1 H); 3.33 (s, 3 H); 3.37 to 3.42 (m, 4 H); 3.55 to 3.62 (m, 4 H); 3.87 (s, 2 H); 5.35 (s, 1 H); 7.07 (dd, J=8.8 and 10.3 Hz, 1 H); 7.16 (dd, J=2.6 and 7.0 Hz, 1 H); 7.29 to 7.38 (m, 1 H); 10.16 (s, 1 H)
Mass spectrometry: method B
Retention time Tr (min)=3.53
[M+H]$^+$: m/z 387; [M–H]$^-$: m/z 385
Melting point (Kofler bench): 245° C.

EXAMPLE 87

Synthesis of N-(3-fluoro-2-hydroxyphenyl)-2-[4-(morpholin-4-yl)-6-oxo-1,6-dihydropyrimidin-2-yl]acetamide

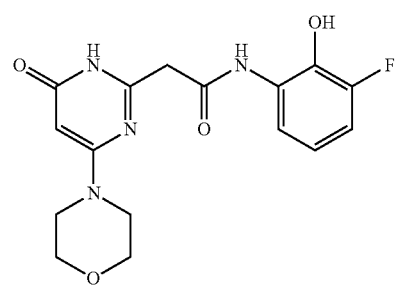 [SMILES: O=C(Cc1nc(N2CCOCC2)cc(=O)[nH]1)Nc1cccc(F)c1O]

The product is prepared according to the procedure described in example 5, using 500 mg of sodium [4-(morpholin-4-yl)-6-oxo-1,6-dihydropyrimidin-2-yl]acetate, 357 mg of 2-amino-6-fluorophenol, and 600 mg of N-[3-(dimethylamino)propyl]-N'-ethylcarbodiimide hydrochloride in a mixture of 4 ml of pyridine and 4 ml of N,N-dimethylformamide. 335 mg of N-(3-fluoro-2-hydroxyphenyl)-2-[4-(morpholin-4-yl)-6-oxo-1,6-dihydropyrimidin-2-yl]acetamide are obtained in the form of a beige solid, the characteristics of which are the following:
$^1$H NMR spectrum (400 MHz):
3.44 (m, 4 H); 3.62 (m, 4 H); 3.71 (s, 2 H); 5.21 (s, 1 H); 6.78 (dt, J=6.0 and 8.1 Hz, 1 H); 6.94 (broad t, J=8.1 Hz, 1 H); 7.64 (broad d, J=8.1 Hz, 1 H); 9.55 to 10.10 (broad m, 2 H); 11.69 (broad m, 1 H)
Mass spectrometry: method B
Retention time Tr (min)=2.66
[M+H]$^+$: m/z 349; [M–H]$^-$: m/z 347
Melting point (Kofler bench): above 260° C.

EXAMPLE 88

Synthesis of 2-[2-(4-fluoro-2,3-dihydro-1H-indol-1-yl)-2-oxoethyl]-6-(morpholin-4-yl)pyrimidin-4(3H)-one

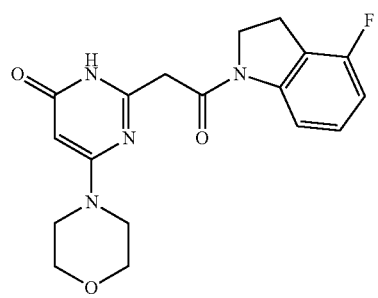 [SMILES: O=C(Cc1nc(N2CCOCC2)cc(=O)[nH]1)N1CCc2c(F)cccc21]

The product is prepared according to the procedure described in example 5, using 261 mg of sodium [4-(morpholin-4-yl)-6-oxo-1,6-dihydropyrimidin-2-yl]acetate, 274 mg of 4-fluoro-2,3-dihydro-1H-indole, and 254 mg of N-[3-

(dimethylamino)propyl]-N'-ethylcarbodiimide hydrochloride in a mixture of 0.16 ml of pyridine and 4 ml of N,N-dimethylformamide. 249 mg of 2-[2-(4-fluoro-2,3-dihydro-1H-indol-1-yl)-2-oxoethyl]-6-(morpholin-4-yl)pyrimidin-4(3H)-one are obtained in the form of a white solid, the characteristics of which are the following:

$^1$H NMR spectrum (400 MHz):
3.20 (t, J=8.4 Hz, 2 H); 3.41 (m, 4 H); 3.61 (m, 4 H); 3.76 (s, 2 H); 4.21 (t, J=8.4 Hz, 2 H); 5.21 (s, 1 H); 6.86 (t, J=8.6 Hz, 1 H); 7.12 to 7.31 (m, 1 H); 7.84 (d, J=8.1 Hz, 1 H); 11.61 (broad s, 1 H)

Mass spectrometry: method B
Retention time Tr (min)=3.20
[M+H]$^+$: m/z 359; [M−H]$^-$: m/z 357
Melting point (Kofler bench): above 260° C.

EXAMPLE 89

Synthesis of 2-[2-(4-chloro-2,3-dihydro-1H-indol-1-yl)-2-oxoethyl]-6-(morpholin-4-yl)pyrimidin-4(3H)-one

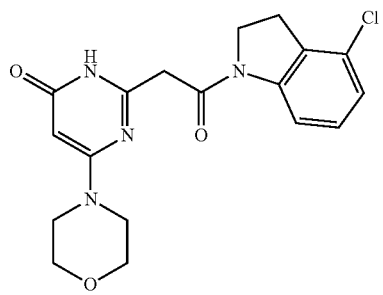 [SMILES: O=C(Cc1nc(N2CCOCC2)cc(=O)[nH]1)N1CCc2c(Cl)cccc21]

The product is prepared according to the procedure described in example 5, using 261 mg of sodium [4-(morpholin-4-yl)-6-oxo-1,6-dihydropyrimidin-2-yl]acetate, 307 mg of 4-chloro-2,3-dihydro-1H-indole, and 254 mg of N-[3-(dimethylamino)propyl]-N'-ethylcarbodiimide hydrochloride in a mixture of 0.16 ml of pyridine and 4 ml of N,N-dimethylformamide. 247 mg of 2-[2-(4-chloro-2,3-dihydro-1H-indol-1-yl)-2-oxoethyl]-6-(morpholin-4-yl)pyrimidin-4(3H)-one are obtained in the form of a white solid, the characteristics of which are the following:

$^1$H NMR spectrum (400 MHz):
3.18 (t, J=8.4 Hz, 2 H); 3.41 (m, 4 H); 3.60 (m, 4 H); 3.76 (s, 2 H); 4.20 (t, J=8.4 Hz, 2 H); 5.21 (s, 1 H); 7.09 (d, J=8.1 Hz, 1 H); 7.22 (t, J=8.1 Hz, 1 H); 7.97 (d, J=8.1 Hz, 1 H); 11.62 (broad s, 1 H)

Mass spectrometry: method B
Retention time Tr (min)=3.46;
[M+H]$^+$: m/z 375; [M−H]$^-$: m/z 373
Melting point (Kofler bench): above 260° C.

EXAMPLE 90

Synthesis of N-(3-ethynyl-4-fluorophenyl)-2-[4-(morpholin-4-yl)-6-oxo-1,6-dihydropyrimidin-2-yl]acetamide

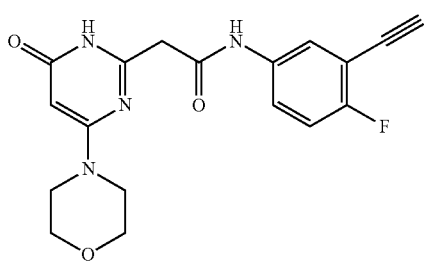 [SMILES: C#Cc1cc(NC(=O)Cc2nc(N3CCOCC3)cc(=O)[nH]2)ccc1F]

Stage 1

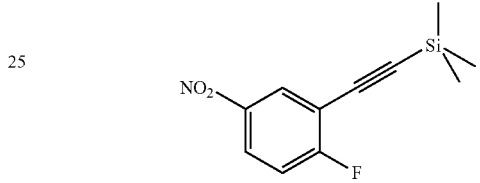

1.126 ml of ethynyl(trimethyl)silane, 55 mg of triphenylphosphine and 24 mg of palladium (2+) acetate are added to a solution of 1.169 g of 2-bromo-1-fluoro-4-nitrobenzene in 13 ml of triethylamine with stirring and under argon. After four and a half hours at a temperature of 100° C., the reaction medium is cooled and the insoluble material is filtered off through sintered glass. The filtrate is concentrated to dryness under reduced pressure. After two silica column purifications, eluent: 90/10 heptane/EtOAc then 95/5 heptane/EtOAc, 460 mg of [(2-fluoro-5-nitrophenyl)ethynyl](trimethyl)silane are obtained in the form of a yellow solid, the characteristics of which are the following:

Mass spectrometry: The spectra were performed by direct introduction on a Waters GCTOF apparatus (direct introduction without LC):
EI: [M]$^+$. m/z 237; base peak: m/z 222.

Stage 2

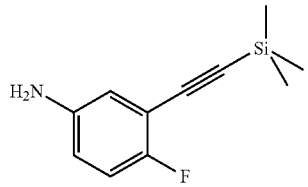

460 mg of iron are added to a solution of 460 mg of [(2-fluoro-5-nitrophenyl)ethynyl](trimethypsilane in 10 ml of methanol, and the medium is adjusted to pH 4-5 with concentrated hydrochloric acid. After refluxing for three and a half hours, the medium is cooled and then filtered through silica, and concentrated to dryness under reduced pressure. The residue is taken up with diethyl ether, the insoluble material is filtered off, and then the filtrate is concentrated to dryness under reduced pressure. 370 mg of 4-fluoro-3-[(trimethylsilyl)ethynyl]aniline are obtained in the form of an orangey oil, the characteristics of which are the following:

Mass spectrometry: method A

Retention time Tr (min)=1.11

[M+H]+: m/z 208; base peak: m/z 249.

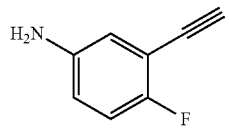

16 mg of potassium carbonate are added to a solution of 360 mg of 4-fluoro-3-[(trimethylsilyl)ethynyl]aniline in 5 ml of methanol. After stirring over night under argon and at a temperature in the region of 20° C., the medium is concentrated to dryness under reduced pressure, then taken up in 8 ml of water and neutralized with a few drops of hydrochloric acid (1N), and then extracted three times with diethyl ether. The combined organic phases are dried over anhydrous magnesium sulphate, filtered and concentrated to dryness under reduced pressure. 225 mg of 3-ethynyl-4-fluoroaniline are obtained in the form of a brown oil, the characteristics of which are the following:

Mass spectrometry: method A

Retention time Tr (min)=0.49

[M+H]+: m/z 136;

Stage 4:

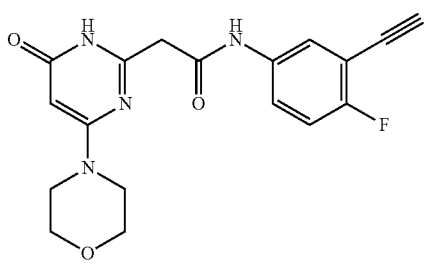 [SMILES: C#Cc1cc(NC(=O)Cc2nc(N3CCOCC3)cc(=O)[nH]2)ccc1F]

The product is prepared according to the procedure described in example 5, using 204 mg of sodium [4-(morpholin-4-yl)-6-oxo-1,6-dihydropyrimidin-2-yl]acetate, 211 mg of 3-ethynyl-4-fluoroaniline, and 195 mg of N-[3-(dimethylamino)propyl]-N'-ethylcarbodiimide hydrochloride in a mixture of 0.126 ml of pyridine and 3 ml of N,N-dimethylformamide. 200 mg of N-(3-ethynyl-4-fluorophenyl)-2-[4-(morpholin-4-yl)-6-oxo-1,6-dihydropyrimidin-2-yl]acetamide are obtained in the form of a white solid, the characteristics of which are the following:

¹H NMR spectrum (400 MHz):

3.41 (m, 4 H); 3.60 (m, 6 H); 4.48 (s, 1 H); 5.20 (s, 1 H); 7.27 (t, J=9.0 Hz, 1 H); 7.56 (m, 1 H); 7.78 (dd, J=1.5 and 5.9 Hz, 1 H); 10.31 (broad m, 1 H); 11.66 (broad m, 1 H)

Mass spectrometry: method A

Retention time Tr (min)=0.75

[M+H]+: m/z 357; [M−H]−: m/z 355

Melting point (Kofler bench): above 260° C.

EXAMPLE 91

Synthesis of 2-[2-(4-hydroxy-2,3-dihydro-1H-indol-1-yl)-2-oxoethyl]-6-(morpholin-4-yl)pyrimidin-4 (3H)-one

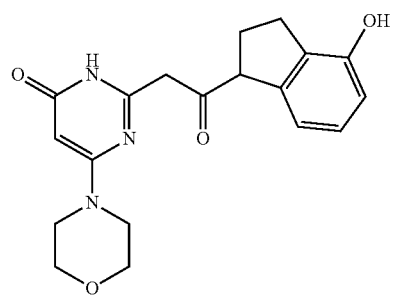 [SMILES: O=C(Cc1nc(N2CCOCC2)cc(=O)[nH]1)C1CCc2c(O)cccc21]

The product is prepared according to the procedure described in example 5, using 261 mg of sodium [4-(morpholin-4-yl)-6-oxo-1,6-dihydropyrimidin-2-yl]acetate, 270 mg of 2,3-dihydro-1H-indol-4-ol, and 254 mg of N-[3-(dimethylamino)propyl]-N'-ethylcarbodiimide hydrochloride in a mixture of 0.16 ml of pyridine and 4 ml of N,N-dimethylformamide. 205 mg of 2-[2-(4-hydroxy-2,3-dihydro-1H-indol-1-yl)-2-oxoethyl]-6-(morpholin-4-yl)pyrimidin-4(3H)-one are obtained in the form of a pink solid, the characteristics of which are the following:

¹H NMR spectrum (400 MHz):

3.01 (t, J=8.1 Hz, 2 H); 3.41 (m, 4 H); 3.61 (m, 4 H); 3.71 (s, 2 H); 4.12 (t, J=8.1 Hz, 2 H); 5.20 (s, 1 H); 6.49 (d, J=8.1 Hz, 1 H); 6.97 (t, J=8.1 Hz, 1 H); 7.50 (d, J=8.1 Hz, 1 H); 9.44 (broad s, 1 H); 11.60 (broad s, 1 H)

Mass spectrometry: method A

Retention time Tr (min)=0.57

[M+H]+: m/z 357; [M−H]−: m/z 355

Melting point (Kofler bench): above 260° C.

EXAMPLE 92

Synthesis of 2-[2-(4,6-difluoro-2,3-dihydro-1H-indol-1-yl)-2-oxoethyl]-6-(morpholin-4-yl)pyrimidin-4 (3H)-one

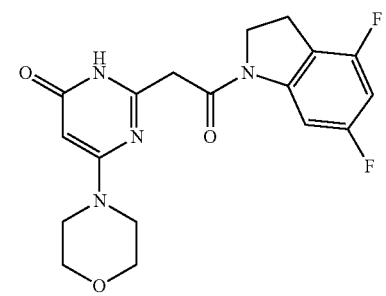 [SMILES: O=C(Cc1nc(N2CCOCC2)cc(=O)[nH]1)N1CCc2c(F)cc(F)cc21]

The product is prepared according to the procedure described in example 5, using 261 mg of sodium [4-(morpholin-4-yl)-6-oxo-1,6-dihydropyrimidin-2-yl]acetate, 310 mg of 4,6-difluoro-2,3-dihydro-1H-indole, and 254 mg of N-[3-(dimethylamino)propyl]-N'-ethylcarbodiimide hydrochloride in a mixture of 0.16 ml of pyridine and 4 ml of N,N-dimethylformamide. 225 mg of 2-[2-(4,6-difluoro-2,3-dihydro-1H-indol-1-yl)-2-oxoethyl]-6-(morpholin-4- pyrimidin-4(3H)-one are obtained in the form of a white solid, the characteristics of which are the following:

¹H NMR spectrum (400 MHz):
3.17 (t, J=8.4 Hz, 2 H); 3.41 (m, 4 H); 3.61 (m, 4 H); 3.78 (s, 2 H); 4.24 (t, J=8.4 Hz, 2 H); 5.21 (s, 1 H); 6.89 (broad t, J=8.9 Hz, 1 H); 7.64 (broad d, J=8.9 Hz, 1 H); 11.62 (broad m, 1 H)

Mass spectrometry: method A
Retention time Tr (min)=0.73
[M+H]⁺: m/z 377; [M−H]⁻: m/z 375
Melting point (Kofler bench): above 260° C.

EXAMPLE 93

Synthesis of N-(3-iodo-4-fluorophenyl)-2-[1-methyl-4-(morpholin-4-yl)-6-oxo-1,6-dihydropyrimidin-2-yl]acetamide

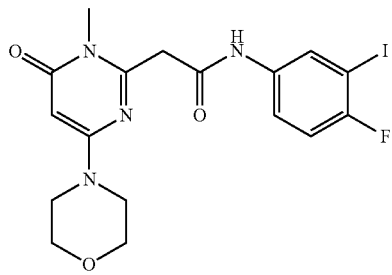

The product is prepared according to the procedure described in example 68, using 200 mg of sodium [1-methyl-4-(morpholin-4-yl)-6-oxo-1,6-dihydropyrimidin-2-yl]acetate and 210 mg of 3-iodo-4-fluoroaniline. 186 mg of N-(3-iodo-4-fluorophenyl)-2-[1-methyl-4-(morpholin-4-yl)-6-oxo-1,6-dihydropyrimidin-2-yl]acetamide are obtained in the form of a white solid, the characteristics of which are the following:

¹H NMR spectrum (400 MHz): 3.33 (s, 3 H); 3.40 (m, 4 H); 3.58 (m, 4 H); 3.90 (s, 2 H); 5.36 (s, 1 H); 7.22 (t, J=8.4 Hz, 1 H); 7.49 (m, 1 H); 8.11 (dd, J=2.4 and 5.6 Hz, 1 H); 10.33 (broad m, 1 H)

Mass spectrometry: method B
Retention time Tr (min)=3.50;
[M+H]⁺: m/z 473; [M−H]⁻: m/z 471.

EXAMPLE 94

Synthesis of 2-[2-(4,5-difluoro-2,3-dihydro-1H-indol-1-yl)-2-oxoethyl]-6-(morpholin-4-yl)pyrimidin-4(3H)-one

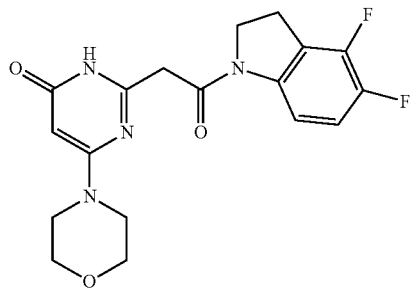 [SMILES: O=C(Cc1nc(N2CCOCC2)cc(=O)[nH]1)N1CCc2c1ccc(F)c2F]

The product is prepared according to the procedure described in example 5, but using 261 mg of sodium [4-(morpholin-4-yl)-6-oxo-1,6-dihydropyrimidin-2-yl]acetate prepared in stage 2 of example 1, 383 mg of 4,5-difluoro-2,3-dihydro-1H-indole hydrochloride, and 254 mg of N-[3-(dimethylamino)propyl]-N'-ethylcarbodiimide hydrochloride in a mixture of 0.32 ml of pyridine and 4 ml of N,N-dimethylformamide. 210 mg of 2-[2-(4,5-difluoro-2,3-dihydro-1H-indol-1-yl)-2-oxoethyl]-6-(morpholin-4-yl)pyrimidin-4(3H)-one are obtained in the form of a pale pink, powdery solid, the characteristics of which are the following:

¹H NMR spectrum (400 MHz):
3.25 (t, J=8.3 Hz, 2 H); 3.41 (m, 4 H); 3.61 (m, 4 H); 3.76 (s, 2 H); 4.23 (t, J=8.3 Hz, 2 H); 5.21 (s, 1 H); 7.05 to 7.34 (m, 1 H); 7.79 (dd, J=3.4 and 8.8 Hz, 1 H); 11.60 (broad m, 1 H)

Mass spectrometry: method B
Retention time Tr (min)=3.30;
[M+H]⁺: m/z 377; [M−H]⁻: m/z 375
Melting point (Kofler bench): above 260° C.

EXAMPLE 95

Synthesis of 2-[2-(6-fluoro-2,3-dihydro-'1H-indol-1-yl)-2-oxoethyl]-6-(morpholin-4-yl)pyrimidin-4(3H)-one

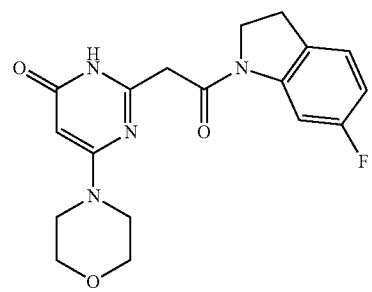 [SMILES: O=C(Cc1nc(N2CCOCC2)cc(=O)[nH]1)N1CCc2ccc(F)cc21]

The product is prepared according to the procedure described in example 5, but using 200 mg of sodium [4-(morpholin-4-yl)-6-oxo-1,6-dihydropyrimidin-2-yl]acetate prepared in stage 2 of example 1, 210 mg of 6-fluoro-2,3-dihydro-1H-indole, and 194 mg of N-[3-(dimethylamino)propyl]-N'-ethylcarbodiimide hydrochloride in a mixture of 0.12 ml of pyridine and 3 ml of N,N-dimethylformamide. 184 mg of 2-[2-(6-fluoro-2,3-dihydro-1H-indol-1-yl)-2-oxoethyl]-6-(morpholin-4-yl)pyrimidin-4(3H)-one are obtained in the form of a white powder, the characteristics of which are the following:

¹H NMR spectrum (400 MHz):
3.14 (t, J=8.3 Hz, 2 H); 3.37 to 3.45 (m, 4 H); 3.54 to 3.64 (m, 4 H); 3.76 (s, 2 H); 4.19 (t, J=8.3 Hz, 2 H); 5.21 (s, 1 H); 6.83 (dt, J=2.0 and 8.6 Hz, 1 H); 7.19 to 7.31 (m, 1 H); 7.77 (dd, J=2.6 and 10.8 Hz, 1 H); 11.61 (broad m, 1 H)

Mass spectrometry: method A
Retention time Tr (min)=0.67;
[M+H]⁺: m/z 359; [M−H]⁻: m/z 357
Melting point (Kofler bench): above 260° C.

EXAMPLE 96

Synthesis of 2-[2-(2-methyl-2,3-dihydro-1H-indol-1-yl)-2-oxoethyl]-6-(morpholin-4-pyrimidin-4(3H)-one

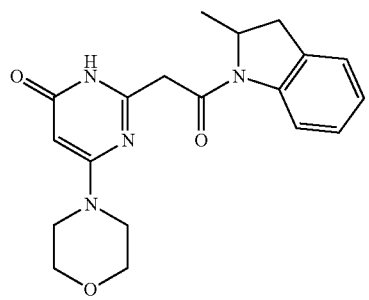 [SMILES: CC1Cc2ccccc2N1C(=O)Cc1nc(N2CCOCC2)cc(=O)[nH]1]

The product is prepared according to the procedure described in example 5, using 500 mg of sodium [4-(morpholin-4-yl)-6-oxo-1,6-dihydropyrimidin-2-yl]acetate, 510 mg of 2-methyl-2,3-dihydro-1H-indole, and 487 mg of N-[3-(dimethylamino)propyl]-N'-ethylcarbodiimide hydrochloride in a mixture of 0.308 ml of pyridine and 8 ml of N,N-dimethylformamide. 400 mg of 2-[2-(2-methyl-2,3-dihydro-1H-indol-1-yl)-2-oxoethyl]-6-(morpholin-4-yl)pyrimidin-4(3H)-one are obtained in the form of a white powder, the characteristics of which are the following:

$^1$H NMR spectrum (400 MHz):
1.26 (d, J=6.1 Hz, 3 H); 2.65 to 2.72 (m, 1 H); 3.18 to 3.44 (m partially masked, 5 H); 3.54 to 3.63 (m, 4 H); 3.72 (d, J=15.7 Hz, 1 H); 3.92 (d, J=15.7 Hz, 1 H); 4.71 (m, 1 H); 5.20 (s, 1 H); 7.04 (t, J=7.8 Hz, 1 H); 7.18 (t, J=7.8 Hz, 1 H); 7.29 (d, J=7.8 Hz, 1 H); 7.96 (d, J=7.8 Hz, 1 H); 11.69 (broad m, 1 H)

Mass spectrometry: method A
Retention time Tr (min)=0.70;
[M+H]$^+$: m/z 355; [M−H]$^−$: m/z 353
Melting point (Kofler bench): 172° C.

EXAMPLE 97

Synthesis of N-[3-(difluoromethyl)-4-fluorophenyl]-2-[1-methyl-4-(morpholin-4-yl)-6-oxo-1,6-dihydropyrimidin-2-yl]acetamide

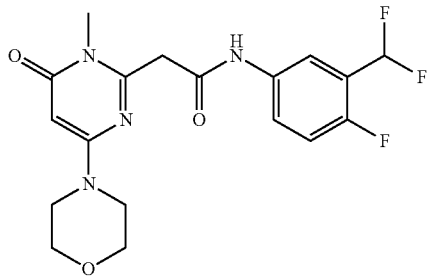 [SMILES: Cn1c(CC(=O)Nc2ccc(F)c(C(F)F)c2)nc(N2CCOCC2)cc1=O]

The product is prepared according to the procedure described in example 5, but using 275 mg of sodium [1-methyl-4-(morpholin-4-yl)-6-oxo-1,6-dihydropyrimidin-2-yl]acetate prepared in stage 1 of example 68, 322 mg of 3-(difluoromethyl)-4-fluoroaniline (example 76, stage 2), and 250 mg of N-[3-(dimethylamino)propyl]-N'-ethylcarbodiimide hydrochloride in a mixture of 0.16 ml of pyridine and 4 ml of N,N-dimethylformamide. 98 mg of N-[3-(difluoromethyl)-4-fluorophenyl]-2-[1-methyl-4-(morpholin-4-yl)-6-oxo-1,6-dihydropyrimidin-2-yl]acetamide are obtained in the form of a white solid, the characteristics of which are the following:

$^1$H NMR spectrum (400 MHz):
3.34 (s, 3 H); 3.39 (m, 4 H); 3.58 (m, 4 H); 3.92 (s, 2 H); 5.36 (s, 1 H); 7.20 (t, J=54.3 Hz, 1 H); 7.34 (t, J=9.5 Hz, 1 H); 7.68 (m, 1 H); 7.89 (m, 1 H); 10.45 (s, 1 H)

Mass spectrometry: method B
Retention time Tr (min)=3.29;
[M+H]$^+$: m/z 397; [M−H]$^−$: m/z 395.

EXAMPLE 98

Synthesis of 2-(1-methyl-4-morpholin-4-yl-6-oxo-1,6-dihydropyrimidin-2-yl)-N-(3,4,5-trifluorophenyl)acetamide

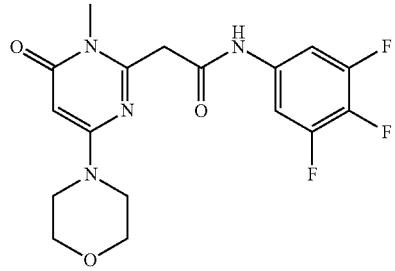 [SMILES: Cn1c(CC(=O)Nc2cc(F)c(F)c(F)c2)nc(N2CCOCC2)cc1=O]

The product is prepared according to the procedure described in example 68, using 200 mg of sodium [1-methyl-4-(morpholin-4-yl)-6-oxo-1,6-dihydropyrimidin-2-yl]acetate, 214 mg of 3,4,5-trifluoroaniline, and 180 mg of N-[3-(dimethylamino)propyl]-N'-ethylcarbodiimide hydrochloride in a mixture of 0.12 ml of pyridine and 2.5 ml of N,N-dimethylformamide. 72 mg of 2-(1-methyl-4-morpholin-4-yl-6-oxo-1,6-dihydropyrimidin-2-yl)-N-(3,4,5-trifluorophenyl)acetamide are obtained in the form of a cream solid, the characteristics of which are the following:

$^1$H NMR spectrum (400 MHz): 3.33 (s, 3 H); 3.39 (m, 4 H); 3.58 (m, 4 H); 3.93 (s, 2 H); 5.36 (s, 1 H); 7.46 (dd, J=6.4 and 10.3 Hz, 2 H); 10.58 (broad s, 1 H)

Mass spectrometry: method B
Retention time Tr (min)=3.47;
[M+H]$^+$: m/z 383; [M−H]$^−$: m/z 381
Melting point (Kofler bench): above 266° C.

EXAMPLE 99

Synthesis of N-(1-methyl-1H-indol-4-yl)-2-[4-(morpholin-4-yl)-6-oxo-1,6-dihydropyrimidin-2-yl]acetamide

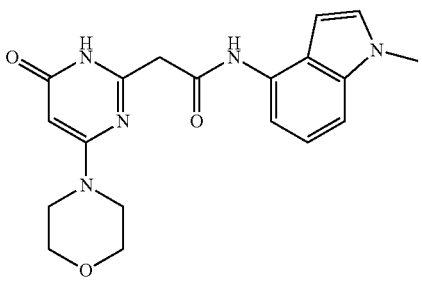 [SMILES: Cn1ccc2c(NC(=O)Cc3nc(N4CCOCC4)cc(=O)[nH]3)cccc21]

2 ml of pyridine, 300 mg of N-[3-(dimethylamino)propyl]-N'-ethylcarbodiimide hydrochloride and 272 mg of 1-methyl- 1H-indol-4-ylamine are added to a solution of 250 mg of sodium [4-(morpholin-4-yl)-6-oxo-1,6-dihydropyrimidin-2-yl]acetate prepared in stage 2 of example 1, in 2 ml of N,N-dimethylformamide. The reaction mixture is stirred at ambient temperature for 15 hours, and then concentrated under reduced pressure. Water and ethyl acetate are added and the resulting mixture is thus stirred for 30 minutes. The precipitate formed is filtered off, and rinsed with water, ethyl ether and petroleum ether. The solid obtained is dried under vacuum. 280 mg of N-(1-methyl-1H-indol-4-yl)-2-[4-(morpholin-4-yl)-6-oxo-1,6-dihydropyrimidin-2-yl]acetamide are obtained in the form of a pinkish solid, the characteristics of which are the following:

$^1$H NMR spectrum (400 MHz): 3.42 (m, 4 H); 3.60 (m, 4 H); 3.73 (s, 2 H); 3.78 (s, 3 H); 5.21 (s, 1 H); 6.67 (d, J=2.9 Hz, 1 H); 7.08 (t, J=8.1 Hz, 1 H); 7.19 (d, J=8.1 Hz, 1 H); 7.29 (d, J=2.9 Hz, 1 H); 7.60 (d, J=8.1 Hz, 1 H); 9.85 (broad s, 1 H); 11.68 (broad m, 1 H)

Mass spectrometry: method

[M+H]$^+$: m/z 366; [M−H]$^−$: m/z 368.

EXAMPLE 100

Synthesis of 2-[2-(4-methyl-2,3-dihydro-1H-indol-1-yl)-2-oxoethyl]-6-(morpholin-4-yl)pyrimidin-4(3H)-one

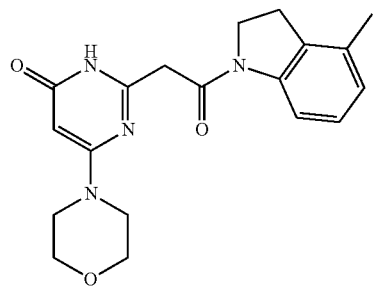 [SMILES: Cc1cccc2c1CCN2C(=O)Cc1nc(N2CCOCC2)cc(=O)[nH]1]

The product is prepared according to the procedure described in example 5, using 261 mg of sodium [4-(morpholin-4-yl)-6-oxo-1,6-dihydropyrimidin-2-yl]acetate, 339 mg of 4-methylindoline hydrochloride, and 254 mg of N-[3-(dimethylamino)propyl]-N'-ethylcarbodiimide hydrochloride in a mixture of 241 µl of pyridine and 4.0 ml of N,N-dimethylformamide. 22 mg of 2-[2-(4-methyl-2,3-dihydro-1H-indol-1-yl)-2-oxoethyl]-6-(morpholin-4-pyrimidin-4(3H)-one are obtained in the form of a fuchsia crystalline powder, the characteristics of which are the following:

$^1$H NMR spectrum (400 MHz): 2.21 (s, 3 H); 3.08 (t, J=8.3 Hz, 2 H); 3.42 (m, 4 H); 3.61 (m, 4 H); 3.75 (s, 2 H); 4.15 (t, J=8.3 Hz, 2 H); 5.20 (s, 1 H); 6.85 (d, J=8.0 Hz, 1 H); 7.07 (t, J=8.0 Hz, 1 H); 7.85 (d, J=8.0 Hz, 1 H); 11.62 (broad m, 1 H)

Mass spectrometry: method B

Retention time Tr (min)=3.31;

[M+H]$^+$: m/z 355; [M−H]$^−$: m/z 353

Melting point (Kofler bench): above 260° C.

EXAMPLE 101

Synthesis of 2-[2-(3-methyl-2,3-dihydro-1H-indol-1-yl)-2-oxoethyl]-6-(morpholin-4-yl)pyrimidin-4(3H)-one

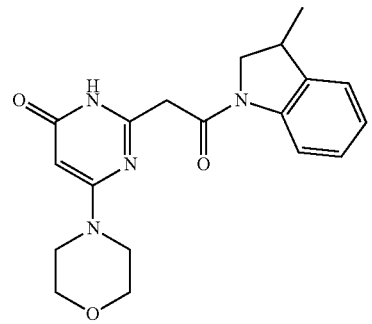 [SMILES: CC1CN(C(=O)Cc2nc(N3CCOCC3)cc(=O)[nH]2)c2ccccc21]

The product is prepared according to the procedure described in example 5, using 500 mg of sodium [4-(morpholin-4-yl)-6-oxo-1,6-dihydropyrimidin-2-yl]acetate, 170 mg of 3-methylindoline and 487 mg of N-[3-(dimethylamino)propyl]-N'-ethylcarbodiimide hydrochloride in a mixture of 310 µl of pyridine and 6.0 ml of N,N-dimethylformamide. 367 mg of 2-[2-(3-methyl-2,3-dihydro-1H-indol-1-yl)-2-oxoethyl]-6-(morpholin-4-yl)pyrimidin-4(3H)-one are obtained in the form of a white crystalline powder, the characteristics of which are the following:

$^1$H NMR spectrum (400 MHz): 1.29 (d, J=6.8 Hz, 3 H); 3.42 (m, 4 H); 3.49 (m, 1 H); 3.60 (m, 4 H); 3.68 (dd, J=6.8 and 9.8 Hz, 1 H); 3.75 (s, 2 H); 4.33 (t, J=9.8 Hz, 1 H); 5.21 (s, 1 H); 7.04 (t, J=7.8 Hz, 1 H); 7.18 (t, J=7.8 Hz, 1 H); 7.27 (d, J=7.8 Hz, 1 H); 8.01 (d, J=7.8 Hz, 1 H); 11.62 (broad m, 1 H)

Mass spectrometry: method A

Retention time Tr (min)=0.73;

[M+H]$^+$: m/z 355; [M−H]$^−$: m/z 353

Melting point (Kofler bench): above 260° C.

EXAMPLE 102

Synthesis of 2-[2-(4-fluoro-2,3-dihydro-1H-indol-1-yl)-2-oxoethyl]-3-methyl-6-(morpholin-4-yl)pyrimidin-4(3H)-one

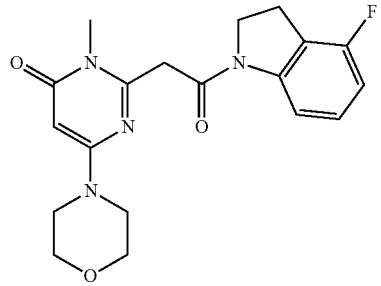 [SMILES: Cn1c(CC(=O)N2CCc3c(F)cccc32)nc(N2CCOCC2)cc1=O]

The product is prepared according to the procedure described in example 68, using 275 mg of sodium [1-methyl-4-(morpholin-4-yl)-6-oxo-1,6-dihydropyrimidin-2-yl]acetate, 274 mg of 4-fluoroindoline and 254 mg of N-[3-(dimethylamino)propyl]-N'-ethylcarbodiimide hydrochloride in a mixture of 161 µl of pyridine and 4.0 ml of N,N-dimethylformamide. 102 mg of 2-[2-(4-fluoro-2,3-dihydro-1H-indol-1-yl)-2-oxoethyl]-3-methyl-6-(morpholin-4-yl)pyrimidin-4(3H)-one are obtained in the form of a pale pink powder, the characteristics of which are the following:

¹H NMR spectrum (400 MHz): 3.19 (t, J=8.4 Hz, 2 H); 3.31 (s, 3 H); 3.39 (m, 4 H); 3.57 (m, 4 H); 4.12 (s, 2 H); 4.25 (t, J=8.4 Hz, 2 H); 5.36 (s, 1 H); 6.87 (t, J=8.7 Hz, 1 H); 7.22 (m, 1 H); 7.84 (d, J=8.1 Hz, 1 H)

Mass spectrometry: method A
Retention time Tr (min)=0.73;
[M+H]⁺: m/z 373; [M−H]⁻: m/z 371
Melting point (Kofler bench): 244° C.

EXAMPLE 103

2-[2-(5-Fluoro-2,3-dihydroindol-1-yl)-2-oxoethyl]-6-morpholin-4-yl-3H-pyrimidin-4-one

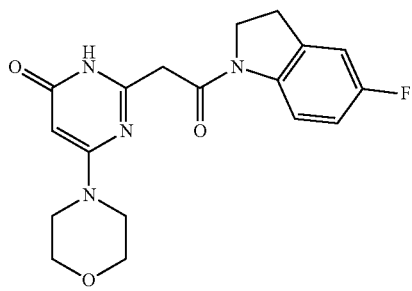 [SMILES: O=C(Cc1nc(N2CCOCC2)cc(=O)[nH]1)N1CCc2cc(F)ccc21]

The product is prepared according to the procedure described in example 5, using 261 mg of sodium [4-(morpholin-4-yl)-6-oxo-1,6-dihydropyrimidin-2-yl]acetate, 274 mg of 5-fluoroindoline and 254 mg of N-[3-(dimethylamino)propyl]-N'-ethylcarbodiimide hydrochloride in a mixture of 0.16 ml of pyridine and 4 ml of dimethylformamide. 197 mg of 2-[2-(5-fluoro-2,3-dihydroindol-1-yl)-2-oxoethyl]-6-morpholin-4-yl-3H-pyrimidin-4-one are obtained in the form of a very pale pink powder, the characteristics of which are the following:

¹H NMR spectrum (400 MHz, δ in ppm, DMSO-d₆): 3.18 (t, J=8.2 Hz, 2 H); 3.42 (m, 4 H); 3.60 (m, 4H); 3.74 (s, 2 H); 4.16 (t, J=8.2 Hz, 2 H); 5.20 (s, 1 H); 6.98 (broad t, J=8.9 Hz, 1 H); 7.12 (broad d, J=8.9 Hz, 1 H); 8.00 (dd, J=5.3 and 8.9 Hz, 1 H); 11.61 (broad m, 1 H).

Mass spectrometry: method A
Retention time Tr (min)=0.70;
[M+H]⁺: m/z 359; [M−H]⁻: m/z 357
Melting point (Kofler bench): 264° C.

EXAMPLE 104

Synthesis of 2-[2-(4-chloro-2,3-dihydro-1H-indol-1-yl)-2-oxoethyl]-3-methyl-6-(morpholin-4-yl)pyrimidin-4(3H)-one

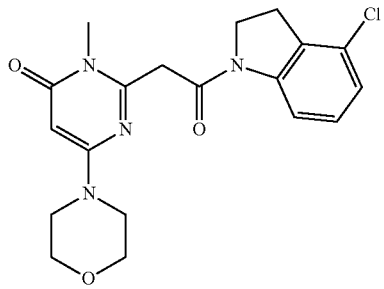 [SMILES: Cn1c(CC(=O)N2CCc3c(Cl)cccc32)nc(N2CCOCC2)cc1=O]

The product is prepared according to the procedure described in example 68, using 275 mg of sodium [1-methyl-4-(morpholin-4-yl)-6-oxo-1,6-dihydropyrimidin-2-yl]acetate, 307 mg of 4-chloroindoline and 254 mg of N-[3-(dimethylamino)propyl]-N'-ethylcarbodiimide hydrochloride in a mixture of 161 μl of pyridine and 4.0 ml of N,N-dimethylformamide. 84 mg of 2-[2-(4-chloro-2,3-dihydro-1H-indol-1-yl)-2-oxoethyl]-3-methyl-6-(morpholin-4-yl)pyrimidin-4(3H)-one are obtained in the form of a slightly pinkish powder, the characteristics of which are the following:

¹H NMR spectrum (400 MHz): 3.18 (t, J=8.4 Hz, 2 H); 3.31 (broad s, 3 H); 3.39 (m, 4 H); 3.58 (m, 4 H); 4.11 (s, 2 H); 4.23 (t, J=8.4 Hz, 2 H); 5.36 (s, 1 H); 7.09 (d, J=8.1 Hz, 1 H); 7.22 (t, J=8.1 Hz, 1 H); 7.96 (d, J=8.1 Hz, 1 H)

Mass spectrometry: method A
Retention time Tr (min)=0.81;
[M+H]⁺: m/z 389; [M−H]⁻: m/z 387
Melting point (Kofler bench): 235° C.

EXAMPLE 105

Synthesis of N-(1-benzothiophen-4-yl)-2-[4-(morpholin-4-yl)-6-oxo-1,6-dihydropyrimidin-2-yl]acetamide

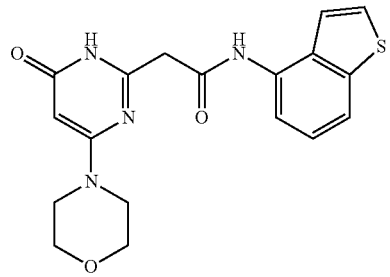 [SMILES: O=C(Cc1nc(N2CCOCC2)cc(=O)[nH]1)Nc1cccc2sccc12]

2 ml of pyridine, 257 mg of N-[3-(dimethylamino)propyl]-N'-ethylcarbodiimide hydrochloride and 223 mg of benzo[B]thiophen-4-ylamine are added to a solution of 250 mg of sodium [4-(morpholin-4-yl)-6-oxo-1,6-dihydropyrimidin-2-yl]acetate prepared in stage 2 of example 1, in 2 ml of N,N-dimethylformamide. The reaction mixture is stirred at ambient temperature for 15 hours, and then concentrated under reduced pressure. Water and ethyl acetate are added and the resulting mixture is thus stirred for 30 minutes. The precipitate formed is filtered off, and rinsed with water, ethyl ether and petroleum ether. The solid obtained is dried under vacuum. 262 mg of N-(1-benzothiophen-4-yl)-2-[4-(morpholin-4-yl)-6-oxo-1,6-dihydropyrimidin-2-yl]acetamide are obtained in the formed of an off-white solid, the characteristics of which are the following:

¹H NMR spectrum (400 MHz): 3.43 (m, 4 H); 3.60 (m, 4 H); 3.74 (s, 2 H); 5.21 (s, 1 H); 7.34 (t, J=7.9 Hz, 1 H); 7.65 (d, J=5.6 Hz, 1 H); 7.71 to 7.82 (m, 3 H); 10.17 (broad m, 1 H); 11.70 (broad m, 1 H)

Mass spectrometry: method A
Retention time Tr (min)=0.66;
[M+H]⁺: m/z 369; [M−H]⁻: m/z 371.

EXAMPLE 106

Synthesis of 2-{2-[2-(hydroxymethyl)-2,3-dihydro-1H-indol-1-yl]-2-oxoethyl}-6-(morpholin-4-yl)pyrimidin-4(3H)-one

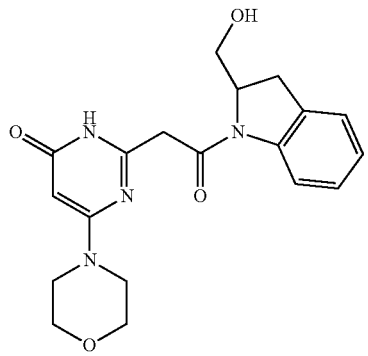 [SMILES: O=C(Cc1nc(N2CCOCC2)cc(=O)[nH]1)N1c2ccccc2CC1CO]

The product is prepared according to the procedure described in example 5, using 261 mg of sodium [4-(morpholin-4-yl)-6-oxo-1,6-dihydropyrimidin-2-yl]acetate, 298 mg of 2,3-dihydro-1H-indol-2-ylmethanol and 249 mg of N-[3-(dimethylamino)propyl]-N'-ethylcarbodiimide hydrochloride in a mixture of 322 μl of pyridine and 4.0 ml of N,N-dimethylformamide. 212 mg of 2-{2-[2-(hydroxymethyl)-2,3-dihydro-1H-indol-1-yl]-2-oxoethyl}-6-(morpholin-4-yl)pyrimidin-4(3H)-one are obtained in the form of a pale pink crystalline powder, the characteristics of which are the following:

$^1$H NMR spectrum (400 MHz): 2.86 (d, J=16.1 Hz, 1 H); 3.25 (dd, J=8.6 and 16.1 Hz, 1 H); 3.34 to 3.43 (m, 5 H); 3.51 (m, 1 H); 3.60 (m, 4 H); 3.81 (d, J=15.9 Hz, 1 H); 4.01 (d, J=15.9 Hz, 1 H); 4.64 (m, 1 H); 5.13 (broad m, 1 H); 5.20 (s, 1 H); 7.03 (t, J=7.8 Hz, 1 H); 7.16 (t, J=7.8 Hz, 1 H); 7.26 (d, J=7.8 Hz, 1 H); 7.94 (d, J=7.8 Hz, 1 H); 11.63 (broad m, 1 H)

Mass spectrometry: method B
Retention time Tr (min)=2.80;
[M+H]$^+$: m/z 371; [M–H]$^-$: m/z 369
Melting point (Kofler bench): 200° C.

EXAMPLE 107

Synthesis of 2-[4-(morpholin-4-yl)-6-oxo-1,6-dihydropyrimidin-2-yl]-N-{2-[2-(piperidin-1-yl)ethoxy]phenyl}acetamide

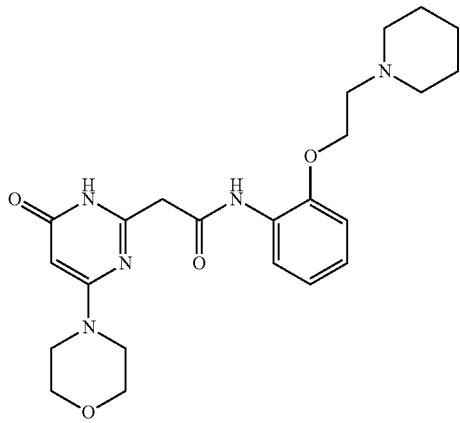 [SMILES: O=C(Cc1nc(N2CCOCC2)cc(=O)[nH]1)Nc1ccccc1OCCN1CCCCC1]

The product is prepared according to the procedure described in example 5, using 250 mg of sodium [4-(morpholin-4-yl)-6-oxo-1,6-dihydropyrimidin-2-yl]acetate, 303 mg of 2-(2-piperidin-1-ylethoxy)phenylamine and 300 mg of N-[3-(dimethylamino)propyl]-N'-ethylcarbodiimide hydrochloride in a mixture of 2 ml of pyridine and 2 ml of dimethylformamide. 255 mg of 2-[4-(morpholin-4-yl)-6-oxo-1,6-dihydropyrimidin-2-yl]-N-{2-[2-(piperidin-1-yl)ethoxy]phenyl}acetamide are obtained in the form of a beige solid, the characteristics of which are the following:

$^1$H NMR spectrum (400 MHz): 1.37 (m, 2 H); 1.43 to 1.53 (m, 4 H); 2.40 (m, 4 H); 2.65 (t, J=6.0 Hz, 2 H); 3.43 (m, 4 H); 3.60 (m, 4 H); 3.68 (s, 2 H); 4.13 (t, J=6.0 Hz, 2 H); 5.22 (s, 1 H); 6.89 (m, 1 H); 7.00 to 7.13 (m, 2 H); 7.93 (d, J=8.3 Hz, 1 H); 9.30 (broad m, 1 H)

Mass spectrometry: method B
Retention time Tr (min)=2.20;
[M+H]$^+$: m/z 442; [M–H]$^-$: m/z 440.

EXAMPLE 108

Synthesis of N-[2-(2-methoxyethoxy)phenyl]-2-[4-(morpholin-4-yl)-6-oxo-1,6-dihydropyrimidin-2-yl]acetamide

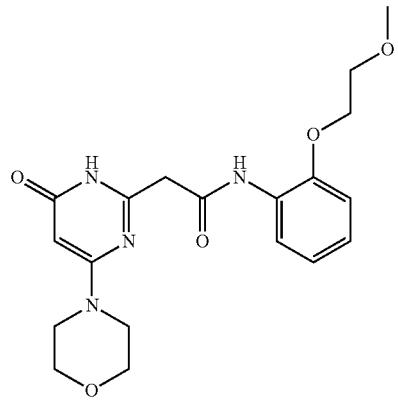 [SMILES: COCCOc1ccccc1NC(=O)Cc1nc(N2CCOCC2)cc(=O)[nH]1]

2 ml of pyridine, 300 mg of N-[3-(dimethylamino)propyl]-N'-ethylcarbodiimide hydrochloride and 303 mg of 2-(2-methoxyethoxy)phenylamine are added to a solution of 250 mg of sodium [4-(morpholin-4-yl)-6-oxo-1,6-dihydropyrimidin-2-yl]acetate prepared in stage 2 of example 1, in 2 ml of N,N-dimethylformamide. The reaction mixture is stirred at ambient temperature for 15 hours, and then concentrated under reduced pressure. Water and ethyl acetate are added and the resulting mixture is thus stirred for 30 minutes. The precipitate formed is filtered off, and rinsed with water, ethyl ether and petroleum ether. The solid obtained is dried under vacuum. 223 mg of N-[2-(2-methoxyethoxy)phenyl]-2-[4-(morpholin-4-yl)-6-oxo-1,6-dihydropyrimidin-2-yl]acetamide are obtained in the form of a pinkish solid, the characteristics of which are the following:

$^1$H NMR spectrum (400 MHz): 3.19 to 3.33 (s partially masked, 3 H); 3.43 (m, 4H); 3.61 (m, 4 H); 3.67 to 3.72 (m, 4 H); 4.16 (t, J=4.5 Hz, 2 H); 5.21 (s, 1 H); 6.94 (m, 1 H); 7.02 to 7.13 (m, 2 H); 7.95 (d, J=8.1 Hz, 1 H); 9.25 (broad s, 1 H); 11.67 (broad m, 1 H)

Mass spectrometry: method B
Retention time Tr (min)=3.00;
[M+H]$^+$: m/z 387; [M–H]$^-$: m/z 389.

EXAMPLE 109

Synthesis of 2-[2-(4-hydroxy-2,3-dihydro-1H-indol-1-yl)-2-oxoethyl]-3-methyl-6-(morpholin-4-yl)pyrimidin-4(3H)-one

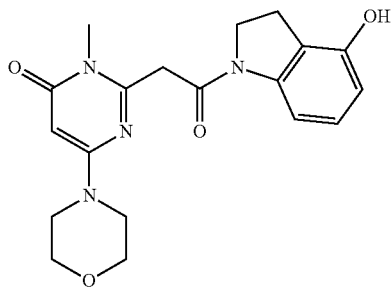 [SMILES: Cn1c(CC(=O)N2CCc3c(O)cccc32)nc(N2CCOCC2)cc1=O]

The product is prepared according to the procedure described in example 68, using 275 mg of sodium [1-methyl-4-(morpholin-4-yl)-6-oxo-1,6-dihydropyrimidin-2-yl]acetate, 270 mg of indolin-4-ol and 254 mg of N-[3-(dimethylamino)propyl]-N'-ethylcarbodiimide hydrochloride in a mixture of 161 µl of pyridine and 4.0 ml of N,N-dimethylformamide. 85 mg of 2-[2-(4-hydroxy-2,3-dihydro-1H-indol-1-yl)-2-oxoethyl]-3-methyl-6-(morpholin-4-yl)pyrimidin-4(3H)-one are obtained in the form of a pink powder, the characteristics of which are the following:

$^1$H NMR spectrum (400 MHz): 3.01 (t, J=8.6 Hz, 2 H); 3.31 (s masked, 3 H); 3.40 (m, 4 H); 3.58 (m, 4 H); 4.07 (s, 2 H); 4.16 (t, J=8.6 Hz, 2 H); 5.36 (s, 1 H); 6.50 (d, J=8.2 Hz, 1 H); 6.97 (t, J=8.2 Hz, 1 H); 7.49 (d, J=8.2 Hz, 1 H); 9.47 (broad s, 1 H)

Mass spectrometry: method A
Retention time Tr (min)=0.49;
[M+H]$^+$: m/z 371; [M–H]$^-$: m/z 369
Melting point (Kofler bench): above 260° C.

EXAMPLE 110

Synthesis of 2-[2-(4-methoxy-2,3-dihydro-1H-indol-1-yl)-2-oxoethyl]-3-methyl-6-(morpholin-4-yl)pyrimidin-4(3H)-one

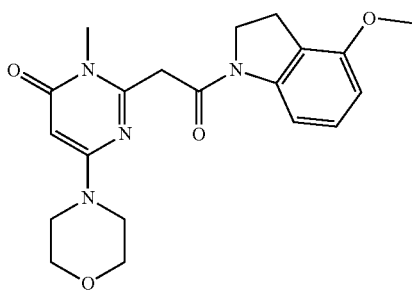 [SMILES: COc1cccc2c1CCN2C(=O)Cc1nc(N2CCOCC2)cc(=O)n1C]

The product is prepared according to the procedure described in example 68, using 275 mg of sodium [1-methyl-4-(morpholin-4-yl)-6-oxo-1,6-dihydropyrimidin-2-yl]acetate, 298 mg of 4-methoxyinoline and 254 mg of N-[3-(dimethylamino)propyl]-N'-ethylcarbodiimide hydrochloride in a mixture of 161 µl of pyridine and 4.0 ml of N,N-dimethylformamide. 107 mg of 2-[2-(4-methoxy-2,3-dihydro-1H-indol-1-yl)-2-oxoethyl]-3-methyl-6-(morpholin-4-pyrimidin-4(3H)-one are obtained in the form of a salmon pink powder, the characteristics of which are the following:

$^1$H NMR spectrum (400 MHz): 3.04 (t, J=8.5 Hz, 2 H); 3.31 (s masked, 3 H); 3.40 (m, 4 H); 3.59 (m, 4 H); 3.80 (s, 3 H); 4.09 (s, 2 H); 4.18 (t, J=8.5 Hz, 2 H); 5.36 (s, 1 H); 6.71 (d, J=8.2 Hz, 1 H); 7.15 (t, J=8.2 Hz, 1 H); 7.64 (d, J=8.2 Hz, 1 H)

Mass spectrometry: method A
Retention time Tr (min)=0.69;
[M+H]$^+$: m/z 385
Melting point (Kofler bench): 229° C.

EXAMPLE 111

Synthesis of 2-[2-(3,4-dihydroisoquinolin-2(1H)-yl)-2-oxoethyl]-6-(morpholin-4-yl)pyrimidin-4(3H)-one

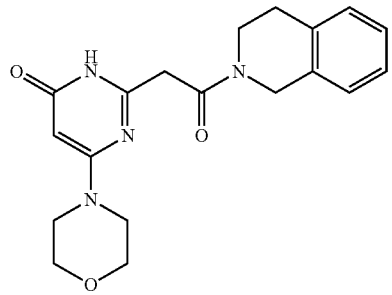 [SMILES: O=C(Cc1nc(N2CCOCC2)cc(=O)[nH]1)N1CCc2ccccc2C1]

The product is prepared according to the procedure described in example 70, using 304 µl of 1,2,3,4-tetrahydroisoquinoline, 300 mg of ethyl [4-(morpholin-4-yl)-6-oxo-1,6-dihydropyrimidin-2-yl]acetate prepared in stage 1 of example 1 and 1.3 ml of a 2M solution of trimethylaluminium, in a mixture of 21 ml of touene and 10 ml of tetrahydrofuran. 130 mg of 2-[2-(3,4-dihydroisoquinolin-2(1H)-yl)-2-oxoethyl]-6-(morpholin-4-yl)pyrimidin-4(3H)-one are thus obtained in the form of a whitish foam, the characteristics of which are the following:

$^1$H NMR spectrum (400 MHz): for this batch, all the signals are broad, with: 2.86 (m, 2 H); 3.33 (m, 4 H); 3.56 (m, 4 H); 3.72 (m, 4 H); 4.67 (s, 2 H); 5.13 (s, 1 H); 7.18 (s, 4 H); 11.23 (broad m, 1 H)

Mass spectrometry: method A
Retention time Tr (min)=0.62;
[M+H]$^+$: m/z 355; [M–H]$^-$: m/z 353
Melting point (Kofler bench): 107.5° C.

EXAMPLE 112

Synthesis of 2-[4-(morpholin-4-yl)-6-oxo-1,6-dihydropyrimidin-2-yl]1-N-{2-[2-(pyrrolidin-1-yl)ethoxy]phenyl}acetamide

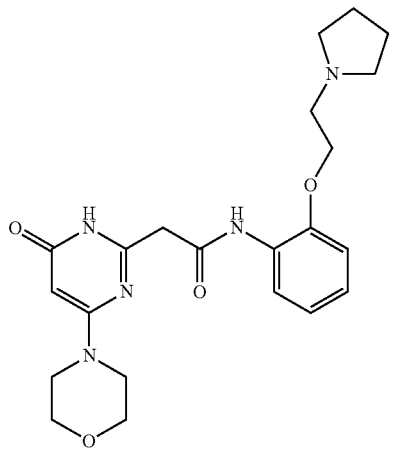 [SMILES: O=C(Cc1nc(N2CCOCC2)cc(=O)[nH]1)Nc1ccccc1OCCN1CCCC1]

2 ml of pyridine, 300 mg of N-[3-(dimethylamino)propyl]-N'-ethylcarbodiimide hydrochloride and 273 mg of 2-(2-pyrrolidin-1-yl-ethoxy)phenylamine are added to a solution of 250 mg of sodium [4-(morpholin-4-yl)-6-oxo-1,6-dihydropyrimidin-2-yl]acetate prepared in stage 2 of example 1, in 2 ml of N,N-dimethylformamide. The reaction mixture is stirred at ambient temperature for 2 hours, and then concentrated under reduced pressure.

After silica column purification, elution being carried out with a mixture of dichloromethane and methanol (95/05 by volume), 45 mg of 2-[4-(morpholin-4-yl)-6-oxo-1,6-dihydropyrimidin-2-yl]-N-{2-[2-(pyrrolidin-1-yl)ethoxy]phenyl}acetamide are obtained in the form of a white solid, the characteristics of which are the following:

$^1$H NMR spectrum (400 MHz): 1.71 (m, 4 H); 2.60 (broad m, 4 H); 2.84 (broad m, 2 H); 3.43 (m, 4 H); 3.61 (m, 4 H); 3.67 (s, 2 H); 4.16 (t, J=5.9 Hz, 2 H); 5.22 (s, 1 H); 6.93 (m, 1 H); 7.03 to 7.13 (m, 2 H); 7.94 (d, J=8.1 Hz, 1 H); 9.46 (broad s, 1 H); 13.33 (very broad m, 1 H)

Mass spectrometry: method A
Retention time Tr (min)=0.39;
[M+H]$^+$: m/z 426; [M–H]$^-$: m/z 428.

EXAMPLE 113

Synthesis of 2-[4-(morpholin-4-yl)-6-oxo-1,6-dihydropyrimidin-2-yl]-N-[2-(pyridin-3-ylmethoxy)phenyl]acetamide

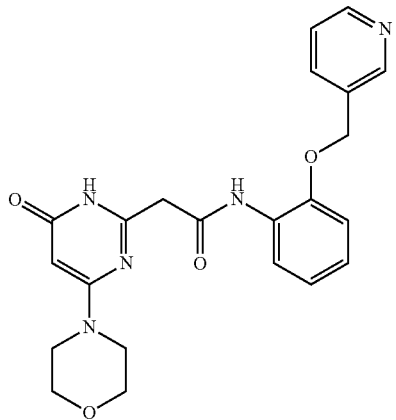 [SMILES: O=C(Cc1nc(N2CCOCC2)cc(=O)[nH]1)Nc1ccccc1OCc1cccnc1]

2 ml of pyridine, 300 mg of N-[3-(dimethylamino)propyl]-M'-ethylcarbodiimide hydrochloride and 366 mg of 2-(pyridin-3-ylmethoxy)phenylamine are added to a solution of 250 mg of sodium [4-(morpholin-4-yl)-6-oxo-1,6-dihydropyrimidin-2-yl]acetate prepared in stage 2 of example 1, in 2 ml of N,N-dimethylformamide. The reaction mixture is stirred at ambient temperature for 20 hours, and then concentrated under reduced pressure. Water and ethyl acetate are added and the resulting mixture is thus stirred for 30 minutes. The precipitate formed is filtered off, and rised with water, ethyl ether and petroleum ether. The solid obtained is dried under vacuum. 150 mg of 2-[4-(morpholin-4-yl)-6-oxo-1,6-dihydropyrimidin-2-yl]-N-[2-(pyridin-3-ylmethoxy)phenyl]acetamide are obtained in the form of a brown solid, the characteristics of which are the following:

$^1$H NMR spectrum (400 MHz): all the signals are broad, with: 3.37 (m, 4 H); 3.55 (m, 4 H); 3.70 (s, 2 H); 5.19 (s, 1 H); 5.26 (s, 2 H); 6.93 (t, J=7.6 Hz, 1 H); 7.07 (t, J=7.6 Hz, 1 H); 7.14 (d, J=7.6 Hz, 1 H); 7.40 (m, 1 H); 7.88 (m, 2 H); 8.53 (d, J=5.2 Hz, 1 H); 8.70 (s, 1 H); 9.47 (s, 1 H); 11.66 (broad m, 1 H)

Mass spectrometry: method A
Retention time Tr (min)=0.44;
[M+H]$^+$: m/z 420; [M–H]$^-$: m/z 422.

EXAMPLE 114

Synthesis of 3-methyl-2-[2-(4-methyl-2,3-dihydro-1H-indol-1-yl)-2-oxoethyl]-6-(morpholin-4-yl)pyrimidin-4(3H)-one

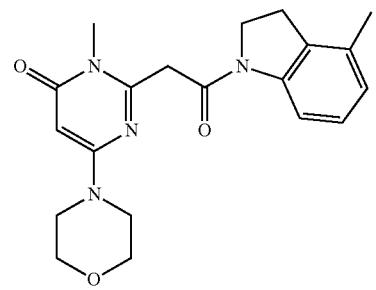 [SMILES: Cc1cccc2c1CCN2C(=O)Cc1nc(N2CCOCC2)cc(=O)n1C]

The product is prepared according to the procedure described in example 68, using 275 mg of sodium [1-methyl-4-(morpholin-4-yl)-6-oxo-1,6-dihydropyrimidin-2-yl]acetate, 339 mg of 4-methylindoline hydrochloride and 254 mg of N-[3-(dimethylamino)propyl]-N'-ethylcarbodiimide hydrochloride in a mixture of 240 μl of pyridine and 4.0 ml of N,N-dimethylformamide. 93 mg of 3-methyl-2-[2-(4-methyl-2,3-dihydro-1H-indol-1-yl)-2-oxoethyl]-6-(morpholin-4-yl)pyrimidin-4(3H)-one are obtained in the form of a pink powder, the characteristics of which are the following:

$^1$H NMR spectrum (400 MHz): 2.21 (s, 3 H); 3.08 (t, J=8.3 Hz, 2 H); 3.29 (s, 3 H); 3.41 (m, 4 H); 3.58 (m, 4 H); 4.10 (s, 2 H); 4.19 (t, J=8.3 Hz, 2 H); 5.36 (s, 1 H); 6.86 (d, J=8.1 Hz, 1 H) 7.07 (t, J=8.1 Hz, 1 H); 7.84 (d, J=8.1 Hz, 1 H)

Mass spectrometry: method A
Retention time Tr (min)=0.75;
[M+H]$^+$: m/z 369; [M–H]$^-$: m/z 367
Melting point (Kofler bench): 239° C.

EXAMPLE 115

Synthesis of 2-[2-(3-dimethylaminomethyl-2,3-dihydroindol-1-yl)-2-oxoethyl]-6-morpholin-4-yl-3H-pyrimidin-4-one

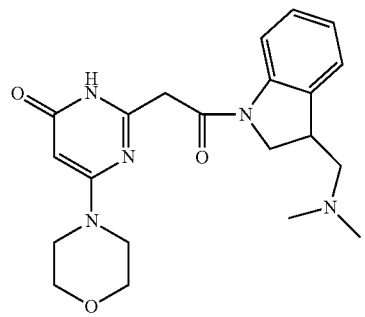 [SMILES: CN(C)CC1CN(C(=O)Cc2nc(N3CCOCC3)cc(=O)[nH]2)c2ccccc21]

Stage 1:

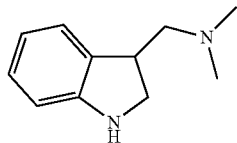

1.1 g of sodium cyanoborohydride is gradually added to a solution of 1 g of gramine in 20 ml of trifluoroacetic acid, under argon, cooled in an ice bath, and stirred for half an hour at 0° C. and then for 2 h at ambient temperature. The reaction medium is plunged into 50 g of ice and alkalinized using 30% sodium hydroxide, and is then extracted with four times 30 ml of ethyl acetate. The organic phase is washed with 20 ml of water, dried over anhydrous magnesium sulphate, filtered, and then concentrated to dryness under reduced pressure. After a silica column purification, eluent: 85/15 v/v $CH_2Cl_2$/MeOH, 660 mg of (2,3-dihydro-1H-indol-3-ylmethyl)dimethylamine are obtained in the form of a yellow solid, the characteristics of which are the following:

Mass spectrometry: method A
Retention time Tr (min)=0.16; mixture with that expected $[M+H]^+$: m/z 177.

Stage 2:

The product is prepared according to the procedure described in example 5, using 220 mg of sodium [4-(morpholin-4-yl)-6-oxo-1,6-dihydropyrimidin-2-yl]acetate, 300 mg of (2,3-dihydro-1H-indol-3-ylmethyl)dimethylamine and 210 mg of N-[3-(dimethylamino)propyl]-N'-ethylcarbodiimide hydrochloride in a mixture of 0.14 ml of pyridine and 2.5 ml of N,N-dimethylformamide. 206 mg of 2-[2-(3-dimethylaminomethyl-2,3-dihydroindol-1-yl)-2-oxoethyl]-6-morpholin-4-yl-3H-pyrimidin-4-one are obtained in the form of a pink solid, the characteristics of which are the following:

$^1$H NMR spectrum (400 MHz): 2.22 (s, 6 H); 2.35 (m, 1 H); 2.45 (m, 1 H); 3.28 (m masked, 1 H); 3.41 (m, 4 H); 3.60 (m, 4 H); 3.76 (m, 2 H); 3.91 (dd, J=5.7 and 9.9 Hz, 1 H); 4.23 (t, J=9.9 Hz, 1 H); 5.21 (s, 1 H); 7.02 (t, J=8.1 Hz, 1 H); 7.19 (t, J=8.1 Hz, 1 H); 7.29 (d, J=8.1 Hz, 1 H); 8.02 (d, J=8.1 Hz, 1 H); 11.61 (broad m, 1 H)

Mass spectrometry: method A
Retention time Tr (min)=0.37;
$[M+H]^+$: m/z 398; $[M+2H]^{2+}$: m/z 199.5 (base peak)
$[M-H]^-$: m/z 396;
Melting point (Kofler bench): 243° C.

EXAMPLE 116

Synthesis of 2-[2-(4-bromo-2,3-dihydro-1H-indol-1-yl)-2-oxoethyl]-3-methyl-6-(morpholin-4-yl)pyrimidin-4(3H)-one

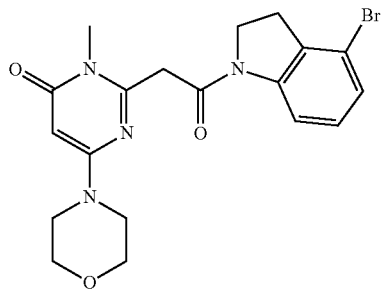 [SMILES: Cn1c(CC(=O)N2CCc3c(Br)cccc32)nc(N2CCOCC2)cc1=O]

The product is prepared according to the procedure described in example 68, using 275 mg of sodium [1-methyl-4-(morpholin-4-yl)-6-oxo-1,6-dihydropyrimidin-2-yl]acetate, 352 mg of 4-bromoindoline hydrochloride and 254 mg of N-[3-(dimethylamino)propyl]-N'-ethylcarbodiimide hydrochloride in a mixture of 201 µl of pyridine and 4.0 ml of N,N-dimethylformamide. 161 mg of 2-[2-(4-bromo-2,3-dihydro-1H-indol-1-yl)-2-oxoethyl]-3-methyl-6-(morpholin-4-yl)pyrimidin-4(3H)-one are obtained in the form of a pink powder, the characteristics of which are the following:

$^1$H NMR spectrum (400 MHz): 3.14 (t, J=8.3 Hz, 2 H); 3.30 (s masked, 3 H); 3.39 (m, 4 H); 3.58 (m, 4 H); 4.11 (s, 2 H); 4.22 (t, J=8.3 Hz, 2 H); 5.36 (s, 1 H); 7.14 (t, J=7.8 Hz, 1 H); 7.24 (d, J=7.8 Hz, 1 H); 8.01 (d, J=7.8 Hz, 1 H)

Mass spectrometry: method A
Retention time Tr (min)=0.83;
$[M+H]^+$: m/z 431; $[M-H]^-$: m/z 433
Melting point (Kofler bench): 226° C.

EXAMPLE 117 AND EXAMPLE 118

Separation of 2-{2-[(2S)-2-methyl-2,3-dihydro-1H-indol-1-yl]-2-oxoethyl}-6-(morpholin-4-yl)pyrimidin-4(3H)-one and 2-{2-[(2R)-2-methyl-2,3-dihydro-1H-indol-1-yl]-2-oxoethyl}-6-(morpholin-4-yl)pyrimidin-4(3H)-one

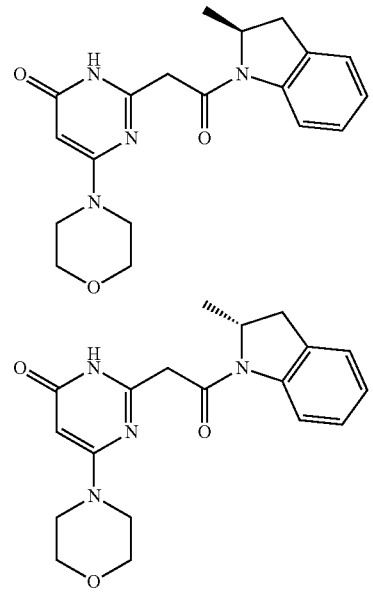

The products were obtained by chiral chromatographic separation of 311 mg of 2-{2-[(2-methyl-2,3-dihydro-1H-indol-1-yl]-2-oxoethyl}-6-(morpholin-4-yl)pyrimidin-4(3H)-one (example 96) on a Chiralpak T304 20 µm chiral column (1080 g, 20 µm, 8/35 cm), eluent: acetonitrile/isopropanol:90/10; flow rate: 185 ml/min. After purification, 160 mg of (+)-2-{2-[(2-methyl-2,3-dihydro-1H-indol-1-yl]-2-oxoethyl}-6-(morpholin-4-yl)pyrimidin-4(3H)-one are obtained, as first enantiomer, in the form of a pink amorphous solid, the characteristics of which are the following:

$^1$H NMR spectrum (400 MHz): for this batch, the signals are broad, with: 1.26 (d, J=6.8 Hz, 3 H); 2.44 (m partially masked, 1 H); 2.69 (d, J=15.2 Hz, 1 H); 3.42 (m, 4 H); 3.60 (m, 4H); 3.72 (d, J=15.7 Hz, 1 H); 3.92 (d, J=15.7 Hz, 1 H); 4.72 (m, 1 H); 5.20 (s, 1 H); 7.04 (t, J=7.8 Hz, 1H); 7.18 (t, J=7.8 Hz, 1 H); 7.28 (d, J=7.8 Hz, 1 H); 7.96 (d, J=7.8 Hz, 1 H); 11.67 (broad m, 1 H)

Mass spectrometry: method A

Retention time Tr (min)=0.70;

[M+H]⁺: m/z 355; [M–H]⁻: m/z 353;

Optical rotation: $\alpha_D$=+65.0°±/−1.3 (c=1.736 mg in 0.5 mL of methanol);

Then the second enantiomer, i.e.: 143 mg of (−)-2-{2-[(2-methyl-2,3-dihydro-1H-indol-1-yl]-2-oxoethyl}-6-(morpholin-4-yl)pyrimidin-4(3H)-one, is obtained in the form of a white amorphous solid, the characteristics of which are the following:

¹H NMR spectrum (400 MHz): for this batch, the signals are broad, with: 1.26 (d, J=6.8 Hz, 3 H); 2.45 (m partially masked, 1 H); 2.69 (m, 1 H); 3.41 (m, 4 H); 3.61 (m, 4 H); 3.72 (d, J=15.7 Hz, 1 H); 3.92 (d, J=15.7 Hz, 1H); 4.70 (m, 1 H); 5.20 (s, 1 H); 7.04 (t, J=7.8 Hz, 1 H); 7.18 (t, J=7.8 Hz, 1 H); 7.28 (d, J=7.8 Hz, 1 H); 7.96 (d, J=7.8 Hz, 1 H); 11.64 (broad m, 1 H)

Mass spectrometry: method A

Retention time Tr (min)=0.70;

[M+H]⁺: m/z 355; [M–H]⁻: m/z 353;

Optical rotation: $\alpha_D$=−72.8°±/−1.2 (c=2.338 mg in 0.5 ml of methanol).

EXAMPLE 119

Synthesis of 3-methyl-2-[2-(3-methyl-2,3-dihydro-1H-indol-1-yl)-2-oxoethyl]-6-(morpholin-4-pyrimidin-4(3H)-one

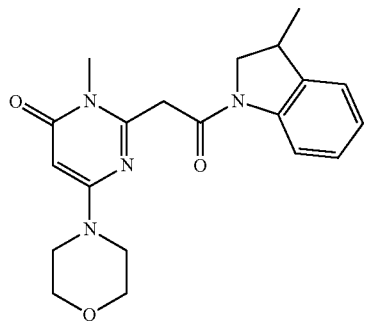 [SMILES: CC1CN(C(=O)Cc2nc(N3CCOCC3)cc(=O)n2C)c2ccccc21]

The product is prepared according to the procedure described in example 68, using 275 mg of sodium [1-methyl-4-(morpholin-4-yl)-6-oxo-1,6-dihydropyrimidin-2-yl]acetate, 254 mg of 3-methylindoline hydrochloride and 254 mg of N-[3-(dimethylamino)propyl]-N'-ethylcarbodiimide hydrochloride in a mixture of 161 µl of pyridine and 4.0 ml of N,N-dimethylformamide. 96 mg of 3-methyl-2-[2-(3-methyl-2,3-dihydro-1H-indol-1-yl)-2-oxoethyl]-6-(morpholin-4-yl)pyrimidin-4(3H)-one are obtained in the form of a pink powder, the characteristics of which are the following:

¹H NMR spectrum (400 MHz): 1.30 (d, J=6.8 Hz, 3 H); 3.32 (s, 3 H); 3.39 (m, 4 H); 3.49 (m, 1 H); 3.57 (m, 4 H); 3.71 (dd, J=6.8 and 10.1 Hz, 1 H); 4.10 (s, 2 H); 4.36 (t, J=10.1 Hz, 1 H); 5.36 (s, 1 H); 7.05 (t, J=8.0 Hz, 1 H); 7.17 (t, J=8.0 Hz, 1 H); 7.28 (d, J=8.0 Hz, 1 H); 8.01 (d, J=8.0 Hz, 1 H)

Mass spectrometry: method A

Retention time Tr (min)=0.77;

[M+H]⁺: m/z 369; [M–H]⁻: m/z 367

Melting point (Kofler bench): 225° C.

EXAMPLE 120

Synthesis of 2-{2-[2-(methoxymethyl)-2,3-dihydro-1H-indol-1-yl]-2-oxoethyl}-6-(morpholin-4-yl)pyrimidin-4(3H)-one

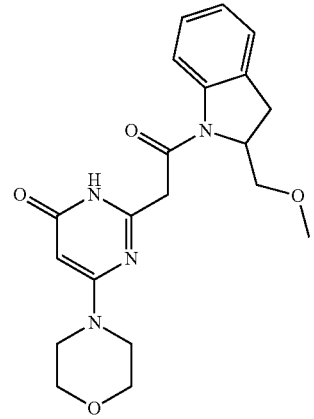 [SMILES: COCC1Cc2ccccc2N1C(=O)Cc1nc(N2CCOCC2)cc(=O)[nH]1]

The product is prepared according to the procedure described in example 5, using 261 mg of sodium [4-(morpholin-4-yl)-6-oxo-1,6-dihydropyrimidin-2-yl]acetate, 326 mg of 2-(methoxymethyl)indoline and 249 mg of N-[3-(dimethylamino)propyl]-N'-ethylcarbodiimide hydrochloride in a mixture of 162 µl of pyridine and 4.0 ml of N,N-dimethylformamide. 143 mg of 2-{2-[2-(methoxymethyl)-2,3-dihydro-1H-indol-1-yl]-2-oxoethyl}-6-(morpholin-4-pyrimidin-4(3H)-one are obtained in the form of a beige powder, the characteristics of which are the following:

¹H NMR spectrum (400 MHz): 2.84 (d, J=16.4 Hz, 1 H); 3.26 (s, 3 H); 3.34 to 3.46 (m, 7 H); 3.60 (m, 4 H); 3.79 (d, J=15.6 Hz, 1 H); 4.00 (d, J=15.6 Hz, 1 H); 4.80 (m, 1 H); 5.20 (s, 1 H); 7.03 (t, J=7.8 Hz, 1 H); 7.17 (t, J=7.8 Hz, 1 H); 7.27 (d, J=7.8 Hz, 1 H); 7.93 (d, J=7.8 Hz, 1 H); 11.66 (broad s, 1 H)

Mass spectrometry: method B

Retention time Tr (min)=3.26;

[M+H]⁺: m/z 385; [M–H]⁻: m/z 383

Melting point (Kofler bench): 112-115° C.

EXAMPLE 121

Synthesis of 2-[2-(4-ethoxy-2,3-dihydro-1H-indol-1-yl)-2-oxoethyl]-6-(morpholin-4-yl)pyrimidin-4(3H)-one

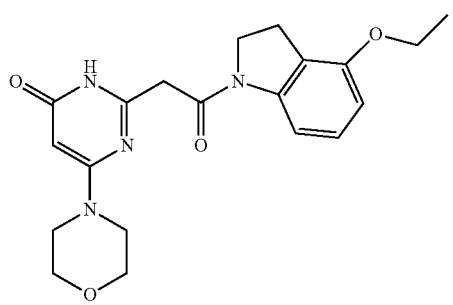 [SMILES: CCOc1cccc2c1CCN2C(=O)Cc1nc(N2CCOCC2)cc(=O)[nH]1]

The product is prepared according to the procedure described in example 5, using 261 mg of sodium [4-(morpholin-4-yl)-6-oxo-1,6-dihydropyrimidin-2-yl]acetate, 163 mg of 4-(ethoxy)indoline and 249 mg of N-[3-(dimethylamino)

propyl]-N'-ethylcarbodiimide hydrochloride in a mixture of 162 μl of pyridine and 4.0 ml of N,N-dimethylformamide. 260 mg of 2-[2-(4-ethoxy-2,3-dihydro-1H-indol-1-yl)-2-oxoethyl]-6-(morpholin-4-yl)pyrimidin-4(3H)-one are obtained in the form of a white powder, the characteristics of which are the following:

$^1$H NMR spectrum (400 MHz): 1.33 (t, J=6.8 Hz, 3 H); 3.03 (t, J=8.6 Hz, 2 H); 3.42 (m, 4 H); 3.61 (m, 4 H); 3.73 (s, 2 H); 4.06 (q, J=6.8 Hz, 2 H); 4.14 (t, J=8.6 Hz, 2 H); 5.20 (s, 1 H); 6.68 (d, J=8.1 Hz, 1 H); 7.12 (t, J=8.1 Hz, 1 H); 7.63 (d, J=8.1 Hz, 1 H); 11.61 (broad s, 1 H)

Mass spectrometry: method B

Retention time Tr (min)=3.48;

[M+H]$^+$: m/z 385; [M−H]$^−$: m/z 383

Melting point (Kofler bench): 257° C.

EXAMPLE 122

Synthesis of 1-{[4-(morpholin-4-yl)-6-oxo-1,6-dihydropyrimidin-2-yl]acetyl}-2,3-dihydro-1H-indole-2-carboxamide

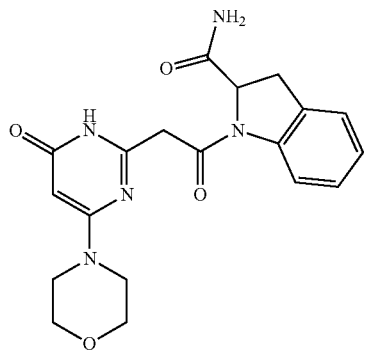 [SMILES: NC(=O)C1Cc2ccccc2N1C(=O)Cc1nc(N2CCOCC2)cc(=O)[nH]1]

The product is prepared according to the procedure described in example 5, using 261 mg of sodium [4-(morpholin-4-yl)-6-oxo-1,6-dihydropyrimidin-2-yl]acetate, 324 mg of 2-carboxamidoindoline and 249 mg of N-[3-(dimethylamino)propyl]-N'-ethylcarbodiimide hydrochloride in a mixture of 162 μl of pyridine and 4.0 ml of N,N-dimethylformamide. 93 mg of 1-{[4-(morpholin-4-yl)-6-oxo-1,6-dihydropyrimidin-2-yl]acetyl}-2,3-dihydro-1H-indole-2-carboxamide are obtained in the form of a white powder, the characteristics of which are the following:

$^1$H NMR spectrum (400 MHz): 3.11 (d, J=16.9 Hz, 1 H); 3.36 to 3.47 (m, 5 H); 3.54 to 3.63 (m, 5 H); 3.77 (d, J=15.7 Hz, 1 H); 5.07 (dd, J=3.8 and 9.1 Hz, 1 H); 5.20 (s, 1 H); 7.02 (t, J=7.8 Hz, 1 H); 7.18 (t, J=7.8 Hz, 1 H); 7.23 (d, J=7.8 Hz, 1 H); 7.36 (broad s, 1 H); 7.76 (broad s, 1 H); 8.01 (d, J=7.8 Hz, 1 H); 11.59 (broad m, 1 H)

Mass spectrometry: method A

Retention time Tr (min)=0.50;

[M+H]$^+$: m/z 384; [M−H]$^−$: m/z 382

Melting point (Kofler bench): above 260° C.

EXAMPLE 123

Synthesis of 3-methyl-2-[2-(2-methyl-2,3-dihydro-1H-indol-1-yl)-2-oxoethyl]-6-(morpholin-4-yl)pyrimidin-4(3H)-one

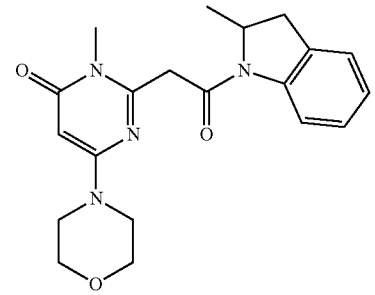 [SMILES: CC1Cc2ccccc2N1C(=O)Cc1nc(N2CCOCC2)cc(=O)n1C]

The product is prepared according to the procedure described in example 68, using 550 mg of sodium [1-methyl-4-(morpholin-4-yl)-6-oxo-1,6-dihydropyrimidin-2-yl]acetate, 400 mg of 2-methylindoline and 500 mg of N-[3-(dimethylamino)propyl]-N'-ethylcarbodiimide hydrochloride in a mixture of 320 μl of pyridine and 8.0 ml of N,N-dimethylformamide. 37 mg of 3-methyl-2-[2-(2-methyl-2,3-dihydro-1H-indol-1-yl)-2-oxoethyl]-6-(morpholin-4-yl)pyrimidin-4(3H)-one are obtained in the form of a pink powder, the characteristics of which are the following:

$^1$H NMR spectrum (400 MHz): 1.28 (d, J=6.8 Hz, 3 H); 2.70 (d, J=15.9 Hz, 1 H); 3.23 to 3.30 (s masked, 3 H); 3.40 (m, 5 H); 3.60 (m, 4 H); 4.02 (d, J=16.9 Hz, 1 H); 4.29 (d, J=16.9 Hz, 1 H); 4.70 (m, 1 H); 5.36 (s, 1 H); 7.05 (t, J=7.8 Hz, 1 H); 7.18 (t, J=7.8 Hz, 1 H); 7.29 (d, J=7.8 Hz, 1 H); 7.95 (d, J=7.8 Hz, 1 H)

Mass spectrometry: method A

Retention time Tr (min)=0.75;

[M+H]$^+$: m/z 369; [M−H]$^−$: m/z 367

Melting point (Kofler bench): 148° C.

EXAMPLE 124

Synthesis of 2-[2-(6-fluoro-2,3-dihydro-1H-indol-1-yl)-2-oxoethyl]-3-methyl-6-(morpholin-4-yl)pyrimidin-4(3H)-one

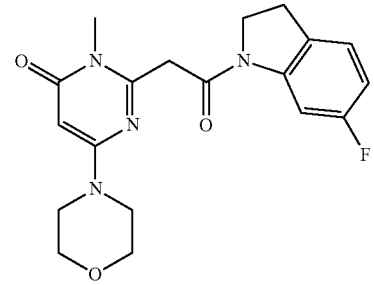 [SMILES: Cn1c(CC(=O)N2CCc3ccc(F)cc32)nc(N2CCOCC2)cc1=O]

The product is prepared according to the procedure described in example 68, using 275 mg of sodium [1-methyl-4-(morpholin-4-yl)-6-oxo-1,6-dihydropyrimidin-2-yl]acetate, 205 mg of 6-fluoroindoline and 254 mg of N-[3-(dimethylamino)propyl]-N'-ethylcarbodiimide hydrochloride in a mixture of 161 μl of pyridine and 4.0 ml of N,N-dimethylformamide. 140 mg of 2-[2-(6-fluoro-2,3-dihydro-1H-indol-1-yl)-2-oxoethyl]-3-methyl-6-(morpholin-4-yl)pyrimidin-4

(3H)-one are obtained in the form of a very pale pink powder, the characteristics of which are the following:

$^1$H NMR spectrum (400 MHz): 3.14 (t, J=8.2 Hz, 2 H); 3.25 to 3.45 (m partially masked, 7 H); 3.58 (m, 4 H); 4.11 (s, 2 H); 4.22 (t, J=8.2 Hz, 2 H); 5.36 (s, 1 H); 6.84 (t, J=8.7 Hz, 1 H); 7.26 (m, 1 H); 7.77 (broad d, J=10.3 Hz, 1 H)

Mass spectrometry: method A
Retention time Tr (min)=0.73;
[M+H]$^+$: m/z 373; m/z 371
Melting point (Kofler bench): 223° C.

EXAMPLE 125 AND EXAMPLE 126

Separation of 2-{2-[(3S)-3-methyl-2,3-dihydro-1H-indol-1-yl]-2-oxoethyl}-6-(morpholin-4-yl)pyrimidin-4(3H)-one and 2-{2-[(3R)-3-methyl-2,3-dihydro-1H-indol-1-yl]-2-oxoethyl}-6-(morpholin-4-yl) pyrimidin-4(3H)-one

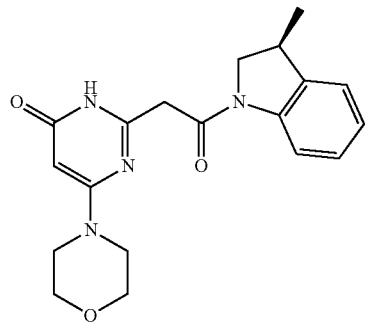

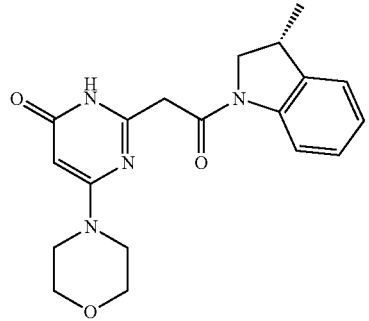

The products were obtained by chiral chromatographic separation of 369 mg of 2-{2-[3-methyl-2,3-dihydro-1H-indol-1-yl]-2-oxoethyl}-6-(morpholin-4-yl)pyrimidin-4(3H)-one (example 101) on a Chiralpak T304 20 μm chiral column (1100 g, 20 μm, 8/35 cm), eluent: heptane/ethanol/methanol: 25/40/35; flow rate: 200 ml/min. After purification, 168 mg of (+)-2-{2-[3-methyl-2,3-dihydro-1H-indol-1-yl]-2-oxoethyl}-6-(morpholin-4-yl)pyrimidin-4(3H)-one are obtained, as first enantiomer, in the form of a white powder, the characteristics of which are the following:

$^1$H NMR spectrum (400 MHz): 1.29 (d, J=6.8 Hz, 3 H); 3.42 (m, 4 H); 3.49 (m, 1H); 3.60 (m, 4 H); 3.68 (dd, J=6.6 and 10.1 Hz, 1 H); 3.75 (s, 2 H); 4.33 (t, J=10.1 Hz, 1 H); 5.21 (s, 1 H); 7.04 (t, J=8.0 Hz, 1 H); 7.18 (t, J=8.0 Hz, 1H); 7.27 (d, J=8.0 Hz, 1 H); 8.01 (d, J=8.0 Hz, 1H); 11.61 (broad m, 1 H)

Mass spectrometry: method A
Retention time Tr (min)=0.72;
[M+H]$^+$: m/z 355; [M−H]$^-$: m/z 353;
Optical rotation: α$_D$=+17.1°±/−0.8 (c=1.656 mg in 0.5 ml of DMSO);

Then the second enantiomer, i.e.: 164 mg of (−)-2-{2-[3-methyl-2,3-dihydro-1H-indol-1-yl]-2-oxoethyl}-6-(morpholin-4-yl)pyrimidin-4(3H)-one, is obtained in the form of a white powder, the characteristics of which are the following:

$^1$H NMR spectrum (400 MHz): 1.29 (d, J=6.8 Hz, 3 H); 3.41 (m, 4 H); 3.49 (m, 1H); 3.60 (m, 4 H); 3.68 (dd, J=6.6 and 10.3 Hz, 1 H); 3.75 (s, 2 H); 4.33 (t, J=10.3 Hz, 1 H); 5.21 (s, 1 H); 7.05 (t, J=8.0 Hz, 1 H); 7.18 (t, J=8.0 Hz, 1H); 7.27 (d, J=8.0 Hz, 1 H); 8.01 (d, J=8.0 Hz, 1 H); 11.60 (broad m, 1 H)

Mass spectrometry: method A
Retention time Tr (min)=0.72;
[M+H]$^+$: m/z 355; [M−H]$^-$: m/z 353;
Optical rotation: α$_D$=−13.0° (c=1.386 mg in 0.5 ml of DMSO).

EXAMPLE 127

Synthesis of 2-[2-(5,6-difluoro-2,3-dihydro-1H-indol-1-yl)-2-oxoethyl]-3-methyl-6-(morpholin-4-yl) pyrimidin-4(3H)-one

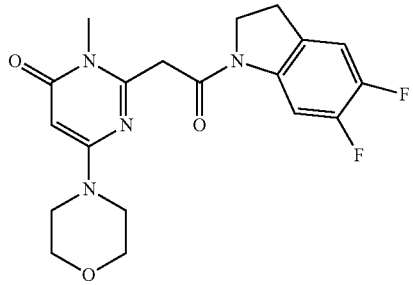 [SMILES: Cn1c(CC(=O)N2CCc3cc(F)c(F)cc32)nc(N2CCOCC2)cc1=O]

The product is prepared according to the procedure described in example 68, using 275 mg of sodium [1-methyl-4-(morpholin-4-yl)-6-oxo-1,6-dihydropyrimidin-2-yl]acetate, 232 mg of 5,6-difluoroindoline and 254 mg of N-[3-(dimethylamino)propyl]-N'-ethylcarbodiimide hydrochloride in a mixture of 161 μl of pyridine and 4.0 ml of N,N-dimethylformamide. 167 mg of 2-[2-(5,6-difluoro-2,3-dihydro-1H-indol-1-yl)-2-oxoethyl]-3-methyl-6-(morpholin-4-yl)pyrimidin-4(3H)-one are obtained in the form of an off-white powder, the characteristics of which are the following:

$^1$H NMR spectrum (400 MHz): 3.16 (t, J=8.6 Hz, 2 H); 3.31 (s, 3 H); 3.39 (m, 4 H); 3.58 (m, 4 H); 4.11 (s, 2 H); 4.22 (t, J=8.6 Hz, 2 H); 5.36 (s, 1H); 7.37 (dd, J=8.9 and 10.3 Hz, 1 H); 7.95 (dd, J=7.5 and 12.1 Hz, 1 H)

Mass spectrometry: method A
Retention time Tr (min)=0.76;
[M+H]$^+$: m/z 391; [M−H]$^-$: m/z 389
Melting point (Kofler bench): 250° C.

EXAMPLE 128

Synthesis of 2-[2-(4,5-difluoro-2,3-dihydro-1H-indol-1-yl)-2-oxoethyl]-3-methyl-6-(morpholin-4-yl)pyrimidin-4(3H)-one

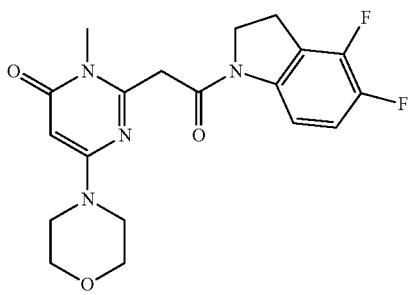

The product is prepared according to the procedure described in example 68, using 275 mg of sodium [1-methyl-4-(morpholin-4-yl)-6-oxo-1,6-dihydropyrimidin-2-yl]acetate, 287 mg of 4,5-difluoroindoline hydrochloride and 254 mg of N-[3-(dimethylamino)propyl]-N'-ethylcarbodiimide hydrochloride in a mixture of 241 µl of pyridine and 4.0 ml of N,N-dimethylformamide. 155 mg of 2-[2-(4,5-difluoro-2,3-dihydro-1H-indol-1-yl)-2-oxoethyl]-3-methyl-6-(morpholin-4-yl)pyrimidin-4(3H)-one are obtained in the form of a brick-red coloured powder, the characteristics of which are the following:

$^1$H NMR spectrum (400 MHz): 3.25 (t, J=8.4 Hz, 2 H); 3.31 (s, 3 H); 3.39 (m, 4 H); 3.58 (m, 4 H); 4.11 (s, 2 H); 4.27 (t, J=8.4 Hz, 2 H); 5.36 (s, 1 H); 7.23 (m, 1 H); 7.79 (dd, J=4.3 and 8.9 Hz, 1 H)

Mass spectrometry: method A
Retention time Tr (min)=0.77;
[M+H]$^+$: m/z 391; [M-H]$^-$: m/z 389
Melting point (Kofler bench): above 260° C.

EXAMPLE 129

Synthesis of 2-[2-(1,3-dihydro-2H-isoindol-2-yl)-2-oxoethyl]-6-(morpholin-4-yl)pyrimidin-4(3H)-one

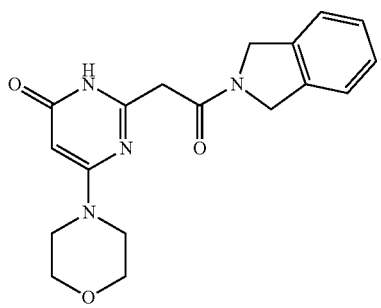 [SMILES: O=C(Cc1nc(N2CCOCC2)cc(=O)[nH]1)N1Cc2ccccc2C1]

The product is prepared according to the procedure described in example 70, using 250 mg of isoindoline, 267 mg of ethyl [4-(morpholin-4-yl)-6-oxo-1,6-dihydropyrimidin-2-yl]acetate prepared in stage 1 of example 1 and 1.15 ml of a 2M solution of trimethylaluminium, in a mixture of 20 ml of toluene and 10 ml of tetrahydrofuran. 80 mg of 2-[2-(1,3-dihydro-2H-isoindol-2-yl)-2-oxoethyl]-6-(morpholin-4-yl)pyrimidin-4(3H)-one are thus obtained in the form of a white powder, the characteristics of which are the following:

$^1$H NMR spectrum (400 MHz): 3.39 (m, 4 H); 3.59 (m, 4 H); 3.67 (s, 2 H); 4.67 (s, 2 H); 4.90 (s, 2 H); 5.19 (s, 1 H); 7.26 to 7.42 (m, 4 H); 11.60 (broad m, 1 H)

Mass spectrometry: method A
Retention time Tr (min)=0.60;
[M+H]$^+$: m/z 341; [M-H]$^-$: m/z 339
Melting point (Kofler bench): above 260° C.

EXAMPLE 130

Synthesis of N-(1-benzothiophen-4-yl)-2-[1-methyl-4-(morpholin-4-yl)-6-oxo-1,6-dihydropyrimidin-2-yl]acetamide

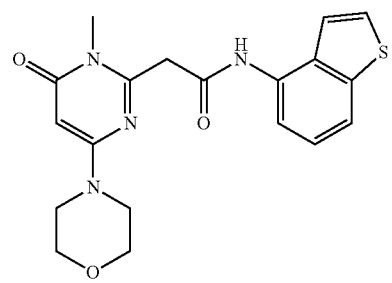

The product is prepared according to the procedure described in example 86, using 551 mg of sodium [1-methyl-4-(morpholin-4-yl)-6-oxo-1,6-dihydropyrimidin-2-yl]acetate, 328 mg of benzo[b]thiophen-4-ylamine and 498 mg of N-[3-(dimethylamino)propyl]-N'-ethylcarbodiimide hydrochloride in a mixture of 324 µl of pyridine and 8.0 ml of N,N-dimethylformamide. 110 mg of N-(1-benzothiophen-4-yl)-2-[1-methyl-4-(morpholin-4-yl)-6-oxo-1,6-dihydropyrimidin-2-yl]acetamide are obtained in the form of a white powder, the characteristics of which are the following:

$^1$H NMR spectrum (400 MHz): 3.38 (s, 3 H); 3.41 (m, 4 H); 3.57 (m, 4H); 4.05 (s, 2 H); 5.36 (s, 1 H); 7.34 (t, J=7.9 Hz, 1 H); 7.63 (d, J=5.6 Hz, 1 H); 7.72 to 7.81 (m, 3 H); 10.14 (broad m, 1 H)

Mass spectrometry: method A
Retention time Tr (min)=0.71;
[M+H]$^+$: m/z 385; [M-H]$^-$: m/z 383
Melting point (Kofler bench): 254° C.

EXAMPLE 131

Synthesis of 2-[2-(5-chloro-3,4-dihydroquinolin-1 (2H)-yl)-2-oxoethyl]-6-(morpholin-4-yl)pyrimidin-4 (3H)-one

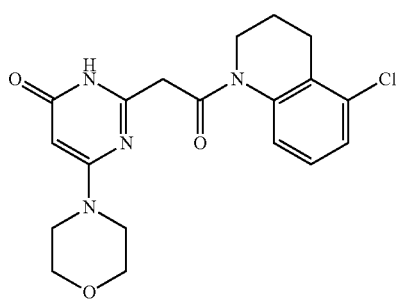 [SMILES: O=C(Cc1nc(N2CCOCC2)cc(=O)[nH]1)N1CCCc2c(Cl)cccc21]

The product is prepared according to the procedure described in example 5, using 261 mg of sodium [4-(morpholin-4-yl)-6-oxo-1,6-dihydropyrimidin-2-yl]acetate, 184 mg of 5-chloro-1,2,3,4-tetrahydroquinoline (can be prepared according to WO 2004/116388), and 249 mg of N-[3-(dimethylamino)propyl]-N'-ethylcarbodiimide hydrochloride in a mixture of 162 µl of pyridine and 4.0 ml of N,N-dimethylformamide. 141 mg of 2-[2-(5-chloro-3,4-dihydroquinolin-1 (2H)-yl)-2-oxoethyl]-6-(morpholin-4-yl)pyrimidin-4(3H)-one are obtained in the form of a white powder, the characteristics of which are the following:

$^1$H NMR spectrum (400 MHz): 1.96 (m, 2 H); 2.77 (t, J=6.8 Hz, 2 H); 3.41 (m, 4H); 3.61 (m, 4 H); 3.70 (t, J=6.8 Hz, 2 H); 3.79 (s, 2 H); 5.16 (s, 1 H); 7.21 (t, J=8.0 Hz, 1 H); 7.27 (d, J=8.0 Hz, 1 H); 7.55 (broad d, J=8.0 Hz, 1 H); 11.57 (broad m, 1 H)

Mass spectrometry: method A
Retention time Tr (min)=0.78;
[M+H]$^+$: m/z 389; [M−H]$^-$: m/z 387
Melting point (Kofler bench): 238° C.

EXAMPLE 132

Synthesis of 2-{2-[4-(hydroxymethyl)-2,3-dihydro-1H-indol-1-yl]-2-oxoethyl}-6-(morpholin-4-yl)pyrimidin-4(3H)-one

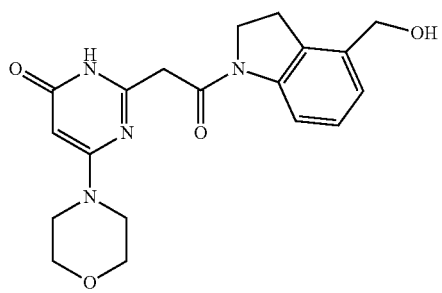 [SMILES: O=C(Cc1nc(N2CCOCC2)cc(=O)[nH]1)N1CCc2c(CO)cccc21]

The product is prepared according to the procedure described in example 5, using 261 mg of sodium [4-(morpholin-4-yl)-6-oxo-1,6-dihydropyrimidin-2-yl]acetate, 173 mg of 4-(hydroxymethyl)indoline and 254 mg of N-[3-(dimethylamino)propyl]-N'-ethylcarbodiimide hydrochloride in a mixture of 161 µl of pyridine and 4.0 ml of N,N-dimethylformamide. 288 mg of 2-{2-[4-(hydroxymethyl)-2,3-dihydro-1H-indol-1-yl]-2-oxoethyl}-6-(morpholin-4-yl)pyrimidin-4 (3H)-one are obtained in the form of a pink powder, the characteristics of which are the following:

$^1$H NMR spectrum (400 MHz): 3.12 (t, J=8.3 Hz, 2 H); 3.42 (m, 4 H); 3.59 (m, 4H); 3.75 (s, 2 H); 4.15 (t, J=8.3 Hz, 2 H); 4.46 (d, J=5.4 Hz, 2 H); 5.10 (t, J=5.4 Hz, 1 H); 5.21 (s, 1 H); 7.04 (d, J=7.8 Hz, 1 H); 7.15 (t, J=7.8 Hz, 1 H); 7.92 (d, J=7.8 Hz, 1 H); 11.62 (broad s, 1 H)

Mass spectrometry: method B
Retention time Tr (min)=2.48;
[M+H]$^+$: m/z 371; [M−H]$^-$: m/z 369
Melting point (Kofler bench): 234° C.

EXAMPLE 133

Synthesis of N-[4-fluoro-2-(piperidin-4-ylmethoxy) phenyl]-2-[4-(morpholin-4-yl)-6-oxo-1,6-dihydropyrimidin-2-yl]acetamide

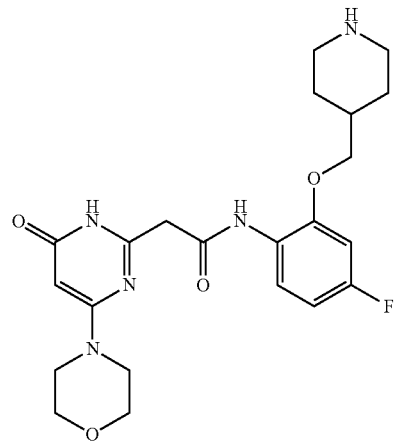 [SMILES: O=C(Cc1nc(N2CCOCC2)cc(=O)[nH]1)Nc1ccc(F)cc1OCC1CCNCC1]

Stage 1:

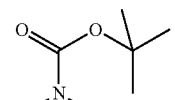

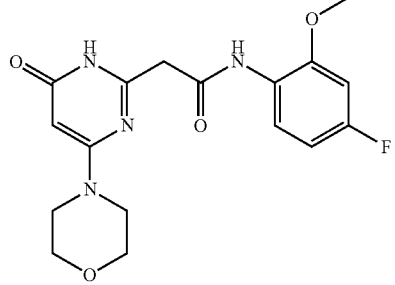

3 ml of pyridine, 500 mg of N-[3-(dimethylamino)propyl]-N'-ethylcarbodiimide hydrochloride and 930 mg of 4-(2- amino-5-fluorophenoxymethyl)piperidine-1-carboxylic acid tert-butyl ester are added to a solution of 500 mg of sodium [4-(morpholin-4-yl)-6-oxo-1,6-dihydropyrimidin-2-yl]acetate prepared in stage 2 of example 1, in 3 ml of N,N-dimethylformamide. The reaction mixture is stirred at ambient temperature for 2 days, and then concentrated under reduced pressure. After silica column purification, elution being carried out with a mixture of dichloromethane and methanol (95/05 by volume), 225 mg of 4-{5-fluoro-2-[2-(4-morpholin-4-yl-6-oxo-1,6-dihydropyrimidin-2-yl)acetylamino]phenoxymethyl}piperidine-1-carboxylic acid tert-butyl ester are obtained in the form of a purplish solid, the characteristics of which are the following:

Mass spectrometry: method B
Retention time Tr (min)=4.02;
[M+H]⁺: m/z 544; [M−H]⁻: m/z 546.

Stage 2:

1.5 ml of 4M hydrochloric acid in dioxane are added to a solution of 223 mg of 4-{5-fluoro-2-[2-(4-morpholin-4-yl-6-oxo-1,6-dihydropyrimidin-2-yl)acetylamino]phenoxymethyl}piperidine-1-carboxylic acid tert-butyl ester in 6 ml of ethanol. After stirring at ambient temperature for 20 h, the reaction medium is concentrated under reduced pressure, taken up with a solution of aqueous ammonia in methanol, and then again concentrated to dryness. After purification by silica column chromatography, eluent: 90/10 CH₂Cl₂/MeOH, 65 mg of N-[4-fluoro-2-(piperidin-4-ylmethoxy)phenyl]-2-[4-(morpholin-4-yl)-6-oxo-1,6-dihydropyrimidin-2-yl]acetamide are obtained, the characteristics of which are the following:

¹H NMR spectrum (400 MHz): 1.52 (m, 2 H); 1.89 (m, 2 H); 2.06 (m, 1 H); 2.86 (m, 2 H); 3.25 (m partially masked, 2 H); 3.43 (m, 4 H); 3.62 (m, 4 H); 3.71 (s, 2 H); 3.92 (d, J=6.4 Hz, 2 H); 5.22 (s, 1 H); 6.74 (dt, J=2.7 and 8.8 Hz, 1 H); 7.00 (dd, J=2.7 and 11.0 Hz, 1 H); 7.75 (dd, J=6.6 and 8.8 Hz, 1 H); 7.87 (very broad m, 2 H); 9.22 (broad s, 1 H)

Mass spectrometry: method A
Retention time Tr (min)=0.48;
[M+H]⁺: m/z 444; [M−H]⁻: m/z 446.

EXAMPLE 134

2-[2-(5-Chloro-2,3-dihydroindol-1-yl)-2-oxoethyl]-6-morpholin-4-yl-3H-pyrimidin-4-one

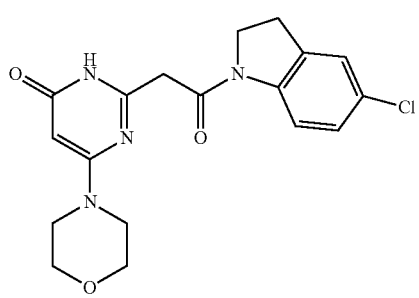 [SMILES: O=C(Cc1nc(N2CCOCC2)cc(=O)[nH]1)N1CCc2cc(Cl)ccc21]

The product is prepared according to the procedure described in example 5, using 261 mg of sodium [4-(morpholin-4-yl)-6-oxo-1,6-dihydropyrimidin-2-yl]acetate, 307 mg of 5-chloroindoline and 254 mg of N-[3-(dimethylamino)propyl]-N'-ethylcarbodiimide hydrochloride in a mixture of 0.16 ml of pyridine and 4 ml of dimethylformamide. 255 mg of 2-[2-(5-chloro-2,3-dihydroindol-1-yl)-2-oxoethyl]-6-morpholin-4-yl-3H-pyrimidin-4-one are obtained in the form of a white powder, the characteristics of which are the following:

¹H NMR spectrum (400 MHz, δ in ppm, DMSO-d₆): 3.18 (t, J=8.3 Hz, 2H); 3.41 (m, 4 H); 3.60 (m, 4H); 3.75 (s, 2 H); 4.16 (t, J=8.3 Hz, 2 H); 5.20 (s, 1 H); 7.21 (broad d, J=8.6 Hz, 1 H); 7.32 (broad s, 1 H); 7.99 (d, J=8.6 Hz, 1 H); 11.61 (broad m, 1H).

Mass spectrometry: method B
Retention time Tr (min)=3.42;
[M−H]⁻: m/z 373
Melting point (Kofler bench): above 260° C.

EXAMPLE 135

2-[2-(4-Bromo-2,3-dihydroindol-1-yl)-2-oxoethyl]-6-morpholin-4-yl-3H-pyrimidin-4-one

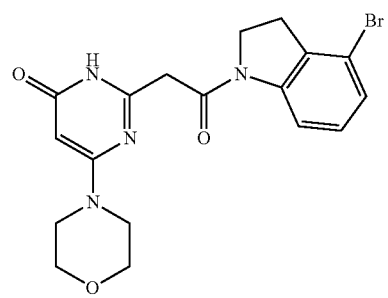 [SMILES: O=C(Cc1nc(N2CCOCC2)cc(=O)[nH]1)N1CCc2c(Br)cccc21]

The product is prepared according to the procedure described in example 5, using 261 mg of sodium [4-(morpholin-4-yl)-6-oxo-1,6-dihydropyrimidin-2-yl]acetate, 402 mg of 4-bromoindoline and 254 mg of N-[3-(dimethylamino)propyl]-N'-ethylcarbodiimide hydrochloride in a mixture of 0.16 ml of pyridine and 4 ml of dimethylformamide. 303 mg of 2-[2-(4-bromo-2,3-dihydroindol-1-yl)-2-oxoethyl]-6-morpholin-4-yl-3H-pyrimidin-4-one are obtained in the form of a white powder, the characteristics of which are the following:

¹H NMR spectrum (400 MHz, δ in ppm, DMSO-d₆): 3.14 (t, J=8.4 Hz, 2H); 3.41 (m, 4 H); 3.61 (m, 4H); 3.76 (s, 2 H); 4.19 (t, J=8.4 Hz, 2 H); 5.21 (s, 1 H); 7.14 (t, J=8.1 Hz, 1 H); 7.23 (broad d, J=8.1 Hz, 1 H); 8.01 (broad d, J=8.1 Hz, 1 H); 11.62 (broad m, 1 H).

Mass spectrometry: method A
Retention time Tr (min)=0.88;
[M+H]⁺: m/z 419; [M−H]⁻: m/z 417
Melting point (Kofler bench): 219° C.

EXAMPLE 136 AND EXAMPLE 137

Separation of 2-(2-{(3S)-3-[(dimethylamino)methyl]-2,3-dihydro-1H-indol-1-yl}-2-oxoethyl)-6-(morpholin-4-yl)pyrimidin-4(3H)-one and 2-(2-{(3R)-3-[(dimethylamino)methyl]-2,3-dihydro-1H-indol-1-yl}-2-oxoethyl)-6-(morpholin-4-yl)pyrimidin-4(3H)-one

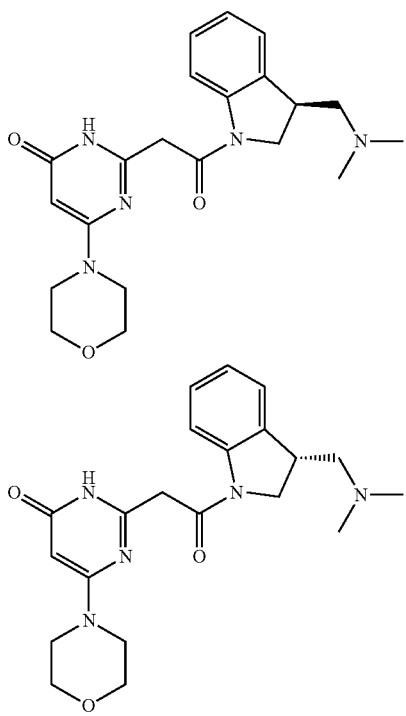

The products were obtained by chiral chromatographic separation of 500 mg of 2-[2-(3-dimethylaminomethyl-2,3-dihydroindol-1-yl)-2-oxoethyl]-6-morpholin-4-yl-3H-pyrimidin-4-one (example 115) on a Chiralpak AD 20 µm chiral column (batch CFB003) (1200 g, 20 µm, 80/35 mm), eluent: heptane/methanol/ethanol:50/20/30; flow rate: 160 all/min. After purification, 226 mg of (+)-2-[2-(3-dimethylaminomethyl-2,3-dihydroindol-1-yl)-2-oxoethyl]-6-morpholin-4-yl-3H-pyrimidin-4-one are obtained, as first enantiomer, in the form of a yellow solid, the characteristics of which are the following:

$^1$H NMR spectrum (400 MHz): 2.22 (s, 6 H); 2.36 (dd, J=10.0 and 11.7 Hz, 1 H); 2.46 (dd, J=5.4 and 11.7 Hz, 1 H); 3.41 (m, 4 H); 3.60 (m, 5 H); 3.76 (m, 2 H); 3.91 (dd, J=5.7 and 10.0 Hz, 1 H); 4.23 (t, J=10.0 Hz, 1 H); 5.21 (s, 1 H); 7.02 (t, J=7.8 Hz, 1 H); 7.19 (t, J=7.8 Hz, 1 H); 7.29 (d, J=7.8 Hz, 1 H); 8.03 (d, J=7.8 Hz, 1 H); 11.61 (broad m, 1 H)

Mass spectrometry: method A
Retention time Tr (min)=0.40;
[M+H]$^+$: m/z 398; [M−H]$^-$: m/z 396
Melting point (Kofler bench): 246° C.
Optical rotation: 1.830 mg in 1 ml of DMSO positive sign.

Then the second enantiomer, i.e.: 239 mg of (−)-2-[2-(3-dimethylaminomethyl-2,3-dihydroindol-1-yl)-2-oxoethyl]-6-morpholin-4-yl-3H-pyrimidin-4-one, is obtained in the form of a yellow solid, the characteristics of which are the following:

$^1$H NMR spectrum (400 MHz): 2.22 (s, 6 H); 2.36 (dd, J=10.0 and 11.7 Hz, 1 H); 2.46 (dd, J=5.4 and 11.7 Hz, 1 H); 3.41 (m, 4 H); 3.60 (m, 5 H); 3.76 (m, 2 H); 3.91 (dd, J=5.7 and 10.0 Hz, 1 H); 4.23 (t, J=10.0 Hz, 1 H); 5.21 (s, 1 H); 7.02 (t, J=7.8 Hz, 1 H); 7.19 (t, J=7.8 Hz, 1 H); 7.29 (d, J=7.8 Hz, 1 H); 8.03 (d, J=7.8 Hz, 1 H); 11.62 (broad m, 1 H)

Mass spectrometry: method A
Retention time Tr (min)=0.40;
[M+H]$^+$: m/z 398; [M−H]$^-$: m/z 396
Melting point (Kofler bench): 256° C.
Optical rotation: 1.721 mg in 1 ml of DMSO negative sign.

EXAMPLE 138

Synthesis of N-[4-fluoro-2-(2-methoxyethoxy)phenyl]-2-[4-(morpholin-4-yl)-6-oxo-1,6-dihydropyrimidin-2-yl]acetamide

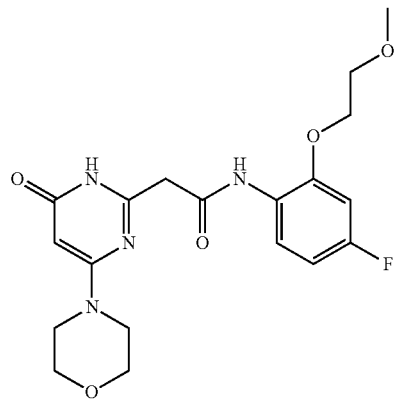 [SMILES: COCCOc1cc(F)ccc1NC(=O)Cc1nc(N2CCOCC2)cc(=O)[nH]1]

3 ml of pyridine, 500 mg of N-[3-(dimethylamino)propyl]-N-ethylcarbodiimide hydrochloride and 590 mg of 4-fluoro-2-(2-methoxyethoxy)phenylamine are added to a solution of 500 mg of sodium [4-(morpholin-4-yl)-6-oxo-1,6-dihydropyrimidin-2-yl]acetate prepared in stage 2 of example 1, in 3 ml of N,N-dimethylformamide. The reaction mixture is stirred at ambient temperature for 15 hours, and then concentrated under reduced pressure. Water and ethyl acetate are added and the resulting mixture is thus stirred for 30 minutes. The precipitate formed is filtered off, and rinsed with water, ethyl ether and petroleum ether. The solid obtained is dried under vacuum. 155 mg of N-[4-fluoro-2-(2-methoxyethoxy)phenyl]-2-[4-(morpholin-4-yl)-6-oxo-1,6-dihydropyrimidin-2-yl]acetamide are obtained in the form of a pinkish solid, the characteristics of which are the following:

$^1$H NMR spectrum (400 MHz): 3.17 to 3.33 (m partially masked, 3 H); 3.43 (m, 4 H); 3.62 (m, 4 H); 3.68 (m, 4 H); 4.21 (m, 2 H); 5.21 (s, 1 H); 6.75 (dt, J=2.7 and 8.8 Hz, 1 H); 7.02 (dd, J=2.7 and 10.8 Hz, 1 H); 7.85 (dd, J=6.8 and 8.8 Hz, 1 H); 9.28 (broad s, 1 H); 11.65 (broad m, 1 H)

Mass spectrometry: method B
Retention time Tr (min)=3.60;
[M+H]$^+$: m/z 405; [M−H]$^-$: m/z 407.

EXAMPLE 139

Synthesis of N-(1H-benzimidazol-4-yl)-2-[4-(morpholin-4-yl)-6-oxo-1,6-dihydropyrimidin-2-yl]acetamide

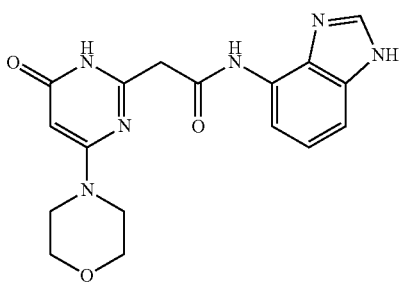 [SMILES: O=C(Cc1nc(N2CCOCC2)cc(=O)[nH]1)Nc1cccc2[nH]cnc12]

The product is prepared according to the procedure described in example 5, using 130 mg of sodium [4-(morpholin-4-yl)-6-oxo-1,6-dihydropyrimidin-2-yl]acetate, 113 mg of 4-aminobenzimidazole hydrochloride and 127 mg of N-[3-(dimethylamino)propyl]-N'-ethylcarbodiimide hydrochloride in a mixture of 80 µl of pyridine and 2.0 ml of N,N-dimethylformamide. 112 mg of N-(1H-benzimidazol-4-yl)-2-[4-(morpholin-4-yl)-6-oxo-1,6-dihydropyrimidin-2-yl]acetamide are obtained in the form of an off-white powder, the characteristics of which are the following:

$^1$H NMR spectrum (400 MHz): 3.48 (m, 4 H); 3.60 (m, 4 H); 3.79 (broad s, 2 H); 5.21 (s, 1 H); 7.14 (t, J=8.1 Hz, 1 H); 7.26 (broad s, 1 H); 7.94 (broad s, 1 H); 8.21 (s, 1 H); 10.20 (broad s, 1 H); 11.70 (broad m, 1 H); 12.54 (broad m, 1 H)

Mass spectrometry: method A
Retention time Tr (min)=0.32;
[M+H]$^+$: m/z 355; [M−H]$^-$: m/z 353
Melting point (Kofler bench): above 260° C.

EXAMPLE 140

Synthesis of methyl 2-hydroxy-3-({[4-(morpholin-4-yl)-6-oxo-1,6-dihydropyrimidin-2-yl]acetyl}amino)benzoate

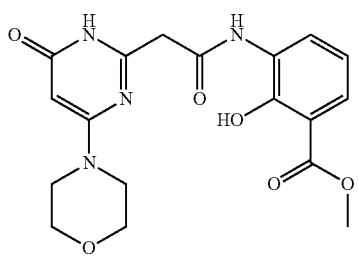 [SMILES: COC(=O)c1cccc(NC(=O)Cc2nc(N3CCOCC3)cc(=O)[nH]2)c1O]

6 ml of pyridine, 1 g of N-[3-(dimethylamino)propyl]-N'-ethylcarbodiimide hydrochloride and 1 g of methyl 3-amino-2-hydroxybenzoate are added to a solution of 1 g of [4-(morpholin-4-yl)-6-oxo-1,6-dihydropyrimidin-2-yl]acetate prepared in stage 2 of example 1, in 6 ml of N,N-dimethylformamide. The reaction mixture is stirred at ambient temperature for 15 hours, and then concentrated under reduced pressure. Water and ethyl acetate are added and the resulting mixture is thus stirred for 30 minutes. The precipitate formed is filtered off, and rinsed with water, ethyl ether and petroleum ether. The solid obtained is dried under vacuum. 1.27 g of methyl 2-hydroxy-3-({[4-(morpholin-4-yl)-6-oxo-1,6-dihydropyrimidin-2-yl]acetyl}amino)benzoate are obtained in the form of a grey solid, the characteristics of which are the following:

$^1$H NMR spectrum (400 MHz): 3.45 (m, 4 H); 3.58 (m, 4 H); 3.73 (s, 2H); 3.94 (s, 3 H); 5.21 (s, 1 H); 6.95 (t, J=7.9 Hz, 1 H); 7.56 (dd, J=1.3 and 7.9 Hz, 1 H); 8.21 (broad d, J=7.9 Hz, 1 H); 9.71 (broad s, 1 H); 11.03 (broad s, 1H); 11.70 (broad m, 1 H)

Mass spectrometry: method A
Retention time Tr (min)=0.66;
[M+H]$^+$: m/z 387; [M−H]$^-$: m/z 389.

EXAMPLE 141

2-[2-(4-Methoxy-2,3-dihydroindol-1-yl)-2-oxoethyl]-6-morpholin-4-yl-3H-pyrimidin-4-one

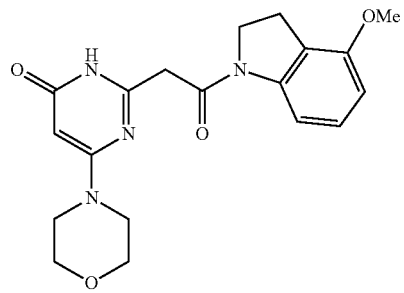 [SMILES: COc1cccc2c1CCN2C(=O)Cc1nc(N2CCOCC2)cc(=O)[nH]1]

The product is prepared according to the procedure described in example 5, using 261 mg of sodium [4-(morpholin-4-yl)-6-oxo-1,6-dihydropyrimidin-2-yl]acetate, 308 mg of 4-methoxyindoline and 254 mg of N-[3-(dimethylamino)propyl]-N'-ethylcarbodiimide hydrochloride in a mixture of 0.16 ml of pyridine and 4 ml of dimethylformamide. 269 mg of 2-[2-(4-methoxy-2,3-dihydroindol-1-yl)-2-oxoethyl]-6-morpholin-4-yl-3H-pyrimidin-4-one are obtained in the form of a pinkish powder, the characteristics of which are the following:

$^1$H NMR spectrum (400 MHz, δ in ppm, DMSO-d$_6$): 3.04 (t, J=8.2 Hz, 2H); 3.41 (m, 4 H); 3.61 (m, 4H); 3.74 (s, 2 H); 3.79 (s, 3 H); 4.14 (t, J=8.2 Hz, 2 H); 5.20 (s, 1H); 6.70 (broad d, J=7.9 Hz, 1 H); 7.15 (t, J=7.9 Hz, 1 H); 7.64 (broad d, J=7.9 Hz, 1H); 11.61 (broad m, 1 H).

Mass spectrometry: method A
Retention time Tr (min)=0.75;
[M+H]$^+$: m/z 371; [M−H]$^-$: m/z 369
Melting point (Kofler bench): above 260° C.

EXAMPLE 142

N-(3-bromo-2-hydroxyphenyl)-2-[4-(morpholin-4-yl)-6-oxo-1,6-dihydropyrimidin-2-yl]acetamide

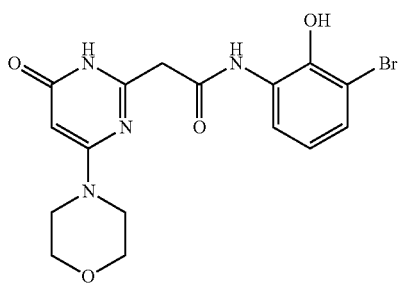 [SMILES: O=C(Cc1nc(N2CCOCC2)cc(=O)[nH]1)Nc1cccc(Br)c1O]

600 mg of N-[3-(dimethylamino)propyl]-N'-ethylcarbodiimide hydrochloride and 550 mg of 2-amino-6-bromophenol are added to a solution of 500 mg of sodium [4-(morpholin-4-yl)-6-oxo-1,6-dihydropyrimidin-2-yl]acetate prepared in stage 2 of example 1, in 4 ml of pyridine. The reaction mixture is stirred at ambient temperature for 20 hours, and then concentrated under reduced pressure. Water and ethyl acetate are added and the resulting mixture is thus stirred for 30 minutes. The precipitate formed is filtered off, and rinsed with water, ethyl ether and petroleum ether. The solid obtained is dried under vacuum. 543 mg of N-(3-bromo-2-hydroxyphenyl)-2-[4-(morpholin-4-yl)-6-oxo-1,6-dihydropyrimidin-2-yl]acetamide are obtained in the form of a beige solid, the characteristics of which are the following:

$^1$H NMR spectrum (400 MHz): 3.44 (m, 4 H); 3.62 (m, 4 H); 3.70 (s, 2 H); 5.21 (s, 1 H); 6.78 (t, J=8.1 Hz, 1 H); 7.32 (d, J=8.1 Hz, 1 H); 7.56 (d, J=8.1 Hz, 1 H); 9.82 (broad m, 2 H); 11.62 (broad m, 1 H)

Mass spectrometry: method A
Retention time Tr (min)=0.64;
[M+H]$^+$: m/z 408; [M−H]$^-$: m/z 410.

EXAMPLE 143

Synthesis of N-(3,4-dihydro-2H-1,4-benzoxazin-8-yl)-2-[4-(morpholin-4-yl)-6-oxo-1,6-dihydropyrimidin-2-yl]acetamide

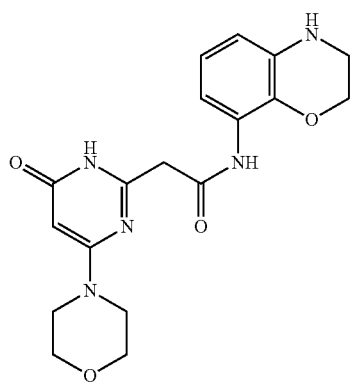 [SMILES: O=C(Cc1nc(N2CCOCC2)cc(=O)[nH]1)Nc1cccc2c1OCCN2]

The product is prepared according to the procedure described in example 5, using 261 mg of sodium [4-(morpholin-4-yl)-6-oxo-1,6-dihydropyrimidin-2-yl]acetate, 166 mg of 3,4-dihydro-2H-1,4-benzoxazin-8-ylamine and 249 mg of N-[3-(dimethylamino)propyl]-N'-ethylcarbodiimide hydrochloride in a mixture of 162 µl of pyridine and 4.0 ml of N,N-dimethylformamide. 100 mg of N-(3,4-dihydro-2H-1,4-benzoxazin-8-yl)-2-[4-(morpholin-4-yl)-6-oxo-1,6-dihydropyrimidin-2-yl]acetamide are obtained in the form of a white powder, the characteristics of which are the following:

$^1$H NMR spectrum (400 MHz): 3.32 (m partially masked, 2 H); 3.44 (m, 4 H); 3.62 (m, 6 H); 4.08 (m, 2 H); 5.08 (m, 1 H); 5.19 (s, 1 H); 6.49 (t, J=7.8 Hz, 1 H); 6.56 (dd, J=1.5 and 7.8 Hz, 1 H); 6.80 (dd, J=1.5 and 7.8 Hz, 1 H); 9.43 (broad m, 1 H); 11.63 (broad m, 1 H)

Mass spectrometry: method A
Retention time Tr (min)=2.64;
[M+H]$^+$: m/z 372; [M−H]$^-$: m/z 370
Melting point (Kofler bench): 243° C.

EXAMPLE 144

Methyl 5-fluoro-2-({[4-(morpholin-4-yl)-6-oxo-1,6-dihydropyrimidin-2-yl]acetyl}amino)benzoate

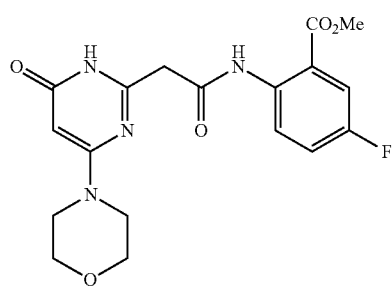 [SMILES: COC(=O)c1cc(F)ccc1NC(=O)Cc1nc(N2CCOCC2)cc(=O)[nH]1]

The product is prepared according to the procedure described in example 5, using 300 mg of sodium [4-(morpholin-4-yl)-6-oxo-1,6-dihydropyrimidin-2-yl]acetate, 303 mg of methyl 2-amino-5-fluorobenzoate and 308 mg of N-[3-(dimethylamino)propyl]-N'-ethylcarbodiimide hydrochloride in a mixture of 2 ml of pyridine and 2 ml of dimethylformamide. 310 mg of methyl 5-fluoro-2-({[4-(morpholin-4-yl)-6-oxo-1,6-dihydropyrimidin-2-yl]acetyl}amino) benzoate are obtained in the form of a white solid, the characteristics of which are the following:

$^1$H NMR spectrum (400 MHz): 3.44 (m, 4 H); 3.61 (m, 4 H); 3.67 (s, 2H); 3.84 (s, 3 H); 5.21 (s, 1 H); 7.50 (m, 1 H); 7.64 (dd, J=3.0 and 9.2 Hz, 1 H); 8.13 (dd, J=5.3 and 8.9 Hz, 1 H); 10.57 (broad s, 1 H); 11.70 (broad m, 1 H)

Mass spectrometry: method A
Retention time Tr (min)=0.71;
[M+H]$^+$: m/z 391; [M−H]$^-$: m/z 389.

EXAMPLE 145

Synthesis of 2-(2-{3-[(diethylamino)methyl]-2,3-dihydro-1H-indol-1-yl}-2-oxoethyl)-6-(morpholin-4-yl)pyrimidin-4(3H)-one

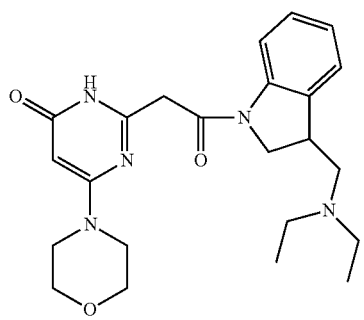 [SMILES: CCN(CC)CC1CN(C(=O)Cc2nc(N3CCOCC3)cc(=O)[nH]2)c2ccccc21]

Stage 1:

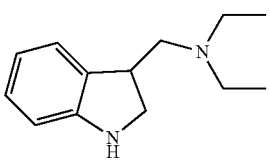

0.48 g of sodium cyanoborohydride is gradually added to a solution of 5' 0.5 g of diethyl(1H-indol-3-ylmethyl)amine (prepared according to Synth. Commun. 2006, 1829) in 10 ml of trifluoroacetic acid, under argon, cooled in an ice bath, and then the resulting mixture is stirred for half an hour at 0° C. and 3 h at ambient temperature. The reaction medium is then plunged into 100 ml of water and alkalinized using 30% sodium hydroxide. After the addition of 100 ml of ethyl acetate, the resulting mixture is stirred for 10 min at ambient temperature and then the mixture is separated by settling out and the aqueous phase is extracted with three times 50 ml of ethyl acetate. The organic phases are combined, and then washed with 40 ml of water. The organic phase is dried over anhydrous magnesium sulphate, filtered and concentrated to dryness under reduced pressure. The residue is taken up with 20 ml of 2N sodium hydroxide plus 40 ml of water and 60 ml of ethyl acetate, stirred for 5 min, and then separated by settling out. The aqueous phase is extracted with twice 40 ml of ethyl acetate and the organic phases are combined, dried over anhydrous magnesium sulphate, filtered and concentrated to dryness under reduced pressure. After a silica column purification, eluent: 89/10/1 $CH_2Cl_2$/MeOH/$NH_4OH$, 246 mg of (2,3-dihydro-1H-indol-3-ylmethyl)diethylamine are obtained in the form of a yellow oil, the characteristics of which are the following:

Mass spectrometry: method A
Retention time Tr (min)=0.20;
$[M+H]^+$: m/z 205;

Stage 2:

The product is prepared according to the procedure described in example 5, using 150 mg of sodium [4-(morpholin-4-yl)-6-oxo-1,6-dihydropyrimidin-2-yl]acetate, 238 mg of (2,3-dihydro-1H-indol-3-ylmethyl)diethylamine and 140 mg of N-[3-(dimethylamino)propyl]-N-ethylcarbodiimide hydrochloride in a mixture of 0.1 ml of pyridine and 3 ml of N,N-dimethylformamide. 108 mg of 2-(2-{3-[(diethylamino)methyl]-2,3-dihydro-1H-indol-1-yl}-2-oxoethyl)-6-(morpholin-4-pyrimidin-4(3H)-one are obtained in the form of a cream solid, the characteristics of which are the following:

$^1$H NMR spectrum (400 MHz): 0.96 (t, J=7.0 Hz, 6 H); 2.36 to 2.71 (m partially masked, 6 H); 3.41 (m, 4 H); 3.56 (m, 1 H); 3.61 (m, 4 H); 3.75 (s, 2 H); 3.88 (dd, J=5.4 and 10.8 Hz, 1 H); 4.21 (t, J=10.8 Hz, 1 H); 5.21 (s, 1 H); 7.02 (t, J=7.7 Hz, 1 H); 7.18 (t, J=7.7 Hz, 1 H); 7.32 (d, J=7.7 Hz, 1 H); 8.03 (d, J=7.7 Hz, 1 H); 11.62 (broad m, 1 H)

Mass spectrometry: method A
Retention time Tr (min)=0.43;
$[M+H]^+$: m/z 426; $[M-H]^-$: m/z 424
Melting point (Kofler bench): 202° C.

EXAMPLE 146

Synthesis of 2-[2-(2,3-dihydro-1H-pyrrolo[3,2-b]pyridin-1-yl)-2-oxoethyl]-6-(morpholin-4-yl)pyrimidin-4(3H)-one

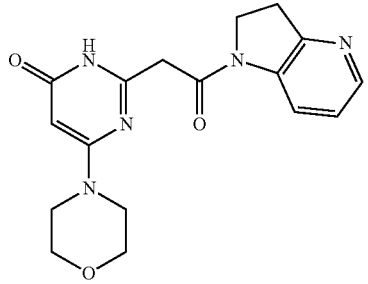 [SMILES: O=C(Cc1nc(N2CCOCC2)cc(=O)[nH]1)N1CCc2ncccc21]

Stage 1:

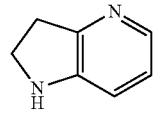

1.49 g of Raney nickel at 50% in water are added to a solution of 1.5 g of 4-azaindole in 45 ml of absolute ethanol, in an autoclave under argon. The mixture is hydrogenated under 100 bar of hydrogen at a temperature of 95° C. for 41 h. After a return to ambient temperature, the catalyst is filtered off through Clarcel and the filtrate is concentrated to dryness under reduced pressure. The residue is purified by chromatography on a 70 g 15-40 µm silica cartridge, elution being carried out with pure dichloromethane and then with a 99/1 v/v mixture of dichloromethane/methanol with a flow rate of 80 ml/min, and then on a 30 g 15-40 µm silica cartridge, elution being carried out with pure dichloromethane with a flow rate of 30 ml/min. 0.18 g of 4-azaindoline is thus obtained in the form of a pale yellow solid which melts at 63° C. (Kofler bench).

Stage 2:

The product is prepared according to the procedure described in example 5, using 350 mg of sodium [4-(morpholin-4-yl)-6-oxo-1,6-dihydropyrimidin-2-yl]acetate, 177 mg of 4-azaindoline and 340 mg of N-[3-(dimethylamino)propyl]-N'-ethylcarbodiimide hydrochloride in a mixture of 216 µl of pyridine and 6.5 ml of N,N-dimethylformamide. 252 mg of 2-[2-(2,3-dihydro-1H-pyrrolo[3,2-b]pyridin-1-yl)-2-oxoethyl]-6-(morpholin-4-yl)pyrimidin-4(3H)-one are obtained in the form of a white powder, the characteristics of which are the following:

$^1$H NMR spectrum (400 MHz): 3.24 to 3.37 (m partially masked, 2H); 3.41 (m, 4 H); 3.60 (m, 4 H); 3.79 (s, 2 H); 4.19 (t, J=8.3 Hz, 2 H); 5.21 (s, 1 H); 7.17 (dd, J=4.4 and 8.3 Hz, 1 H); 8.13 (d, J=4.4 Hz, 1 H); 8.19 (d, J=8.3 Hz, 1 H); 11.63 (broad m, 1 H)

Mass spectrometry: method A
Retention time Tr (min)=0.37;
[M+H]$^+$: m/z 342; [M–H]$^-$: m/z 340
Melting point (Kofler bench): above 260° C.

EXAMPLE 147

2-[2-(5,6-Difluoro-2,3-dihydroindol-1-yl)-2-oxoethyl]-6-morpholin-4-yl-3H-pyrimidin-4-one

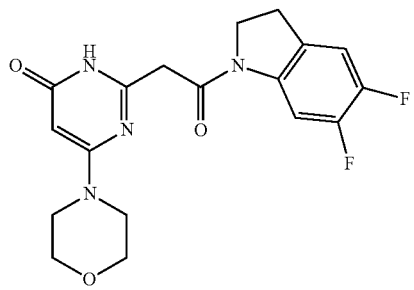 [SMILES: O=C(Cc1nc(N2CCOCC2)cc(=O)[nH]1)N1CCc2cc(F)c(F)cc21]

The product is prepared according to the procedure described in example 5, using 261 mg of sodium [4-(morpholin-4-yl)-6-oxo-1,6-dihydropyrimidin-2-yl]acetate, 310 mg of 4-methoxyindoline and 254 mg of N-[3-(dimethylamino)propyl]-N'-ethylcarbodiimide hydrochloride in a mixture of 0.16 ml of pyridine and 4 ml of dimethylformamide. 245 mg of 2-[2-(5,6-difluoro-2,3-dihydroindol-1-yl)-2-oxoethyl]-6-morpholin-4-yl-3H-pyrimidin-4-one are obtained in the form of a white powder, the characteristics of which are the following:

$^1$H NMR spectrum (400 MHz, δ in ppm, DMSO-d$_6$): 3.16 (t, J=8.4 Hz, 2 H); 3.41 (m, 4 H); 3.60 (m, 4 H); 3.76 (s, 2 H); 4.19 (t, J=8.4 Hz, 2 H); 5.21 (s, 1 H); 7.37 (t, J=9.2 Hz, 1 H); 7.95 (dd, J=7.6 and 12.0 Hz, 1 H); 11.61 (broad m, 1 H).

Mass spectrometry: method A
Retention time Tr (min)=0.70;
[M+H]$^+$: m/z 377; [M–H]$^-$: m/z 375
Melting point (Kofler bench): above 260° C.

EXAMPLE 148

Synthesis of 2-[4-(morpholin-4-yl)-6-oxo-1,6-dihydropyrimidin-2-yl]-N-(1,2,3,4-tetrahydroquinolin-8-yl)acetamide

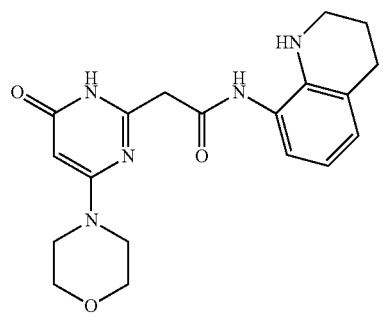 [SMILES: O=C(Cc1nc(N2CCOCC2)cc(=O)[nH]1)Nc1cccc2c1NCCC2]

The product is prepared according to the procedure described in example 5, using 340 mg of sodium [4-(morpholin-4-yl)-6-oxo-1,6-dihydropyrimidin-2-yl]acetate, 212 mg of 8-amino-1,2,3,4-tetrahydroquinoline and 330 mg of N-[3-(dimethylamino)propyl]-N'-ethylcarbodiimide hydrochloride in a mixture of 210 µl of pyridine and 5.0 ml of N,N-dimethylformamide. 243 mg of 2-[4-(morpholin-4-yl)-6-oxo-1,6-dihydropyrimidin-2-yl]-N-(1,2,3,4-tetrahydroquinolin-8-yl)acetamide are obtained in the form of a beige powder, the characteristics of which are the following:

$^1$H NMR spectrum (400 MHz): 1.79 (m, 2 H); 2.70 (t, J=6.5 Hz, 2 H); 3.23 (broad t, J=6.5 Hz, 2 H); 3.44 (m, 4 H); 3.59 (s, 2 H); 3.63 (m, 4 H); 5.03 (broad s, 1 H); 5.20 (s, 1 H); 6.43 (t, J=7.7 Hz, 1 H); 6.75 (d, J=7.7 Hz, 1 H); 6.93 (d, J=7.7 Hz, 1 H); 9.22 (broad s, 1 H); 11.62 (broad m, 1 H)

Mass spectrometry: method A
Retention time Tr (min)=0.57;
[M+H]$^+$: m/z 370; [M–H]$^-$: m/z 368
Melting point (Kofler bench): 232° C.

EXAMPLE 149

Synthesis of 2-[2-(8-chloro-2,3-dihydro-4H-1,4-benzoxazin-4-yl)-2-oxoethyl]-6-(morpholin-4-yl)pyrimidin-4(3 H)-one

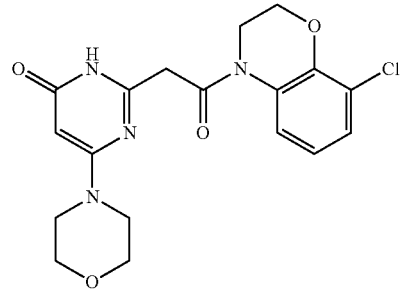 [SMILES: O=C(Cc1nc(N2CCOCC2)cc(=O)[nH]1)N1CCOc2c(Cl)cccc21]

The product is prepared according to the procedure described in example 5, using 220 mg of sodium [4-(morpholin-4-yl)-6-oxo-1,6-dihydropyrimidin-2-yl]acetate, 157 mg of 8-chloro-2H-benzo[b][1,4]oxazine (which can be prepared according to WO 2008/100463) and 214 mg of N-[3-(dimethylamino)propyl]-N'-ethylcarbodiimide hydrochloride in a mixture of 135 µl of pyridine and 3.5 ml of N,N-dimethylformamide. 140 mg of 2-[2-(8-chloro-2,3-dihydro-4H-1,4-benzoxazin-4-yl)-2-oxoethyl]-6-(morpholin-4-yl)pyrimidin-4(3 H)-one are obtained in the form of a white powder, the characteristics of which are the following:

$^1$H NMR spectrum (400 MHz): for this batch, all the signals are broad, with: 3.41 (m, 4 H); 3.57 (m, 4 H); 3.88 (m, 4 H); 4.42 (m, 2 H); 5.17 (s, 1 H); 6.88 (m, 1 H); 7.24 (m, 1 H); 7.71 (very broad m, 1 H); 11.57 (broad m, 1 H)

Mass spectrometry: method A
Retention time Tr (min)=0.71;
[M+H]$^+$: m/z 391; [M–H]$^-$: m/z 389
Melting point (Kofler bench): above 260° C.

EXAMPLE 150

Synthesis of N-(2-hydroxy-3-methylphenyl)-2-[4-(morpholin-4-yl)-6-oxo-1,6-dihydropyrimidin-2-yl]acetamide

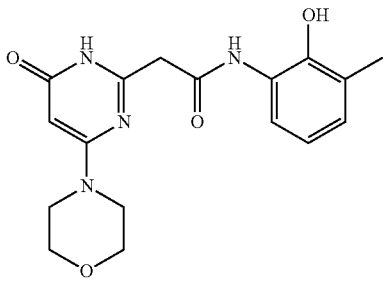 [SMILES: Cc1cccc(NC(=O)Cc2nc(N3CCOCC3)cc(=O)[nH]2)c1O]

The product is prepared according to the procedure described in example 5, using 1 g of sodium [4-(morpholin-4-yl)-6-oxo-1,6-dihydropyrimidin-2-yl]acetate, 680 mg of 6-amino-2-methylphenol and 1.2 g of N-[3-(dimethylamino)propyl]-N'-ethylcarbodiimide hydrochloride in a mixture of 6 ml of pyridine and 8 ml of N,N-dimethylformamide. 1.1 g of N-(2-hydroxy-3-methyl phenyl)-2-[4-(morpholin-4-yl)-6-oxo-1,6-dihydropyrimidin-2-yl]acetamide are obtained in the form of a beige solid, the characteristics of which are the following:

$^1$H NMR spectrum (400 MHz): 2.18 (s, 3 H); 3.45 (m, 4 H); 3.62 (m, 4 H); 3.70 (s, 2 H); 5.21 (s, 1 H); 6.73 (t, J=7.8 Hz, 1 H); 6.91 (d, J=7.8 Hz, 1 H); 7.37 (d, J=7.8 Hz, 1 H); 8.80 (broad s, 1 H); 9.77 (s, 1 H); 11.68 (broad m, 1 H)

Mass spectrometry: method A
Retention time Tr (min)=0.61;
[M+H]$^+$: m/z 345; [M−H]$^−$: m/z 343.

EXAMPLE 151

N-(2-hydroxy-3-nitrophenyl)-2-[4-(morpholin-4-yl)-6-oxo-1,6-dihydropyrimidin-2-yl]acetamide

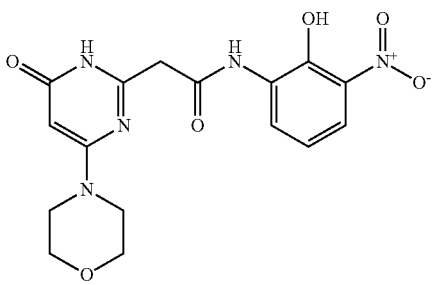 [SMILES: O=C(Cc1nc(N2CCOCC2)cc(=O)[nH]1)Nc1cccc([N+](=O)[O-])c1O]

The product is prepared according to the procedure described in example 5, using 1 g of sodium [4-(morpholin-4-yl)-6-oxo-1,6-dihydropyrimidin-2-yl]acetate, 590 mg of 2-amino-6-nitrophenol, and 734 mg of N-[3-(dimethylamino)propyl]-N'-ethylcarbodiimide hydrochloride in a mixture of 5 ml of pyridine and 6 ml of N,N-dimethylformamide. 976 mg of N-(2-hydroxy-3-nitrophenyl)-2-[4-(morpholin-4-yl)-6-oxo-1,6-dihydropyrimidin-2-yl]acetamide are obtained in the form of a yellow solid, the characteristics of which are the following:

$^1$H NMR spectrum (400 MHz): 3.48 (m, 4 H); 3.63 (m, 4 H); 3.65 (s, 2 H); 5.19 (s, 1 H); 5.85 (dd, J=7.2 and 8.7 Hz, 1 H); 7.37 (dd, J=1.7 and 8.7 Hz, 1 H); 7.91 (dd, J=1.7 and 7.2 Hz, 1 H); 9.74 (broad m, 1 H); 11.75 (broad m, 1 H)

Mass spectrometry: method A
Retention time Tr (min)=0.61;
[M+H]$^+$: m/z 376; [M−H]$^−$: m/z 374.

EXAMPLE 152

N-(3-cyano-2-hydroxyphenyl)-2-[4-(morpholin-4-yl)-6-oxo-1,6-dihydropyrimidin-2-yl]acetamide

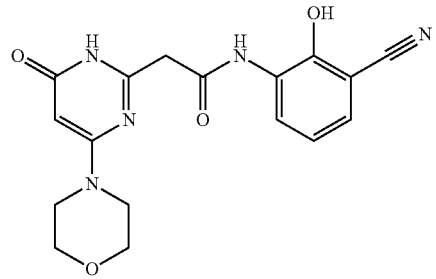 [SMILES: N#Cc1cccc(NC(=O)Cc2nc(N3CCOCC3)cc(=O)[nH]2)c1O]

The product is prepared according to the procedure described in example 5, using 1 g of sodium [4-(morpholin-4-yl)-6-oxo-1,6-dihydropyrimidin-2-yl]acetate, 513 mg of 3-amino-2-hydroxybenzonitrile and 734 mg of N-[3-(dimethylamino)propyl]-N'-ethylcarbodiimide hydrochloride in a mixture of 5 ml of pyridine and 5 ml of N,N-dimethylformamide. 257 mg of N-(3-cyano-2-hydroxyphenyl)-2-[4-(morpholin-4-yl)-6-oxo-1,6-dihydropyrimidin-2-yl]acetamide are obtained in the form of a white solid, the characteristics of which are the following:

$^1$H NMR spectrum (400 MHz): 3.44 (m, 4 H); 3.62 (m, 4 H); 3.70 (s, 2 H); 5.21 (s, 1 H); 6.91 (t, J=7.8 Hz, 1 H); 7.40 (d, J=7.8 Hz, 1 H); 7.78 (d, J=7.8 Hz, 1 H); 9.95 (broad m, 1 H); 10.71 (very broad m, 1 H); 11.64 (broad m, 1 H)

Mass spectrometry: method A
Retention time Tr (min)=0.57;
[M+H]$^+$: m/z 356; [2M+H]$^+$: m/z 711 (base peak)
[M−H]$^−$: m/z 354 (base peak); [2M−H]$^−$: m/z 709.

EXAMPLE 153

N-[2-hydroxy-3-(trifluoromethyl)phenyl]-2-[4-(morpholin-4-yl)-6-oxo-1,6-dihydropyrimidin-2-yl]acetamide

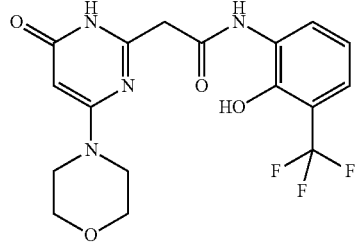 [SMILES: O=C(Cc1nc(N2CCOCC2)cc(=O)[nH]1)Nc1cccc(C(F)(F)F)c1O]

The product is prepared according to the procedure described in example 5, using 1 g of sodium [4-(morpholin-4-yl)-6-oxo-1,6-dihydropyrimidin-2-yl]acetate, 978 mg of 2-hydroxy-3-(trifluoromethyl)aniline and 1.2 g of N-[3-(dimethylamino)propyl]-N'-ethylcarbodiimide hydrochloride in a mixture of 6 ml of pyridine and 8 ml of N,N-dimethylformamide. 600 mg of N-[2-hydroxy-3-(trifluoromethyl)phenyl]-2-[4-(morpholin-4-yl)-6-oxo-1,6-dihydropyrimidin-2-yl]acetamide are obtained in the form of a beige solid, the characteristics of which are the following:

$^1$H NMR spectrum (400 MHz): 3.44 (m, 4 H); 3.61 (m, 4 H); 3.69 (s, 2 H); 5.21 (s, 1 H); 6.95 (t, J=7.8 Hz, 1 H); 7.38 (d, J=7.8 Hz, 1 H); 7.57 (d, J=7.8 Hz, 1 H); 10.44 (very broad m, 3 H)

Mass spectrometry: method A
Retention time Tr (min)=0.71;
[M+H]$^+$: m/z 399; [M−H]: m/z 397.

EXAMPLE 154

Synthesis of 2-[2-(3,3-dimethyl-2,3-dihydro-1H-indol-1-yl)-2-oxoethyl]-6-(morpholin-4-yl)pyrimidin-4(3 H)-one

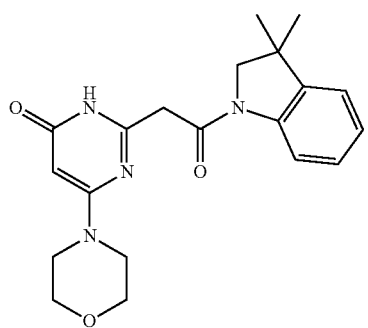 [SMILES: CC1(C)CN(C(=O)Cc2nc(N3CCOCC3)cc(=O)[nH]2)c2ccccc21]

The product is prepared according to the procedure described in example 5, using 177 mg of sodium [4-(morpholin-4-yl)-6-oxo-1,6-dihydropyrimidin-2-yl]acetate, 236 mg of 3,3-dimethylindoline (which can be prepared according to T. W. Ramsay et al., Synth. Commun. 1995, 25, 4029) and 169 mg of N-[3-(dimethylamino)propyl]-N'-ethylcarbodiimide hydrochloride in a mixture of 0.11 ml of pyridine and 5 ml of N,N-dimethylformamide. The reaction mixture is stirred for 15 h at ambient temperature and then concentrated to dryness under reduced pressure. 40 ml of water are added to the residue and triturated with a spatula at ambient temperature. The precipitate formed is filtered off, and then solubilized with a dichloromethane/methanol mixture and dried. After concentration to dryness under reduced pressure, the crude product is purified by chromatography on a 30 g silica (0.02-0.045 mm) column, eluent: 90/10 v/v dichloromethane/methanol. After the various fractions have been evaporated, the pink solid residue is triturated from 10 ml of diisopropyl ether, filtered off, and then dried under a bell jar (1 h/40° C./20 mbar). 134 mg of 2-[2-(3,3-dimethyl-2,3-dihydroindol-1-yl)-2-oxoethyl]-6-morpholin-4-yl-3H-pyrimidin-4-one are thus obtained in the form of a pink solid, the characteristics of which are the following:

$^1$H NMR spectrum (400 MHz): 1.31 (s, 6 H); 3.42 (m, 4 H); 3.59 (m, 4 H); 3.75 (s, 2 H); 3.91 (s, 2 H); 5.20 (s, 1 H); 7.05 (t, J=7.6 Hz, 1 H); 7.18 (t, J=7.6 Hz, 1 H); 7.27 (d, J=7.6 Hz, 1H); 8.00 (d, J=7.6 Hz, 1 H); 11.61 (broad m, 1 H)

Mass spectrometry: method A
Retention time Tr (min)=0.77;
[M+H]$^+$: m/z 369; [M−H]$^-$: m/z 367
Melting point (Kofler bench): 248° C.

EXAMPLE 155

Pharmaceutical composition

Tablets corresponding to the following formulation were prepared:

| | |
|---|---|
| Product of Example 1 | 0.2 g |
| Excipient for a tablet with a final weight of | 1 g |
| (details of the excipient: lactose, talc, starch, magnesium stearate). | |

Example 1 is taken by way of example of a pharmaceutical preparation, it being possible for this preparation to be carried out, if desired, with other products as examples in the present application.

Pharmacological Section:
Experimental Protocols
In Vitro Experimental Procedures The inhibitory activity of the molecules on AKT phosphorylation is measured either by western blotting using the technique described below, or by the MSD Multi-spot Biomarker detection technique from Meso Scale Discovery also described below. It was demonstrated, on one set of molecules, that both techniques give compatible results.

Study of pAKT Expression in PC3 Human Prostate Carcinoma Cells Measured by Western Blotting (Test A):

This test is based on measuring the expression of the AKT protein phosphorylated on serine 473. The phosphorylation of AKT (pAKT) is measured by western blotting in the PC3 human prostate carcinoma line (ATCC CRL-1435), using an antibody that specifically recognises pAKT-S473.

On day 1, the PC3 cells are seeded into 6-well plates (TPP, #92006) at the concentration of $0.8 \times 10^6$ cells/well in 1800 µl of DMEM medium (DMEM Gibco #11960-044) containing 10% of foetal calf serum (SVF Gibco, #10500-056) and 1% glutamine (L-Glu Gibco #25030-024), and incubated at 37° C., 5% $CO_2$, overnight.

On day 2, the cells are incubated in the presence or absence of the test products for 1 to 2 hours at 37° C. in the presence of 5% $CO_2$. The molecules, diluted in dimethyl sulphoxide (DMSO Sigma #D2650), are added from a 10-times concentrated stock solution, the final percentage of DMSO being 0.1%. The molecules are tested either at a single concentration of less than or equal to 10 µM, or at increasing concentrations in a range that can extend from less than 1 nM to 10 µM.

After this incubation, the cells are lysed for the preparation of the proteins. After the culture medium has been drawn off, the cells are rinsed with 1 ml of PBS (DPBS Gibco, #14190-094), recovered by scraping in 200 µl of complete HNTG buffer and transferred into a 96-well plate (Greiner #651201), and lysed for 1 h on ice. The HNTG buffer is composed of the following mixture: 50 mM hepes, 150 mM NaCl, 1% triton, 10% glycerol, with extemporaneous addition of one Mini Protease Inhibitor Cocktail tablet (Roche 1836153) and of one Phosphatase Inhibitor Cocktail tablet (Roche 104906837001) per 10 ml of buffer.

The lysate is centrifuged for 10 min at 6000 rpm. 155 µl of supernatant are recovered. 150 µl are incubated for denaturation for 5 min at 95° C. in the presence of 4× NuPAGE LDS Sample Buffer diluted 4-fold (InVitrogen ref NP0007) and of 10× NuPAGE Sample Reducing Agent diluted 10-fold (InVitrogen ref NP0009). These samples are then frozen at −20° C. 5 µl are assayed by the microBCA technique according to the technical bulletin of the MicroBCA Protein Assay Kit (Pierce #23235).

For protein separation, 20 µg of proteins are loaded on to a NU-PAGE 4-12% Bis Tris Gel 12 well (InVitrogen ref NP0322BOX) and the migration is carried out for 1 h 30 in 20× NU-PAGE MOPS SDS Running Buffer diluted 20-fold (InVitrogen ref NP0001), at 150 volts.

The gel is then transferred on to an Invitrolon PVDF membrane (Invitrogen #LC2007) permeabilised beforehand and for a few seconds in ethanol (Ethanol Fischer Scientific #E/0600DF/15).

The transfer is carried out in a Biorad tank at 30 volts overnight or at 60 volts for 3 hours, in the presence of 20× NUPAGE Transfer Buffer diluted 20-fold (InVitrogen ref NP0006).

The membrane is then saturated in saturating solution composed of TBS (10× Tris Buffered Saline, Sigma #T5912, diluted 10-fold), 0.1% Tween 20 (Sigma #P5927) and 3% BSA (Bovine Albumin Serum Fraction V, Sigma #A4503) for 6 h after overnight transfer or else for 1 h after transfer for a period of 3 h.

The primary antibodies are diluted to/1000th for the anti-phospho AKT-Ser473 antibody (193H2, rabbit monoclonal, cat#4058 from Cell Signaling Technology Abcam), in saturating solution composed of PBS, 0.1% Tween 20 and 3% BSA, and then shaken overnight at 4° C. Two rinses for 5 min in washing solution composed of TBS and 0.1% Tween 20 are carried out before hybridisation of the secondary antibodies.

The secondary antibodies are diluted 1/10000th for the rabbit anti-Mouse IgG HRP antibody (W402 Promega) and to 1/10000th for the goat anti-Rabbit IgG HRP antibody (W401 Promega) in saturating solution, and then shaken for 1 h at ambient temperature.

Two rinses for 30 min in washing solution are carried out and then a rinse for 5 min in $H_2O$ is carried out in order to eliminate the remaining Tween 20.

The revealing solution is prepared volume-for-volume according to the technical bulletin of the Western Lightning Chemiluminescence Reagent Plus (Western Lightning Chemiluminescence Reagent Plus Perkin Elmer #NEL104).

The membrane is placed in the revealing solution for 1 min, drained, inserted between two transparent plates and then placed in the measuring device for reading the luminescence and the quantification of the signal. The luminescence is read with the FujiFilm device (Ray Test).

The FUJI device measures the total luminescence signal obtained (AU) for each band selected. It then subtracts the background noise (BG) proportional to the size of the band selected (Area), said background noise being calculated from a specific background noise band, with a view to obtaining the specific signal (AU-BG) for each band. The band obtained in the absence of product and in the presence of 0.1% DMSO is considered to be the 100% signal. The software calculates the % specific activity (Ratio) obtained for each band selected as a function of this 100% signal. The percentage inhibition is calculated for each concentration according to the formula (100%−Ratio).

Two independent experiments make it possible to calculate the mean of the percentages of inhibition obtained at a given concentration for the products tested only at one concentration.

Where appropriate, the activity of the products is translated into approximately IC50, obtained from a dose-response curve of various concentrations tested and representing the dose giving 50% of specific inhibition (absolute IC50). Two independent experiments make it possible to calculate the mean of the IC50s.

Study of pAKT Expression in PC3 Human Prostate Carcinoma Cells Measured by the MSD Multi-Spot Biomarker Detection Technique from Meso Scale Discovery (Test B):

This test is based on measuring the expression of the AKT protein phosphorylated on serine 473 (P-AKT-S473), in the PC3 human prostate carcinoma line, by means of the technique based on a sandwich immunoassay using the MSD Multi-spot Biomarker Detection kit from Meso Scale Discovery: phospho-Akt (Ser473) whole cell lysate kit (#K151CAD) or phospho-Akt (Ser473)/Total Akt whole cell lysate kit (#K151OOD). The primary antibody specific for P-AKT-S473 (Kit #K151CAD) is coated on to an electrode in each well of the 96-well plates of the MSD, kit: after the addition of a protein lysate to each well, the signal is visualised by adding a secondary detection antibody labelled with an electrochemoluminescent compound. The procedure followed is that described in the kit.

On day 1, the PC3 cells are seeded into 96-well plates (TPP, #92096) at the concentration of 35 000 cells/well in 200 μl of DMEM medium (DMEM Gibco #11960-044) containing 10% of foetal calf serum (FCS Gibco, #10500-056) and 1% glutamine (L-Glu Gibco #25030-024), and incubated at 37° C., 5% $CO_2$, overnight.

On day 2, the cells are incubated in the presence or absence of the test products for 1 to 2 h at 37° C. in the presence of 5% of $CO_2$. The molecules, diluted in dimethyl sulphoxide (DMSO Sigma #D2650), are added from a 20-times concentrated stock solution, the final percentage of DMSO being 0.1%. The molecules are tested either at a single concentration of less than or equal to 10 μM, or at increasing concentrations in a range that can extend from less than 1 nM to 10 μM.

After this incubation, the cells are lysed for the preparation of the proteins. For this, after the culture medium has been drawn off, 50 μl of complete Tris Lysis Buffer of the MSD kit containing the protease and phosphatase inhibitor solutions are added to the wells and the cells are lysed for 1 h at 4° C. with shaking. At this stage, the plates containing the lysates can be stored at −20° C. or at −80° C.

The wells of the 96-well plates of the MSD kit are saturated for 1 h at ambient temperature with the blocking solution of the MSD kit. Four washes are carried out with 150 μl of Tris Wash Buffer of the MSD kit. The lysates previously prepared are transferred into the 96-well multi-spot plates of the MSD kit and incubated for 1 h at ambient temperature, with shaking. Four washes are carried out with 150 μl of Tris Wash Buffer of the MSD kit. 25 μl of the MSD sulfo-tag detection antibody solution are added to the wells and incubated for 1 h at ambient temperature, with shaking. Four washes are carried out with 150 μl of Tris Wash Buffer of the MSD kit. 150 μl of Read Buffer of the MSD kit are added to the wells and the plates are read immediately on the S12400 instrument from Meso Scale Discovery.

The instrument measures a signal for each well. Wells without cells and containing the lysis buffer serve to determine the background noise that will be subtracted from all the measurements (min). The wells containing cells in the absence of product and in the presence of 0.1% DMSO are considered to be the 100% signal (max). The percentage inhibition is calculated for each concentration of test product according to the following formula: $(1-((test-min)/(max-min)))\times 100$.

The activity of the product is translated to $IC_{50}$, obtained from a dose-response curve of various concentrations tested and representing the dose giving 50% specific inhibition (absolute $IC_{50}$). 2 independent experiments make it possible to calculate the mean of the $IC_{50}$ values.

The results obtained for the products as examples in the experimental section are given in the pharmacological results table below:

Pharmacological Results Table:

| example | Test A | Test B |
|---|---|---|
| Example 1 | 102 | |
| Example 2 | 321 | |
| Example 3 | 100 | |
| Example 4 | | 145 |
| Example 5 | | 51 |
| Example 6 | 23 | |
| Example 7 | | 23 |
| Example 8 | 318 | |
| Example 9 | 727 | |
| Example 10 | 3498 | |
| Example 11 | 632 | |
| Example 12 | 737 | |
| Example 13 | | 71 |
| Example 14 | 570 | 74 |
| Example 15 | 1420 | |
| Example 16 | 850 | |
| Example 17 | 1481 | |
| Example 18 | 23 | |
| Example 19 | | 42 |
| Example 20 | 1314 | |
| Example 21 | 10 000 | |
| Example 22 | 350 | |
| Example 23 | 39 | |
| Example 24 | | 247 |
| Example 25 | | |
| Example 26 | 2287 | |
| Example 27 | | 71 |
| Example 28 | 171 | |
| Example 29 | 116 | |
| Example 30 | | 1030 |
| Example 31 | | 58 |
| Example 32 | 3635 | |
| Example 33 | 93 | |
| Example 34 | 609 | |
| Example 35 | 10 000 | |
| Example 36 | 200 | |
| Example 37 | 10 000 | |
| Example 38 | 480 | |
| Example 39 | 1763 | |
| Example 40 | 1494 | |
| Example 41 | 290 | 60 |
| Example 42 | 400 | 148 |
| Example 43 | 549 | |
| Example 44 | 308 | |
| Example 45 | 261 | |
| Example 46 | 2498 | |
| Example 47 | 346 | |
| Example 48 | 184 | |
| Example 49 | | 146 |
| Example 50 | 6721 | |
| Example 51 | 133 | |
| Example 52 | 227 | |
| Example 53 | | 66 |
| Example 54 | 807 | 67 |
| Example 55 | 10 000 | |
| Example 56 | 137 | |
| Example 57 | 5865 | |
| Example 58 | 760 | 71 |
| Example 59 | 417 | 50 |
| Example 60 | | 290 |
| Example 61 | | 77 |
| Example 62 | 530 | |
| Example 63 | 6155 | |
| Example 64 | | 10 000 |
| Example 65 | 6460 | |
| Example 66 | | 131 |
| Example 67 | 2207 | |
| Example 68 | 202 | 79 |
| Example 69 | 250 | |
| Example 70 | | 195 |
| Example 71 | 5375 | 120 |
| Example 72 | | 89 |
| Example 73 | 650 | |
| Example 74 | | 10 |
| Example 75 | | 69 |
| Example 76 | | 77 |
| Example 77 | | 698 |
| Example 78 | | 129 |
| Example 79 | | 20 |
| Example 80 | | 94 |
| Example 81 | | 1940 |
| Example 82 | | 133 |
| Example 83 | | 115 |
| Example 84 | | 17 |
| Example 85 | | 340 |
| Example 86 | | 26 |
| Example 87 | | 75 |
| Example 88 | | 5 |
| Example 89 | | 3 |
| Example 90 | | 14 |
| Example 91 | | 71 |
| Example 92 | | 57 |
| Example 93 | | 63 |
| Example 94 | | 11 |
| Example 95 | | 35 |
| Example 96 | | 6 |
| Example 97 | | 260 |
| Example 98 | | 219 |
| Example 99 | | 666 |
| Example 100 | | 3 |
| Example 101 | | 13 |
| Example 102 | | 43 |
| Example 103 | | 7 |
| Example 104 | | 42 |
| Example 105 | | 15 |
| Example 106 | | 27 |
| Example 107 | | 24 |
| Example 108 | | 56 |
| Example 109 | | 43 |
| Example 110 | | 278 |
| Example 111 | | 301 |
| Example 112 | | 23 |
| Example 113 | | 664 |
| Example 114 | | 26 |
| Example 115 | | 10 |
| Example 116 | | 51 |
| Example 117 | | 19 |
| Example 118 | | 12 |
| Example 119 | | 194 |
| Example 120 | | 11 |
| Example 121 | | 44 |
| Example 122 | | 503 |
| Example 123 | | 77 |
| Example 124 | | 124 |
| Example 125 | | 16 |
| Example 126 | | 57 |
| Example 127 | | 61 |
| Example 128 | | 69 |
| Example 129 | | 1000 |
| Example 130 | | 70 |
| Example 131 | | 41 |
| Example 132 | | 533 |
| Example 133 | | 174 |
| Example 134 | | 124 |
| Example 135 | | 1 |
| Example 136 | | 26 |
| Example 137 | | 68 |
| Example 138 | | 35 |
| Example 139 | | 3000 |
| Example 140 | | 302 |
| Example 141 | | 60 |
| Example 142 | | 22 |
| Example 143 | | 473 |
| Example 144 | | 432 |
| Example 145 | | 38 |
| Example 146 | | 180 |
| Example 147 | | 4 |
| Example 148 | | 234 |
| Example 149 | | 43 |
| Example 150 | | 189 |
| Example 151 | | 29 |
| Example 152 | | 938 |

-continued

| example | Test A | Test B |
| --- | --- | --- |
| Example 153 | | 49 |
| Example 154 | | 28 |

Tests A and B: IC$_{50}$ (nM)

The invention claimed is:
1. A compound according to formula (I):

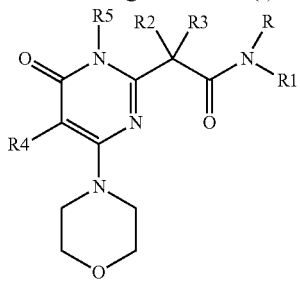

in which:
R1 represents an aryl or heteroaryl radical optionally substituted with one or more substituents, which may be identical or different, chosen from halogen, hydroxyl, CN, nitro, —COOH, —COOalkyl,—NRxRy, —CONRxRy, —NRxCORy, —CORy, —NRxCO$_2$Rz, alkoxy, phenoxy, alkylthio, alkyl, alkenyl, alkynyl, cycloalkyl, O—cycloalkyl, heterocycloalkyl, aryl and heteroaryl; wherein:
  each said alkoxy, phenoxy, alkylthio, alkyl, alkenyl, alkynyl, heterocycloalkyl, aryl and heteroaryl substituent is optionally substituted with one or more radicals, which may be identical or different, chosen from halogen, hydroxyl, alkoxy, NRvRw, heterocycloalkyl and heteroaryl,
  each said aryl and heteroaryl substituent is optionally additionally substituted with one or more alkyl and alkoxy groups, said alkyl and alkoxy groups optionally further substituted with one or more halogen atoms; and
  each of said heterocycloalkyl and heteroaryl substituent may additionally optionally be substituted with an oxo radical;
R represents a hydrogen atom or, together with R1, forms a saturated or partially or totally unsaturated 5- or 6-membered ring fused to an aryl or heteroaryl residue to form a bicyclic radical, said bicyclic radical optionally containing one or more heteroatoms chosen from O, S, N, NH and N(alkyl);
  wherein said bicyclic radical is optionally substituted with one or more substituents, which may be identical or different, chosen from halogen, CO—NH$_2$, hydroxyl, alkyl and alkoxy; each of said alkyl substituents being itself optionally substituted with hydroxyl, alkoxy, NH$_2$, NHalkyl or N(alkyl)$_2$;
R2 and R3, which may be identical or different, independently represent a hydrogen atom, a halogen atom or an alkyl radical optionally substituted with one or more halogen atoms;
R4 represents a hydrogen atom;
R5 represents a hydrogen atom or an alkyl radical optionally substituted with one or more halogen atoms;
NRxRy being such that Rx represents a hydrogen atom or an alkyl radical and Ry represents a hydrogen atom, a cycloalkyl radical or an alkyl radical, wherein each of said cycloalkyl radical and said alkyl radical may optionally be substituted with one or more radicals, which may be identical or different, chosen from hydroxyl, alkoxy, NRvRw and heterocycloalkyl; or Rx and Ry form, with the nitrogen atom to which they are attached, a cyclic radical containing from 3 to 10 ring members and optionally one or more other heteroatoms chosen from O, S, NH and N-alkyl, this radical being optionally substituted with one or more radicals, which may be identical or different, chosen from halogen atoms and alkyl, hydroxyl, oxo, alkoxy, NH$_2$; N(alkyl) and N(alkyl)$_2$ radicals;
NRvRw being such that Rv represents a hydrogen atom or an alkyl radical and Rw represents a hydrogen atom or a cycloalkyl radical, CO$_2$(alkyl), or an alkyl radical optionally substituted with one or more radicals, which may be identical or different, chosen from hydroxyl, alkoxy and heterocycloalkyl; or Rv and Rw form, with the nitrogen atom to which they are attached, a cyclic radical containing from 3 to 10 ring members and optionally one or more other heteroatoms chosen from O, S, NH and N-alkyl, this cyclic radical being optionally substituted with one or more radicals, which may be identical or different, chosen from halogen atoms and alkyl, hydroxyl, oxo, alkoxy, NH$_2$; N(alkyl) radicals;
Rz represents a cycloalkyl radical or an alkyl radical, wherein each of said cycloalkyl radical and said alkyl radical may optionally be substituted with one or more radicals, which may be identical or different, chosen from hydroxyl, alkoxy, NRvRw and heterocycloalkyl;
each of said alkyl, alkoxy and alkylthio radicals being linear or branched and containing from 1 to 6 carbon atoms,
or a pharmaceutically acceptable salt thereof.
2. A compound according to claim 1, in which:
R1 represents a phenyl, pyridine, thienyl, benzoxazolyl, benzofuryl, indazolyl, indolyl, benzothienyl, benzimidazolyl, benzoxazinyl or tetrahydroquinolyl radical, optionally substituted with one or more substituents, which may be identical or different, chosen from halogen, CN, nitro, —COOH, —COO(alkyl), —NRxRy, alkoxy, alkyl, alkynyl and cycloalkyl; wherein:
  each said alkoxy, alkyl and alkynyl substituents is optionally substituted with one or more groups, which may be identical or different, chosen from halogen atoms and hydroxyl, alkoxy, NRvRw, piperidyl, pyrrolidinyl or heteroaryl radicals;
R represents a hydrogen atom or, together with R1, forms a benzoxazinyl, dihydroindolyl, tetrahydroisoquinolyl, tetrahydroquinolyl or dihydropyrrolopyridyl ring, said benzoxazinyl, dihydroindolyl, tetrahydroisoquinolyl, tetrahydroquinolyl or dihydropyrrolopyridyl ring being optionally substituted with one or more substituents, which may be identical or different, chosen from halogen, CO—NH$_2$, hydroxyl, alkyl and alkoxy;
  wherein said alkyl substituent is itself optionally substituted with a hydroxyl, alkoxy, NH$_2$, NH(alkyl) or N(alkyl)$_2$ group;
R2 and R3, which may be identical or different, independently represent a hydrogen atom, a fluorine atom or an alkyl radical;
R4 represents a hydrogen atom;
R5 represents a hydrogen atom or an alkyl radical;
NRxRy being such that Rx represents a hydrogen atom or an alkyl radical and Ry represents a hydrogen atom or an alkyl radical; or Rx and Ry form, with the nitrogen atom to which they are attached, a cyclic radical containing from 3 to 10 ring members and optionally one or more other heteroatoms chosen from O, S, NH and N-alkyl, this cyclic radical being optionally substituted;

NRvRw being such that Rv represents a hydrogen atom or an alkyl radical and Rw represents a hydrogen atom or an alkyl radical;

or a pharmaceutically acceptable salt thereof.

3. A compound of formula (I) according to claim 1, wherein said compound is:

2-[4-(morpholin-4-yl)-6-oxo-1,6-dihydropyrimidin-2-yl]-N-phenylacetamide;
N-(4-fluorophenyl)-2-[4-(morpholin-4-yl)-6-oxo-1,6-dihydropyrimidin-2-yl]acetamide;
N-(3-chlorophenyl)-2-[4-(morpholin-4-yl)-6-oxo-1,6-dihydropyrimidin-2-yl]acetamide ;
N-[3-(dimethylamino)phenyl]-2-[4-(morpholin-4-yl)-6-oxo-1,6-dihydropyrimidin-2-yl]acetamide;
N-(2,4-difluorophenyl)-2-[4-(morpholin-4-yl)-6-oxo-1,6-dihydropyrimidin-2-yl]acetamide;
N-(3,4-difluorophenyl)-2-[4-(morpholin-4-yl)-6-oxo-1,6-dihydropyrimidin-2-yl]acetamide;
2-[4-(morpholin-4-yl)-6-oxo-1,6-dihydropyrimidin-2-yl]-N-(thiophen-3-yl)acetamide;
N-(4-fluoro-3-methoxyphenyl)-2-[4-(morpholin-4-yl)-6-oxo-1,6-dihydropyrimidin-2-yl]acetamide;
N-(2-fluorophenyl)-2[4-(morpholin-4-yl)-6-oxo-1,6-dihydropyrimidin-2-yl]acetamide;
N-(2-methylphenyl)-2-[4-(morpholin-4-yl)-6-oxo-1,6-dihydropyrimidin-2-yl]acetamide;
N-(2-methoxypheny)-2-[4-(morpholin-4-yl)-6-oxo-1,6-dihydropyrimidin-2-yl]acetamide;
N-(2,3-difluorophenyl)-2-[4-(morpholin-4-yl)-6-oxo-1,6-dihydropyrimidin-2-yl]acetamide;
N-(3,5-difluorophenyl)-2-[4-(morpholin-4-yl)-6-oxo-1,6-dihydopyrimidin-2-yl]acetamide;
N-(3-fluorophenyl)-2-[4-(morpholin-4-yl)-6-oxo-1,6-dihydropyrimidin-2-yl]acetamide;
N-(4-chlorophenyl)-2-[4-(morpholin-4-yl)-6-oxo-1,6-dihydropyrimidin-2-yl]acetamide;
N-(3-methoxyphenyl)-2-[4-(morpholin-4-yl)-6-oxo-1,6-dihydropyrimidin-2-yl]acetamide;
2-[4-(morpholin-4-yl)-6-oxo-1,6-dihydropyrimidin-2-yl]-N-[3-(trifluoromethyl)phenyl]acetamide;
N-(3-bromophenyl)-2-[4-(morpholin-4-yl)-6-oxo-1,6-dihydropyrimidin-2-yl]acetamide;
N-[3-(2-methylpropan-2-yl)phenyl]-2-[4-(morpholin-4-yl)-6-oxo-1,6-dihydropyrimidin-2-yl]acetamide;
methyl3-({[4-(morpholin-4-yl)-6-oxo-1,6-dihydropyrimidin-2-yl]acetyl}amino)benzoate;
3-({[4-(morpholin-4-yl)-6-oxo-1,6-dihydropyrimidin-2-yl]acetyl}amino)benzoic acid;
2-[4-(morpholin-4-yl)-6-oxo-1,6-dihydropyrimidin-2yl]-N-[3-(propan-2-yl)phenyl]acetamide;
N-(3-methylphenyl)-2-[4-(morpholin-4-yl)-6-oxo-1,6-dihydropyrimidin-2-yl]acetamide;
N-(3-cyano-4-fluoropheny)-2-[4-(morpholin-4-yl)-6-oxo-1,6-dihydropyrimidin-2-yl]acetamide;
N-(1H-indazol-6yl)-2-[4-(morpholin-4-yl)-6-oxo-1,6-dihydropyrimidin-2-yl]acetamide;
N-(3-cyanophenyl)-2-[4-(morpholin-4-yl)-6-oxo-1,6-dihydropyrimidin-2-yl]acetamide;
N-(5-fluoropyridin-2-yl)-2-[4-(morpholin-4-yl)-6-oxo-1,6-dihyropyrimidin-2-yl]acetamide;
N-(4-fluoro-3-methylphenyl)-2-[4-(morpholin-4-yl)-6-oxo-1,6-dihydropyrimidin-2-yl]acetamide;
N-(3-chloro-4-fluorophenyl)-2-[4-(morpholin-4-yl)-6-oxo-1,6-dihydropyrimidin-2-yl]acetamide;
2-[4-(morpholin-4-yl)-6-oxo-1,6-dihydropyrimidin-2-yl]-N-(pyridin-3-yl)acetamide;
N-(4-fluoro-2-methylphenyl)-2-[4-(morpholin-4-yl)-6-oxo-1,6-dihydropyrirmidin-2-yl]acetamide;
N-(3-hydroxyphenyl)-2-[4-(morpholin-4yl)-6-oxo-1,6-dihydropyrimidin-2-yl]acetamide;
N-(3-bromo-4-fluorophenyl)-2-[4-(morpholin-4-yl)-6-oxo-1,6-dihydropyrimidin-2-yl]acetamide;
2-[4-(morpholin-4-yl)-6-oxo-1,6-dihydropyrimidin-2-yl]-N-(3,4,5-trifluorophenyl)acetamide;
N-[4-fluoro-3-(hydroxymethyl)phenyl]-2-[4-(morpholin-4yl)-6-oxo-1,6-dihydropyrimidin -2-yl]acetamide;
N-(3-cyclopropylephenyl)-2-[4-(morpholin-4-yl)-6-oxo-1,6-dihydropyrimidin-2-yl]acetamide;
N-(2-hydroxyphenyl)-2-[4-(morpholin-4-yl)-6-oxo-1,6-dihydropyrimidin-2-yl]acetamide;
N-[3-(difluoromethoxy)phenyl]-2-[4-(morpholin-4-yl)-6-oxo-1,6-dihydropyrimidin-2-yl]acetamide;
N-(4-fluoro-3-methoxyphenyl)-2-[4-(morpholin-4-yl)-6-oxo-1,6-dihydropyrimidin-2-yl]propanamide;
N-(2,3-dimethylphenyl)-2-[4-(morpholin-4-yl)-6-oxo-1,6-dihydropyrimidin-2-yl]actetamide;
N-(2-fluoro-3-methylphenyl)-2-[4-(morpholin-4-yl)-6-oxo-1,6-dihydropyrimidin-2-yl]acetamide;
N-(1,3-benzoxazol-4-yl)-2-[4-(morpholin-4-yl)-6-oxo-1,6-dihydropyrimidin-2-yl]acetamide;
2-[4-(morpholin-4-yl)-6-oxo-1,6-dihydropyrimidin-2-yl]-N-[3-(trifluoromethoxy)phenyl]acetamide;
2-[4-(morpholin-4-yl)-6-oxo-1,6-dihydropyrimidin-2-yl]-N-[3-(propan-2-yloxy)phenyl]acetamide;
N-(4-fluoro-2-methoxyphenyl)-2-[4-(morpholin-4-yl)-6-oxo-1,6-dihydropyrimidin-2-yl]acetamide;
2-methylpropan-2-yl{2-[3-({[4-(morpholin-4-yl)-6-oxo-1,6-dihydropyrimidin-2-yl]acetyl}amino)phenyl]ethyl}carbamate;
N-[4-fluoro-3-(trifluoromethyl)phenyl]-2-[4-(morpholin-4-yl)-6-oxo-1,6-dihydropyrimidin-2-yl]acetamide;
N-(3-ethynylphenyl)-2-[4-(morpholin-4-yl)-6-oxo-1,6-dihydropyrimidin-2-yl]acetamide;
N-[3-(cyclopentyloxy)phenyl]-2-[4-(morpholin-4-yl)-6-oxo-1,6-dihydropyrimidin-2-yl]acetamide;
N-(4-fluoro-2-hydroxyphenyl)-2-[4-(morpholin-4-yl)-6-oxo-1,6-dihydropyrimidin-2-yl]acetamide;
2-[2-(2,3-dihydro-1H-indol-1-yl)-2-oxoethyl]-6-(morpholin-4-pyrimidin-4(3H)-one;
N-(3-cyclopropyl-4-fluorophenyl)-2-[4-(morpholin-4-yl)-6-oxo-1,6-dihydropyrimidin-2-yl]acetamide;
2-[4-(morpholin-4-yl)-6-oxo-1,6-dihydropyrimidin-2-yl]-N-(2,3,4-trifluorophenyl)acetamide;
N-[4-fluoro-3-(trifluoromethoxy)phenyl]-2-[4-(morpholin-4-yl)-6-oxo-1,6-dihydropyrimidin-2-yl]acetamide;
N-[3-(2-hydroxyethoxy)phenyl]-2-[4-(morpholin-4-yl)-6-oxo-1,6-dihydropyrimidin-2-yl]acetamide;
N-(3-iodophenyl)-2-[4-(morpholin-4-yl)-6-oxo-1,6-dihydropyrimidin-2-yl]acetamide;
methyl 2-fluoro-5-({[4-(morpholin-4-yl)-6-oxo-1,6-dihydropyrimidin-2-yl]acetyl}amino)benzoate;
N-(3-ethoxyphenyl)-2-[4-(morpholin-4-yl)-6-oxo-1,6-dihydropyrimidin-2-yl]acetamide;
N-(2,4-difluoro-3-methoxyphenyl)-2-[4-(morpholin-4-yl)-6-oxo-1,6-dihydropyrimidin-2-yl]acetamide;
2-[4-(morpholin-4-yl)-6-oxo-1,6-dihydropyrimidin-2-yl]-N-(2,4,5-trifluorophenyl)acetamide;
N-(3,5-dichloro-4-fluorophenyl)-2-[4-(morpholin-4yl)-6-oxo-1,6-dihydropyrimidin-2-yl]acetamide;
2-[2-(2,3-dihydro-4H-1,4-benzoxazin-4-yl)-2-oxoethyl]-6-(morpholin-4-yl)pyrimidin-4(3H)-one;

N-(4-fluoro-3-nitrophenyl)-2-[4-(morpholin-4-yl)-6-oxo-1,6-dihydropyrimidin-2-yl]acetamide;
2-fluoro-5-({[4-(morpholin-4-yl)-6-oxo-1,6-dihydropyrimidin-2-yl]acetyl}amino)benzoic acid;
N-(5-fluoro-2-hydroxyphenyl)-2-[4-(morpholin-4-yl)-6oxo-1,6dihydropyrimidin-2-yl]acetamide;
N-(2-bromo-4-fluorophenyl)-2-[4-(morpholin-4-yl)-6-oxo-1,6-dihydropyrimidin-2-yl]acetamide;
N-(4-fluorophenyl)-2-[1-methyl-4-(morpholin-4-yl)-6-oxo-1,6-dihydropyrimidin-2-yl]acetamide;
N-(3-chloro-4-fluorophenyl)-2-[1-methyl-4-(morpholin-4-yl)-6-oxo-1,6-dihydropyrimidin-2-yl]acetamide;
N-(3-bromophenyl)-2-[1-methyl-4-(morpholin-4-yl)-6-oxo-1,6-dihydropyrimidin-2-yl]acetamide;
2-[1-ethyl-4-(morpholin-4-yl)-6-oxo-1,6-dihydropyrimidin-2-yl]-N-(4-fluorophenyl)acetamide;
N-(1H-indol-4-yl)-2-[4-(morpholin-4yl)-1,6-dihydropyrimidin-2-yl]acetamide;
N-(4-fluorophenyl)-3-methyl-2-[4-(morpholin-4-yl)-6-oxo-1,6-dihydropyrimidin-2-yl]butanamide;
N-[4-fluoro-3-(methoxymethyl)phenyl]-2-[4-(morpholin-4-yl)-6-oxo-1,6-dihydropyrimidin-2-yl]acetamide;
N-(4-fluoro-3-iodophenyl)-2-[4-(morpholin-4-yl)-6-oxo-1,6-yl]acetamide;
N-2-[4-(morpholin-4-yl)-6-oxo-1,6-dihydropyrimidin-2-yl]-N-[3-(1,1,2,2-tetrafluoroethoxy)phenyl]acetamide;
N-[3-(difluoromethyl)-4-fluorophenyl]-2-[4-(morpholin-4-yl)-6-oxo-1,6-dihydropyrimidin-2-yl]acetamide;
2,2-difluoro-N-(4-fluorophenyl)-2-[4-(morpholin-4-yl)-6-oxo-1,6-dihydropyrimidin-2-yl]acetamide;
N-(3,4-difluorophenyl)-2-[1-methyl-4-(morpholin-4-yl)-6-oxo-1,6-dihydropyrimidin-2-yl]acetamide;
2-[2-(2,3-dihydro-1H-indol-1-yl)-2-oxoethyl]-3-methyl-6-(morpholin-4-yl)pyrimidin-4(3H)-one;
N-(3-bromo-4-fluorophenyl)-2-[1methyl-4-(morpholin-4-yl)-6-oxo-1,6-dihydropyrimidin-2-yl]acetamide;
N-[4-fluoro-3-(hydroxymethyl)phenyl]-2-[1-methyl-4-(morpholin-4-yl)-6-oxo-1,6-dihydropyrimidin-2-yl]acetamide;
N-(3-cyclopropylphenyl)-2-[1-methyl-4-(morpholin-4-yl)-6-oxo-1,6-dihydropyrimidin-2-yl]acetemide;
N-(4-fluoro-3-methoxyphenyl)-2-[1-methyl-4-(morpholin-4-yl)-6-oxo-1,6-dihydropyrimidin-2-yl]acetamide;
N-(1-benzofur-4-yl)-2-[4-(morpholin-4-yl)-6-oxo-1,6-dihydropyrimidin-2-yl]acetamide;
2-[1-methyl-4-(morpholin-4-yl)-6-oxo-1,6-dihydropyrimidin-2-yl]-N-phenylacetamide;
N-(3-cyclopropyl-4-fluorophenyl)-2-[1-methyl-4-(morpholin-4-yl)-6-oxo-1,6-dihydropyrimidin-2-yl]acetamide;
N-(3-fluoro-2-hydroxyphenyl)-2-[4-(morpholin-4-yl)-6-oxo-1,6-dihydropyrimidin-2-yl]actetamide;
2-[2-(4-fluoro-2,3-dihydro-1H-indol-1-yl)-2-oxoethyl]-6-(morpholin-4-yl)pyrimidin-4(3H)-one;
2-[2-(4-chloro-2,3-dihydro-1H-indol-1-yl)-2-oxoethyl]-6-(morpholin-4-yl)pyrimidin-4(3H)-one;
N-(3-ethynyl-4-fluorophenyl)-2-[4-(morpholin-4-yl)-6-oxo-1,6-dihydropyrimidin-2-yl]acetamide;
2-[2-(4-hydroxy-2,3-dihydro-1H-indol-1-yl)-2-oxoethyl]-6-(morpholin-4-yl)pyrimidin-4(3H)-one;
2-[2-(4,6-difluoro-2,3-dihydro-1H-indol-1-yl)-2-oxoethyl]-6-(morpholin-4-yl)pyrimidin-4(3H)-one;
N-(4-fluoro-3-iodophenyl)-2-(1-methyl-4-morpholin-4-yl-6-oxo-1,6-dihydropyrimidin-2-yl)acetamide;
2-[2-(4,5-difluoro-2,3-dihydro-1H-indol-1-yl)-2-oxoethyl]-6-(morpholin-4-yl)pyrimidin-4(3H)-one;
2-[2-(6-fluoro-2,3-dihydro-1H-indol-1-yl)-2-oxoethyl]-6-(morpholin-4-yl)pyrimidin-4(3H)-one;
2-[2-(2-methyl-2,3-dihydro-1H-indol-1-yl)-2-oxoethyl]-6-(morpholin-4-yl)pyrimidin-4(3H)-one;
N-[3-(difluoromethyl)-4-fluorophenyl]-2-[1-methyl-4-(morpholin-4-yl)-6-oxo-1,6-dihydropyrimidin-2-yl]acetamide;
2-[1-methyl-4-(morpholin-4-yl)-6-oxo-1,6-dihydropyrimidin-2-yl]-N-(3,4,5-trifluorophenyl)acetamide;
N-(1-methyl-1H-indol-4-yl)-2-[4-(morpholin-4-yl)-6-oxo-1,6-dihydropyrimidin-2-yl]acetamide;
2-[2-(4-methyl-2,3-dihydro-1H-indol-1-yl)-2-oxoethyl]-6-(morpholin-4-yl)pyrimidin-4(3H)-one;
2-[2-(3-methyl-2,3-dihydro-1H-indol-1-yl)-2-oxoethyl]-6-(morpholin-4-yl)pyrimidin-4(3H)-one;
2-[2-(4-fluoro-2,3-dihydro-1H-indol-1-yl)-2-oxoethyl]-3-methyl-6-(morpholin-4-yl)pyrimidin-4(3H)-one;
2-[2-(5-fluoro-2,3-dihydroindol-1-yl)-2-oxoethyl]-6-morpholin-4-yl-3H-pyrimidin-4-one;
2-[2-(4-chloro-2,3-dihydro-1H-indol-1-yl)-2-oxoethyl]-3-methyl-6-(morpholin-4-yl)pyrimidin-4(3H)-one;
N-(1-benzothiophen-4-yl)-2-[4-(morpholin-4-yl)-6-oxo-1,6-dihydropyrimidin-2-yl]acetamide;
2-{2-[2-(hydroxymethyl)-2,3-dihydro-1H-indol-1-yl]-2-oxoethyl}-6-(morpholin-4-yl)pyrimidin-4(3H)-one;
2-[4-(morpholin-4-yl)-6-oxo-1,6-dihydropyrimidin-2-yl]-N-{2-[2-(piperidin-1-yl)ethoxy]phenyl}acetamide;
N-[2-(2-methoxyethoxy)phenyl]-2-[4-(morpholin-4-yl)-6-oxo-1,6-dihydropyrimidin-2-yl]acetamide;
2-[2-(4-hydroxy-2,3-dihydro-1H-indol-1-yl)-2-oxoethyl]-3-methyl-6-(morpholin-4-yl)pyrimidin-4(3H)-one;
2-[2-(4-methoxy-2,3-dihydro-1H-indol-1-yl)-2-oxoethyl]-3-methyl-6-(morpholin-4-yl)pyrimidin-4(3H)-one;
2-[2-(3,4-dihydroisoquinolin-2(1H)-yl)-2-oxoethyl]-6-(morpholin-4-yl)pyrimidin-4(3H)-one;
2-[4-(morpholin-4-yl)-6-oxo-1,6-dihydropyrimidin-2-yl]-N-{2-[2-(pyrrolidin-1-yl)ethoxy]phenyl}acetamide;
2-[4-(morpholin-4-yl)-6-oxo-1,6-dihydropyrimidin-2-yl]-N-[2-(pyridin-3-ylmethoxy)phenyl]acetamide;
3-methyl-2-[2-(4-methyl-2,3-dihydro-1H-indol-1-yl)-2-oxoethyl]-6-(morpholin-4-yl)pyrimidin-4(3H)-one;
2-(2-{3-[(dimethylamino)methyl]-2,3-dihydro-1H-indol1-yl}-2-oxoethyl)-6-(morpholin-4-yl)pyrimidin-4(3H)-one;
2-[2-(4-bromo-2,3-dihydro-1H-indol-1-yl)-2-oxoethyl]-3-methyl-6-(morpholin-4-yl)pyrimidin-4(3H)-one;
2-{2-[(2S)-2-methyl-2,3-dihydro-1H-indol-1-yl]-2-oxoethyl}-6-(morpholin-4-yl)pyrimidin-4(3H)-one;
2-{2-[(2R)methyl-2,3-dihydro-1H-indol-1-yl]-2-oxoethyl}-6-(morpholin-4-yl)pyrimidin-4(3H)-one;
3-methyl-2-[2-(3methyl-2,3-dihydro-1H-indol-1-yl)-2-oxoethyl]-6-(morpholin-4-yl)pyrimidin-4(3H)-one;
2-{2-[2-(methoxymethyl)-2,3-dihydro-1H-indol-1-yl]-2-oxoethyl}-6-(morpholin-4-yl)pyrimidin-4(3H)-one;
2-[2-(4-ethoxy-2,3-dihydro-1H-indol-1-yl)-2-oxoethyl]-6-(morpholin-4-yl)pyrimidin-4(3H)-one;
1-{[4-(morpholin-4-yl)-6-oxo-1,6-dihydropyrimidin-2-yl]acetyl}-2,3-dihydro-1H-indole-2-carboxamide;
3-methyl-2-[2-(2-methyl-2,3-dihydro-1H-indol-1-yl)-2-oxoethyl]-6-(morpholin-4-yl)pyrimidin-4(3H)-one;
2-[2-(6-fluoro-2,3-dihydro-1H-indol-1-yl)-2-oxoethyl]-3-methyl-6-(morpholin-4-yl)pyrimidin-4(3H)-one;
2-{2-[(3S)-3-methyl-2,3-dihydro-1H-indol-1-yl]-2-oxoethyl}-6-(morpholin-4-yl)pyrimidin-4(3H)-one;

2-{2-[(3R)-3-methyl-2,3-dihydro-1H-indol-1-yl]-2-oxoethyl}-6-(morpholin-4-yl)pyrimidin-4(3H)-one;
2-[2-(5,6-difluoro-2,3-dihydro-1H-indol-1-yl)-2-oxoethyl]-3-methyl-6-(morpholin-4-yl)pyrimidin-4(3H)-one;
2-[2-(4,5-difluoro-2,3-dihydro-1H-indol-1-yl)-2-oxoethyl]-3-methyl-6-(morpholin-4-yl)pyrimidin-4(3H)-one;
2-[2-(1,3-dihydro-2H-isoindol-2-oxoethyl]-6-(morpholin-4-yl)pyrimidin-4(3H)-one;
N-(1-benzothiophen-4-yl)-2-[1-methyl-4-(morpholin-4-yl)-6-oxo-1,6-dihydropyrimidin-2-yl]acetamide;
2-[2-(5-chloro-3,4-dihydroquinolin-1(2H)-yl)-2-oxoethyl]-6-(morpholin-4-yl)pyrimidin-4(3H)-one;
2-{2-[4-(hydroxymethyl)-2,3-dihydro-1H-indol-1-yl]-2-oxoethyl}-6-(morpholin-4-yl)pyrimidin-4(3H)-one;
N-[4-fluoro-2-(piperidin-4-ylmethoxy)phenyl]-2-[4-(morpholin-4-yl)-6-oxo-1,6-dihydropyrimidin-2-yl]acetamide;
2-[2-(5chloro-2,3dihydroindol-1-yl)-2-oxoethyl]-6-morpholin-4-yl-3H-pyrimidin-4-one;
2-[2-(4-bromo-2,3-dihydroindol-1-yl)-2-oxoethyl]-6-morpholin-4-yl-3H-pyrimidin-4-one;
2-(2-{(3S)-3-[(dimethylamino)methyl]-2,3-dihydro-1H-indol-1-yl}-2-oxoethyl)-6-(morpholin-4-yl)pyrimidin-4(3H)-one;
2-(2-{(3R)-3-[(dimethylamino)methyl]-2,3-dihydro-1H-indol-1-yl}-2-oxoethyl)-6-(morpholin-4-yl)pyrmidin-4(3H)-one;
N-[4-fluoro-2-(2-methoxyethoxy)phenyl]-2-[4-(morpholin-4-yl)-6-oxo-1,6-dihydropyrimidin-2-yl]acetamide;
N-(1H-benzimidazol-4-yl)-2-[4-(morpholin-4-yl)-6-oxo-1,6-dihydropyrimidin-2-yl]acetamide;
methyl 2-hydroxy-3-({[4-(morpholin-4-yl)-6-oxo-1,6-dihydropyrimidin-2-yl]acetyl}amino)benzoate;
2-[2-(4-methoxy-2,3-dihydroindol-1-yl)-2-oxoethyl]-6-morpholin-4-yl-3H-pyrimidin-4-one;
N-(3-bromo-2-hydroxyphenyl)-2-[4-(morpholin-4-yl)-6-oxo-1,6-dihydropyrimidin-2-yl]acetamide;
N-(3,4-dihydro-2H-1,4-benzoxazin-8-yl)-2-[4-(morpholin-4-yl)-6-oxo-1,6-dihydropyrimidin-2-yl]acetamide;
methyl 5-fluoro-2-({[4-(morpholin-4-yl)-6-oxo-1,6-dihydopyrimidin-2-yl]acetyl}amino)benzoate;
2-(2-{3-[(diethylamino)methyl]-2,3-dihydro-1H-indol-1-yl}-2-oxoethyl)-6-(morpholin-4-yl)pyrimidin-4(3H)-one;
2-[2-(2,3-dihydro-1H-pyrrolo[3,2-b]pyridin-1-yl)-2-oxoethyl]-6-(morpholin-4-yl)pyrimidin-4(3H)-one;
2-[2-(5,6-difluoro-2,3-dihydroindol-1-yl)-2-oxoethyl]-6-morpholin-4-yl-3H-pyrimidin-4-one;
2-[4-(morpholin-4-yl)-6-oxo-1,6-dihydropyrimidin-2-yl]-N-(1,2,3,4-tetrahydroquinolin-8-yl)acetamide;
2-[2-(8-chloro-2,3-dihydro-4H-1,4-benzoxazin-4-yl)-2-oxoethyl]-6-(morpholin-4-yl)pyrimidin-4(3H)-one;
N-(2-hydroxy-3-methylphenyl)-2-[4-(morpholin-4-yl)-6-oxo-1,6-dihydropyrimidin-2-yl]acetamide;
N-(2-hydroxy-3-nitrophenyl)-2-[4-(morpholin-4-yl)-6-oxo-1,6-dihydropyrimidin-2-yl]acetamide;
N-(3-cyano-2-hydroxyphenyl)-2-[4-(morpholin-4-yl)-6-oxo-1,6-dihydropyrimidin-2-yl]acetamide;
N-[2-hydroxy-3-(trifluoromethyl)phenyl]-2-[4-(morpholin-4-yl)-6-oxo-1,6-dihydropyrimidin-2-yl]acetamide;
2-[2-(3,3-dimethyl-2,3-dihydro-1H-indol-1-yl)-2-oxoethyl]-6-(morpholin-4-yl)pyrimidin-4(3H)-one;
or a pharmaceutically acceptable salt thereof.

* * * * *